US007084257B2

(12) United States Patent
Deshpande et al.

(10) Patent No.: US 7,084,257 B2
(45) Date of Patent: Aug. 1, 2006

(54) FULLY HUMAN ANTIBODY FAB FRAGMENTS WITH HUMAN INTERFERON-GAMMA NEUTRALIZING ACTIVITY

(75) Inventors: Rajendra V. Deshpande, Thousand Oaks, CA (US); Mei-Mei Tsai, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 391 days.

(21) Appl. No.: 09/972,656

(22) Filed: Oct. 5, 2001

(65) Prior Publication Data

US 2003/0099647 A1 May 29, 2003

(51) Int. Cl.
*C07K 16/00* (2006.01)
*C07K 14/00* (2006.01)
*A61K 38/21* (2006.01)

(52) U.S. Cl. .............................. 530/387.9; 530/388.1; 530/389.1; 530/351; 424/85.5

(58) Field of Classification Search ............ 530/387.9, 530/388.1, 389.1, 351; 424/85.5
See application file for complete search history.

(56) References Cited

U.S. PATENT DOCUMENTS

| | | | | |
|---|---|---|---|---|
| 4,474,893 | A | 10/1984 | Reading | 436/547 |
| 4,634,664 | A * | 1/1987 | Oestberg | 435/70.21 |
| 4,666,865 | A | 5/1987 | Chang et al. | 436/518 |
| 4,699,880 | A | 10/1987 | Goldstein | 435/172.2 |
| 5,693,761 | A | 12/1997 | Queen et al. | |
| 5,985,265 | A | 11/1999 | Kinstler et al. | 424/85.4 |
| 6,135,941 | A | 10/2000 | Hillman et al. | |
| 6,150,584 | A | 11/2000 | Kucherlapati et al. | 800/18 |
| 6,255,458 | B1 | 7/2001 | Lonberg et al. | |
| 6,300,129 | B1 | 10/2001 | Lonberg et al. | 435/326 |
| 6,312,690 | B1 | 11/2001 | Edelman et al. | |
| 6,329,511 | B1 | 12/2001 | Vasquez et al. | |
| 6,410,824 | B1 | 6/2002 | Ehrhardt et al. | |
| 6,444,799 | B1 | 9/2002 | Ross | |
| 6,498,027 | B1 | 12/2002 | Van Es et al. | |
| 2002/0146750 | A1 | 10/2002 | Hoogenboom et al | |
| 2003/0056233 | A1 | 3/2003 | Ehrhardt et al. | |

FOREIGN PATENT DOCUMENTS

| | | |
|---|---|---|
| EP | 0 154 316 B1 | 9/1989 |
| EP | 0 401 384 B1 | 3/1996 |
| JP | 11000174 | 1/1999 |
| WO | WO83/04053 | 11/1983 |
| WO | WO 91/02005 | 2/1991 |
| WO | WO 92/11018 | 7/1992 |
| WO | WO 99/55369 | 11/1999 |
| WO | WO 00/05268 | 2/2000 |
| WO | WO 00/06605 | 2/2000 |
| WO | WO 00/55351 | 9/2000 |
| WO | WO 01/09350 | 2/2001 |
| WO | WO 01/25492 | 4/2001 |
| WO | WO 01/34800 | 5/2001 |
| WO | WO 01/40306 | 6/2001 |
| WO | WO 01/57182 | 8/2001 |
| WO | WO 01/88132 | 11/2001 |
| WO | WO 01/98353 | 12/2001 |
| WO | WO 02/083872 | 10/2002 |
| WO | WO 02/094325 | 11/2002 |
| WO | WO 02/094879 | 11/2002 |
| WO | WO 02/102854 | 12/2002 |

OTHER PUBLICATIONS

Morrison and Boyd, Organic Chemistry, 3rd edition, 1973, pp. 1134-1135.*

Langer, "Interferon receptors", *Immunology Today*, vol. 9, (12), pp. 393-400, (1988.

Skurkovich, "Successful first-time use of Antibodies to Interferon-• alone . . . ", *Int. J. Immunotherapy*, vol. XIV (1) , pp. 23-32, (1998).

Gerez, Hyperinducible expression of the interferon-gamma (IFN-•) gene and its suppression in systemic lupus erthematosus (SLE), *Clin. Exp. Immunol*, vol. 109, pp. 296-303, (1997).

Cabilly, "Generation of antibody activity from immunoglobulin polypeptide chains produced in *Escherichia coli", Proc. Nalt. Acad. Sci.*, vol. 81, pp. 3273-3277, (1984).

Morrison, "Chimeric human antibody molecules: Mouse antigen-binding domains with human constant region domains", *Proc. Natl. Acad. Sci.*, vol. 81, pp. 6851-6855, (1984).

Thakur and Landolfi, "A potent neutralizing monoclonal antibody can discriminate amongst IFNγ from various primates with greater specificity than can the human IFNγ receptor complex," *Mol Immunol*, 36:1107-1115 (1999).

Takekoshi et al., "Human Monoclonal anti-HCMV neutralizing antibody from phage display libraries," *J Virol Methods*, 74:89-98 (1998).

National Center for Biotechnology Information (NCBI) Accession No. 1AK5 [gi:2554679]. Inosine monophosphate dehydrogenase (Impdh) from Tritrichomonas foetus.

(Continued)

*Primary Examiner*—Janet L. Andres
*Assistant Examiner*—Jegatheesan Seharaseyon
(74) *Attorney, Agent, or Firm*—Rosemary Sweeney

(57) ABSTRACT

Selective binding agents of interferon-gamma (IFNγ) are provided by the invention. More particularly, the invention provides for antibodies and antigen binding domains which selectively bind to IFNγ and may be used to prevent or treat conditions relating to autoimmune and inflammatory diseases such as rheumatoid arthritis, systemic lupus erythematosus and multiple sclerosis. Nucleic acid molecules encoding said antibodies and antigen binding domains, and expression vectors and host cells for the production of same are also provided.

38 Claims, 47 Drawing Sheets

OTHER PUBLICATIONS

NCBI Acc. No. 1AYX [gi:3212473]; crystal structure of glucoamylase from *Saccharomycopsis fibuligera* at 1.7 angstroms.

NCBI Acc. No. 1B37_A [gi:6730082]; chain A, A 30 angstrom U-shaped catalytic tunnel in the crystal structure of polyamine oxidase.

GenBank Acc. No. BG756803; GenBank gi:14067456; dbEST Id: 8516861.

NCBI Acc. No. CAA03180; EMBL Acc. No. A49389.1; unnamed protein product [unidentified].

NCBI Acc. No. G00590 [gi:683994]; fruit fly STS Dm0315 clone 1 (3) 03670, sequence tagged site.

NCBI Acc. No. G01099 [gi:684503]; fruit fly STS Dm1782 clone DS00349 T7, sequence tagged site.

NCBI Acc. No. G37297 [gi:2996948]; SHGC-57484 *Homo sapiens* STS genomic, sequence tagged site.

NCBI Acc. No. G46898 [gi:4493189]; Z14933_1 zebrafish AB Danio rerio STS genomic clone z14933 5', sequence tagged site.

NCBI Acc. No. G49294 [gi:4757467]; stcB33B7_3867 chromosome 22 genomic clone *Homo sapiens* STS genomic clone 33B7, sequence tagged site.

NCBI Acc. No. G56897 [gi:6122216]; SHGC-102633 *Homo sapiens* STS genomic, sequence tagged site.

NCBI Acc. No. G61782 [gi:6126951]; SHGC-89104 *Homo sapiens* STS genomic, sequence tagged site.

NCBI Acc. No. G72435 [gi:15146465]; MARC 7597-7598:992008547:1 SCF—porcine spleen Sus scrofa STS genomic, sequence tagged site.

NCBI Acc. No. G73246 [gi:17046947]; csnprev11-pcr3-1 *Homo sapiens* STS genomic, sequence tagged site.

NCBI Acc. No. L25291 [gi:409036]; human polyreactive Ig rearranged mu-chain, V-D21/10-JH4, partial cds.

NCBI Acc. No. NP_274431 [gi:15677278]; crossover junction endodeoxyribonuclease RuvC [Neisseria meningitidis MC58].

NCBI Acc. No. X56592 [gi:36655]; human mRNA for immunoglobulin heavy chain (T14:Vh4-T14).

Boulianne, "Production of functional chimaeric mouse/human antibody", *Nature*, vol. 312, pp. 643-646, (1984).

Neuberger, "A hapten-specific chimaeric IgE antibody with human physiological effector function", *Nature*, vol. 314, pp. 268-270, (1985).

Liu, "Chimeric mouse-human IgG1 antibody that can mediate lysis of cancer cells", *Proc. Natl. Acad. Sci.*, vol. 84, pp. 3439-3443, (1987).

Wahl, "Improved radioimaging and tumor localization with monoclonal F(ab')$_2$", *The Journal of Nuclear Medicine*, vol. 24, (4), pp. 316-325, (1983).

Lewis, "Use of a novel mutagenesis strategy, optimized residue substitution, to decrease the off-rate of an anti-gp120 antibody", *Molecular Immnunology, vol. 32 )14_.* pp. 1065-1072, (1995).

Marks, "By-passing immunization: Building high affinity human antibodies by chain shuffling", *Bio/Technology*, vol. 10, pp. 779-783, (1992).

Kranz, "Restricted reassociation of heavy and light chains from hapten-specific monoclonal antibodies", *Proc. Natl. Acad Sci.*, vol. 78 (9), pp. 5807-5811, (1981).

Jones, "Replacing the complementarity-determining regions in a human antibody with those from a mouse", *Nature*, vol. 321, pp. 522-525, (1986).

Riechmann, "Reshaping human antibodies for therapy", *Nature*, vol. 332, pp. 323-327, (1988).

Verhoeyen, "Reshaping human antibodies: Grafting an Antilysozyme Activity", *Science*, vol. 239, pp. 1534-1536, (1988).

Jakobovits, "Analysis of homozygous mutant chimeric mice: Deletion of the immunoglobulin heavychain joining region blocks B-cell development and antibody production", *Proc. Natl. Acad. Sci.*, vol. 90, pp. 2551-2555, (1993).

Jakobovits, "Germ-line transmission and expression of a human-derived yeast artificial chromosome", *Nature*, vol. 362. pp. 255-258, (1993).

Br•ggemann, "Designer Mice: The production of human antibody repertoires in Transgenic animals", *Generation of Antibodies by Cell and Gene Immortalization*, vol. 7, pp. 33-40, (1993).

Hoogenboom, "By-passing immunisation human antibodies form synthetic repertoires of germline $V_H$ Gene segments rearranged in Vitro", *J. Mol. Biol.*, vol. 227, pp. 381-388, (1992).

Marks, "By-passing immunization Human antibodies from V-gene libraries displayed on Phage", *J. Mol. Biol.*, vol. 222, pp. 581-597, (1991).

* cited by examiner

Figure 3

```
CAG GTG CAG CTG CAG CAG TGG GGC GCA GGA CTG TTG AAG CCT TCG GAG
Gln Val Gln Leu Gln Gln Trp Gly Ala Gly Leu Leu Lys Pro Ser Glu

ACC CTG TCC CTC ACC TGC GCT GTC TAT GGT GGG TCC TTC AGT GGT TAC
Thr Leu Ser Leu Thr Cys Ala Val Tyr Gly Gly Ser Phe Ser Gly Tyr

TAC TGG AGC TGG ATC CGC CAG CCC CCA GGG AAG GGG CTG GAG TGG ATT
Tyr Trp Ser Trp Ile Arg Gln Pro Pro Gly Lys Gly Leu Glu Trp Ile

GGG GAA ATC AAT CAT AGT GGA AGC ACC AAC TAC AAC CCG TCC CTC AAG
Gly Glu Ile Asn His Ser Gly Ser Thr Asn Tyr Asn Pro Ser Leu Lys

AGT CGA GTC ACC ATA TCA GTA GAC ACG TCC AAG AAC CAG TTC TCC CTG
Ser Arg Val Thr Ile Ser Val Asp Thr Ser Lys Asn Gln Phe Ser Leu

AAG CTG AGC TCT GTG ACC GCC GCG GAC ACG GCT GTG TAT TAC TGT GCG
Lys Leu Ser Ser Val Thr Ala Ala Asp Thr Ala Val Tyr Tyr Cys Ala

AGA GGC CGG GCA CGG AAC TGG AGA TCG CGT TTT GAC TAC TGG GGC CAG
Arg Gly Arg Ala Arg Asn Trp Arg Ser Arg Phe Asp Tyr Trp Gly Gln

GGA ACC CTG GTC ACC GTC TCT AGT GCC TCC ACC AAG GGC CCA TCG GTC
Gly Thr Leu Val Thr Val Ser Ser Ala Ser Thr Lys Gly Pro Ser Val

TTC CCC CTG GCA CCC TCC TCC AAG AGC ACC TCT GGG GGC ACA GCG GCC
Phe Pro Leu Ala Pro Ser Ser Lys Ser Thr Ser Gly Gly Thr Ala Ala

CTG GGC TGC CTG GTC AAG GAC TAC TTC CCC GAA CCG GTG ACG GTG TCG
Leu Gly Cys Leu Val Lys Asp Tyr Phe Pro Glu Pro Val Thr Val Ser

TGG AAC TCA GGC GCC CTG ACC AGC GGC GTG CAC ACC TTC CCG GCT GTC
Trp Asn Ser Gly Ala Leu Thr Ser Gly Val His Thr Phe Pro Ala Val

CTA CAG TCC TCA GGA CTC TAC TCC CTC AGC AGC GTG GTG ACC GTG CCC
Leu Gln Ser Ser Gly Leu Tyr Ser Leu Ser Ser Val Val Thr Val Pro

TCC AGC AGC TTG GGC ACC CAG ACC TAC ATC TGC AAC GTG AAT CAC AAG
Ser Ser Ser Leu Gly Thr Gln Thr Tyr Ile Cys Asn Val Asn His Lys

CCC AGC AAC ACC AAG GTG GAC AAG AAA GTT GAG CCC AAA TCT TGT
Pro Ser Asn Thr Lys Val Asp Lys Lys Val Glu Pro Lys Ser Cys
```

Figure 4

```
GAG GTG CAG CTG GTG GAG TCT GGG GGA GGC TTG GTA CAG CCT GGG GGG
Glu Val Gln Leu Val Glu Ser Gly Gly Gly Leu Val Gln Pro Gly Gly

TCC CTG AGA CTC TCC TGT GCA GCC TCT GGA TTC ACC TTT AGC AGC TAT
Ser Leu Arg Leu Ser Cys Ala Ala Ser Gly Phe Thr Phe Ser Ser Tyr

GCC ATG AGC TGG GTC CGC CAG GCT CCA GGG AAG GGG CTG GAG TGG GTC
Ala Met Ser Trp Val Arg Gln Ala Pro Gly Lys Gly Leu Glu Trp Val

TCA GCT ATT AGT GGT AGT GGT GGT AGC ACA TAC TAC GCA GAC TCC GTG
Ser Ala Ile Ser Gly Ser Gly Gly Ser Thr Tyr Tyr Ala Asp Ser Val

AAG GGC CGG TTC ACC ATC TCC AGA GAC AAT TCC AAG AAC ACG CTG TAT
Lys Gly Arg Phe Thr Ile Ser Arg Asp Asn Ser Lys Asn Thr Leu Tyr

CTG CAA ATG AAC AGC CTG AGA GCC GAG GAC ACG GCC GTA TAT TAC TGT
Leu Gln Met Asn Ser Leu Arg Ala Glu Asp Thr Ala Val Tyr Tyr Cys

GCG AAA GAT CGG GTG GGG TAT AGC AGC AGC CTT CTT GAC TAC TGG GGC
Ala Lys Asp Arg Val Gly Tyr Ser Ser Ser Leu Leu Asp Tyr Trp Gly

CAG GGA ACC CTG GTC ACC GTC TCT AGT GCC TCC ACC AAG GGC CCA TCG
Gln Gly Thr Leu Val Thr Val Ser Ser Ala Ser Thr Lys Gly Pro Ser

GTC TTC CCC CTG GCA CCC TCC TCC AAG AGC ACC TCT GGG GGC ACA GCG
Val Phe Pro Leu Ala Pro Ser Ser Lys Ser Thr Ser Gly Gly Thr Ala

GCC CTG GGC TGC CTG GTC AAG GAC TAC TTC CCC GAA CCG GTG ACG GTG
Ala Leu Gly Cys Leu Val Lys Asp Tyr Phe Pro Glu Pro Val Thr Val

TCG TGG AAC TCA GGC GCC CTG ACC AGC GGC GTG CAC ACC TTC CCG GCT
Ser Trp Asn Ser Gly Ala Leu Thr Ser Gly Val His Thr Phe Pro Ala

GTC CTA CAG TCC TCA GGA CTC TAC TCC CTC AGC AGC GTG GTG ACC GTG
Val Leu Gln Ser Ser Gly Leu Tyr Ser Leu Ser Ser Val Val Thr Val

CCC TCC AGC AGC TTG GGC ACC CAG ACC TAC ATC TGC AAC GTG AAT CAC
Pro Ser Ser Ser Leu Gly Thr Gln Thr Tyr Ile Cys Asn Val Asn His

AAG CCC AGC AAC ACC AAG GTG GAC AAG AAA GTT GAG CCC AAA TCT TGT
Lys Pro Ser Asn Thr Lys Val Asp Lys Lys Val Glu Pro Lys Ser Cys
```

Figure 5

```
CAG GTC ACC TTG AAG GAG TCT GGT CCT GTG CTG GTG AAA CCC ACA GAG
Gln Val Thr Leu Lys Glu Ser Gly Pro Val Leu Val Lys Pro Thr Glu

ACC CTC ACG CTG ACC TGC ACC GTG TCT GGG TTC TCA CTC AGC AAT GCT
Thr Leu Thr Leu Thr Cys Thr Val Ser Gly Phe Ser Leu Ser Asn Ala

AGA ATG GGT GTG AGT TGG ATC CGT CAG CCC CCA GGG AAG GCC CTG GAG
Arg Met Gly Val Ser Trp Ile Arg Gln Pro Pro Gly Lys Ala Leu Glu

TGG CTT GCA CAC ATT TTT TCG AAT GAC GAA GAA TCC TAC AGC ACA TCT
Trp Leu Ala His Ile Phe Ser Asn Asp Glu Glu Ser Tyr Ser Thr Ser

CTG AAG AGC AGG CTC ACC ATC TCC AAG GAC ACC TCC CAA AGC CAG GTG
Leu Lys Ser Arg Leu Thr Ile Ser Lys Asp Thr Ser Gln Ser Gln Val

GTC CTT ACC ATG ACC AAC ATG GAC CCT GTG GAC ACA GCC ACG TAT TAC
Val Leu Thr Met Thr Asn Met Asp Pro Val Asp Thr Ala Thr Tyr Tyr

TGT GCA CGG CTT TTA TTG TAC GAG GGG TTC GAC CCC TGG GGC CAG GGA
Cys Ala Arg Leu Leu Leu Tyr Glu Gly Phe Asp Pro Trp Gly Gln Gly

ACC CTG GTC ACC GTC TCT AGT GCC TCC ACC AAG GGC CCA TCG GTC TTC
Thr Leu Val Thr Val Ser Ser Ala Ser Thr Lys Gly Pro Ser Val Phe

CCC CTG GCA CCC TCC TCC AAG AGC ACC TCT GGG GGC ACA GCG GCC CTG
Pro Leu Ala Pro Ser Ser Lys Ser Thr Ser Gly Gly Thr Ala Ala Leu

GGC TGC CTG GTC AAG GAC TAC TTC CCC GAA CCG GTG ACG GTG TCG TGG
Gly Cys Leu Val Lys Asp Tyr Phe Pro Glu Pro Val Thr Val Ser Trp

AAC TCA GGC GCC CTG ACC AGC GGC GTG CAC ACC TTC CCG GCT GTC CTA
Asn Ser Gly Ala Leu Thr Ser Gly Val His Thr Phe Pro Ala Val Leu

CAG TCC TCA GGA CTC TAC TCC CTC AGC AGC GTG GTG ACC GTG CCC TCC
Gln Ser Ser Gly Leu Tyr Ser Leu Ser Ser Val Val Thr Val Pro Ser

AGC AGC TTG GGC ACC CAG ACC TAC ATC TGC AAC GTG AAT CAC AAG CCC
Ser Ser Leu Gly Thr Gln Thr Tyr Ile Cys Asn Val Asn His Lys Pro

AGC AAC ACC AAG GTG GAC AAG AAA GTT GAG CCC AAA TCT TGT
Ser Asn Thr Lys Val Asp Lys Lys Val Glu Pro Lys Ser Cys
```

Figure 6

```
CAG GTG CAG CTA CAG CAG TGG GGC GCA GGA CTG TTG AAG CCT TCG GAG
Gln Val Gln Leu Gln Gln Trp Gly Ala Gly Leu Leu Lys Pro Ser Glu

ACC CTG TCC CTC ACC TGC GCT GTC TAT GGT GGG TCC TTC AGT GGT TAC
Thr Leu Ser Leu Thr Cys Ala Val Tyr Gly Gly Ser Phe Ser Gly Tyr

TAC TGG AGC TGG ATC CGC CAG CCC CCA GGG AAG GGG CTG GAG TGG ATT
Tyr Trp Ser Trp Ile Arg Gln Pro Pro Gly Lys Gly Leu Glu Trp Ile

GGG GAA ATC AAT CAT AGT GGA AGC ACC AAC TAC AAC CCG TCC CTC AAG
Gly Glu Ile Asn His Ser Gly Ser Thr Asn Tyr Asn Pro Ser Leu Lys

AGT CGA GTC ACC ATA TCA GTA GAC ACG TCC AAG AAC CAG TTC TCC CTG
Ser Arg Val Thr Ile Ser Val Asp Thr Ser Lys Asn Gln Phe Ser Leu

AAG CTG AGC TCT GTG ACC GCC GCG GAC ACG GCT GTG TAT TAC TGT GCG
Lys Leu Ser Ser Val Thr Ala Ala Asp Thr Ala Val Tyr Tyr Cys Ala

AGA GAT AAG GGC TCC CGT ATT ACG ATT TTT GGA GTG GTT GGG TCC GCT
Arg Asp Lys Gly Ser Arg Ile Thr Ile Phe Gly Val Val Gly Ser Ala

GGC TTT GAC TAC TGG GGC CAG GGC ACC CTG GTC ACC GTC TCT AGT GCC
Gly Phe Asp Tyr Trp Gly Gln Gly Thr Leu Val Thr Val Ser Ser Ala

TCC ACC AAG GGC CCA TCG GTC TTC CCC CTG GCA CCC TCC TCC AAG AGC
Ser Thr Lys Gly Pro Ser Val Phe Pro Leu Ala Pro Ser Ser Lys Ser

ACC TCT GGG GGC ACA GCG GCC CTG GGC TGC CTG GTC AAG GAC TAC TTC
Thr Ser Gly Gly Thr Ala Ala Leu Gly Cys Leu Val Lys Asp Tyr Phe

CCC GAA CCG GTG ACG GTG TCG TGG AAC TCA GGC GCC CTG ACC AGC GGC
Pro Glu Pro Val Thr Val Ser Trp Asn Ser Gly Ala Leu Thr Ser Gly

GTG CAC ACC TTC CCG GCT GTC CTA CAG TCC TCA GGA CTC TAC TCC CTC
Val His Thr Phe Pro Ala Val Leu Gln Ser Ser Gly Leu Tyr Ser Leu

AGC AGC GTG GTG ACC GTG CCC TCC AGC AGC TTG GGC ACC CAG ACC TAC
Ser Ser Val Val Thr Val Pro Ser Ser Ser Leu Gly Thr Gln Thr Tyr

ATC TGC AAC GTG AAT CAC AAG CCC AGC AAC ACC AAG GTG GAC AAG AAA
Ile Cys Asn Val Asn His Lys Pro Ser Asn Thr Lys Val Asp Lys Lys

GTT GAG CCC AAA TCT TGT
Val Glu Pro Lys Ser Cys
```

Figure 7

```
GAG GTG CAG CTG CTG GAG TCT GGG GGA GGC CTG GTC AAG CCT GGG GGG
Glu Val Gln Leu Leu Glu Ser Gly Gly Gly Leu Val Lys Pro Gly Gly

TCC CTG AGA CTC TCC TGT GCA GCC TCT GGA TTC ACC TTC AGT AGC TAT
Ser Leu Arg Leu Ser Cys Ala Ala Ser Gly Phe Thr Phe Ser Ser Tyr

AGC ATG AAC TGG GTC CGC CAG GCT CCA GGG AAG GGG CTG GAG TGG GTC
Ser Met Asn Trp Val Arg Gln Ala Pro Gly Lys Gly Leu Glu Trp Val

TCA TCC ATT AGT AGT GGT AGC AGT TAC AGA TAC GAC GCA GAC TCA GTG
Ser Ser Ile Ser Ser Gly Ser Ser Tyr Arg Tyr Asp Ala Asp Ser Val

AAG GGC CGA TTC ACC ATC TCC AGA GAC AAT TCC AAG AAC ACG CTG TAT
Lys Gly Arg Phe Thr Ile Ser Arg Asp Asn Ser Lys Asn Thr Leu Tyr

CTG CAA ATG AAT AGC CTG AGA GCC GAG GAC ACG GCC ATA TAT TAC TGT
Leu Gln Met Asn Ser Leu Arg Ala Glu Asp Thr Ala Ile Tyr Tyr Cys

GCG GAT CAG ATG GGT ACA ATT AGT GGC AAT GAC TAC TGG GGC CAG GGC
Ala Asp Gln Met Gly Thr Ile Ser Gly Asn Asp Tyr Trp Gly Gln Gly

ACC CTG GTC ACC GTC TCT AGT GCC TCC ACC AAG GGC CCA TCG GTC TTC
Thr Leu Val Thr Val Ser Ser Ala Ser Thr Lys Gly Pro Ser Val Phe

CCC CTG GCA CCC TCC TCC AAG AGC ACC TCT GGG GGC ACA GCG GCC CTG
Pro Leu Ala Pro Ser Ser Lys Ser Thr Ser Gly Gly Thr Ala Ala Leu

GGC TGC CTG GTC AAG GAC TAC TTC CCC GAA CCG GTG ACG GTG TCG TGG
Gly Cys Leu Val Lys Asp Tyr Phe Pro Glu Pro Val Thr Val Ser Trp

AAC TCA GGC GCC CTG ACC AGC GGC GTG CAC ACC TTC CCG GCT GTC CTA
Asn Ser Gly Ala Leu Thr Ser Gly Val His Thr Phe Pro Ala Val Leu

CAG TCC TCA GGA CTC TAC TCC CTC AGC AGC GTG GTG ACC GTG CCC TCC
Gln Ser Ser Gly Leu Tyr Ser Leu Ser Ser Val Val Thr Val Pro Ser

AGC AGC TTG GGC ACC CAG ACC TAC ATC TGC AAC GTG AAT CAC AAG CCC
Ser Ser Leu Gly Thr Gln Thr Tyr Ile Cys Asn Val Asn His Lys Pro

AGC AAC ACC AAG GTG GAC AAG AAA GTT GAG CCC AAA TCT TGT
Ser Asn Thr Lys Val Asp Lys Lys Val Glu Pro Lys Ser Cys
```

Figure 8

```
CAG GTG CAG CTG GTG GAG ACC GGG GGA GGC GTG GTC CAG CCT GGG AGG
Gln Val Gln Leu Val Glu Thr Gly Gly Gly Val Val Gln Pro Gly Arg

TCC CTG AGA CTC TCC TGT GCA GCC TCT GGA TTC ACC TTC AGT AGC TAT
Ser Leu Arg Leu Ser Cys Ala Ala Ser Gly Phe Thr Phe Ser Ser Tyr

GCT ATG CAC TGG GTC CGC CAG GCT CCA GGC AAG GGG CTG GAG TGG GTG
Ala Met His Trp Val Arg Gln Ala Pro Gly Lys Gly Leu Glu Trp Val

GCA GTT ATA TCA TAT GAT GGA AGC AAT AAA TAC TAC GCA GAC TCC GTG
Ala Val Ile Ser Tyr Asp Gly Ser Asn Lys Tyr Tyr Ala Asp Ser Val

AAG GGC CGA TTC ACC ATC TCC AGA GAC AAT TCC AAG AAC ACG CTG TAT
Lys Gly Arg Phe Thr Ile Ser Arg Asp Asn Ser Lys Asn Thr Leu Tyr

CTG CAA ATG AAC AGC CTG AGA GCT GAG GAC ACG GCT GTG TAT TAC TGT
Leu Gln Met Asn Ser Leu Arg Ala Glu Asp Thr Ala Val Tyr Tyr Cys

GCG AGC GAC CTA GTC CTT ACT ATG ACC TCA CGA CGG GCT GCT TTT GAT
Ala Ser Asp Leu Val Leu Thr Met Thr Ser Arg Arg Ala Ala Phe Asp

ATC TGG GGC CAA GGG ACA ATG GTC ACC GTC TCT AGT GCC TCC ACC AAG
Ile Trp Gly Gln Gly Thr Met Val Thr Val Ser Ser Ala Ser Thr Lys

GGC CCA TCG GTC TTC CCC CTG GCA CCC TCC TCC AAG AGC ACC TCT GGG
Gly Pro Ser Val Phe Pro Leu Ala Pro Ser Ser Lys Ser Thr Ser Gly

GGC ACA GCG GCC CTG GGC TGC CTG GTC AAG GAC TAC TTC CCC GAA CCG
Gly Thr Ala Ala Leu Gly Cys Leu Val Lys Asp Tyr Phe Pro Glu Pro

GTG ACG GTG TCG TGG AAC TCA GGC GCC CTG ACC AGC GGC GTG CAC ACC
Val Thr Val Ser Trp Asn Ser Gly Ala Leu Thr Ser Gly Val His Thr

TTC CCG GCT GTC CTA CAG TCC TCA GGA CTC TAC TCC CTC AGC AGC GTG
Phe Pro Ala Val Leu Gln Ser Ser Gly Leu Tyr Ser Leu Ser Ser Val

GTG ACC GTG CCC TCC AGC AGC TTG GGC ACC CAG ACC TAC ATC TGC AAC
Val Thr Val Pro Ser Ser Ser Leu Gly Thr Gln Thr Tyr Ile Cys Asn

GTG AAT CAC AAG CCC AGC AAC ACC AAG GTG GAC AAG AAA GTT GAG CCC
Val Asn His Lys Pro Ser Asn Thr Lys Val Asp Lys Lys Val Glu Pro

AAA TCT TGT
Lys Ser Cys
```

Figure 9

```
GAG GTC CAG CTG GTG CAG TCT GGG GGA GGC TTG GTC CAG CCT GGG GGG
Glu Val Gln Leu Val Gln Ser Gly Gly Gly Leu Val Gln Pro Gly Gly

TCC CTG AGA CTC TCC TGT GCA GCC TCT GGA TTC ACC GTC AGT AGC AAC
Ser Leu Arg Leu Ser Cys Ala Ala Ser Gly Phe Thr Val Ser Ser Asn

TAC ATG AGC TGG GTC CGC CAG GCT CCA GGG AAG GGG CTG GAG TGG GTC
Tyr Met Ser Trp Val Arg Gln Ala Pro Gly Lys Gly Leu Glu Trp Val

TCA GTT ATT TAT AGC GGT GGT AGC ACA TAC TAC GCA GAC TCC GTG AAG
Ser Val Ile Tyr Ser Gly Gly Ser Thr Tyr Tyr Ala Asp Ser Val Lys

GGC AGA TTC ACC ATC TCC AGA GAC AAT TCC AAG AAC ACG CTG TAT CTT
Gly Arg Phe Thr Ile Ser Arg Asp Asn Ser Lys Asn Thr Leu Tyr Leu

CAA ATG AAC AGC CTG AGA GCC GAG GAC ACG GCT GTG TAT TAC TGT GCG
Gln Met Asn Ser Leu Arg Ala Glu Asp Thr Ala Val Tyr Tyr Cys Ala

AGA GAT TCG GAC GGC GGT GAC TAT GGC TAC TGG GGC CAG GGA ACC CTG
Arg Asp Ser Asp Gly Gly Asp Tyr Gly Tyr Trp Gly Gln Gly Thr Leu

GTC ACC GTC TCT AGT GCC TCC ACC AAG GGC CCA TCG GTC TTC CCC CTG
Val Thr Val Ser Ser Ala Ser Thr Lys Gly Pro Ser Val Phe Pro Leu

GCA CCC TCC TCC AAG AGC ACC TCT GGG GGC ACA GCG GCC CTG GGC TGC
Ala Pro Ser Ser Lys Ser Thr Ser Gly Gly Thr Ala Ala Leu Gly Cys

CTG GTC AAG GAC TAC TTC CCC GAA CCG GTG ACG GTG TCG TGG AAC TCA
Leu Val Lys Asp Tyr Phe Pro Glu Pro Val Thr Val Ser Trp Asn Ser

GGC GCC CTG ACC AGC GGC GTG CAC ACC TTC CCG GCT GTC CTA CAG TCC
Gly Ala Leu Thr Ser Gly Val His Thr Phe Pro Ala Val Leu Gln Ser

TCA GGA CTC TAC TCC CTC AGC AGC GTG GTG ACC GTG CCC TCC AGC AGC
Ser Gly Leu Tyr Ser Leu Ser Ser Val Val Thr Val Pro Ser Ser Ser

TTG GGC ACC CAG ACC TAC ATC TGC AAC GTG AAT CAC AAG CCC AGC AAC
Leu Gly Thr Gln Thr Tyr Ile Cys Asn Val Asn His Lys Pro Ser Asn

ACC AAG GTG GAC AAG AAA GTT GAG CCC AAA TCT TGT
Thr Lys Val Asp Lys Lys Val Glu Pro Lys Ser Cys
```

Figure 10

```
CAG GTG CAG CTG CAG GAG TCG GGC CCA GGA CTG GTG AAG CCT TCG GAG
Gln Val Gln Leu Gln Glu Ser Gly Pro Gly Leu Val Lys Pro Ser Glu

ACC CTG TCC CTC ACC TGC GCT GTC TCT GGT GGC TCC ATC AGC AGT GGT
Thr Leu Ser Leu Thr Cys Ala Val Ser Gly Gly Ser Ile Ser Ser Gly

GGT TAC TCC TGG AGC TGG ATC CGG CAG CCA CCA GGG AAG GGC CTG GAG
Gly Tyr Ser Trp Ser Trp Ile Arg Gln Pro Pro Gly Lys Gly Leu Glu

TGG ATT GGG TAC ATC TAT CAT AGT GGG AGC ACC TAC TAC AAC CCG TCC
Trp Ile Gly Tyr Ile Tyr His Ser Gly Ser Thr Tyr Tyr Asn Pro Ser

CTC AAG AGT CGA GTC ACC ATA TCA GTA GAC AGG TCC AAG AAC CAG TTC
Leu Lys Ser Arg Val Thr Ile Ser Val Asp Arg Ser Lys Asn Gln Phe

TCC CTG AAG CTG AGC TCT GTG ACC GCC GCG GAC ACG GCC GTG TAT TAC
Ser Leu Lys Leu Ser Ser Val Thr Ala Ala Asp Thr Ala Val Tyr Tyr

TGT GCC AGA GGG GAC TGG GGC TAC TTT GAC TAC TGG GGC CAG GGA ACC
Cys Ala Arg Gly Asp Trp Gly Tyr Phe Asp Tyr Trp Gly Gln Gly Thr

CTG GTC ACC GTC TCT AGT GCC TCC ACC AAG GGC CCA TCG GTC TTC CCC
Leu Val Thr Val Ser Ser Ala Ser Thr Lys Gly Pro Ser Val Phe Pro

CTG GCA CCC TCC TCC AAG AGC ACC TCT GGG GGC ACA GCG GCC CTG GGC
Leu Ala Pro Ser Ser Lys Ser Thr Ser Gly Gly Thr Ala Ala Leu Gly

TGC CTG GTC AAG GAC TAC TTC CCC GAA CCG GTG ACG GTG TCG TGG AAC
Cys Leu Val Lys Asp Tyr Phe Pro Glu Pro Val Thr Val Ser Trp Asn

TCA GGC GCC CTG ACC AGC GGC GTG CAC ACC TTC CCG GCT GTC CTA CAG
Ser Gly Ala Leu Thr Ser Gly Val His Thr Phe Pro Ala Val Leu Gln

TCC TCA GGA CTC TAC TCC CTC AGC AGC GTG GTG ACC GTG CCC TCC AGC
Ser Ser Gly Leu Tyr Ser Leu Ser Ser Val Val Thr Val Pro Ser Ser

AGC TTG GGC ACC CAG ACC TAC ATC TGC AAC GTG AAT CAC AAG CCC AGC
Ser Leu Gly Thr Gln Thr Tyr Ile Cys Asn Val Asn His Lys Pro Ser

AAC ACC AAG GTG GAC AAG AAA GTT GAG CCC AAA TCT TGT
Asn Thr Lys Val Asp Lys Lys Val Glu Pro Lys Ser Cys
```

Figure 11

```
GAG GTG CAG CTA CAG CAG TGG GGC GCA GGA CTG TTG AAG CCT TCG GAG
Glu Val Gln Leu Gln Gln Trp Gly Ala Gly Leu Leu Lys Pro Ser Glu

ACC CTG TCC CTC ACC TGC GCT GTC TAT GGT GGG TCC TTC AGT GGT TAC
Thr Leu Ser Leu Thr Cys Ala Val Tyr Gly Gly Ser Phe Ser Gly Tyr

TAC TGG AGC TGG ATC CGC CAG CCC CCA GGG AAG GGG CTG GAG TGG ATT
Tyr Trp Ser Trp Ile Arg Gln Pro Pro Gly Lys Gly Leu Glu Trp Ile

GGG GAA ATC AAT CAT AGT GGA AGC ACC AAC TAC AAC CCG TCC CTC AAG
Gly Glu Ile Asn His Ser Gly Ser Thr Asn Tyr Asn Pro Ser Leu Lys

AGT CGA GTC ACC ATA TCA GTA GAC ACG TCC AAG AAC CAG TTC TCC CTG
Ser Arg Val Thr Ile Ser Val Asp Thr Ser Lys Asn Gln Phe Ser Leu

AAG CTG AGC TCT GTG ACC GCC GCG GAC ACG GCT GTG TAT TAC TGT GCG
Lys Leu Ser Ser Val Thr Ala Ala Asp Thr Ala Val Tyr Tyr Cys Ala

AGA GGC TGG CCC ACT TAC GTT TGG GGG AGT TAT CGT CCC AAA GGC TAC
Arg Gly Trp Pro Thr Tyr Val Trp Gly Ser Tyr Arg Pro Lys Gly Tyr

TTT GAC TAC TGG GGC CAG GGA ACC CTG GTC ACC GTC TCT AGT GCC TCC
Phe Asp Tyr Trp Gly Gln Gly Thr Leu Val Thr Val Ser Ser Ala Ser

ACC AAG GGC CCA TCG GTC TTC CCC CTG GCA CCC TCC TCC AAG AGC ACC
Thr Lys Gly Pro Ser Val Phe Pro Leu Ala Pro Ser Ser Lys Ser Thr

TCT GGG GGC ACA GCG GCC CTG GGC TGC CTG GTC AAG GAC TAC TTC CCC
Ser Gly Gly Thr Ala Ala Leu Gly Cys Leu Val Lys Asp Tyr Phe Pro

GAA CCG GTG ACG GTG TCG TGG AAC TCA GGC GCC CTG ACC AGC GGC GTG
Glu Pro Val Thr Val Ser Trp Asn Ser Gly Ala Leu Thr Ser Gly Val

CAC ACC TTC CCG GCT GTC CTA CAG TCC TCA GGA CTC TAC TCC CTC AGC
His Thr Phe Pro Ala Val Leu Gln Ser Ser Gly Leu Tyr Ser Leu Ser

AGC GTG GTG ACC GTG CCC TCC AGC AGC TTG GGC ACC CAG ACC TAC ATC
Ser Val Val Thr Val Pro Ser Ser Ser Leu Gly Thr Gln Thr Tyr Ile

TGC AAC GTG AAT CAC AAG CCC AGC AAC ACC AAG GTG GAC AAG AAA GTT
Cys Asn Val Asn His Lys Pro Ser Asn Thr Lys Val Asp Lys Lys Val

GAG CCC AAA TCT TGT
Glu Pro Lys Ser Cys
```

Figure 12

```
GCC AAT ACC CTT GAA GAG TCT GGT CCT ACG CTG GTG CAA CCG ACA CAG
Ala Asn Thr Leu Glu Glu Ser Gly Pro Thr Leu Val Gln Pro Thr Gln

ACC CTC ACG CTG ACC TGC TCC TAC TCT GGG TTC TCA CTC AGC AGT AAT
Thr Leu Thr Leu Thr Cys Ser Tyr Ser Gly Phe Ser Leu Ser Ser Asn

GAA GCG GGT GTG GGC TGG ATC CGT CAG CCC CCA GGA AAG GCC CCG GAG
Glu Ala Gly Val Gly Trp Ile Arg Gln Pro Pro Gly Lys Ala Pro Glu

TGG CTT GCA CTT CTT TAT TGG GAT GAT GAT AAG CGC TAC AGC CCG TCT
Trp Leu Ala Leu Leu Tyr Trp Asp Asp Asp Lys Arg Tyr Ser Pro Ser

CTG AGG AGC AGG CTC ATC GTT AAC AAG GAC ACC TCC AAA AGC CAG GTT
Leu Arg Ser Arg Leu Ile Val Asn Lys Asp Thr Ser Lys Ser Gln Val

GTC CTT ACA ATG ACC AAC ATG GAC CCT GTG GAC ACG GCC ACA TAT TAC
Val Leu Thr Met Thr Asn Met Asp Pro Val Asp Thr Ala Thr Tyr Tyr

TGT GCA CAC AGA CTC GTC AGA TAT GGT GGC TAC TCA ACG GGT GGT TTT
Cys Ala His Arg Leu Val Arg Tyr Gly Gly Tyr Ser Thr Gly Gly Phe

GAT GTC TGG GGC CAA GGG ACC ACG GTC ACC GTC TCA AGC GCC TCC ACC
Asp Val Trp Gly Gln Gly Thr Thr Val Thr Val Ser Ser Ala Ser Thr

AAG GGC CCA TCG GTC TTC CCC CTG GCA CCC TCC TCC AAG AGC ACC TCT
Lys Gly Pro Ser Val Phe Pro Leu Ala Pro Ser Ser Lys Ser Thr Ser

GGG GGC ACA GCG GCC CTG GGC TGC CTG GTC AAG GAC TAC TTC CCC GAA
Gly Gly Thr Ala Ala Leu Gly Cys Leu Val Lys Asp Tyr Phe Pro Glu

CCG GTG ACG GTG TCG TGG AAC TCA GGC GCC CTG ACC AGC GGC GTC CAC
Pro Val Thr Val Ser Trp Asn Ser Gly Ala Leu Thr Ser Gly Val His

ACC TTC CCG GCT GTC CTA CAG TCC TCA GGA CTC TAC TCC CTC AGC AGC
Thr Phe Pro Ala Val Leu Gln Ser Ser Gly Leu Tyr Ser Leu Ser Ser

GTA GTG ACC GTG CCC TCC AGC AGC TTG GGC ACC CAG ACC TAC ATC TGC
Val Val Thr Val Pro Ser Ser Ser Leu Gly Thr Gln Thr Tyr Ile Cys

AAC GTG AAT CAC AAG CCC AGC AAC ACC AAG GTG GAC AAG AAA GTT GAG
Asn Val Asn His Lys Pro Ser Asn Thr Lys Val Asp Lys Lys Val Glu

CCC AAA TCT TGT
Pro Lys Ser Cys
```

Figure 13

```
GAC GTG CAG CTG GTG GAG ACT GGG GGA GGC TTG GTA CAG CCT GGG GGG
Asp Val Gln Leu Val Glu Thr Gly Gly Gly Leu Val Gln Pro Gly Gly

TCC CTG AGA CTC TCC TGT GCG GCC TCT GGA TTC ACC TTT AGC AGC TAT
Ser Leu Arg Leu Ser Cys Ala Ala Ser Gly Phe Thr Phe Ser Ser Tyr

GCC ATG AGC TGG GTC CGC CAG GCT CCA GGG AAG GGG CTG GAG TGG GTC
Ala Met Ser Trp Val Arg Gln Ala Pro Gly Lys Gly Leu Glu Trp Val

TCA GCT ATT AGT GGT AGT GGT GGT AGC ACA TAC TAC GCA GAC TCC GTG
Ser Ala Ile Ser Gly Ser Gly Gly Ser Thr Tyr Tyr Ala Asp Ser Val

AAG GGC CGG TTC ACC ATC TCC AGA GAC AAT TCC AAG AAC ACG CTG TAT
Lys Gly Arg Phe Thr Ile Ser Arg Asp Asn Ser Lys Asn Thr Leu Tyr

CTG CAA ATG GAC AGC CTG AGA GCC GAG GAC ACG GCC GTA TAT TAC TGT
Leu Gln Met Asp Ser Leu Arg Ala Glu Asp Thr Ala Val Tyr Tyr Cys

GCG AAG ACG TCC TGG AAC GCA GGT GGC CCG ATT GAC TAC TGG GGC CAG
Ala Lys Thr Ser Trp Asn Ala Gly Gly Pro Ile Asp Tyr Trp Gly Gln

GGA AAC CTG GTC ACC GTC TCA AGC GCC TCC ACC AAG GGC CCA TCG GTC
Gly Asn Leu Val Thr Val Ser Ser Ala Ser Thr Lys Gly Pro Ser Val

TTC CCC CTG GCA CCC TCC TCC AAG AGC ACC TCT GGG GGC ACA GCG GCC
Phe Pro Leu Ala Pro Ser Ser Lys Ser Thr Ser Gly Gly Thr Ala Ala

CTG GGC TGC CTG GTC AAG GAC TAC TTC CCC GAA CCG GTG ACG GTG TCG
Leu Gly Cys Leu Val Lys Asp Tyr Phe Pro Glu Pro Val Thr Val Ser

TGG AAC TCA GGC GCC CTG ACC AGC GGC GTC CAC ACC TTC CCG GCT GTC
Trp Asn Ser Gly Ala Leu Thr Ser Gly Val His Thr Phe Pro Ala Val

CTA CAG TCC TCA GGA CTC TAC TCC CTC AGC AGC GTA GTG ACC GTG CCC
Leu Gln Ser Ser Gly Leu Tyr Ser Leu Ser Ser Val Val Thr Val Pro

TCC AGC AGC TTG GGC ACC CAG ACC TAC ATC TGC AAC GTG AAT CAC AAG
Ser Ser Ser Leu Gly Thr Gln Thr Tyr Ile Cys Asn Val Asn His Lys

CCC AGC AAC ACC AAG GTG GAC AAG AAA GTT GAG CCC AAA TCT TGT
Pro Ser Asn Thr Lys Val Asp Lys Lys Val Glu Pro Lys Ser Cys
```

Figure 14

```
AAT TTT ATG CTG ACT CAG CCC CAC TCT GTG TCG GAG TCT CCG GGG AAG
Asn Phe Met Leu Thr Gln Pro His Ser Val Ser Glu Ser Pro Gly Lys

ACG GTA ACC ATC TCC TGC ACC GGC AGC AGT GGC AGC ATT GCC AGC CAC
Thr Val Thr Ile Ser Cys Thr Gly Ser Ser Gly Ser Ile Ala Ser His

TAT GTG CAG TGG TAC CAG CAG CGC CCG GGC AGT GCC CCC ACT AAT GTG
Tyr Val Gln Trp Tyr Gln Gln Arg Pro Gly Ser Ala Pro Thr Asn Val

ATT TAT GAG GAT AAG GAA AGA CCC TCT GGG GTC CCT GAT CGG TTC TCT
Ile Tyr Glu Asp Lys Glu Arg Pro Ser Gly Val Pro Asp Arg Phe Ser

GGC TCC ATC GAC AGC TCC ACC AAC TCT GCC TCC CTC ACC ATC TCT GGA
Gly Ser Ile Asp Ser Ser Thr Asn Ser Ala Ser Leu Thr Ile Ser Gly

CTG AAG ACT GAG GAC GAG GCT GAC TAC TAT TGT CAG TCT TAT GAT AGC
Leu Lys Thr Glu Asp Glu Ala Asp Tyr Tyr Cys Gln Ser Tyr Asp Ser

AGC AAT CAG TGG GTG TTC GGC GGA GGG ACC AAG CTG ACC GTC CTA GGT
Ser Asn Gln Trp Val Phe Gly Gly Gly Thr Lys Leu Thr Val Leu Gly

CAG CCC AAG GCT GCC CCC TCG GTC ACT CTG TTC CCG CCC TCC TCT GAG
Gln Pro Lys Ala Ala Pro Ser Val Thr Leu Phe Pro Pro Ser Ser Glu

GAG CTT CAA GCC AAC AAG GCC ACA CTG GTG TGT CTC ATA AGT GAC TTC
Glu Leu Gln Ala Asn Lys Ala Thr Leu Val Cys Leu Ile Ser Asp Phe

TAC CCG GGA GCC GTG ACA GTG GCC TGG AAG GCA GAT AGC AGC CCC GTC
Tyr Pro Gly Ala Val Thr Val Ala Trp Lys Ala Asp Ser Ser Pro Val

AAG GCG GGA GTG GAG ACC ACC ACA CCC TCC AAA CAA AGC AAC AAC AAG
Lys Ala Gly Val Glu Thr Thr Thr Pro Ser Lys Gln Ser Asn Asn Lys

TAC GCG GCC AGC AGC TAC CTG AGC CTG ACG CCT GAG CAG TGG AAG TCC
Tyr Ala Ala Ser Ser Tyr Leu Ser Leu Thr Pro Glu Gln Trp Lys Ser

CAC AGA AGC TAC AGC TGC CAG GTC ACG CAT GAA GGG AGC ACC GTG GAG
His Arg Ser Tyr Ser Cys Gln Val Thr His Glu Gly Ser Thr Val Glu

AAG ACA GTG GCT CCT ACA GAA TGT TCA
Lys Thr Val Ala Pro Thr Glu Cys Ser
```

Figure 15

```
AAT TTT ATG CTG ACT CAG CCC CAC TCT GTG TCG GAG TCT CCG GGG AAG
Asn Phe Met Leu Thr Gln Pro His Ser Val Ser Glu Ser Pro Gly Lys

ACG GTA ACC ATC TCC TGC ACC CGC AGC AGC GGC AGC ATT GCC AGC TAC
Thr Val Thr Ile Ser Cys Thr Arg Ser Ser Gly Ser Ile Ala Ser Tyr

TAT GTG CAG TGG TAC CAG CAG CGC CCG GGC AGT TCC CCC ACC ACT GTG
Tyr Val Gln Trp Tyr Gln Gln Arg Pro Gly Ser Ser Pro Thr Thr Val

ATC TAT GAA GAT GAC CAA AGA CCC TCT GGG GTC CCT GAT CGA TTC TCT
Ile Tyr Glu Asp Asp Gln Arg Pro Ser Gly Val Pro Asp Arg Phe Ser

GGC TCC ATC GAC AGT GCC TCC AAC TCA GCC TCC CTC ACC ATC TCT GGC
Gly Ser Ile Asp Ser Ala Ser Asn Ser Ala Ser Leu Thr Ile Ser Gly

CTG CAG ACT GAG GAC GAG GCT GAC TAC TAT TGT CAG TCT TAT GAC AGG
Leu Gln Thr Glu Asp Glu Ala Asp Tyr Tyr Cys Gln Ser Tyr Asp Arg

AAC AGT CTG GTG TTC GGC GGG GGG ACC AAG CTG ACC GTC CTG GGT CAG
Asn Ser Leu Val Phe Gly Gly Gly Thr Lys Leu Thr Val Leu Gly Gln

CCC AAG GCT GCC CCC TCG GTC ACT CTG TTC CCG CCC TCC TCT GAG GAG
Pro Lys Ala Ala Pro Ser Val Thr Leu Phe Pro Pro Ser Ser Glu Glu

CTT CAA GCC AAC AAG GCC ACA CTG GTG TGT CTC ATA AGT GAC TTC TAC
Leu Gln Ala Asn Lys Ala Thr Leu Val Cys Leu Ile Ser Asp Phe Tyr

CCG GGA GCC GTG ACA GTG GCC TGG AAG GCA GAT AGC AGC CCC GTC AAG
Pro Gly Ala Val Thr Val Ala Trp Lys Ala Asp Ser Ser Pro Val Lys

GCG GGA GTG GAG ACC ACC ACA CCC TCC AAA CAA AGC AAC AAC AAG TAC
Ala Gly Val Glu Thr Thr Thr Pro Ser Lys Gln Ser Asn Asn Lys Tyr

GCG GCC AGC AGC TAC CTG AGC CTG ACG CCT GAG CAG TGG AAG TCC CAC
Ala Ala Ser Ser Tyr Leu Ser Leu Thr Pro Glu Gln Trp Lys Ser His

AAA AGC TAC AGC TGC CAG GTC ACG CAT GAA GGG AGC ACC GTG GAG AAG
Lys Ser Tyr Ser Cys Gln Val Thr His Glu Gly Ser Thr Val Glu Lys

ACA GTG GCT CCT ACA GAA TGT TCA
Thr Val Ala Pro Thr Glu Cys Ser
```

Figure 16

```
GAT ATT GTG ATG ACC CAC ACT CCA CTC TCC TCA CCT GTC ACC CTT GGA
Asp Ile Val Met Thr His Thr Pro Leu Ser Ser Pro Val Thr Leu Gly

CAG CCG GCC TCC ATC TCC TGC AGG TCT AGT CAG AGC CTC GTA CAC AGT
Gln Pro Ala Ser Ile Ser Cys Arg Ser Ser Gln Ser Leu Val His Ser

GAT GGA AAC ACC TAC TTG AGT TGG CTT CAC CAG AGG CCA GGC CAG CCT
Asp Gly Asn Thr Tyr Leu Ser Trp Leu His Gln Arg Pro Gly Gln Pro

CCA AGA CTC CTA ATT TAT AAG ATT TCT AAC CGG TTC TCT GGG GTC CCA
Pro Arg Leu Leu Ile Tyr Lys Ile Ser Asn Arg Phe Ser Gly Val Pro

GAC AGA TTC AGT GGC AGT GGG GCA GGG ACA GAT TTC ACA CTG AAA ATC
Asp Arg Phe Ser Gly Ser Gly Ala Gly Thr Asp Phe Thr Leu Lys Ile

AGC AGG GTG GAA GCT GAG GAT GTC GGG CTT TAT TAC TGC ATG CAA GCT
Ser Arg Val Glu Ala Glu Asp Val Gly Leu Tyr Tyr Cys Met Gln Ala

ACA CAA CTT CCG TAC ACT TTT GGC CAG GGG ACC AAG CTG GAG ATC AAA
Thr Gln Leu Pro Tyr Thr Phe Gly Gln Gly Thr Lys Leu Glu Ile Lys

CGA ACT GTG GCT GCA CCA TCT GTC TTC ATC TTC CCG CCA TCT GAT GAG
Arg Thr Val Ala Ala Pro Ser Val Phe Ile Phe Pro Pro Ser Asp Glu

CAG TTG AAA TCT GGA ACT GCC TCT GTT GTG TGC CTG CTG AAT AAC TTC
Gln Leu Lys Ser Gly Thr Ala Ser Val Val Cys Leu Leu Asn Asn Phe

TAT CCC AGA GAG GCC AAA GTA CAG TGG AAG GTG GAT AAC GCC CTC CAA
Tyr Pro Arg Glu Ala Lys Val Gln Trp Lys Val Asp Asn Ala Leu Gln

TCG GGT AAC TCC CAG GAG AGT GTC ACA GAG CAG GAC AGC AAG GAC AGC
Ser Gly Asn Ser Gln Glu Ser Val Thr Glu Gln Asp Ser Lys Asp Ser

ACC TAC AGC CTC AGC AGC ACC CTG ACG CTG AGC AAA GCA GAC TAC GAG
Thr Tyr Ser Leu Ser Ser Thr Leu Thr Leu Ser Lys Ala Asp Tyr Glu

AAA CAC AAA GTC TAC GCC TGC GAA GTC ACC CAT CAG GGC CTG AGC TCG
Lys His Lys Val Tyr Ala Cys Glu Val Thr His Gln Gly Leu Ser Ser

CCC GTC ACA AAG AGT TTC AAC AGG GGA GAG TGT
Pro Val Thr Lys Ser Phe Asn Arg Gly Glu Cys
```

Figure 17

```
GAT GTT GTG ATG ACT CAG TCT CCA CTC TCC CTG CCC GTC ACC CCT GGA
Asp Val Val Met Thr Gln Ser Pro Leu Ser Leu Pro Val Thr Pro Gly

GAG CCG GCC TCC ATC TCC TGC AGG GCA ACT CAG AGC CTC CTG CAT GGA
Glu Pro Ala Ser Ile Ser Cys Arg Ala Thr Gln Ser Leu Leu His Gly

AAT GGA CAC AAC TAT TTG GAT TGG TAC CTG CAG AAG CCA GGG CAG TCT
Asn Gly His Asn Tyr Leu Asp Trp Tyr Leu Gln Lys Pro Gly Gln Ser

CCA CAC CTC CTG ATC TAT ATG GGT TCT AAT CGG GCC TCC GGG GTC CCT
Pro His Leu Leu Ile Tyr Met Gly Ser Asn Arg Ala Ser Gly Val Pro

GGC AGG TTC AGT GGC ACT GAA TCA GGC AGA AAT TTT ACA CTG AAG ATC
Gly Arg Phe Ser Gly Thr Glu Ser Gly Arg Asn Phe Thr Leu Lys Ile

AGC AGA GTG GAG GCT GAG GAT GTT GGG GTC TAT TAC TGT ATG CAG GCT
Ser Arg Val Glu Ala Glu Asp Val Gly Val Tyr Tyr Cys Met Gln Ala

CTA CAA CTT CCT CCG ACG TTC GGC CAA GGT ACC AGG GTG GAT ATC AAA
Leu Gln Leu Pro Pro Thr Phe Gly Gln Gly Thr Arg Val Asp Ile Lys

CGA ACT GTG GCT GCA CCA TCT GTC TTC ATC TTC CCG CCA TCT GAT GAG
Arg Thr Val Ala Ala Pro Ser Val Phe Ile Phe Pro Pro Ser Asp Glu

CAG TTG AAA TCT GGA ACT GCC TCT GTT GTG TGC CTG CTG AAT AAC TTC
Gln Leu Lys Ser Gly Thr Ala Ser Val Val Cys Leu Leu Asn Asn Phe

TAT CCC AGA GAG GCC AAA GTA CAG TGG AAG GTG GAT AAC GCC CTC CAA
Tyr Pro Arg Glu Ala Lys Val Gln Trp Lys Val Asp Asn Ala Leu Gln

TCG GGT AAC TCC CAG GAG AGT GTC ACA GAG CAG GAC AGC AAG GAC AGC
Ser Gly Asn Ser Gln Glu Ser Val Thr Glu Gln Asp Ser Lys Asp Ser

ACC TAC AGC CTC AGC AGC ACC CTG ACG CTG AGC AAA GCA GAC TAC GAG
Thr Tyr Ser Leu Ser Ser Thr Leu Thr Leu Ser Lys Ala Asp Tyr Glu

AAA CAC AAA GTC TAC GCC TGC GAA GTC ACC CAT CAG GGC CTG AGC TCG
Lys His Lys Val Tyr Ala Cys Glu Val Thr His Gln Gly Leu Ser Ser

CCC GTC ACA AAG AGC TTC AAC AGG GGA GAG TGT
Pro Val Thr Lys Ser Phe Asn Arg Gly Glu Cys
```

Figure 18

```
CAG TCT GTG CTT ACG CAG CCG CCC TCG GTG TCT GTG GCC CCA GGA AAG
Gln Ser Val Leu Thr Gln Pro Pro Ser Val Ser Val Ala Pro Gly Lys

ACG GCC ACT ATT ACC TGT GGG GGA GAC AAC CTT GGA GGT AAA AGT CTA
Thr Ala Thr Ile Thr Cys Gly Gly Asp Asn Leu Gly Gly Lys Ser Leu

CAC TGG TAC CAG CAG AAG CCA GGC CAG GCC CCT GTA CTG GTC GTC TAC
His Trp Tyr Gln Gln Lys Pro Gly Gln Ala Pro Val Leu Val Val Tyr

GAT GAT AGC GAC CGG CCC TCA GGG ATC CCT GAG CGA TTT TCT GGC TCC
Asp Asp Ser Asp Arg Pro Ser Gly Ile Pro Glu Arg Phe Ser Gly Ser

AAC TCT GGG AAC ACG GCC ACC CTG ACC ATT GAT AGG GTC GAA GAC GGG
Asn Ser Gly Asn Thr Ala Thr Leu Thr Ile Asp Arg Val Glu Asp Gly

GAT GAG GCC GAC TAT TAT TGT CAG GTG TGG GAT GGT AGT AGT GAT CAA
Asp Glu Ala Asp Tyr Tyr Cys Gln Val Trp Asp Gly Ser Ser Asp Gln

CGA GTC TTC GGC GGA GGG ACC AGG CTG ACC GTC CTA GGT CAG CCC AAG
Arg Val Phe Gly Gly Gly Thr Arg Leu Thr Val Leu Gly Gln Pro Lys

GCT GCC CCC TCG GTC ACT CTG TTC CCG CCC TCC TCT GAG GAG CTT CAA
Ala Ala Pro Ser Val Thr Leu Phe Pro Pro Ser Ser Glu Glu Leu Gln

GCC AAC AAG GCC ACA CTG GTG TGT CTC ATA AGT GAC TTC TAC CCG GGA
Ala Asn Lys Ala Thr Leu Val Cys Leu Ile Ser Asp Phe Tyr Pro Gly

GCC GTG ACA GTG GCC TGG AAG GCA GAT AGC AGC CCC GTC AAG GCG GGA
Ala Val Thr Val Ala Trp Lys Ala Asp Ser Ser Pro Val Lys Ala Gly

GTG GAG ACC ACC ACA CCC TCC AAA CAA AGC AAC AAC AAG TAC GCG GCC
Val Glu Thr Thr Thr Pro Ser Lys Gln Ser Asn Asn Lys Tyr Ala Ala

AGC AGC TAT CTG AGC CTG ACG CCT GAG CAG TGG AAG TCC CAC AGA AGC
Ser Ser Tyr Leu Ser Leu Thr Pro Glu Gln Trp Lys Ser His Arg Ser

TAC AGC TGC CAG GTC ACG CAT GAA GGG AGC ACC GTG GAG AAG ACA GTG
Tyr Ser Cys Gln Val Thr His Glu Gly Ser Thr Val Glu Lys Thr Val

GCT CCT ACA GAA TGT TCA
Ala Pro Thr Glu Cys Ser
```

Figure 19

```
TCC TAT GAG CTG ACT CAG CCA CCC TCT GTG TCA GTG TCT CCG GGA CAG
Ser Tyr Glu Leu Thr Gln Pro Pro Ser Val Ser Val Ser Pro Gly Gln

ACA GCC AGG ATC ACC TGC TCA GGA GAT GTA CTG GCA AGA AAA TAT GCT
Thr Ala Arg Ile Thr Cys Ser Gly Asp Val Leu Ala Arg Lys Tyr Ala

CGG TGG TTC CAG CAG AAG CCA GGC CAG GCC CCT GTG CTG GTG ATT TAT
Arg Trp Phe Gln Gln Lys Pro Gly Gln Ala Pro Val Leu Val Ile Tyr

AAA GAC CGT GAG CGG CCC TCA GGG ATC CCT GAG CGA TTC TCC GGC TCC
Lys Asp Arg Glu Arg Pro Ser Gly Ile Pro Glu Arg Phe Ser Gly Ser

ACC TCA GGG ACC ACA GTC ACC TTG ACC ATC AGC GGG GCC CAG GTT GAA
Thr Ser Gly Thr Thr Val Thr Leu Thr Ile Ser Gly Ala Gln Val Glu

GAT GAG GCT GAC TAT TAC TGT TAC TCT GCG GCT GAC AAC AGG GGG GTG
Asp Glu Ala Asp Tyr Tyr Cys Tyr Ser Ala Ala Asp Asn Arg Gly Val

TTC GGC GGA GGG ACC AAG CTG ACC GTC CTA CGT CAG CCC AAG GCT GCC
Phe Gly Gly Gly Thr Lys Leu Thr Val Leu Arg Gln Pro Lys Ala Ala

CCC TCG GTC ACT CTG TTC CCA CCC TCC TCT GAG GAG CTT CAA GCC AAC
Pro Ser Val Thr Leu Phe Pro Pro Ser Ser Glu Glu Leu Gln Ala Asn

AAG GCC ACA CTG GTG TGT CTC ATA AGT GAC TTC TAC CCG GGA GCC GTG
Lys Ala Thr Leu Val Cys Leu Ile Ser Asp Phe Tyr Pro Gly Ala Val

ACA GTG GCC TGG AAG GCA GAT AGC AGT CCC GTC AAG GCG GGA GTG GAG
Thr Val Ala Trp Lys Ala Asp Ser Ser Pro Val Lys Ala Gly Val Glu

ACC ACC ACA CCC TCC AAA CAA AGC AAC AAC AAG TAC GCG GCC AGC AGC
Thr Thr Thr Pro Ser Lys Gln Ser Asn Asn Lys Tyr Ala Ala Ser Ser

TAC CTG AGC CTG ACG CCT GAG CAG TGG AAG TCC CAC AAA AGC TAC AGC
Tyr Leu Ser Leu Thr Pro Glu Gln Trp Lys Ser His Lys Ser Tyr Ser

TGC CAG GTC ACG CAT GAA GGG AGC ACC GTG GAG AAG ACA GTG GCT CCT
Cys Gln Val Thr His Glu Gly Ser Thr Val Glu Lys Thr Val Ala Pro

ACA GAA TGT TCA
Thr Glu Cys Ser
```

Figure 20

```
GAA ATT GTG CTC ACG CAG TCT CCA GGC ACC CTG TCT TTG TCT CCA GGG
Glu Ile Val Leu Thr Gln Ser Pro Gly Thr Leu Ser Leu Ser Pro Gly

GAA AGA GCC ACC CTC TCC TGC CGG GCC AGT CAG TAT GTT AGC AGC AAC
Glu Arg Ala Thr Leu Ser Cys Arg Ala Ser Gln Tyr Val Ser Ser Asn

TCC TTA GCC TGG TAC CAG CAG AAA GCT GGC CAG GCT CCC AGG CTC CTC
Ser Leu Ala Trp Tyr Gln Gln Lys Ala Gly Gln Ala Pro Arg Leu Leu

ATC TAT GGT GCA TCC AAC AGG GCC ACT GGC ATC CCA GAC AGG TTC AGT
Ile Tyr Gly Ala Ser Asn Arg Ala Thr Gly Ile Pro Asp Arg Phe Ser

GGC AGT GGG TCT GGG ACA GAC TTC ACT CTC ACC ATC AGC AGA CTG GAG
Gly Ser Gly Ser Gly Thr Asp Phe Thr Leu Thr Ile Ser Arg Leu Glu

CCT GAA GAT TTT GCA GTG TAT TAC TGT CAG CAG TAT GGT AGC TCG CCG
Pro Glu Asp Phe Ala Val Tyr Tyr Cys Gln Gln Tyr Gly Ser Ser Pro

ATC ACC TTC GGC CAA GGG ACA CGA CTG GAG ATT AAA CGA ACT GTG GCT
Ile Thr Phe Gly Gln Gly Thr Arg Leu Glu Ile Lys Arg Thr Val Ala

GCA CCA TCT GTC TTC ATC TTC CCG CCA TCT GAT GAG CAG TTG AAA TCT
Ala Pro Ser Val Phe Ile Phe Pro Pro Ser Asp Glu Gln Leu Lys Ser

GGA ACT GCC TCT GTT GTG TGC CTG CTG AAT AAC TTC TAT CCC AGA GAG
Gly Thr Ala Ser Val Val Cys Leu Leu Asn Asn Phe Tyr Pro Arg Glu

GCC AAA GTA CAG TGG AAG GTG GAT AAC GCC CTC CAA TCG GGT AAC TCC
Ala Lys Val Gln Trp Lys Val Asp Asn Ala Leu Gln Ser Gly Asn Ser

CAG GAG AGT GTC ACA GAG CAG GAC AGC AAG GAC AGC ACC TAC AGC CTC
Gln Glu Ser Val Thr Glu Gln Asp Ser Lys Asp Ser Thr Tyr Ser Leu

AGC AGC ACC CTG ACG CTG AGC AAA GCA GAC TAC GAG AAA CAC AAA GTC
Ser Ser Thr Leu Thr Leu Ser Lys Ala Asp Tyr Glu Lys His Lys Val

TAC GCC TGC GAA GTC ACC CAT CAG GGC CTG AGC TCG CCC GTC ACA AAG
Tyr Ala Cys Glu Val Thr His Gln Gly Leu Ser Ser Pro Val Thr Lys

AGC TTC AAC AGG GGA GAG TGT
Ser Phe Asn Arg Gly Glu Cys
```

Figure 21

```
AAT TTT ATG CTG ACT CAG CCC CAC TCT GTG TCG GAG TCT CCG GGG AAG
Asn Phe Met Leu Thr Gln Pro His Ser Val Ser Glu Ser Pro Gly Lys

ACG GTA ACC ATC TCC TGC ACC GGC AGC AGT GGC AGC ATT GCC AAC AAC
Thr Val Thr Ile Ser Cys Thr Gly Ser Ser Gly Ser Ile Ala Asn Asn

TAT GTT CAC TGG TAC CAG CAA CGC CCG GGC AGT GCC CCC ACC ACT GTG
Tyr Val His Trp Tyr Gln Gln Arg Pro Gly Ser Ala Pro Thr Thr Val

ATC TTT GAG GAT GAC CAA AGA CCC TCT GGA GTC CCT GAT CGG TTC TCT
Ile Phe Glu Asp Asp Gln Arg Pro Ser Gly Val Pro Asp Arg Phe Ser

GGC TCC GTC GAC AGC TCC TCC AAC TCT GCC TCC CTC AGC ATT TCT GGA
Gly Ser Val Asp Ser Ser Ser Asn Ser Ala Ser Leu Ser Ile Ser Gly

CTG AAG ACT GAG GAC GAG GCT GAC TAC TAC TGT CAG TCT TAT GAT AAC
Leu Lys Thr Glu Asp Glu Ala Asp Tyr Tyr Cys Gln Ser Tyr Asp Asn

AGC AAT TCA TTT GTG GTG TTC GGC GGA GGG ACC AAG CTG ACC GTC CTA
Ser Asn Ser Phe Val Val Phe Gly Gly Gly Thr Lys Leu Thr Val Leu

GGT CAG CCC AAG GCT GCC CCC TCG GTC ACT CTG TTC CCG CCC TCC TCT
Gly Gln Pro Lys Ala Ala Pro Ser Val Thr Leu Phe Pro Pro Ser Ser

GAG GAG CTT CAA GCC AAC AAG GCC ACA CTG GTG TGT CTC ATA AGT GAC
Glu Glu Leu Gln Ala Asn Lys Ala Thr Leu Val Cys Leu Ile Ser Asp

TTC TAC CCG GGA GCC GTG ACA GTG GCC TGG AAG GCA GAT AGC AGC CCC
Phe Tyr Pro Gly Ala Val Thr Val Ala Trp Lys Ala Asp Ser Ser Pro

GTC AAG GCG GGA GTG GAG ACC ACC ACA CCC TCC AAA CAA AGC AAC AAC
Val Lys Ala Gly Val Glu Thr Thr Thr Pro Ser Lys Gln Ser Asn Asn

AAG TAC GCG GCC AGC AGC TAC CTG AGC CTG ACG CCT GAG CAG TGG AAG
Lys Tyr Ala Ala Ser Ser Tyr Leu Ser Leu Thr Pro Glu Gln Trp Lys

TCC CAC AAA AGC TAC AGC TGC CAG GTC ACG CAT GAA GGG AGC ACC GTG
Ser His Lys Ser Tyr Ser Cys Gln Val Thr His Glu Gly Ser Thr Val

GAG AAG ACA GTG GCC CCT ACA GAA TGC TCT
Glu Lys Thr Val Ala Pro Thr Glu Cys Ser
```

Figure 22

```
GAA ATT GTG CTG ACT CAG TCT CCA CTC TCC CTT CCC GTC ACC CCT GGA
Glu Ile Val Leu Thr Gln Ser Pro Leu Ser Leu Pro Val Thr Pro Gly

GAG CCG GCC TCC ATC TCC TGC AGG TCT AGT CAG AGC CTC CTG CAT ACT
Glu Pro Ala Ser Ile Ser Cys Arg Ser Ser Gln Ser Leu Leu His Thr

AAT GAA TAC AAC TAT TTG GAT TGG TAC CTG CAG AAG CCA GGG CAG TCT
Asn Glu Tyr Asn Tyr Leu Asp Trp Tyr Leu Gln Lys Pro Gly Gln Ser

CCA CAG CTC CTC ATC TAT TTG GGT TCT AAT CGG GCC CCC GGG GTC CCT
Pro Gln Leu Leu Ile Tyr Leu Gly Ser Asn Arg Ala Pro Gly Val Pro

GAC AGG TTC AGT GGC AGT GGA TCA GGC ACA GAT TTT ACA CTG AGA ATC
Asp Arg Phe Ser Gly Ser Gly Ser Gly Thr Asp Phe Thr Leu Arg Ile

AGC AGG GTG GAG GCT GAC GAT GTT GGG GTT TAC TAC TGC ATG CAA GCT
Ser Arg Val Glu Ala Asp Asp Val Gly Val Tyr Tyr Cys Met Gln Ala

CTA CAA ACT CCT CGT ACT TTT GGC CAG GGG ACC AAG CTG GAG ATC AAA
Leu Gln Thr Pro Arg Thr Phe Gly Gln Gly Thr Lys Leu Glu Ile Lys

CGA ACT GTG GCT GCA CCA TCT GTC TTC ATC TTC CCG CCA TCT GAT GAG
Arg Thr Val Ala Ala Pro Ser Val Phe Ile Phe Pro Pro Ser Asp Glu

CAG TTG AAA TCT GGA ACT GCC TCT GTT GTG TGC CTG CTG AAT AAC TTC
Gln Leu Lys Ser Gly Thr Ala Ser Val Val Cys Leu Leu Asn Asn Phe

TAT CCC AGA GAG GCC AAA GTA CAG TGG AAG GTG GAT AAC GCC CTC CAA
Tyr Pro Arg Glu Ala Lys Val Gln Trp Lys Val Asp Asn Ala Leu Gln

TCG GGT AAC TCC CAG GAG AGT GTC ACA GAG CAG GAC AGC AAG GAC AGC
Ser Gly Asn Ser Gln Glu Ser Val Thr Glu Gln Asp Ser Lys Asp Ser

ACC TAC AGC CTC AGC AGC ACC CTG ACG CTG AGC AAA GCA GAC TAC GAG
Thr Tyr Ser Leu Ser Ser Thr Leu Thr Leu Ser Lys Ala Asp Tyr Glu

AAA CAC AAA GTC TAC GCC TGC GAA GTC ACC CAT CAG GGC CTG AGC TCG
Lys His Lys Val Tyr Ala Cys Glu Val Thr His Gln Gly Leu Ser Ser

CCC GTC ACA AAG AGC TTC AAC AGG GGA GAG TGT
Pro Val Thr Lys Ser Phe Asn Arg Gly Glu Cys
```

Figure 23

```
GAT ATT GTG ATG ACC CAC ACT CCA CTC TCC CTG CCC GTC ACC CCT GGA
Asp Ile Val Met Thr His Thr Pro Leu Ser Leu Pro Val Thr Pro Gly

GAG CCG GCC TCC ATC TCC TGC AGG TCC AGT CAG AGC CTC CTG CGT AGT
Glu Pro Ala Ser Ile Ser Cys Arg Ser Ser Gln Ser Leu Leu Arg Ser

AAT GGA TAC AAC TAT TTG GCT TGG TAC GTG CAG AAG CCA GGG CAG TCT
Asn Gly Tyr Asn Tyr Leu Ala Trp Tyr Val Gln Lys Pro Gly Gln Ser

CCA CAA CTC CTG ATC TAC TTG GCT TCT AAT CGG GCC TCC GGG GTC CCT
Pro Gln Leu Leu Ile Tyr Leu Ala Ser Asn Arg Ala Ser Gly Val Pro

GAC AGG TTT AGT GGC AGT GGA TCA GGC ACA GAT TTT ACA CTG AAG ATC
Asp Arg Phe Ser Gly Ser Gly Ser Gly Thr Asp Phe Thr Leu Lys Ile

AGC AGC GTG GAG GCT GAG GAT GTT GGG GTG TAT TAC TGC GTG CAT GGT
Ser Ser Val Glu Ala Glu Asp Val Gly Val Tyr Tyr Cys Val His Gly

GTA CAC ATT CCC TAC ACT TTT GGC CAG GGG ACC AAG CTG GAG ATC AAA
Val His Ile Pro Tyr Thr Phe Gly Gln Gly Thr Lys Leu Glu Ile Lys

CGA ACT GTG GCT GCA CCA TCT GTC TTC ATC TTC CCG CCA TCT GAT GAG
Arg Thr Val Ala Ala Pro Ser Val Phe Ile Phe Pro Pro Ser Asp Glu

CAG TTG AAA TCT GGA ACT GCC TCT GTT GTG TGC CTG CTG AAT AAC TTC
Gln Leu Lys Ser Gly Thr Ala Ser Val Val Cys Leu Leu Asn Asn Phe

TAT CCC AGA GAG GCC AAA GTA CAG TGG AAG GTG GAT AAC GCC CTC CAA
Tyr Pro Arg Glu Ala Lys Val Gln Trp Lys Val Asp Asn Ala Leu Gln

TCG GGT AAC TCC CAG GAG AGT GTC ACA GAG CAG GAC AGC AAG GAC AGC
Ser Gly Asn Ser Gln Glu Ser Val Thr Glu Gln Asp Ser Lys Asp Ser

ACC TAC AGC CTC AGC AGC ACC CTG ACG CTG AGC AAA GCA GAC TAC GAG
Thr Tyr Ser Leu Ser Ser Thr Leu Thr Leu Ser Lys Ala Asp Tyr Glu

AAA CAC AAA GTC TAC GCC TGC GAA GTC ACC CAT CAG GGC CTG AGC TCG
Lys His Lys Val Tyr Ala Cys Glu Val Thr His Gln Gly Leu Ser Ser

CCC GTC ACA AAG AGC TTC AAC AGG GGA GAG TGT
Pro Val Thr Lys Ser Phe Asn Arg Gly Glu Cys
```

Figure 24

```
AAT TTT ATG CTG ACT CAG CCC CAC TCT GTG TCG GAG TCT CCG GGG AAG
Asn Phe Met Leu Thr Gln Pro His Ser Val Ser Glu Ser Pro Gly Lys

ACG GTA ACC ATC TCC TGC ACC GGC AGC AGT GGC AGC ATT GCC AGC AAC
Thr Val Thr Ile Ser Cys Thr Gly Ser Ser Gly Ser Ile Ala Ser Asn

TAT GTG CAG TGG TAC CAG CAG CGC CCG GGC AGT GCC CCC ACC ACT GTG
Tyr Val Gln Trp Tyr Gln Gln Arg Pro Gly Ser Ala Pro Thr Thr Val

ATC TAT GAG GAT AAC CAA AGA CCC TCT GGG GTC CCT CCT CGG TTC TCT
Ile Tyr Glu Asp Asn Gln Arg Pro Ser Gly Val Pro Pro Arg Phe Ser

GGC TCC ATC GAC AGG TCC TCC AAC TCT GCC TCC CTC ACC ATC TCC GGA
Gly Ser Ile Asp Arg Ser Ser Asn Ser Ala Ser Leu Thr Ile Ser Gly

CTG AAG AGT GAG GAC GAG GCT GAC TAC TAC TGT CAA TCT TAT GAT GGC
Leu Lys Ser Glu Asp Glu Ala Asp Tyr Tyr Cys Gln Ser Tyr Asp Gly

AGC GCT TGG GTG TTC GGC GGA GGG ACC AAG CTG ACC GTC CTA GGT CAG
Ser Ala Trp Val Phe Gly Gly Gly Thr Lys Leu Thr Val Leu Gly Gln

CCC AAG GCT GCC CCC TCG GTC ACT CTG TTC CCA CCC TCC TCT GAG GAG
Pro Lys Ala Ala Pro Ser Val Thr Leu Phe Pro Pro Ser Ser Glu Glu

CTT CAA GCC AAC AAG GCC ACA CTG GTG TGT CTC ATA AGT GAC TTC TAC
Leu Gln Ala Asn Lys Ala Thr Leu Val Cys Leu Ile Ser Asp Phe Tyr

CCG GGA GCC GTG ACA GTG GCC TGG AAG GCA GAT AGC AGC CCC GTC AAG
Pro Gly Ala Val Thr Val Ala Trp Lys Ala Asp Ser Ser Pro Val Lys

GCG GGA GTG GAG ACC ACC GCA CCC TCC AAA CAA AGC AAC AAC AAG TAC
Ala Gly Val Glu Thr Thr Ala Pro Ser Lys Gln Ser Asn Asn Lys Tyr

GCG GCC AGC AGC TAC CTG AGC CTG ACG CCT GAG CAG TGG AAG TCC CAC
Ala Ala Ser Ser Tyr Leu Ser Leu Thr Pro Glu Gln Trp Lys Ser His

AAA AGC TAC AGC TGC CAG GTC ACG CAT GAA GGG AGC ACC GTG GAG AAG
Lys Ser Tyr Ser Cys Gln Val Thr His Glu Gly Ser Thr Val Glu Lys

ACA GTG GCC CCT GCA GAA TGC TCT
 Thr Val Ala Pro Ala Glu Cys Ser
```

Figure 25

| pattern | Heavy chain | | |
|---|---|---|---|
| | CDR1 | CDR2 | CDR3 |
| BS-A | GYYWS | EINHSGSTNYNPSLKS | GRARNWRSRFDY |
| 59-A2 | SYAMS | AISGSGGSTYYADSVKG | TSWNAGGPIDY |
| BS-B | SYAMS | AISGSGGSTYYADSVKG | DRVGYSSSLLDY |
| RD-A2 | GYYWS | EINHSGSTNYNPSLKS | DKGSRITIFGVVGSAGFDY |
| RD-B | NARMGVS | HIFSNDEESYSTSLKS | LLLYEGFDP |
| GP-A | SYAMH | VISYDGSNKYYADSVKG | DLVLTMTSRRAAFDI |
| 58C | SYSMN | SISSGSSYRYDADSVKG | DQWGTISGNDY |
| IFN-A | GYYWS | EINHSGSTNYNPSLKS | GWPTYVWGSYRPKGYFDY |
| 57E | SGGYSWS | YIYHSGSTYYNPSLKS | GDWGYFDY |
| 57D | SNYMS | VIYSGGSTYYADSVKG | DADGGDYGY |
| 67C | SNEAGVG | LLYWDDDKRYSPSLRS | RLVRYGGYSTGGFDV |

| | Light chain | | |
|---|---|---|---|
| | CDR1 | CDR2 | CDR3 |
| BS-A | TGSSGSIASHYVQ | EDKERPS | QSYDSSNQWV |
| 59-A2 | TGSSGSIASNYVQ | EDNQRPS | QSYDGSAWV |
| BS-B | TRSSGSIASYYVQ | EDDQRPS | QSYDRNSLV |
| RD-A2 | RATQSLLHGNGHNYLD | MGSNRAS | MQALQLPPT |
| RD-B | RSSQSLVHSDGNTYLS | KISNRFS | MQATQLPYT |
| GP-A | SGDVLARKYAR | KDRERPS | YSAADNRGV |
| 58C | GGDNLGGKSLH | DDSDRPS | QVWDGSSDQRV |
| IFN-A | RSSQSLLHTNEYNYLD | LGSNRAP | MQALQTPRT |
| 57E | TGSSGSIANNYVH | EDDQRPS | QSYDNSNSFVV |
| 57D | RASQYVSSNSLA | GASNRAT | QQYGSSPIT |
| 67C | RSSQSLLRSNGYNYLA | LASNRAS | VHGVHIPYT |

Figure 28

| IgG ID | Affinity | Neutralization In BiaCore | Neutralization In Cell based assay |
|---|---|---|---|
| BS-A | 6 nM | No | Yes, at high concentration |
| BS-B | 0.5 nM | Yes, IC$_{50}$ at 9 nM | Yes, at high concentration |
| GP-A | 8 nM | No | No |
| IFN-A | 18 nM | No | No |
| 57D | No | No | No |
| 57E | 200 nM | No | No |
| RD-A2 | N/A | No | No |
| RD-B | No | No | No |
| 58C | N/A | N/A | N/A |
| 67C | N/A | N/A | N/A |

Figure 30

| pattern | Fab affinity | IgG affinity |
|---|---|---|
| BS-A | 84.3 nM | 6 nM |
| BS-B | 83.5 nM | 0.5 nM |
| GP-A | 150 nM | 8 nM |
| IFN-A | 420 nM | 18 nM |

Figure 31

Heavy Chain Comparison Matrix

SIMILARITY →

|  | BS-A | BS-B | RD-A2 | RD-B1 | IFN-A | 57E | 57D | GP-A | 58C | 67C | 59-A2 |
|---|---|---|---|---|---|---|---|---|---|---|---|
| BS-A | — | 61.3 % | 93.4 % | 58.5 % | 95.1 % | 89.0 % | 59.5 % | 59.4 % | 58.8 % | 52.2 % | 59.1% |
| BS-B | 56.3 % | — | 63.0 % | 54.3 % | 60.6 % | 67.0 % | 60.4 % | 83.3 % | 84.7 % | 49.6 % | 90.5% |
| RD-A2 | 92.0% | 57.1 % | — | 61.9 % | 92.1% | 89.7% | 60.5 % | 58.9 % | 61.3 % | 53.4 % | 59.6% |
| RD-B1 | 55.9 % | 50.0 % | 56.8 % | — | 60.2 % | 63.9 % | 53.5 % | 53.4 % | 55.1 % | 77.9 % | 50.9% |
| IFN-A | 93.5% | 56.3 % | 90.5% | 55.9 % | — | 90.7% | 60.7 % | 58.3 % | 60.5 % | 53.4 % | 61.2% |
| 57E | 88.1% | 62.6 % | 88.8% | 58.8 % | 89.0% | — | 67.5 % | 61.9 % | 66.4 % | 50.8 % | 64.3% |
| 57D | 55.2 % | 88.6% | 57.0 % | 47.4 % | 57.3 % | 61.4 % | — | 84.0% | 85.8% | 53.2 % | 88.6% |
| GP-A | 54.5 % | 81.7% | 52.4 % | 49.2 % | 52.0 % | 57.6 % | 80.7 % | — | 81.7% | 50.8 % | 81.0% |
| 58C | 53.8 % | 83.0% | 56.3 % | 50.8 % | 55.5 % | 62.1 % | 84.1% | 78.3 % | — | 50.5 % | 80.0% |
| 67C | 45.2 % | 44.2 % | 44.8 % | 72.6 % | 46.6 % | 51.8 % | 45.9 % | 44.1 % | 44.1 % | — | 46.9% |
| 59-A2 | 54.8% | 88.2% | 55.3% | 47.3% | 55.2% | 60.7% | 86.0% | 80.2% | 78.3% | 41.6% | — |

↑ IDENTITY

Light Chain Comparison Matrix

SIMILARITY →

|  | BS-A | BS-B | RD-A2 | RD-B1 | IFN-A | 57E | 57D | GP-A | 58C | 67C | 59-A2 |
|---|---|---|---|---|---|---|---|---|---|---|---|
| BS-A | — | 89.0% | 41.0 % | 45.2 % | 45.7 % | 90.9% | 55.8 % | 67.6 % | 69.2 % | 47.6 % | 91.7% |
| BS-B | 89.0% | — | 46.8 % | 49.1 % | 51.8 % | 91.5% | 55.5 % | 68.1 % | 67.2 % | 47.6 % | 88.2% |
| RD-A2 | 37.1 % | 40.4 % | — | 75.2 % | 88.0% | 44.0 % | 67.2 % | 51.7 % | 51.8 % | 79.1 % | 41.9% |
| RD-B1 | 41.3 % | 45.5 % | 70.9 % | — | 80.0% | 45.5 % | 67.2 % | 54.0 % | 52.7 % | 79.1 % | 44.2% |
| IFN-A | 41.9 % | 47.3 % | 80.3% | 75.0 % | — | 50.4 % | 72.4 % | 55.9 % | 56.4 % | 84.5 % | 45.7% |
| 57E | 88.2% | 89.7% | 38.5 % | 42.9 % | 45.9 % | — | 55.9 % | 66.4 % | 67.2 % | 45.6 % | 90.9% |
| 57D | 50.0 % | 48.2 % | 62.0 % | 60.3 % | 69.0 % | 48.7 % | — | 55.6 % | 60.7 % | 67.9 % | 54.8% |
| GP-A | 61.0 % | 62.1 % | 44.7 % | 48.6 % | 49.6 % | 59.5 % | 48.7 % | — | 73.5 % | 55.7 % | 65.1% |
| 58C | 60.6 % | 59.5 % | 48.2 % | 46.3 % | 50.9 % | 59.5 % | 55.6 % | 68.4 % | — | 54.5 % | 67.3% |
| 67C | 43.7 % | 44.7 % | 73.6 % | 76.4 % | 80.9% | 42.7 % | 63.2 % | 50.5 % | 49.5 % | — | 46.6% |
| 59-A2 | 90.8% | 88.2% | 38.1% | 40.4% | 41.9% | 89.1% | 49.0% | 59.4% | 60.6% | 43.7% | — |

↑ IDENTITY

Figure 32

Heavy Chain CDR1 pileup

| | |
|---|---|
| BS-A | GYYWS |
| IFN-A | GYYWS |
| RD-A2 | GYYWS |
| 57E | SGGYSWS |
| 67C | SNEAGVG |
| RD-B | NARMGVS |
| BS-B | SYAMS |
| 59-A2 | SYAMS |
| GP-A | SYAMH |
| 58C | SYSMN |
| 57D | SNYMS |

Light Chain CDR1 pileup

| | |
|---|---|
| IFN-A | RSSQSLLHINEYNYLD |
| RD-A2 | RATQSLLHGNGHNYLD |
| 67C | RSSQSLLRSNGYNYLA |
| RD-B | RSSQSLVHSDGNTYLS |
| 57D | RASQ.YVSS...NSLA |
| 59-A2 | TGSSGSIASNYVQ |
| BS-A | TGSSGSIASHYVQ |
| BS-B | TRSSGSIASYYVQ |
| 57E | TGSSGSIANNYVH |
| 58C | GGDNLGGKSLH |
| GP-A | SGDVLARKYAR |

Heavy Chain CDR2 pileup

| | |
|---|---|
| 57D | VI.YSGGSTYYADSVKG |
| BS-B | AISGSGGSTYYADSVKG |
| 59-A2 | AISGSGGSTYYADSVKG |
| GP-A | VISYDGSNKYYADSVKG |
| 58C | SISSGSSYRYLADSVKG |
| BS-A | EINHSGSTNYNPSLKS |
| IFN-A | EINHSGSTNYNPSLKS |
| RD-A2 | EINHSGSTNYNPSLKS |
| 57E | YIYHSGSTYYNPSLKS |
| 67C | LLYWDDDKRYSPSLRS |
| RD-B | HIFSNDEESYSTSLKS |

Light Chain CDR2 pileup

| | |
|---|---|
| BS-B | EDDQRPS |
| 57E | EDDQRPS |
| 59-A2 | EDNQRPS |
| BS-A | EDKERPS |
| GP-A | KDRERPS |
| 58C | DDSDRPS |
| RD-A2 | MGSNRAS |
| 67C | LASNRAS |
| IFN-A | LGSNRAP |
| 57D | GASNRAT |
| RD-B | KISNRFS |

Heavy Chain CDR3 pileup

| | |
|---|---|
| 57E | GDWGYFDY |
| BS-A | GRARNWRSRFDY |
| IFN-A | GWPTYVWGSYRPKGYFDY |
| RD-A2 | DKGSRITIFGVVGSAGFDY |
| 58C | DQWGTISGNDY |
| 67C | RLVRYGGYSTGGFDV |
| RD-B | LLLYEGFDP |
| BS-B | DRVGYSSSLLDY |
| 59-A2 | TSWNAGGPIDY |
| GP-A | DLVLTMTSRRAAFDI |
| 57D | DADGGDYGY |

Light Chain CDR3 pileup

| | |
|---|---|
| IFN-A | MQALQTPRT |
| RD-A2 | MQALQLPPT |
| RD-B | MQATQLPYT |
| 67C | VHGVHIPYT |
| 57E | QSYDNSNSPVV |
| BS-A | QSYDSSNQWV |
| 59-A2 | QSYDGS.AWV |
| BS-B | QSYDR.NSLV |
| 57D | QQYGSSPIT |
| 58C | QVWDGSSDQRV |
| GP-A | ~~YSAADNRGV |

Figure 33

```
                                                         H1
                                                      ----------
                        FR1                          CDR1             FR2
           --------------------------------        --------     ---------------
                    1         2         3                            4
Locus      12345678901234567890123456789 0          1ab2345     67890123456789
VH4 4-34   QVQLQQWGAGLLKPSETLSLTCAVYGGSFS          G--YYWS     WIRQPPGKGLEWIG
"BS-A"     QVQLQQWGAGLLKPSETLSLTCAVYGGSFS          G  YYWS     WIRQPPGKGLEWIG
"RD-A2"    QVQLQQWGAGLLKPSETLSLTCAVYGGSFS          G  YYWS     WIRQPPGKGLEWIG
"IFN-A"    EVQLQQWGAGLLKPSETLSLTCAVYGGSFS          G  YYWS     WIRQPPGKGLEWIG H2
                 -------
                 CDR2                          FR3
           -------------------       ---------------------------------
                5         6              7         8         9
Locus      0123abc456789012345       67890123456789012abc345678901234
VH4 4-34   EINH---SGSTNYNPSLKS       RVTISVDTSKNQFSLKLSSVTAADTAVYYCAR    (SEQ ID NO:122)
"BS-A"     EINH   SGSTNYNPSLKS       RVTISVDTSKNQFSLKLSSVTAADTAVYYCAR
"RD-A2"    EINH   SGSTNYNPSLKS       RVTISVDTSKNQFSLKLSSVTAADTAVYYCAR
"IFN-A"    EINH   SGSTNYNPSLKS       RVTISVDTSKNQFSLKLSSVTAADTAVYYCAR CDR3
Diversity                   ------------------------------------
D1 1-1     GTTGT                VQLER              YNWND
"BS-A"                          GRAR               NWRS D3 3-3     VLRFLEWLLY           YYDFWSGYYT         ITIFGVVII
"RD-A2"                         DKGSR              ITIFGVVGSA D3 3-16    VL*LRLGELSLY         YYDYVWGSRYT        IMITFGGVIVI
"IFN-A"                G        WPTYVWGSYRP        KG H3
              ------
              CDR3
             --------
              100     110
Joining        |       |
JH4        -----YFDYWGQGTLVTVSS
"BS-A"     -----RFDYWGQGTLVTVSS
"RD-A2"    -----GFDYWGQGTLVTVSS
"IFN-A"    -----YFDYWGQGTLVTVSS
```

Figure 34

```
                                              H1
                                           ----------
              FR1                           CDR1          FR2
       ---------------------------------  ---------  ---------------
              1         2         3
Locus  12345678901234567890123456789 0    1ab2345    67890123456789
VH1 1-18 EVQLLESGGGLVQPGGSLRLSCAASGFTFS    S--YAMS    WVRQAPGKGLEWVS
"BS-B"   EVQLVESGGGLVQPGGSLRLSCAASGFTFS    S  YAMS    WVRQAPGKGLEWVS
"59-A2"  DVQLVETGGGLVQPGGSLRLSCAASGFTFS    S  YAMS    WVRQAPGKGLEWVS H2
            -------
           CDR2                              FR3
       ------------------    ----------------------------------
           5          6            7         8         9
Locus   012abc3456789012345   67890123456789012abc345678901234
VH1 1-18 AISG--SGGSTYYADSVKG   RFTISRDNSKNTLYLQMNSLRAEDTAVYYCAR  (SEQ ID NO:123)
"BS-B"   AISG  SGGSTYYADSVKG   RFTISRDNSKNTLYLQMNSLRAEDTAVYYCAK
"59-A2"  AISG  SGGSTYYADSVKG   RFTISRDNSKNTLYLQMDSLRAEDTAVYYCAK CDR3
Diversity    ---------------------------------------------
D6 6-13        GYSSSWY       GIAAAG       V*QQLV
"BS-B"       DRVGYSSS D1 1-1         GTTGT         VQLER        YNWND
D1 1-7         GITGT         V*LEL        YNWNY
"59-A2"         T                          SWNAGG H3
            ------
            CDR3
           --------
            100       110
Joining      |         |
JH4        -----YFDYWGQGTLVTVSS
"BS-B"     -----LLDYWGQGTLVTVSS
"59-A2"    -----PIDYWGQGNLVTVSS
```

Figure 35

```
                                     H1
                                  ----------
               FR1                CDR1          FR2
          --------------------------------  -------  ----------------
                    1         2         3        4
Locus     12345678901234567890123456789 0  1ab2345  67890123456789
VH2 2-26  QVTLKESGPVLVKPTETLTLTCTVSGFSLS   NARMGVS  WIRQPPGKALEWLA
"RD-B"    QVTLKESGPVLVKPTETLTLTCTVSGFSLS   NARMGVS  WIRQPPGKALEWLA H2
              --------
              CDR2                     FR3
          ------------------  ---------------------------------
                5         6          7         8         9
Locus     012abc3456789012345  67890123456789012abc345678901234
VH2 2-26  HIF---SNDEKSYSTSLKS  RLTISKDTSKSQVVLTMTNMDPVDTATYYCAR  (SEQ ID NO:124)
"RD-B"    HIF   SNDEESYSTSLKS  RLTISKDTSQSQVVLTMTNMDPVDTATYYCAR CDR3
                       ----------
Diversity
D3 3-22          VLL**WLLL      YYYDSSGYYY     ITMIVVVIT
"RD-B"           LLL            Y H3
           ------
           CDR3
           --------
              100       110
Joining        |         |
JH5       ----NWFDPWGQGTLVTVSS
"RD-B"        EGFDPWGQGTLVTVSS
```

Figure 36

```
                                          H1
                                        ----------
                    FR1                   CDR1           FR2
         ------------------------------  -------  ---------------
                1         2         3                  4
Locus    12345678901234567890123456789O  1ab2345  67890123456789
VH3 3-21 EVQLVESGGGLVKPGGSLRLSCAASGFTFS  S--YSMN  WVRQAPGKGLEWVS
"58C"    EVQLLESGGGLVKPGGSLRLSCAASGFTFS  S  YSMN  WVRQAPGKGLEWVS H2
              --------
             CDR2                         FR3
         --------------------   ----------------------------------
               5         6          7         8         9
Locus    012abc3456789012345    67890123456789012abc345678901234
VH3 3-21 SISS--SSSYIYYADSVKG    RFTISRDNAKNSLYLQMNSLRAEDTAVYYCAR  (SEQ ID NO:125)
"58C"    SISS  GSSYRYDADSVKG    RFTISRDNSKNTLYLQMNSLRAEDTAIYYCAD Diversity
Unknown
  "58C"          QMGTIS H3
            ------
            CDR3
            --------
             100       110
              |         |
Joining
JH4       -----YFDYWGQGTLVTVSS
"58C"     GNDYWGQGTLVTVSS
```

Figure 37

```
                                                        H1
                                                    -----------
                        FR1                            CDR1            FR2
               -------------------------------      -------    ----------------
                      1         2         3         1ab2345    4
Locus          12345678901234567890123456789 0      1ab2345    67890123456789
VH3 3-30.3     QVQLVESGGGVVQPGRSLRLSCAASGFTFS       S--YAMH    WVRQAPGKGLEWVA
"GP-A"         QVQLVETGGGVVQPGRSLRLSCAASGFTFS       S  YAMH    WVRQAPGKGLEWVA H2
                      -------
                       CDR2                               FR3
               ---------------------     ---------------------------------
                  5         6             7         8         9
Locus          012abc3456789012345       67890123456789012abc345678901234
VH3 3-30.3     VISY--DGSNKYYADSVKG       RFTISRDNSKNTLYLQMNSLRAEDTAVYYCAR    (SEQ ID NO:126)
"GP-A"         VISY  DGSNKYYADSVKG       RFTISRDNSKNTLYLQMNSLRAEDTAVYYCAS CDR3
Diversity                    --------------------------------------------
D3 3-10              VLLWFGELL*         YYYGSGSYYN          ITMVRGVII
"GP-A"               DLVL                                   TMTSRRA H3
                      ------
                       CDR3
                      --------
                       100        110
Joining                 |          |
JH3            -----AFDIWGQGTMVTVSS
"GP-A"         -----AFDIWGQGTMVTVSS
```

Figure 38

```
                                         H1
                                     -----------
                   FR1                  CDR1            FR2
        --------------------------------  -------  ---------------
                  1         2         3   1ab2345  4
Locus   12345678901234567890123456 7890   1ab2345  67890123456789
VH3 3-53 EVQLVESGGGLIQPGGSLRLSCAASGFTVS   S--NYMS  WVRQAPGKGLEWVS
"57D"   EVQLVQSGGGLVQPGGSLRLSCAASGFTVS    S  NYMS  WVRQAPGKGLEWVS H2
           --------
            CDR2                       FR3
        ------------------  -----------------------------------
            5         6         7         8         9
Locus   012abc3456789012345  67890123456789012abc345678901234
VH3 3-53 VIY---SGGSTYYADSVKG  RFTISRDNSKNTLYLQMNSLRAEDTAVYYCAR  (SEQ ID NO:127)
"57D"   VIY   SGGSTYYADSVKG  RFTISRDNSKNTLYLQMNSLRAEDTAVYYCAR CDR3
Diversity                                          -----------
D3 3-16        VL*LRLGELSLY     YYDYVWGSYRYT       IMITFGGVIVI
"57D"                                              DSDGG H3
            ------
            CDR3
           --------
            100       110
Joining      |         |
Unknown
"57D"       DYGYWGQGTLVTVSS
```

Figure 39

```
                                    H1
                                 -----------
                 FR1                CDR1         FR2
         -------------------------------  -------  ---------------
                 1         2         3        4
Locus    12345678901234567890123456789 0  1ab2345  67890123456789
VH4 4-61 QVQLQESGPGLVKPSETLSLTCTVSGGSVS  SGGYYWS  WIRQPPGKGLEWIG
"57E"    QVQLQESGPGLVKPSETLSLTCAVSGGSIS  SGGYSWS  WIRQPPGKGLEWIG H2
           --------
              CDR2                        FR3
         -----------------  ----------------------------------
            5        6         7         8         9
Locus    012abc3456789012345  67890123456789012abc345678901234
VH4 4-61 YIY---YSGSTNYNPSLKS  RVTISVDTSKNQFSLKLSSVTAADTAVYYCAR  (SEQ ID NO:128)
"57E"    YIY   HSGSTYYNPSLKS  RVTISVDRSKNQFSLKLSSVTAADTAVYYCAR CDR3
                             -----------
Diversity
D7 7-27              LTG      *LG         NWG
"57E"                          G          DWG H3
           ------
              CDR3
           --------
            100       110
             |         |
Joining
JH4      ----YFDYWGQGTLVTVSS
"57E"        YFDYWGQGTLVTVSS
```

Figure 40

```
                                       H1
                                   ----------
                     FR1              CDR1            FR2
          -------------------------  -------    ---------------
                 1         2         3              4
Locus     12345678901234567890123456789 0  1ab2345  67890123456789
VH2 2-05  QITLKESGPTLVKPTQTLTLTCTFSGFSLS  TSGVGVG  WIRQPPGKALEWLA
"67-C"    ANTLEESGPTLVQPTQTLTLTCSYSGFSLS  SNEAGVG  WIRQPPGKAPEWLA H2
          --------
             CDR2                         FR3
          ------------------  ----------------------------------
                5       6         7         8         9
Locus     012abc3456789012345  67890123456789012abc345678901234
VH2 2-05  LIY---WNDDKRYSPSLKS  RLTITKDTSKNQVVLTMTNMDPVDTATYYCAH   (SEQ ID NO:129)
"67-C"    LLY   WDDDKRYSPSLRS  RLIVNKDTSKSQVVLTMTNMDPVDTATYYCAH CDR3
                                    ----------------------
Diversity
D5 5-18             VDTAMV          WIQLWL         GYSYGY
"67-C"                              RLVRYG         GYSTG H3
          ------
            CDR3
          --------
              100        110
               |          |
Joining
JH6       YYYYYGMDYWGQGTTVTVSS
"67-C"    -----GFDVWGQGTTVTVSS
```

Figure 41

```
                                              L1                                        L2
                                        -------------                                   ---
              FR1                       CDR1                       FR2                  CDR2
         ------------------------   ------------------    -----------------          --------
                 1         2              3                       4                      5
Locus     12345678901234567890123    45678901abcdef234     567890123456789           0123456

Vλ6 6a   NFMLTQ-PHSVSESPGKTVTISC    TRSSGSIAS----NYVQ     WYQQRPGSSPTTVIY           EDNQRPS
"BS-A"   NFMLTQ PHSVSESPGKTVTISC    TGSSGSIAS    HYVQ     WYQQRPGSAPTNVIY           EDKERPS
"59-A2"  NFMLTQ PHSVSESPGKTVTISC    TGSSGSIAS    NYVQ     WYQQRPGSAPTTVIY           EDNQRPS
"BS-B"   NFMLTQ PHSVSESPGKTVTISC    TRSSGSIAS    YYVQ     WYQQRPGSSPTTVIY           EDDQRPS
"57E"    NFMLTQ PHSVSESPGKTVTISC    TGSSGSIAN    NYVH     WYQQRPGSAPTTVIF           EDDQRPS

L3
                                                          -----
              FR3                                         CDR3
         ------------------------------------------    -------
                  6         7         8                    9
Locus     789012345ab6789012345678901234 5678         9012345abcde Vλ6 6a   GVPDRFSGSIDSSSNSASLTISGLKTEDEADYYC            QSYDSSN    (SEQ ID NO:130)
"BS-A"   GVPDRFSGSIDSSTNSASLTISGLKTEDEADYYC            QSYDSSNQ
"59-A2"  GVPPRFSGSIDRSSNSASLTISGLKSEDEADYYC            QSYDGSA
"BS-B"   GVPDRFSGSIDSASNSASLTISGLQTEDEADYYC            QSYDRNS
"57E"    GVPDRFSGSVDSSSNSASLSISGLKTEDEADYYC            QSYDNSNF L3
              -
              CDR3
              --
                100
                 |
Joining
Unknown       WVFGGGTKLTVL
"BS-A"        WVFGGGTKLTVL
"59-A2"       WVFGGGTKLTVL Unknown       LVFGGGTKLTVL
"BS-B"        LVFGGGTKLTVL JL2 or JL3    VVFGGGTKLTVL
"57E"         VVFGGGTKLTVL
```

Figure 42

```
                                            L1                              L2
                                       -------------                        ---
             FR1                          CDR1                FR2          CDR2
     ------------------------       ------------------   ---------------   ------

1         2                 3                   4              5
Locus    12345678901234567890123    45678901abcdef234    567890123456789   0123456
VK2 A23  DIVMTQTPLSSPVTLGQPASISC    RSSQSLVHS-DGNTYLS    WLQQRPGQPPRLLIY   KISNRFS
"RD-B1"  DIVMTHTPLSSPVTLGQPASISC    RSSQSLVHS DGNTYLS    WLHQRPGQPPRLLIY   KISNRFS L3
                                                        -----
             FR3                                        CDR3
     ------------------------------------------         -------

6         7         8                         9
Locus    789012345678901234567890123456789012345678      9012345
VK2 A23  GVPDRFSGSGAGTDFTLKISRVEAEDVGVYYC                MQATQFP   (SEQ ID NO:131)
"RD-B1"  GVPDRFSGSGAGTDFTLKISRVEAEDVGLYYC                MQATQLP L3
             -
             CDR3
             --
              100
              |
Joining
JK2      YTFGQGTKLEIK
"RD-B1"  YTFGQGTKLEIK
```

Figure 43

```
                                                L1                                    L2
                                         ---------------                             ---
                      FR1                     CDR1                   FR2             CDR2
          ------------------------    ------------------    ----------------        -----
--
                     1         2              3                    4                   5
Locus     12345678901234567890123    45678901abcdef234    567890123456789       0123456
VK2 A19   DIVMTQSPLSLPVTPGEPASISC    RSSQSLLHS-NGYNYLD    WYLQKPGQSPQLLIY       LGSNRAS
"RD-A2"   DVVMTQSPLSLPVTPGEPASISC    RATQSLLHG NGHNYLD    WYLQKPGQSPHLLIY       MGSNRAS
"IFN-A"   EIVLTQSPLSLPVTPGEPASISC    RSSQSLLHT NEYNYLD    WYLQKPGQSPQLLIY       LGSNRAP
"67-C"    DIVMTHTPLSLPVTPGEPASISC    RSSQSLLRS NGYNYLA    WYVQKPGQSPQLLIY       LASNRAS L3
                                                         -----
                          FR3                            CDR3
          ----------------------------------            -------
                6         7         8                      9
Locus     78901234567890123456789012345678         9012345
VK2 A19   GVPDRFSGSGSGTDFTLKISRVEAEDVGVYYC         MQALQTP   (SEQ ID NO:132)
"RD-A2"   GVPGRFSGTESGRNFTLKISRVEAEDVGVYYC         MQALQTP
"IFN-A"   GVPDRFSGSGSGTDFTLRISRVEADDVGVYYC         MQALQTR
"67-C"    GVPDRFSGSGSGTDFTLKISSVEAEDVGVYYC         VHGVHIP L3
          -
          CDR3
          --
                100
                 |
Joining
JK3       FTFGPGTKVDIK
"RD-A2"   PTFGQGTRVDIK

JK2       YTFGQGTKLEIK
"IFN-A"   RTFGQGTKLEIK

JK2       YTFGQGTKLEIK
"67-C"    YTFGQGTKLEIK
```

Figure 44

```
                                                   L1                                L2
                                              ----------                         --------
                    FR1                         CDR1              FR2              CDR2
          -----------------------         ---------------    ---------------    -----------
                    1         2                 3                  4                 5
Locus     12345678901234567890123         45678901abc234     567890123456789    01abcde23456
VL3 3h    SYVLTQPPS-VSVAPGKTARITC         GG-NN-IGSK-SVH     WYQQKPGQAPVLVVY    DD-----SDRPS
"58C"     QSVLTQPPS VSVAPGKTATITC         GG DN LGGK SLH     WYQQKPGQAPVLVVY    DD     SDRPS L3
                                                                  -----
                    FR3                                           CDR3
          ---------------------------------------              -------
                    6         7         8                          9
Locus     789012345678ab9012345678901234 5678                  9012345abcde
VL3 3h    GIPERFSGSNSG--NTATLTISRVEAGDEADYYC                   QVWDSSSDH  (SEQ ID NO:133)
"58C"     GIPERFSGSNSG  NTATLTIDRVEDGDEADYYC                   QVWDGSSDQ L3
          -
          CDR3
          --
                  100
Joining            |
Unknown
"58C"     RVFGGGTRLTVL
```

Figure 45

```
                                       L1                          L2
                                     ----------                    ---
             FR1                     CDR1              FR2         CDR2
             ------------------------ ---------------- ---------------- -------
             1        2               3                4                5
Locus        12345678901234567890123  45678901abc234   567890123456789  01abcde23456
VL3 2-19     SYELTQPSS-VSVSPGQTARITC  SG-DV-LAKK-YAR   WFQQKPGQAPVLVIY  KD-----SERPS
"GP-A"       SYELTQPPS VSVSPGQTARITC  SG DV LARK YAR   WFQQKPGQAPVLVIY  KD     RERPS L3
                                                     -----
             FR3                                     CDR3
             ------------------------------------    -------
             6         7         8                   9
Locus        789012345678ab9012345678901234 5678     9012345abcde
VL3 2-19     GIPERFSGSSSG--TTVTLTISGAQVEDEADYYC      YSAADNN  (SEQ ID NO:134)
"GP-A"       GIPERFSGSTSG  TTVTLTISGAQVEDEADYYC      YSAADNR L3
             -
             CDR3
             --
                      100
                       |
Joining
JL2 or JL3   VVFGGGTKLTVL
"GP-A"       GVFGGGTKLTVL
```

Figure 46

```
                                              L1                              L2
                                        -------------                        ---
                   FR1                      CDR1                FR2          CDR2
         ----------------------      ------------------   ----------------   -------
                 1         2              3                    4             5
Locus    12345678901234567890123      45678901abcdef234    567890123456789    0123456
VK3 A27  EIVLTQSPGTLSLSPGERATLSC      RASQSVSSS-----YLA    WYQQKPGQAPRLLIY    GASSRAT
"57D"    EIVLTQSPGTLSLSPGERATLSC      RASQYVSSN    SLA    WYQQKAGQAPRLLIY    GASNRAT L3
                                                          -----
                   FR3                                    CDR3
         ---------------------------------              -------
                 6         7         8                     9
Locus    789012345678901234567890123456778             9012345
VK3 A27  GIPDRFSGSGSGTDFTLTISRLEPEDFAVYYC              QQYGSSP    (SEQ ID NO:135)
"57D"    GIPDRFSGSGSGTDFTLTISRLEPEDFAVYYC              QQYGSSP L3
                   -
                   CDR3
                   --
                       100
                        |
Joining
JK5                ITFGQGTRLEIK
"57D"              ITFGQGTRLEIK
```

Figure 47

Fab Classes

| pattern | Heavy chain | | | | Light chain | | |
|---|---|---|---|---|---|---|---|
| | Family | V | D | J | Family | V | J |
| BS-A | VH4 | 4-34 | 1-1 | JH4* | VL6 | 6a | ** |
| BS-B | VH1 | 1-18 | 6-13 | JH4* | VL6 | 6a | ** |
| RD-B1 | VH2 | 2-26 | 3-22 | JH5* | VK2 | A23 | JK2 |
| RD-A2 | VH4 | 4-34 | 3-3 | JH4* | VK2 | A19 | JK3 |
| 58C | VH3 | 3-21 | ** | JH4* | VL3 | 3h | ** |
| GP-A | VH3 | 3-30.3 | 3-10 | JH3 | VL3 | 2-19 | JL2/JL3 |
| 57D | VH3 | 3-53 | 3-16 | ** | VK3 | A27 | JK5 |
| 57E | VH4 | 4-61 | 7-27 | JH4 | VL6 | 6a | JL2/JL3 |
| IFN-A | VH4 | 4-34 | 3-16 | JH4 | VK2 | A19 | JK2 |
| 67C | VH2 | 2-05 | 5-18 | JH6* | VK2 | A19 | JK2 |
| 59-A2 | VH1 | 1-18 | 1-1/1-7 | JH4* | VL6 | 6a | ** |

US 7,084,257 B2

FULLY HUMAN ANTIBODY FAB FRAGMENTS WITH HUMAN INTERFERON-GAMMA NEUTRALIZING ACTIVITY

FIELD OF THE INVENTION

The invention relates to novel fully human antibody Fab fragments that bind to human interferon gamma (hIFNγ), and inhibit its interaction with the cognate receptor, IFNγ-R, and/or modify biological actions elicited by IFNγ. More particularly, the invention relates to neutralizing Fab fragments (Fabs) isolated through hIFNγ-affinity-selections of a phage displayed library containing unique Fab fragments, which were then converted into full-length human IgG antibodies. These novel fully human antibodies to hIFNγ, having the desired qualities of hIFNγ-neutralizing activity, high affinity, and long half-life in vivo, may be used to prevent or treat various autoimmune and inflammatory diseases. Nucleic acid molecules, vectors and host cells for the production of the fully human Fabs of the invention are also provided.

BACKGROUND OF THE INVENTION

Antibodies have played an essential role in biopharmaceutical research and drug discovery efforts for many decades. The utility of antibodies as therapeutic agents for the treatment of human diseases has been idealized for many years due to their: (a) long half-life in vivo; (b) ability to bind target(s) with high affinity and specificity; and (c) potential to mediate immune effector functions (such as complement fixation and antibody-dependent cellular cytotoxicity).

The reduction of the therapeutic antibody concept to practice was severely limited, however, until now, by the adverse immunogenicity of antibodies obtained from non-human species which restricted long-term clinical utility of the antibodies. Recent technological advances have provided new ways of overcoming these limitations by providing a means of obtaining fully human antibodies with less immunogenicity and a longer-term therapeutic potential. Additionally, developments in combinatorial library methods and antibody-engineering have opened opportunities for modification of antibody-affinity, half-life, and/or effector functions.

One such technology, which employs filamentous phage-displayed, combinatorial libraries of antibody fragments fused to the phage coat protein (so-called "phage displayed library"), has been effectively used to discover antibodies with high affinity, specificity, and agonistic or antagonistic acitivity in vivo.

Human interferon gamma (hIFNγ) is a lymphokine produced by activated T-lymphocytes and natural killer cells. It manifests antiproliferative, antiviral and immunomodulatory activites and binds to hIFNγ-R, a heterodimeric receptor on most primary cells of the immune system; Langer et al., *Immunology Today,* 9:393 (1988), and triggers a cascade of events leading to inflammation. The antiviral and immunomodulatory activity of IFNγ is known to have beneficial effects in a number of clinical conditions. However, there are many clinical settings in which IFNγ-activity is known to have deleterious effects. For example, autoimmune dieseases are associated with high levels of hIFNγ in the blood, and there is now evidence suggesting that sequestration of IFNγ is associated with symptomatic relief of autoimmune diseases such as rheumatoid arthritis (RA), systemic lupus erythematosus (SLE) and multiple sclerosis (MS); see, e.g., Skurkovich et al., *Intern. Journal of Immunotherapy,* 14:23–32 (1998); Gerez et al., *Clin. Exp. Immunol.,* 109: 296–303 (1997). IFNγ-activity has also been linked to such disease states as cachexia, septic shock and Crohn's disease.

Because blocking the interaction of hIFNγ to its receptor represents the most upstream step of intervention in this regard, a fully human antibody with hIFNγ-neutralizing activity represents an attractive therapeutic product candidate. It is an object of the present invention to employ the phage displayed library technology to identify antibodies using human interferon-gamma (hIFNγ) as the therapeutic target.

SUMMARY OF THE INVENTION

The present invention provides for novel fully human antibody Fab fragments that bind to human interferon-gamma (hIFNγ). In one embodiment, the fully human antibody Fab fragments bind to hIFNγ in a manner that partially or completely inhibits the interaction of hIFNγ with its cognate receptor, hIFNγ-R, and thereby partially or completely inhibits hIFNγ activity; that is, the antibody is an antagonist of hIFNγ. Preferably, the hIFNγ is mammalian hIFNγ. More preferably, the hIFNγ is human hIFNγ which may be in soluble or cell surface associated forms, or fragments, derivatives and variants thereof.

An antibody of the present invention may be prepared by immunizing an animal with hIFNγ such as murine or human hIFNγ, preferably human hIFNγ, or with an immunogenic fragment, derivative or variant thereof. In addition, an animal may be immunized with cells transfected with a vector containing a nucleic acid molecule encoding hIFNγ such that hIFNγ is expressed and associated with the surface of the transfected cells. Alternatively, the antibodies may be obtained by screening a library comprising antibody or antigen binding domain sequences for binding to hIFNγ. Such a library is conveniently prepared in bacteriophage as protein or peptide fusions to a bacteriophage coat protein which are expressed on the surface of assembled phage particles and the encoding DNA sequences contained within the phage particles (so-called "phage displayed library"). In one example, a phage displayed library contains DNA sequences encoding human antibodies, such as variable light and heavy chains.

The antibodies or antigen binding domains may be tetrameric glycoproteins similar to native antibodies, or they may be single chain antibodies; Fv, Fab, Fab' or F(ab)' fragments, bispecific antibodies, heteroantibodies, or other fragments, variants, or derivatives thereof, which are capable of binding hIFNγ and partially or completely neutralize hIFNγ activity. Antibodies or antigen binding domains may be produced in hybridoma cell lines (antibody-producing cells such as spleen cells fused to mouse myeloma cells, for example) or may be produced in heterologous cell lines transfected with nucleic acid molecules encoding said antibody or antigen binding domain.

An antibody or antigen binding domain of the invention comprises:

(a) a Fab heavy chain amino acid sequence as shown in FIGS. 3–13 (SEQ ID NO:65–SEQ ID NO:86);

(b) a heavy chain amino acid sequence comprising conservative amino acid substitutions of the sequence in (a);

(c) a heavy chain amino acid sequence which is at least about 80% identical to the sequence in (a); or (d) a fragment or derivative of (a), (b) or (c);

wherein the antibody or antigen binding domain binds selectively to hIFNγ.

In another embodiment, an antibody or antigen binding domain of the invention recognizes an epitope on human hIFNγ recognized by an antibody or antigen binding domain comprising a Fab heavy chain amino acid sequence as shown in FIGS. 3–13 same as above (SEQ ID NO:65–SEQ ID NO:86) and a Fab light amino acid sequence as shown in FIGS. 14–24 (SEQ ID NO:87–SEQ ID NO:108).

In another embodiment, an antibody or antigen binding domain of the invention comprises a $V_l$ and $V_h$ chain:

wherein each $V_l$ chain comprises CDR amino acid sequences designated CDR1($V_l$), CDR2($V_l$) and CDR3 ($V_l$) separated by framework amino acid sequences, CDR1 ($V_l$) being selected from the group consisting of:
  TGSSGSIASHYVQ (SEQ ID NO:01);
  TGSSGSIASNYVQ (SEQ ID NO:02);
  TRSSGSIASYYVQ (SEQ ID NO:03);
  RATQSLLHGNGHNYLD (SEQ ID NO:04);
  RSSQSLVHSDGNTYLS (SEQ ID NO:05);
  SGDVLARKYAR (SEQ ID NO:06);
  GGDNLGGKSLH (SEQ ID NO:07);
  RSSQSLLHTNEYNYLD (SEQ ID NO:08);
  TGSSGSIANNYVH (SEQ ID NO:09);
  RASQYVSSNSLA (SEQ ID NO:10); and
  RSSQSLLRSNGYNYLA (SEQ ID NO:11)
CDR2($V_l$) being selected from the group consisting of:
  EDKERPS (SEQ ID NO:12);
  EDNQRPS (SEQ ID NO:13);
  EDDQRPS (SEQ ID NO:14);
  MGSNRAS (SEQ ID NO:15);
  KISNRFS (SEQ ID NO:16);
  KDRERPS (SEQ ID NO:17);
  DDSDRPS (SEQ ID NO:18);
  LGSNRAP (SEQ ID NO:19);
  EDDQRPS (SEQ ID NO:20);
  GASNRAT (SEQ ID NO:21); and
  LASNRAS (SEQ ID NO:22)
and CDR3($V_l$) being selected from the group consisting of:
  QSYDSSNQWV (SEQ ID NO:23);
  QSYDGSAWV (SEQ ID NO:24);
  QSYDRNSLV (SEQ ID NO:25);
  MQALQLPPT (SEQ ID NO:26);
  MQATQLPYT (SEQ ID NO:27);
  YSAADNRGV (SEQ ID NO:28);
  QVWDGSSDQRV (SEQ ID NO:29);
  MQALQTPRT (SEQ ID NO:30);
  QSYDNSNSFVV (SEQ ID NO:31);
  QQYGSSPIT (SEQ ID NO:32); AND
  VHGVHIPYT (SEQ ID NO:33)
wherein CDR1($V_l$), CDR2($V_l$) and CDR3($V_l$) are selected independently of each other; and
wherein each $V_h$ chain comprises CDR amino acid sequences designated CDR1($V_h$), CDR2($V_h$) and CDR3 ($V_h$) separated by framework amino acid sequences, CDR1 ($V_h$) being selected from the group consisting of:
  GYYWS (SEQ ID NO:34);
  SYAMS (SEQ ID NO:35);
  GYYWS (SEQ ID NO:36);
  NARMGVS (SEQ ID NO:37);
  SYAMH (SEQ ID NO:38);
  SYSMN (SEQ ID NO:39);
  GYYWS (SEQ ID NO:40);
  SGGYSWS (SEQ ID NO:41);
  SNYMS (SEQ ID NO:42); and
  SNEAGVG (SEQ ID NO:43)

CDR2($V_h$) being selected from the group consisting of:
  EINHSGSTNYNPSLKS (SEQ ID NO:44);
  AISGSGGSTYYADSVKG (SEQ ID NO:45);
  EINHSGSTNYNPSLKS (SEQ ID NO:46);
  HIFSNDEESYSTSLKS (SEQ ID NO:47);
  VISYDGSNKYYADSVKG (SEQ ID NO:48);
  SISSGSSYRYDADSVKG (SEQ ID NO:49);
  EINHSGSTNYNPSLKS (SEQ ID NO:50);
  YIYHSGSTYYNPSLKS (SEQ ID NO:51);
  VIYSGGSTYYADSVKG (SEQ ID NO:52); and
  LLYWDDDKRYSPSLRS (SEQ ID NO:53)
CDR3($V_h$) being selected from the group consisting of:
  GRARNWRSRFDY (SEQ ID NO:54);
  TSWNAGGPIDY (SEQ ID NO:55);
  DRVGYSSSLLDY (SEQ ID NO:56);
  DKGSRITIFGVVGSAGFDY (SEQ ID NO:57);
  LLLYEGFDP (SEQ ID NO:58);
  DLVLTMTSRRAAFDI (SEQ ID NO:59);
  DQWGTISGNDY (SEQ ID NO:60);
  GWPTYVWGSYRPKGYFDY (SEQ ID NO:61);
  GDWGYFDY (SEQ ID NO:62);
  DADGGDYGY (SEQ ID NO:63); and
  RLVRYGGYSTGGFDV (SEQ ID NO:64)
wherein CDR1($V_l$), CDR2($V_h$) and CDR3($V_h$) are selected independently of each other.

In another embodiment, an antibody or antigen binding domain of the invention comprises a $V_l$ and a $V_h$ chain wherein: the $V_l$ chain comprises CDR1 having the sequence TGSSGSIASHYVQ (SEQ ID NO:01), CDR2 having the sequence EDKERPS (SEQ ID NO:12), and CDR3 having the sequence QSYDSSNQWV (SEQ ID NO:23); and
the $V_h$ chain comprises CDR1 having the sequence GYYWS (SEQ ID NO:34), CDR2 having the sequence EINHSGSTNYNPSLKS (SEQ ID NO:44), and CDR3 having the sequence GRARNWRSRFDY (SEQ ID NO:54);
wherein CDR1, CDR2 and CDR3 on each $V_l$ and $V_h$ chain are separated by framework amino acid sequences.

In another embodiment, an antibody or antigen binding domain of the invention comprises a $V_l$ and a $V_h$ chain wherein: the $V_l$ chain comprises CDR1 having the sequence TGSSGSIASNYVQ (SEQ ID NO:02), CDR2 having the sequence EDNQRPS (SEQ ID NO:13), and CDR3 having the sequence QSYDGSAWV (SEQ ID NO:24); and
the $V_h$ chain comprises CDR1 having the sequence SYAMS (SEQ ID NO:35), CDR2 having the sequence AISGSGGSTYYADSVKG (SEQ ID NO:45), and CDR3 having the sequence TSWNAGGPIDY (SEQ ID NO:55);
wherein CDR1, CDR2 and CDR3 on each $V_l$ and $V_h$ chain are separated by framework amino acid sequences.

In another embodiment, an antibody or antigen binding domain of the invention comprises a $V_l$ and a $V_h$ chain wherein: the $V_l$ chain comprises CDR1 having the sequence TRSSGSIASYYVQ (SEQ ID NO:03), CDR2 having the sequence EDDQRPS (SEQ ID NO:14), and CDR3 having the sequence QSYDRNSLV (SEQ ID NO:25); and
the $V_h$ chain comprises CDR1 having the sequence SYAMS (SEQ ID NO:35), CDR2 having the sequence AISGSGGSTYYADSVKG (SEQ ID NO:45), and CDR3 having the sequence DRVGYSSSLLDY (SEQ ID NO:56);
wherein CDR1, CDR2 and CDR3 on each $V_l$ and $V_h$ chain are separated by framework amino acid sequences.

In another embodiment, an antibody or antigen binding domain of the invention comprises a $V_l$ and a $V_h$ chain wherein: the $V_l$ chain comprises CDR1 having the sequence RATQSLLHGNGHNYLD (SEQ ID NO:04), CDR2 having the sequence MGSNRAS (SEQ ID NO:15), and CDR3 having the sequence MQALQLPPT (SEQ ID NO:26); and
the $V_h$ chain comprises CDR1 having the sequence GYYWS (SEQ ID NO:36), CDR2 having the sequence EINHSGSTNYNPSLKS (SEQ ID NO:46), and CDR3 having the sequence DKGSRITIFGVVGSAGFDY (SEQ ID NO:57);
wherein CDR1, CDR2 and CDR3 on each $V_1$ and $V_h$ chain are separated by framework amino acid sequences.

In another embodiment, an antibody or antigen binding domain of the invention comprises a $V_1$ and a $V_h$ chain wherein: the $V_1$ chain comprises CDR1 having the sequence RSSQSLVHSDGNTYLS (SEQ ID NO:05), CDR2 having the sequence KISNRFS (SEQ ID NO:16), and CDR3 having the sequence MQATQLPYT (SEQ ID NO:27); and
the $V_h$ chain comprises CDR1 having the sequence NARMGVS (SEQ ID NO:37), CDR2 having the sequence HIFSNDEESYSTSLKS (SEQ ID NO:47), and CDR3 having the sequence LLLYEGFDP (SEQ ID NO:58);
wherein CDR1, CDR2 and CDR3 on each $V_1$ and $V_h$ chain are separated by framework amino acid sequences.

In another embodiment, an antibody or antigen binding domain of the invention comprises a $V_1$ and a $V_h$ chain wherein: the $V_1$ chain comprises CDR1 having the sequence SGDVLARKYAR (SEQ ID NO:06), CDR2 having the sequence KDRERPS (SEQ ID NO:17), and CDR3 having the sequence YSAADNRGV (SEQ ID NO:28); and
the $V_h$ chain comprises CDR1 having the sequence SYAMH (SEQ ID NO:38), CDR2 having the sequence VISYDGSNKYYADSVKG (SEQ ID NO:48), and CDR3 having the sequence DLVLTMTSRRAAFDI (SEQ ID NO:59);
wherein CDR1, CDR2 and CDR3 on each $V_1$ and $V_h$ chain are separated by framework amino acid sequences.

In another embodiment, an antibody or antigen binding domain of the invention comprises a $V_1$ and a $V_h$ chain wherein: the $V_1$ chain comprises CDR1 having the sequence GGDNLGGKSLH (SEQ ID NO:07), CDR2 having the sequence DDSDRPS (SEQ ID NO:18), and CDR3 having the sequence QVWDGSSDQRV (SEQ ID NO:29); and
the $V_h$ chain comprises CDR1 having the sequence SYSMN (SEQ ID NO:39), CDR2 having the sequence SISSGSSYRYDADSVKG (SEQ ID NO:49), and CDR3 having the sequence DQWGTISGNDY (SEQ ID NO:60);
wherein CDR1, CDR2 and CDR3 on each $V_1$ and $V_h$ chain are separated by framework amino acid sequences.

In another embodiment, an antibody or antigen binding domain of the invention comprises a $V_1$ and a $V_h$ chain wherein: the $V_1$ chain comprises CDR1 having the sequence RSSQSLLHTNEYNYLD (SEQ ID NO:08), CDR2 having the sequence LGSNRAP (SEQ ID NO:19), and CDR3 having the sequence MQALQTPRT (SEQ ID NO:30); and
the $V_h$ chain comprises CDR1 having the sequence GYYWS (SEQ ID NO:40), CDR2 having the sequence EINHSGSTNYNPSLKS (SEQ ID NO:50), and CDR3 having the sequence GWPTYVWGSYRPKGYFDY (SEQ ID NO:61);
wherein CDR1, CDR2 and CDR3 on each $V_1$ and $V_h$ chain are separated by framework amino acid sequences.

In another embodiment, an antibody or antigen binding domain of the invention comprises a $V_1$ and a $V_h$ chain wherein: the $V_1$ chain comprises CDR1 having the sequence TGSSGSIANNYVH (SEQ ID NO:09), CDR2 having the sequence EDDQRPS (SEQ ID NO:20), and CDR3 having the sequence QSYDNSNSFVV (SEQ ID NO:31); and
the $V_h$ chain comprises CDR1 having the sequence SGGYSWS (SEQ ID NO:41), CDR2 having the sequence YIYHSGSTYYNPSLKS (SEQ ID NO:51), and CDR3 having the sequence GDWGYFDY (SEQ ID NO:62);
wherein CDR1, CDR2 and CDR3 on each $V_1$ and $V_h$ chain are separated by framework amino acid sequences.

In another embodiment, an antibody or antigen binding domain of the invention comprises a $V_1$ and a $V_h$ chain wherein: the $V_1$ chain comprises CDR1 having the sequence RASQYVSSNSLA (SEQ ID NO:10), CDR2 having the sequence GASNRAT (SEQ ID NO:21), and CDR3 having the sequence QQYGSSPIT (SEQ ID NO:32); and
the $V_h$ chain comprises CDR1 having the sequence SNYMS (SEQ ID NO:42), CDR2 having the sequence VIYSGGSTYYADSVKG (SEQ ID NO:52), and CDR3 having the sequence DADGGDYGY (SEQ ID NO:63);
wherein CDR1, CDR2 and CDR3 on each $V_1$ and $V_h$ chain are separated by framework amino acid sequences.

In another embodiment, an antibody or antigen binding domain of the invention comprises a $V_1$ and a $V_h$ chain wherein: the $V_1$ chain comprises CDR1 having the sequence RSSQSLLRSNGYNYLA (SEQ ID NO:11), CDR2 having the sequence LASNRAS (SEQ ID NO:22), and CDR3 having the sequence VHGVHIPYT (SEQ ID NO:33); and
the $V_1$ chain comprises CDR1 having the sequence SNEAGVG (SEQ ID NO:43), CDR2 having the sequence LLYWDDDKRYSPSLRS (SEQ ID NO:53), and CDR3 having the sequence RLVRYGGYSTGGFDV (SEQ ID NO:64);
wherein CDR1, CDR2 and CDR3 on each $V_1$ and $V_h$ chain are separated by framework amino acid sequences.

Antibodies and antigen binding domains of the invention are derived from germ line nucleic acid sequences present in genomic DNA which encode light and heavy chain amino acid sequences. Antibodies are encoded by nucleic acid sequences which are the products of germline sequence rearrangement and somatic mutation.

In one embodiment, an antibody or antigen binding domain of the invention comprises a $V_1$ and a $V_h$ chain wherein the $V_1$ chain is comprises a rearranged or somatic variant of a Vλ6 germline genes such as in FIG. 41 (SEQ ID NO:130); and the $V_h$ chain comprises a rearranged or somatic variant of a VH4 germline genes such as in FIG. 33 (SEQ ID NO:122); and the antibody binds selectively to an IFNγ polypeptide.

In another embodiment, the $V_1$ chain comprises or a rearranged or somatic variant of a Vλ6 germline genes such as in FIG. 41 (SEQ ID NO:130); and the $V_h$ chain comprises a rearranged or somatic variant of a VH1 germline gene such as in FIG. 34 (SEQ ID NO:123).

In another embodiment, the $V_1$ chain comprises a rearranged or somatic variant of a Vκ2 germline gene such as in FIG. 42 (SEQ ID NO:131); and the $V_h$ chain comprises a rearranged or somatic variant of a VH2 germline gene such as in FIG. 35 (SEQ ID NO:124).

In another embodiment, the $V_1$ chain comprises a rearranged or somatic variant of a Vκ2 germline gene such as in FIG. 43 (SEQ ID NO:132); and the $V_h$ chain comprises a rearranged or somatic variant of a VH4 germline gene such as in FIG. 33 (SEQ ID NO:122).

In another embodiment, the $V_1$ chain comprises a rearranged or somatic variant of a Vλ3 germline gene such as in FIG. 44 (SEQ ID NO:133); and the $V_h$ chain comprises a rearranged or somatic variant of a VH3 germline gene such as in FIG. 36 (SEQ ID NO:125).

In another embodiment, the $V_1$ chain comprises a rearranged or somatic variant of a Vλ3 germline gene such as in FIG. 45 (SEQ ID NO:134); and the $V_h$ chain comprises a rearranged or somatic variant of a VH3 germline gene such as in FIG. 37 (SEQ ID NO:126).

In another embodiment, the $V_l$ chain comprises a rearranged or somatic variant of a Vκ3 germline gene such as in FIG. 46 (SEQ ID NO:135); and the $V_h$ chain comprises a rearranged or somatic variant of a VH3 germline gene such as in FIG. 38 (SEQ ID NO:127).

In another embodiment, the $V_l$ chain comprises a rearranged or somatic variant of a Vλ6 germline gene such as in FIG. 41 (SEQ ID NO:130); and the $V_h$ chain comprises a rearranged or somatic variant of a VH4 germline gene such as in FIG. 39 (SEQ ID NO:128).

In another embodiment, the $V_l$ chain comprises a rearranged or somatic variant of a Vκ2 germline gene such as in FIG. 43 (SEQ ID NO:132); and the $V_h$ chain comprises a rearranged or somatic variant of a VH4 germline gene such as in FIG. 33 (SEQ ID NO:122).

In another embodiment, the $V_l$ chain comprises a rearranged or somatic variant of a Vκ2 germline gene such as in FIG. 43 (SEQ ID NO:132); and the $V_h$ chain comprises a rearranged or somatic variant of a VH2 germline gene such as in FIG. 40 (SEQ ID NO:129).

In another embodiment, the $V_l$ chain comprises a rearranged or somatic variant of a Vλ6 germline gene such as in FIG. 41 (SEQ ID NO:130); and the $V_h$ chain comprises or a rearranged or somatic variant of a VH1 germline gene such as in FIG. 34 (SEQ ID NO:123).

The selective binding agents of the invention (antibody or antigen binding domain) partially or completely inhibit at least one activity of IFNγ, such as binding of IFNγ to IFNγ-R.

In one embodiment, an IFNγ antagonist, such as an antibody or antigen binding domains, is administered to an animal which has experienced or is at risk of developing lupus-like disease, arthritis, or multiple-sclerosis-like syndrome. An IFNγ antagonist may be used to prevent and/or treat lupus nephritis, rheumatoid arthritis, and/or multiple sclerosis.

Also provided are compositions comprising the antibodies or antigen binding domains of the invention and a pharmaceutically acceptable carrier.

DESCRIPTION OF THE FIGURES

FIG. 3 shows the nucleotide and amino acid sequence of Fab "BS-A" heavy chain.

FIG. 4 shows the nucleotide and amino acid sequence of Fab "BS-B" heavy chain.

FIG. 5 shows the nucleotide and amino acid sequence of Fab "RD-B1" heavy chain.

FIG. 6 shows the nucleotide and amino acid sequence of Fab "RD-A2" heavy chain.

FIG. 7 shows the nucleotide and amino acid sequence of Fab "58C" heavy chain.

FIG. 8 shows the nucleotide and amino acid sequence of Fab "GP-A" heavy chain.

FIG. 9 shows the nucleotide and amino acid sequence of Fab "57D" heavy chain.

FIG. 10 shows the nucleotide and amino acid sequence of Fab "57E" heavy chain.

FIG. 11 shows the nucleotide and amino acid sequence of Fab "IFN-A" heavy chain.

FIG. 12 shows the nucleotide and amino acid sequence of Fab "67C" heavy chain.

FIG. 13 shows the nucleotide and amino acid sequence of Fab "59-A2" heavy chain.

FIG. 14 shows the nucleotide and amino acid sequence of Fab "BS-A" light chain.

FIG. 15 shows the nucleotide and amino acid sequence of Fab "BS-B" light chain.

FIG. 16 shows the nucleotide and amino acid sequence of Fab "RD-B1" light chain.

FIG. 17 shows the nucleotide and amino acid sequence of Fab "RD-A2" light chain.

FIG. 18 shows the nucleotide and amino acid sequence of Fab "58C" light chain.

FIG. 19 shows the nucleotide and amino acid sequence of Fab "GP-A" light chain.

FIG. 20 shows the nucleotide and amino acid sequence of Fab "57D" light chain.

FIG. 21 shows the nucleotide and amino acid sequence of Fab "57E" light chain.

FIG. 22 shows the nucleotide and amino acid sequence of Fab "IFN-A" light chain.

FIG. 23 shows the nucleotide and amino acid sequence of Fab "67C" light chain.

FIG. 24 shows the nucleotide and amino acid sequence of Fab "59-A2" light chain.

FIG. 25 shows a comparison of the amino acid sequences of the heavy and light chain complementarily determining regions (CDRs) of Fabs "BS-A", "BS-B", "RD-A2", "RD-B1", "IFN-A", "57E", "57D", "GP-A", "58-C", "67C" and "59-A2".

FIG. 28 is a chart which provides a comparison of the affinity and neutralization activity of "BS-A", "BS-B", "RD-A2", "RD-B", "IFN-A", "57E", "57D", "GP-A", "58C" and "67C" IgGs as measured by BiaCore and in the A549 cell assay. The BiaCore data was analyzed using BIAEVALUATION.

FIG. 30 is a chart which provides a comparison of affinity of anti-IFNγ Fabs "BS-A", "BS-B", "IFN-A" and "GP-A" and the corresponding IgGs as measured by BIACore.

FIG. 31 shows a comparison of Fab amino acid sequences shown in FIGS. 3–24. The predicted amino acid sequences of heavy and light chain Fabs "BS-A", "BS-B", "RD-A2", "RD-B1", "IFN-A", "57E", "57D", "GP-A", "58-C", "67C" and "59-A2" were compared for identity and similarity. GCG's "BestFit" program was used to obtain percentage of identity and similarity between each pair of Fabs.

FIG. 32 shows complementarily determining regions (CDRs) alignments of the heavy and light chain "BS-A", "BS-B", "RD-A2", "RD-B1", "IFN-A", "57E", "57D", "GP-A", "58-C", "67C" and "59-A2" Fabs.

FIG. 33 shows a comparison of predicted Fab "BS-A", "RD-A2" and "IFN-A" heavy chain amino acid sequences (residues 1-120, 1-127 and 1-126 inclusive in FIGS. 3, 6 and 11, respectively) with germline sequence from the VH4 family. The germline sequence comprises the V region sequence 4-34, the D region sequences 1-1, 3-3 or 3-16, and the J region sequence JH4. FR1, FR2 and FR3 designate the three framework regions, CDR1, CDR2 and CDR3 designate the three complementarily determining regions, and H1, H2 and H3 designate the corresponding junction sequences between framework regions and CDRs. Differences between "BS-A", "RD-A2", "IFN-A" and germline V, D, or J sequences are in boldface. The numbering of germline amino acid residues in FIGS. 33–46 is as described in Kabat et al., *Sequences of Proteins of Immunological Interest*, U.S. Department of Health and Human Services, 4$^{th}$ ed. (1991).

FIG. 34 shows a comparison of predicted Fab "BS-B", and "59-A2" heavy chain amino acid sequences (residues 1-121 and 1-120 inclusive in FIGS. 4 and 13, respectively) with germline sequence from the VH1 family. The germline sequence comprises the V region sequence 1-18, the D region sequences 6-13, 1-1 OR 1-7, and the J region sequence JH4.

FIG. 35 shows a comparison of predicted Fab "RD-B1" heavy chain amino acid sequence (residues 1-119 inclusive in FIG. 5) with germline sequence from the VH2 family. The germline sequence comprises the V region sequence 2-26, the D region sequence 3-22, and the J region sequence JH5.

FIG. 36 shows a comparison of predicted Fab "58C" heavy chain amino acid sequence (residues 1-119 inclusive in FIG. 7) with germline sequence from the VH3 family. The germline sequence comprises the V region sequence 3-21, the D region sequence unknown, and the J region sequence JH4.

FIG. 37 shows a comparison of predicted Fab "GP-A" heavy chain amino acid sequence (residues 1-124 inclusive in FIG. 8) with germline sequence from the VH3 family. The germline sequence comprises the V region sequence 3-30.3, the D region sequence 3-10, and the J region sequence JH3.

FIG. 38 shows a comparison of predicted Fab "57D" heavy chain amino acid sequence (residues 1-117 inclusive in FIG. 9) with germline sequence from the VH3 family. The germline sequence comprises the V region sequence 3-53, the D region sequence 3-16, and the J region sequence unknown.

FIG. 39 shows a comparison of predicted Fab "57E" heavy chain amino acid sequence (residues 1-118 inclusive in FIG. 10) with germline sequence from the VH4 family. The germline sequence comprises the the V region sequence 4-61, the D region sequence 7-27, and the J region sequence JH4.

FIG. 40 shows a comparison of predicted Fab "67C" heavy chain amino acid sequence (residues 1-119 inclusive in FIG. 12) with germline sequence from the VH2 family. The germline sequence comprises the V region sequence 2-05, the D region sequence 5-18, and the J region sequence JH6.

FIG. 41 shows a comparison of predicted Fab "BS-A", "BS-B", "57E" and "59-A2" light chain amino acid sequences (residues 1-111, 1-110, 1-112 and 1-110 inclusive in FIGS. 14, 15, 21 and 24, respectively) with germline sequence from the Vλ6 family. The germline sequence comprises the V region sequence 6a, and the J region sequences unknown or JL2 or JL3.

FIG. 42 shows a comparison of predicted Fab "RD-B1" light chain amino acid sequence (residues 1-112 inclusive in FIG. 16) with germline sequence from the Vκ2 family. The germline sequence comprises the V region sequence A23, and the J region sequence JK2.

FIG. 43 shows a comparison of predicted Fab "RD-A2", "IFN-A" and "67C" light chain amino acid sequences (residues 1-112, 1-110, 1-112 and 1-110 inclusive in FIGS. 17, 22, and 23, respectively) with germline sequence from the Vκ2 family. The germline sequence comprises the V region sequence A19, and the J region sequences JK3, JK2 and JK2, respectively.

FIG. 44 shows a comparison of predicted Fab "58C" light chain amino acid sequence (residues 1-108 inclusive in FIG. 18) with germline sequence from the Vλ3 family. The germline sequence comprises the V region sequence 3h, and the J region sequence unknown.

FIG. 45 shows a comparison of predicted Fab "GP-A" light chain amino acid sequence (residues 1-106 inclusive in FIG. 19) with germline sequence from the Vλ3 family. The germline sequence comprises the V region sequence 2-19, and the J region sequence JL2 or JL3.

FIG. 46 shows a comparison of predicted Fab "57D" light chain amino acid sequence (residues 1-108 inclusive in FIG. 20) with germline sequence from the Vκ3 family. The germline sequence comprises the V region sequence A27, and the J region sequences JK5.

FIG. 47 shows a comparison of Fab classes. Fab class comparison was done using GCG (Genetics Computer Group, 575 Science Drive, Madison, Wis. 53711) PileUp program for multiple sequence comparison analysis. The symbol (**) indicates that the closest matching diversity (D) region or joining region (J), although related to known germ line sequences, could not be determined. The symbol (*) indicates that variations in 1, 2 or 3 residues occur in comparison to the identified joining region.

DETAILED DESCRIPTION OF THE INVENTION

Figure 1:
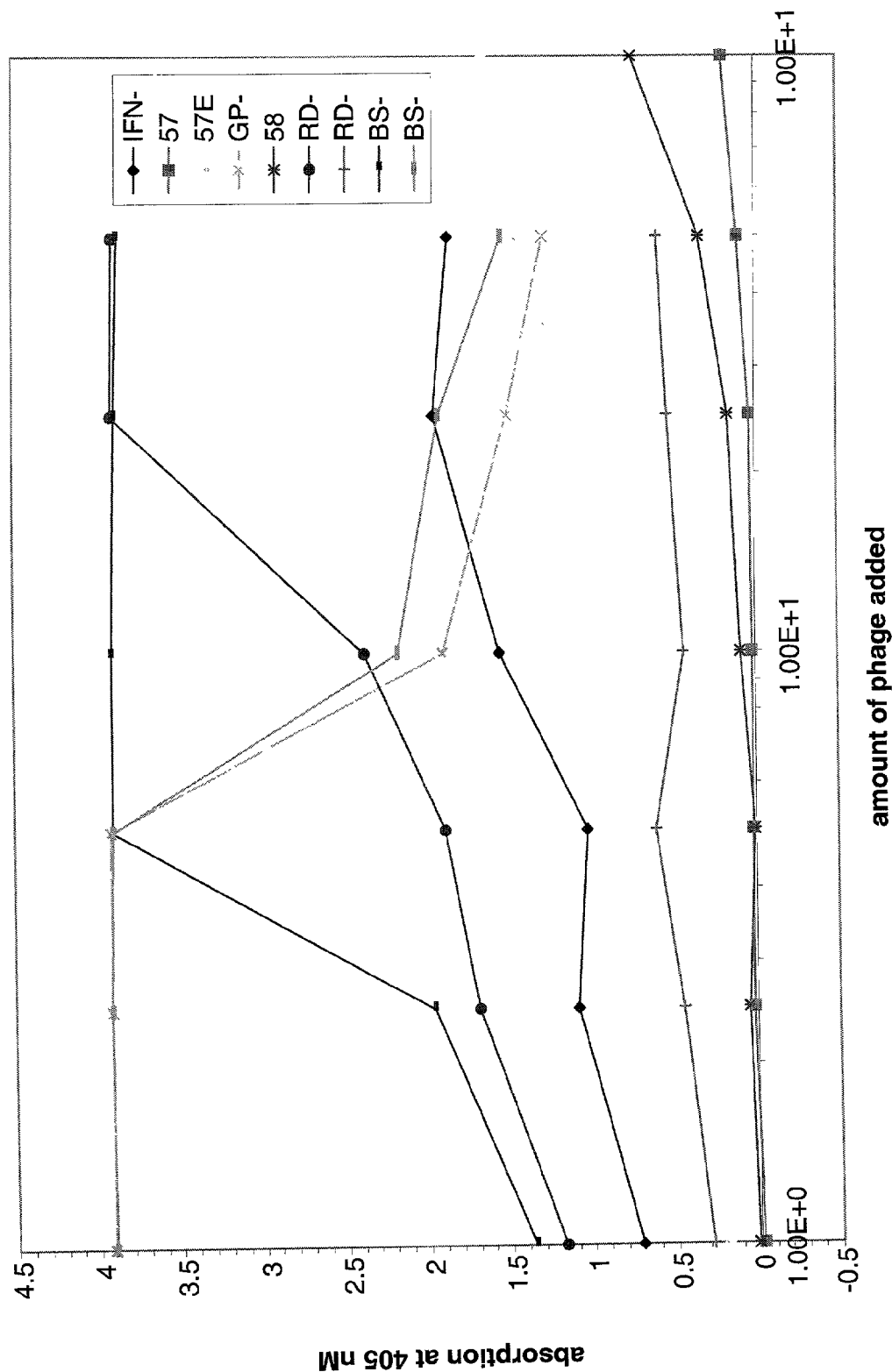
FIG. 1 is a graph depicting the results of ELISA for reactivity of predominant phage Fab clones to hIFNγ. Phage dilutions were performed using a maximum of 100 μl of phage suspension pre-blocked with 2% MPBS per well to given a typical range of $10^9$–$10^{11}$ phage/well in the ELISA. Phage stocks for ELISA were prepared as described in Example 3. Values were from single point determinations and $OD_{405}$ was measured for signal detection.

The present invention provides for agents which selectively bind ("selective binding agents") human gamma interferon-gamma protein (hIFNγ). Preferably, the agents are IFNγ antagonists or inhibitors which inhibit partially or completely at least one activity of IFNγ, such as binding of IFNγ to its cognate receptor. In one embodiment, the fully human antibody fragments selectively binds IFNγ such that it partially or completely blocks the binding of IFNγ to its cognate receptor and partially or completely inhibits IFNγ activity.

The term "selective binding agent" refers to a molecule which preferentially binds IFNγ. A selective binding agent may include a protein, peptide, nucleic acid, carbohydrate, lipid, or small molecular weight compound. In a preferred embodiment, a selective binding agent is an antibody, such as polyclonal antibodies, monoclonal antibodies (mAbs), chimeric antibodies, CDR-grafted antibodies, anti-idiotypic (anti-Id) antibodies to antibodies that can be labeled in soluble or bound form, as well as fragments, regions or derivatives thereof, provided by known techniques, including, but not limited to enzymatic cleavage, peptide synthesis or recombinant techniques. The anti-IFNγ selective binding agents of the present invention are capable of binding portions of IFNγ that inhibit the binding of IFNγ to the IFNγ-R receptor.

The antibodies and antigen binding domains of the invention bind selectively to IFNγ, that is they bind preferentially to IFNγ with a greater binding affinity than to other antigens. The antibodies may bind selectively to human IFNγ, but also bind detectably to non-human IFNγ, such as murine IFNγ. Alternatively, the antibodies may bind selectively to non-human IFNγ, but also bind detectably to human IFNγ. Alternatively, the antibodies may bind exclusively to human IFNγ, with no detectable binding to non-human IFNγ.

The term "monoclonal antibody" refers to an antibody obtained from a population of substantially homogeneous antibodies wherein each monoclonal antibody will typically recognize a single epitope on the antigen. The term "monoclonal" is not limited to any particular method for making the antibody. For example, monoclonal antibodies of the invention may be made by the hybridoma method as described in Kohler et al.; *Nature*, 256:495 (1975) or may be isolated from phage libraries using the techniques as described herein, for example.

The term "antigen binding domain" or "antigen binding region" refers to that portion of the selective binding agent (such as an antibody molecule) which contains the amino acid residues that interact with an antigen and confer on the binding agent its specificity and affinity for the antigen. Preferably, the antigen binding region will be of human origin. In other embodiments, the antigen binding region can be derived from other animal species, in particular rodents such as rabbit, rat or hamster.

The term "epitope" refers to that portion of any molecule capable of being recognized by and bound by a selective binding agent (such as an antibody) at one or more of the binding agent's antigen binding regions. Epitopes usually consist of chemically active surface groupings of molecules such as amino acids or sugar side chains and have specific three dimensional structural characteristics as well as specific charge characteristics. By "inhibiting and/or neutralizing epitope" is intended an epitope, which, when bound by a selective binding agent, results in loss of biological activity of the molecule or organism containing the epitope, in vivo, in vitro, or in situ, more preferably in vivo, including binding of IFNγ to its receptor. The term "light chain" when used in reference to an antibody refers to two distinct types, called kappa (k) of lambda (λ) based on the amino acid sequence of the constant domains.

The term "heavy chain" when used in reference to an antibody refers to five distinct types, called alpha, delta, epsilon, gamma and mu, based on the amino acid sequence of the heavy chain constant domain. These distinct types of heavy chains give rise to five classes of antibodies, IgA, IgD, IgE, IgG and IgM, respectively, including four subclasses of IgG, namely $IgG_1$, $IgG_2$, $IgG_3$ and $IgG_4$.

The term "variable region" or "variable domain" refers to a portion of the light and heavy chains, typically about the amino-terminal 120 to 130 amino acids in the heavy chain and about 100 to 110 amino acids in the light chain, which differ extensively in sequence among antibodies and are used in the binding and specificity of each particular antibody for its particular antigen. The variability in sequence is concentrated in those regions called complimentarily determining regions (CDRs) while the more highly conserved regions in the variable domain are called framework regions (FR). The CDRs of the light and heavy chains are responsible for the interaction of the antibody with antigen.

The term "constant region" or "constant domain" refers to a carboxy terminal portion of the light and heavy chain which is not directly involved in binding of the antibody to antigen but exhibits various effector function, such as interaction with the Fc receptor.

The term "human interferon-gamma" or "human interferon-gamma polypeptide" refers to the polypeptides comprising the amino acid sequences described in PCT Publication WO 83/04053, the disclosure of which is incorporated by reference, and related polypeptides. Related polypeptides include allelic variants; splice variants; fragments; derivatives; substitution, deletion, and insertion variants; fusion polypeptides; and interspecies homologs. Also encompassed are soluble forms of IFNγ which is sufficient to generate an immunological response. IFNγ may be a mature polypeptide, as defined herein, and may or may not have an amino terminal methionine residue, depending upon the method by which it is prepared.

The term "fragment" when used in relation to IFNγ or to a proteinaceous selective binding agent of IFNγ refers to a peptide or polypeptide that comprises less than the full length amino acid sequence. Such a fragment may arise, for example, from a truncation at the amino terminus, a truncation at the carboxy terminus, and/or an internal deletion of a residue(s) from the amino acid sequence. Fragments may result from alternative rna splicing or from in vivo protease activity.

The term "variant" when used in relation to IFNγ or to a proteinaceous selective binding agent of IFNγ refers to a peptide or polypeptide comprising one or more amino acid sequence substitutions, deletions, and/or additions as compared to a native or unmodified sequence. For example, an IFNγ variant may result from one or more changes to an amino acid sequence of native IFNγ. Also by way of example, a variant of a selective binding agent of IFNγ may result from one or more changes to an amino acid sequence of a native or previously unmodified selective binding agent. Variants may be naturally occurring, such as allelic or splice variants, or may be artificially constructed. Polypeptide variants may be prepared from the corresponding nucleic acid molecules encoding said variants.

The term "derivative" when used in relation to IFNγ or to a proteinaceous selective binding agent of IFNγ refers to a polypeptide or peptide, or a variant, fragment or derivative thereof, which has been chemically modified. Examples include covalent attachment of one or more polymers, such as water soluble polymers, N-linked, or O-linked carbohydrates, sugars, phosphates, and/or other such molecules. The derivatives are modified in a manner that is different from naturally occurring or starting peptide or polypeptides, either in the type or location of the molecules attached. Derivatives further include deletion of one or more chemical groups which are naturally present on the peptide or polypeptide.

The term "fusion" when used in relation to IFNγ or to a proteinaceous selective binding agent of IFNγ refers to the joining of a peptide or polypeptide, or fragment, variant and/or derivative thereof, with a heterologous peptide or polypeptide.

The term "biologically active" when used in relation to IFNγ or to a proteinaceous selective binding agent refers to a peptide or a polypeptide having at least one activity characteristic of IFNγ or a selective binding agent. A selective binding agent of IFNγ may have agonist, antagonist, or neutralizing or blocking activity with respect to at least one biological activity of IFNγ.

The term "naturally occurring" when used in connection with biological materials such as nucleic acid molecules, polypeptides, host cells, and the like, refers to those which are found in nature and not manipulated by a human being.

The term "isolated" when used in relation to IFNγ or to a proteinaceous selective binding agent of IFNγ refers to a peptide or polypeptide that is free from at least one contaminating polypeptide that is found in its natural environment, and preferably substantially free from any other contaminating mammalian polypeptides which would interfere with its therapeutic or diagnostic use.

The term "mature" when used in relation to IFNγ or to a proteinaceous selective binding agent of IFNγ refers to a peptide or polypeptide lacking a leader sequence. The term may also include other modifications of a peptide or polypeptide such as proteolytic processing of the amino terminus (with or without a leader sequence) and/or the carboxy terminus, cleavage of a smaller polypeptide from a larger precursor, n-linked and/or o-linked glycosylation, and the like.

The terms "effective amount" and "therapeutically effective amount" when used in relation to a selective binding agent of IFNγ refers to an amount of a selective binding agent that is useful or necessary to support an observable change in the level of one or more biological activities of IFNγ. Said change may be either an increase or decrease in the level of IFNγ activity.

The term "conservative amino acid substitution" refers to a substitution of a native amino acid residue with a non-native residue such that there is little or no effect on the polarity or charge of the amino acid residue at that position. For example, a conservative substitution results from the replacement of a non-polar residue in a polypeptide with any other non-polar residue. Furthermore, any native residue in a polypeptide may also be substituted with alanine, as has been previously described for alanine scanning mutagenesis; Cunningham et al., *Science,* 244:1081–1085 (1989). Exemplary rules for conservative amino acid substitutions are set forth in Table I.

TABLE I

Conservative Amino Acid Substitutions

| Original Residues | Exemplary Substitutions | Preferred Substitutions |
|---|---|---|
| ALA | VAL, LEU, ILE | VAL |
| ARG | LYS, GLN, ASN | LYS |
| ASN | GLN, HIS, LYS, ARG | GLN |
| ASP | GLU | GLU |
| CYS | SER | SER |
| GLN | ASN | ASN |
| GLU | ASP | ASP |
| GLY | PRO, ALA | ALA |
| HIS | ASN, GLN, LYS, ARG | ARG |

TABLE I-continued

Conservative Amino Acid Substitutions

| Original Residues | Exemplary Substitutions | Preferred Substitutions |
|---|---|---|
| ILE | LEU, VAL, MET, ALA, PHE, NORLEUCINE | LEU |
| LEU | NORLEUCINE, ILE, VAL, MET, ALA, PHE | ILE |
| LYS | ARG, GLN, ASN | ARG |
| MET | LEU, PHE, ILE | LEU |
| PHE | LEU, VAL, ILE, ALA, TYR | LEU |
| PRO | ALA | ALA |
| SER | THR | THR |
| THR | SER | SER |
| TRP | TYR, PHE | TYR |
| TYR | TRP, PHE, THR, SER | PHE |
| VAL | ILE, MET, LEU, PHE, ALA, NORLEUCINE | LEU |

Conservative amino acid substitutions also encompass non-naturally occurring amino acid residues which are typically incorporated by chemical peptide synthesis rather than by synthesis in biological systems. These include peptidomimetics, and other reversed or inverted forms of amino acid moieties.

Conservative modifications to the amino acid sequence (and the corresponding modifications to the encoding nucleotides) are able to produce IFNγ polypeptides (and proteinaceous selective binding agents thereof) having functional and chemical characteristics similar to those of naturally occurring IFNγ or selective binding agents. In contrast, substantial modifications in the functional and/or chemical characteristics of IFNγ (and protineaceous selective binding agents thereof) may be accomplished by selecting substitutions that differ significantly in their effect on maintaining (a) the structure of the molecular backbone in the area of the substitution, for example, as a sheet or helical conformation, (b) the charge or hydrophobicity of the molecule at the target site, or (c) the bulk of the side chain. Naturally occurring residues may be divided into groups based on common side chain properties:

1) Hydrophobic: norleucine, Met, Ala, Val, Leu, Ile;
2) Neutral hydrophilic: Cys, Ser, Thr;
3) Acidic: Asp, Glu;
4) Basic: Asn, Gln, His, Lys, Arg;
5) Residues that influence chain orientation: Gly, Pro; and
6) Aromatic: Trp, Tyr, Phe.

Non-conservative substitutions may involve the exchange of a member of one of these classes for a member from another class.

The "identity or similarity" of two or more nucleic acid molecules and/or polypeptides provides a measure of the relatedness of two or more distinct sequences. The term "identity" refers to amino acids which are identical at corresponding positions in two distinct amino acid sequences. The term "similarity" refers to amino acids which are either identical or are conservative substitutions as defined above at corresponding positions in two distinct amino acid sequences.

The extent of identity or similarity can be readily calculated by known methods, including but not limited to those described in Computational Molecular Biology, Lesk, A. M., ed., Oxford University Press, New York, 1988; *Biocomputing: Informatics and Genome Projects*, Smith, D. W., ed., Academic Press, New York, 1993; *Computer Analysis of*

Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math., 48:1073 (1988).

Preferred methods to determine identity and/or similarity are designed to give the largest match between the sequences tested. Methods to determine identity and similarity are codified in publicly available computer programs. Exemplary computer program methods to determine identity and similarity between two sequences include, but are not limited to, the GCG program package, including GAP; Devereux et al., Nucleic Acids Research, 12:387 (1984); Genetics Computer Group, University of Wisconsin, Madison, Wis.; BLASTP, BLASTN, and FASTA Altschul et al., J. Mol. Biol., 215:403–410 (1990). The BLAST X program is publicly available from the National Center for Biotechnology Information (NCBI) and other sources (BLAST Manual, Altschul et al. NCB NLM NIH Bethesda, Md.). The well known Smith Waterman algorithm may also be used to determine identity.

IFNγ Polypeptides

IFNγ polypeptides, and fragments, variants and derivatives thereof, are used as target molecules for screening and identifying the selective binding agents of the invention. When it is desired to prepare antibodies as selective binding agents, IFNγ polypeptides are preferably immunogenic, that is they elicit an immune response when administered to an animal. Alternatively, when antibodies are prepared by in vitro techniques, IFNγ polypeptides used as target molecules are capable of detectably binding an antibody or antigen binding domain.

IFNγ polypeptides are prepared by biological or chemical methods. Biological methods such as expression of DNA sequences encoding recombinant IFNγ are known in the art; see e.g., Sambrook et al. Supra. Chemical synthesis methods such as those set forth by Merrifield et al., J. Am. Chem. Soc., 85:2149 (1963), Houghten et al., Proc Natl Acad. Sci. USA, 82:5132 (1985), and Stewart and Young, Solid phase peptide synthesis, Pierce Chemical Co., Rockford, Ill. (1984) may also be used to prepare IFNγ polypeptides of the invention. Such polypeptides may be synthesized with or without a methionine on the amino terminus. Chemically synthesized IFNγ polypeptides, or fragments or variants thereof, may be oxidized using methods set forth in these references to form disulfide bridges. IFNγ polypeptides of the invention prepared by chemical synthesis will have at least one biological activity comparable to the corresponding IFNγ polypeptides produced recombinantly or purified from natural sources.

IFNγ polypeptides may be obtained by isolation from biological samples such as source tissues and/or fluids in which the IFNγ polypeptides are naturally found. Sources for IFNγ polypeptides may be human or non-human in origin. Isolation of naturally-occurring IFNγ polypeptides can be accomplished using methods known in the art, such as separation by electrophoresis followed by electroelution, various types of chromatography (affinity, immunoaffinity, molecular sieve, and/or ion exchange), and/or high pressure liquid chromatography. The presence of the IFNγ polypeptide during purification may be monitored using, for example, an antibody prepared against recombinantly produced IFNγ polypeptide or peptide fragments thereof.

Polypeptides of the invention include isolated IFNγ polypeptides and polypeptides related thereto including fragments, variants, fusion polypeptides, and derivatives as defined hereinabove. IFNγ fragments of the invention may result from truncations at the amino terminus (with or without a leader sequence), truncations at the carboxy terminus, and/or deletions internal to the polypeptide. Such IFNγ polypeptides fragments may optionally comprise an amino terminal methionine residue. The polypeptides of the invention will be immunogenic in that they will be capable of eliciting an antibody response.

IFNγ polypeptide variants of the invention include one or more amino acid substitutions, additions and/or deletions as compared to the native IFNγ amino acid sequence. Amino acid substitutions may be conservative, as defined above, or non-conservative or any combination thereof. The variants may have additions of amino acid residues either at the carboxy terminus or at the amino terminus (where the amino terminus may or may not comprise a leader sequence).

Embodiments of the invention include IFNγ glycosylation variants and cysteine variants. IFNγ glycosylation variants include variants wherein the number and/or type of glycosylation sites has been altered compared to native IFNγ polypeptide. In one embodiment, IFNγ glycosylation variants comprise a greater or a lesser number of N-linked glycosylation sites compared to native IFNγ.

Also provided for are IFNγ glycoyslation variants comprising a rearrangement of N-linked carbohydrate chains wherein one or more N-linked glycosylation sites (typically those that are naturally occurring) are eliminated and one or more new N-linked sites are created. IFNγ cysteine variants comprise a greater number or alternatively a lesser number of cysteine residues compared to native IFNγ. In one embodiment, one or more cysteine residues are deleted or substituted with another amino acid (e.g., serine). Cysteine variants of IFNγ can improve the recovery of biologically active IFNγ by aiding the refolding of IFNγ into a biologically active conformation after isolation from a denatured state.

Preparing IFNγ polypeptide variants is within the level of skill in the art. In one approach, one may introduce one or more amino acid substitutions, deletions and/or additions in native IFNγ wherein the IFNγ variant retains the native structure of IFNγ and/or at least one of the biological activities. One approach is to compare sequences of IFNγ polypeptides from a variety of different species in order to identify regions of relatively low and high identity and/or similarity. It is appreciated that those regions of an IFNγ polypeptide having relatively low identity and/or similarity, are less likely to be essential for structure and activity and therefore may be more tolerant of amino acid alterations, especially those which are non-conservative. It is also appreciated that even in relatively conserved regions, one could introduce conservative amino acid substitutions while retaining activity.

In another approach, structure-function relationships can be used to identify residues in similar polypeptides that are important for activity or structure. For example, one may compare conserved amino acid residue among IFNγ and other members of the tumor necrosis factor family for which structure-function analyses are available and, based on such a comparison, predict which amino acid residues in IFNγ are important for activity or structure. One skilled in the art may choose chemically similar amino acid substitutions for such predicted important amino acid residues of IFNγ.

In yet another approach, an analysis of a secondary or tertiary structure of IFNγ (either determined by x-ray diffraction of IFNγ crystals or by structure prediction methods) can be undertaken to determine the location of specific amino acid residues in relation to actual or predicted structures within an IFNγ polypeptide. Using this information, one can introduce amino acid changes in a manner that seeks to retain as much as possible the secondary and/or tertiary structure of an IFNγ polypeptide. In yet another approach, the effects of altering amino acids at specific positions may be tested experimentally by introducing amino acid substitutions and testing the altered IFNγ polypeptides for biological activity using assays described herein.

Techniques such as alanine scanning mutagenesis (Cunningham et al., supra) are particularly suited for this approach. Many altered sequence may be conveniently tested by introducing many substitutions at various amino acid positions in IFNγ and screening the population of altered polypeptides as part of a phage display library. Using this approach, those regions of an IFNγ polypeptide that are essential for activity may be readily determined.

The above methods are useful for generating IFNγ variants which retain the native structure. Thus, antibodies raised against each variants are likely to recognize a native structural determinant, or epitope, of IFNγ and are also likely to bind to native IFNγ. However, in some cases is may be desirable to produce IFNγ variants which do not retain native IFNγ structure or are partially or completely unfilled. Antibodies raised against such proteins will recognize buried epitopes on IFNγ.

The invention also provides for IFNγ fusion polypeptides which comprise IFNγ polypeptides, and fragments, variants, and derivatives thereof, fused to a heterologous peptide or protein. Heterologous peptides and proteins include, but are not limited to: an epitope to allow for detection and/or isolation of a IFNγ fusion polypeptide; a transmembrane receptor protein or a portion thereof, such as an extracellular domain, or a transmembrane and intracellular domain; a ligand or a portion thereof which binds to a transmembrane receptor protein; an enzyme or portion thereof which is catalytically active; a protein or peptide which promotes oligomerization, such as leucine zipper domain; and a protein or peptide which increases stability, such as an immunoglobulin constant region.

A IFNγ polypeptide may be fused to itself or to a fragment, variant, or derivative thereof. Fusions may be made either at the amino terminus or at the carboxy terminus of a IFNγ polypeptide, and may be direct with no linker or adapter molecule or may be through a linker or adapter molecule. A linker or adapter molecule may also be designed with a cleavage site for a DNA restriction endonuclease or for a protease to allow for separation of the fused moieties. In a further embodiment of the invention, a IFNγ polypeptide, fragment, variant and/or derivative is fused to an Fc region of human IgG. In one example, a human IgG hinge, ch2 and ch3 region may be fused at either the N-terminus or C-terminus of the IFNγ polypeptides using methods known to the skilled artisan. In another example, a portion of a hinge regions and ch2 and ch3 regions may be fused. The IFNγ Fc-fusion polypeptide so produced may be purified by use of a protein a affinity column. In addition, peptides and proteins fused to an fc region have been found to exhibit a substantially greater half-life in vivo than the unfused counterpart. Also, a fusion to an Fc region allows for dimerization/multimerization of the fusion polypeptide. The Fc region may be a naturally occurring Fc region, or may be altered to improve certain qualities, such as therapeutic qualities, circulation time, reduce aggregation, etc.

IFNγ polypeptide derivatives are included in the scope of the present invention. Such derivatives are chemically modified IFNγ polypeptide compositions in which IFNγ polypeptide is linked to a polymer. The polymer selected is typically water soluble so that the protein to which it is attached does not precipitate in an aqueous environment, such as a physiological environment. The polymer may be of any molecular weight, and may be branched or unbranched. Included within the scope of IFNγ polypeptide polymers is a mixture of polymers. Preferably, for therapeutic use of the end-product preparation, the polymer will be pharmaceutically acceptable.

The water soluble polymer or mixture thereof may be for example, polyethylene glycol (PEG), monomethoxy-polyethylene glycol, dextran (such as low molecular weight dextran, of, for example about 6 kD), cellulose, or other carbohydrate based polymers, poly-(N-vinyl pyrrolidone) polyethylene glycol, propylene glycol homopolymers, a polypropylene oxide/ethylene oxide co-polymer, polyoxyethylated polyols (e.g., glycerol) and polyvinyl alcohol.

A preferred water soluble polymer is polyethylene glycol. As used herein, polyethylene glycol is meant to encompass any of the forms of PEG that have been used to derivatize other proteins, such as mono- ($C_1$–$C_{10}$) alkoxy-, or aryloxy-polyethylene glycol. Also encompassed by the invention are bifunctional PEG crosslinking molecules which may be used to prepare covalently attached IFNγ multimers.

Methods for preparing chemically derivatized IFNγ polypeptides are known in the art. By way of example, derivatization of IFNγ polypeptides with PEG may be carried out using procedures described in Francis et al., *Focus on Growth Factors,* 3:4–10 (1992); EP 0 154 316; and EP 0 401 384. In a preferred embodiment, an IFNγ polypeptide derivative will have a single PEG moiety at the amino terminus; see U.S. Pat. No. 5,985,265, herein incorporated by reference.

IFNγ polypeptide derivatives disclosed herein may exhibit an enhancement or reduction of at least one biological activity of IFNγ compared to unmodified polypeptide, or may exhibit increased or decreased half-life or stability.

IFNγ Selective Binding Agents

IFNγ polypeptides, and fragments, variants and derivatives thereof, may be used to identify selective binding agents of IFNγ. As defined above, a selective binding agent of IFNγ encompasses both proteinaceous and non-proteinaceous binding agents and, in one preferred embodiment of the invention, the selective binding agent is proteinaceous. In yet another preferred embodiment, the selective binding agent is an antibody or fragment thereof which binds IFNγ, preferably human IFNγ. The antibodies of the invention may be agonist antibodies, which enhance the level of at least one biological activity of IFNγ; or antagonist antibodies, which decrease the level of at least one biological activity of IFNγ. Antagonist antibodies of IFNγ may also be referred to as inhibitory or neutralizing antibodies of IFNγ. Although such antibodies are preferred embodiments of the invention, it is understood that other proteinaceous selective binding agents which are agonists or antagonists of IFNγ activity are also encompassed by the invention.

As described in the examples below, anti-IFNγ antibodies and antigen binding domains which inhibit at least one activity of IFNγ have been identified. Embodiments of the invention include antibodies comprising a heavy chain Fab sequence as shown in any of FIGS. 3–13 and further comprising a kappa or lambda light chain sequence. Light chain Fab sequences may be as shown in FIGS. 14–24. For example, "BS-A" antibody has light and heavy chain sequences in FIGS. 14 and 3, respectively; "BS-B" antibody has light and heavy chains sequences of FIGS. 15 and 4, respectively; "RD-B1" antibody has light and heavy chain sequences of FIGS. 16 and 5, respectively; "RD-A2" antibody has light and heavy chain sequences of FIGS. 17 and 6, respectively; "58C" antibody has light and heavy chain sequences of FIGS. 18 and 7, respectively; "GP-A" antibody has light and heavy chain sequences of FIGS. 19 and 8, respectively; "57D" antibody has light and heavy chain sequences of FIGS. 20 and 9, respectively; "57E" antibody has light and heavy chain sequences of FIGS. 21 and 10, respectively; "IFN-A" antibody has light and heavy chain sequences of FIGS. 22 and 11, respectively; "67C" antibody has light and heavy chain sequences of FIGS. 23 and 12, respectively; and "59-A2" antibody has light and heavy chain sequences of FIGS. 24 and 13, respectively. The antibodies of the invention further comprise a human Fc region from any isotype, either IgG, IgM, IgA, IgE, or IgD. Preferably, the Fc region is from human IgG, such as IgG1, IgG2, IgG3, or IgG4.

The invention also provides for antibodies or antigen binding domains which comprise fragments, variants, or derivatives of the Fab sequences disclosed herein. Fragments include variable domains of either the light or heavy chain Fab sequences which are typically joined to light or heavy constant domains. Variants include antibodies comprising light chain Fab sequences which are at least about 80%, 85%, 90%, 95%, 98% or 99% identical or similar to the Fab sequences, or the corresponding variable domains, in any one of FIGS. 14–24, or antibodies comprising heavy chain Fab sequences, or the corresponding variable domains, which are at least about 80%, 85%, 90%, 95%, 98% or 99% identical or similar to the Fab sequences in any one of FIGS. 3–13. The antibodies may be typically associated with constant regions of the heavy and light chains to form full-length antibodies.

Antibodies and antigen binding domains, and fragments, variants and derivatives thereof, of the invention will retain the ability to bind selectively to an IFNγ polypeptide, preferably to a human IFNγ polypeptide. In one embodiment, an antibody will bind an IFNγ polypeptide with a dissociation constant (KD) of about 1 nM or less, or alternatively 0.1 nM or less, or alternatively 10 pM or less or alternatively less than 10 pM.

Antibodies of the invention include polyclonal monospecific polyclonal, monoclonal, recombinant, chimeric, humanized, fully human, single chain and/or bispecific antibodies. Antibody fragments include those portions of an anti-IFNγ antibody which bind to an epitope on an IFNγ polypeptide. Examples of such fragments include Fab F(ab'), F(ab)', Fv, and sFv fragments. The antibodies may be generated by enzymatic cleavage of full-length antibodies or by recombinant DNA techniques, such as expression of recombinant plasmids containing nucleic acid sequences encoding antibody variable regions.

Polyclonal antibodies are heterogeneous populations of antibody molecules derived from the sera of animals immunized with an antigen. An antigen is a molecule or a portion of a molecule capable of being bound by an antibody which is additionally capable of inducing an animal to produce antibody capable of binding to an epitope of that antigen. An antigen can have one or more epitope. The specific reaction referred to above is meant to indicate that the antigen will react, in a highly selective manner, with its corresponding antibody and not with the multitude of other antibodies which can be evoked by other antigens.

Polyclonal antibodies directed toward an IFNγ polypeptide generally are raised in animals (e.g., rabbits or mice) by multiple subcutaneous or intraperitoneal injections of IFNγ and an adjuvant. In accordance with the invention, it may be useful to conjugate an IFNγ polypeptide, or a variant, fragment, or derivative thereof to a carrier protein that is immunogenic in the species to be immunized, such as keyhole limpet heocyanin, serum, albumin, bovine thyroglobulin, or soybean trypsin inhibitor. Also, aggregating agents such as alum are used to enhance the immune response. After immunization, the animals are bled and the serum is assayed for anti-IFNγ antibody titer.

Monoclonal antibodies (mAbs) contain a substantially homogeneous population of antibodies specific to antigens, which population contains substantially similar epitope binding sites. Such antibodies may be of any immunoglobulin class including IgG, IgM, IgE, IgA, IgD and any subclass thereof. A hybridoma producing a monoclonal antibody of the present invention may be cultivated in vitro, in situ, or in vivo. Production of high titers in vivo or in situ is a preferred method of production. Monoclonal antibodies directed toward IFNγ are produced using any method which provides for the production of antibody molecules by continuous cell lines in culture. Examples of suitable methods for preparing monoclonal antibodies include hybridoma methods of Kohler et al., *Nature,* 256:495–497 (1975), and the human B-cell hybridoma method, Kozbor, *J. Immunol,*. 133:3001 (1984); Brodeur et al., Monoclonal Antibody Production Techniques and Applications, pp. 51–63 (Marcel Dekker, Inc., New York, 1987); and Harlow and Lane, Antibodies: A Laboratory Manual, Cold Spring Harbor Laboratory (1988); the contents of which references are incorporated entirely herein by reference.

Preferred anti-IFNγ selective binding agents include monoclonal antibodies which will inhibit partially or completely the binding of human IFNγ to its cognate receptor, hIFNγ-R, or an antibody having substantially the same specific binding characteristics, as well as fragments and regions thereof. Preferred methods for determining monoclonal antibody specificity and affinity by competitive inhibition can be found in Harlow et al., Antibodies: A Laboratory Manual, Cold Spring Harbor Laboratory Press, Cold Spring Harbor, N.Y., 1988); Colligan et al., eds., Current Protocols in Immunology, Greene Publishing Assoc. and Wiley Interscience, N.Y., (1992, 1993); and Muller, *Meth. Enzymol.,* 92:589–601 (1983). These references are incorporated herein by reference. Also provided by the invention are hybridoma cell lines which produce monoclonal antibodies reactive with IFNγ polypeptides.

Chimeric antibodies are molecules in which different portions are derived from different animal species, such as those having a variable region derived from a murine monoclonal antibody and a human immunoglobulin constant region. Chimeric antibodies are primarily used to reduce immunogenicity in application and to increase yields in production, for example, where murine monoclonal antibodies have higher yields from hybridomas but higher immunogenicity in humans, such that human/murine chimeric monoclonal antibodies are used.

Chimeric antibodies and methods for their production are known in the art. Cabilly et al., *Proc. Natl. Acad. Sci.* USA, 81:3273–3277 (1984); Morrison et al., *Proc. Natl. Acad. Sci.* USA, 81:6851–6855 (1984); Boulianne et al., *Nature,* 312: 643–646 (1984); Neuberger et al., *Nature,* 314:268–270 (1985); Liu et al., *Proc. Natl. Acad. Sci.* USA, 84:3439–3443

(1987); and Harlow and Lane *Antibodies: A Laboratory Manual*, Cold Spring Harbor Laboratory (1988). These references are incorporated herein by reference.

For example, chimeric monoclonal antibodies of the invention may be used as a therapeutic. In such a chimeric antibody, a portion of the heavy and/or light chain is identical with or homologous to corresponding sequence in antibodies derived from a particular species or belonging to one particular antibody class or subclass, while the remainder of the chain(s) is identical with or homologous to corresponding sequence in antibodies derived from another species or belonging to another antibody class or subclass, as well as fragments of such antibodies, so long as they exhibit the desired biological activity; see, e.g., U.S. Pat. No. 4,816,567 and Morrison et al., *Proc. Natl. Acad. Sci.*, 81:6851–6855 (1985).

As used herein, the term "chimeric antibody" includes monovalent, divalent or polyvalent immunoglobulins. A monovalent chimeric antibody is a dimer (HL) formed by a chimeric H chain associated through disulfide bridges with a chimeric L chain. A divalent chimeric antibody is tetramer ($H_2L_2$) formed by two HL dimers associated through at least one disulfide bridge. A polyvalent chimeric antibody can also be produced, for example, by employing a $C_H$ region that aggregates (e.g., from an IgM H chain, or μ chain).

Murine and chimeric antibodies, fragments and regions of the present invention may comprise individual heavy (H) and/or light (L) immunoglobulin chains. A chimeric H chain comprises an antigen binding region derived from the H chain of a non-human antibody specific for IFNγ, which is linked to at least a portion of a human H chain C region ($C_H$), such as $CH_1$ or $CH_2$.

A chimeric L chain according to the present invention comprises an antigen binding region derived from the L chain of a non-human antibody specific for IFNγ, linked to at least a portion of a human L chain C region ($C_L$).

Selective binding agents, such as antibodies, fragments, or derivatives, having chimeric H chains and L chains of the same or different variable region binding specificity, can also be prepared by appropriate association of the individual polypeptide chains, according to known method steps; see, e.g., Ausubel et al., eds. *Current Protocols in Molecular Biology*, Wiley Interscience, N.Y. (1993) and Harlow et al., Antibodies: A Laboratory Manual, Cold Spring Harbor Laboratory Press, Cold Spring Harbor, N.Y. (1988). The contents of these references are incorporated entirely herein by reference. With this approach, hosts expressing chimeric H chains (or their derivatives) are separately cultured from hosts expressing chimeric L chains (or their derivatives), and the immunoglobulin chains are separately recovered and then associated. Alternatively, the hosts can be co-cultured and the chains allowed to associate spontaneously in the culture medium, followed by recovery of the assembled immunoglobulin, fragment or derivative.

As an example, the antigen binding region of the selective binding agent (such as a chimeric antibody) of the present invention is preferably derived from a non-human antibody specific for human IFNγ. Preferred sources for the DNA encoding such a non-human antibody include cell lines which produce antibodies, such as hybrid cell lines commonly known as hybridomas.

The invention also provides for fragments, variants and derivatives, and fusions of anti-IFNγ antibodies, wherein the terms "fragments", "variants", "derivatives" and "fusions" are defined herein. The invention encompasses fragments, variants, derivatives, and fusions of anti-IFNγ antibodies which are functionally similar to the unmodified anti-IFNγ antibody, that is, they retain at least one of the activities of the unmodified antibody. In addition to the modifications set forth above, also included is the addition of genetic sequences coding for cytotoxic proteins such as plant and bacterial toxins. The fragments, variants, derivatives and fusions of anti-IFNγ antibodies can be produced from any of the hosts of this invention.

Suitable fragments include, for example, Fab, Fab', F(ab')$_2$, Fv and scFv. These fragments lack the Fc fragment of an intact antibody, clear more rapidly from the circulation, and can have less non-specific tissue binding than an intact antibody; Wahl et al., *J. Nucl. Med.*, 24:316–325 (1983). These fragments are produced from intact antibodies using methods well known in the art, for example by proteolytic cleavage with enzymes such as papain (to produce Fab fragments) or pepsin (to produce F(ab')$_2$ fragments). The identification of these antigen binding regions and/or epitopes recognized by monoclonal antibodies of the present invention provides the information necessary to generate additional monoclonal antibodies with similar binding characteristics and therapeutic or diagnostic utility that parallel the embodiments of this application.

Variants of selective binding agents are also provided. In one embodiment, variants of antibodies and antigen binding domains comprise changes in light and/or heavy chain amino acid sequences that are naturally occurring or are introduced by in vitro engineering of native sequences using recombinant DNA techniques. Naturally occurring variants include "somatic" variants which are generated in vivo in the corresponding germ line nucleotide sequences during the generation of an antibody response to a foreign antigen. Variants encoded by somatic mutations in germline variable light and heavy chain sequences which generate the exemplary Fabs of the present invention in sequences are shown in FIGS. 33 and 41 for Fab "BS-A", FIGS. 34 and 41 for Fab "BS-B", FIGS. 35 and 42 for Fab "RD-B1", FIGS. 35 and 42 for Fab "RD-B1", FIGS. 33 and 43 for Fab "RD-A2", FIGS. 36 and 44 for Fab "58C", FIGS. 37 and 45 for Fab "GP-A", FIGS. 38 and 46 for Fab "57D", FIGS. 39 and 41 for Fab "57E", FIGS. 33 and 43 for Fab "IFN-A", FIGS. 40 and 43 for Fab "67C", and FIGS. 34 and 41 for Fab "59-A2".

Variants of anti-IFNγ antibodies and antigen binding domains can also be prepared by mutagenesis techniques known in the art. In one example, amino acid changes may be introduced at random throughout an antibody coding region and the resulting variants may be screened for a desired activity, such as binding affinity for IFNγ. Alternatively, amino acid changes may be introduced in selected regions of an IFNγ antibody, such as in the light and/or heavy chain CDRs, and framework regions, and the resulting antibodies may be screened for binding to IFNγ or some other activity. Amino acid changes encompass one or more amino acid substitutions in a CDR, ranging from a single amino acid difference to the introduction of all possible permutations of amino acids within a given CDR, such as CDR3. In another method, the contribution of each residue within a CDR to IFNγ binding may be assessed by substituting at least one residue within the CDR with alanine; Lewis et al., *Mol. Immunol.*, 32:1065–1072 (1995). Residues which are not optimal for binding to IFNγ may then be changed in order to determine a more optimum sequence. Also encompassed are variants generated by insertion of amino acids to increase the size of a CDR, such as CDR3. For example, most light chain CDR3 sequences are nine amino acids in length. Light chain CDR3 sequences in an antibody which are shorter than nine residues may be optimized for binding to IFNγ by insertion of appropriate amino acids to increase the length of the CDR.

In one embodiment, antibody or antigen binding domain variants comprise one or more amino acid changes in one or more of the heavy or light chain CDR1, CDR2 or CDR3 and optionally one or more of the heavy or light chain framework regions FR1, FR2 or FR3. Amino acid changes comprise substitutions, deletions and/or insertions of amino acid residues. Exemplary variants include an "BS-A" heavy chain variable region variant with one or more amino acid changes in the sequences GYYWS (SEQ ID NO:34); EINHSGSTNYNPSLKS (SEQ ID NO:44); or GRARNWRSRFDY (SEQ ID NO:54), or an "BS-A" light chain variable region variant with one or more amino acid changes in the sequences TGSSGSIASHYVQ (SEQ ID NO:01); EDKERPS (SEQ ID NO:12); or QSYDSSNQWV (SEQ ID NO:23). The aforementioned "BS-A" heavy and light chain variable region variants may further comprise one or more amino acid changes in the framework regions.

In one example, one or more amino acid changes may be introduced to substitute a somatically mutated framework residue with the germline residue at that position. When the aforementioned amino acid changes are substitutions, the changes may be conservative or non-conservative substitutions. Variants may also be prepared by "chain shuffling" of either light or heavy chains; Marks et al. *Biotechnology,* 10:779–783 (1992). Typically, a single light (or heavy) chain is combined with a library having a repertoire of heavy (or light) chains and the resulting population is screened for a desired activity, such as binding to IFNγ. This technique permits screening of a greater sample of different heavy (or light) chains in combination with a single light (or heavy) chain than is possible with libraries comprising repertoires of both heavy and light chains.

The selective binding agents of the invention can be bispecific. Bispecific selective binding agents of this invention can be of several configurations. For example, bispecific antibodies resemble single antibodies (or antibody fragments) but have two different antigen binding sites (variable regions). Bispecific antibodies can be produced by chemical techniques; see e.g., Kranz et al., *Proc. Natl. Acad. Sci. USA,* 78:5807 (1981); by "polydoma" techniques; U.S. Pat. No. 4,474,893; or by recombinant DNA techniques.

The selective binding agents of the invention may also be heteroantibodies. Heteroantibodies are two or more antibodies, or antibody binding fragments (Fab) linked together, each antibody or fragment having a different specificity.

The invention also relates to "humanized" antibodies. Methods for humanizing non-human antibodies are well known in the art. Generally, a humanized antibody has one or more amino acid residues introduced into a human antibody from a source which is non-human. In general, non-human residues will be present in CDRs. Humanization can be performed following methods known in the art; Jones et al., *Nature* 321:522–525 (1986); Riechmann et al., *Nature,* 332:323–327 (1988); Verhoeyen et al., *Science,* 239:1534–1536 (1988), by substituting rodent complementarily-determining regions (CDRs) for the corresponding regions of a human antibody.

The selective binding agents of the invention, including chimeric, CDR-grafted, and humanized antibodies can be produced by recombinant methods known in the art. Nucleic acids encoding the antibodies are introduced into host cells and expressed using materials and procedures described herein and known in the art. In a preferred embodiment, the antibodies are produced in mammalian host cells, such as CHO cells. Fully human antibodies may be produced by expression of recombinant DNA transfected into host cells or by expression in hybridoma cells as described above.

Techniques for creating recombinant DNA versions of the antigen-binding regions of antibody molecules which bypass the generation of monoclonal antibodies are encompassed within the practice of this invention. To do so, antibody-specific messenger RNA molecules are extracted from immune system cells taken from an immunized animal, and transcribed into complementary DNA (cDNA). The cDNA is then cloned into a bacterial expression system. One example of such a technique suitable for the practice of this invention uses a filamentous bacteriophage M13 derived phagemid vector system having a leader sequence that causes the expressed Fab protein to migrate to the periplasmic space (between the bacterial cell membrane and the cell wall) or to be secreted. One can rapidly generate and screen great numbers of functional Fab fragments for those which bind the antigen. Such IFNγ selective binding agents (Fab fragments with specificity for an IFNγ polypeptide) are specifically encompassed within the term "antibody" as it is defined, discussed, and claimed herein.

Also within the scope of the invention are techniques developed for the production of chimeric antibodies by splicing the genes from a mouse antibody molecule of appropriate antigen-specificity together with genes from a human antibody molecule of appropriate biological activity, such as the ability to activate human complement and mediate ADCC; Morrison et al., *Proc. Natl. Acad. Sci.,* 81:6851 (1984); Neuberger et al., *Nature,* 312:604 (1984). One example is the replacement of a Fc region with that of a different isotype. Selective binding agents such as antibodies produced by this technique are within the scope of the invention.

In a preferred embodiment of the invention, the anti-IFNγ antibodies are fully human antibodies. Thus encompassed by the invention are antibodies which bind IFNγ polypeptides and are encoded by nucleic acid sequences which are naturally occurring somatic variants of human germline immunoglobulin nucleic acid sequence, and fragments, synthetic variants, derivatives and fusions thereof. Such antibodies may be produced by any method known in the art. Exemplary methods include immunization with a IFNγ antigen (any IFNγ polypeptide capable of elicing an immune response, and optionally conjugated to a carrier) of transgenic animals (e.g., mice) that are capable of producing a repertoire of human antibodies in the absence of endogenous immunoglobulin production; see, e.g., Jakobovits et al., *Proc. Natl. Acad. Sci.,* 90:2551–2555 (1993); Jakobovits et al., *Nature,* 362:255–258 (1993); Bruggermann et al., *Year in Immunol.,* 7:33 (1993).

Alternatively, human antibodies may be generated through the in vitro screening of phage display antibody libraries; see e.g., Hoogenboom et al., *J. Mol. Biol.,* 227:381 (1991); Marks et al., *J. Mol. Biol.,* 222:581 (1991), incorporated herein by reference. Various antibody-containing phage display libraries have been described and may be readily prepared by one skilled in the art. Libraries may contain a diversity of human antibody sequences, such as human Fab, Fv, and scFv fragments, that may be screened against an appropriate target. Example 2 describes the screening of a Fab phage library against IFNγ to identify those molecules which selectively bind IFNγ. It will be appreciated that phage display libraries may comprise peptides or proteins other than antibodies which may be screened to identify selective binding agents of IFNγ.

An anti-idiotypic (anti-Id) antibody is an antibody which recognizes unique determinants generally associated with the antigen-binding site of an antibody. An Id antibody can be prepared by immunizing an animal of the same species and genetic type (e.g., mouse strain) as the source of the monoclonal antibody with the monoclonal antibody to which an anti-Id is being prepared. The immunized animal will recognize and respond to the idiotypic determinants of the immunizing antibody by producing an antibody to these idiotypic determinants (the anti-Id antibody); see, e.g., U.S. Pat. No. 4,699,880, which is herein entirely incorporated by reference. The anti-Id antibody may also be used as an "immunogen" to induce an immune response in yet another animal, producing a so-called anti-anti-Id antibody. The anti-anti-Id may be epitopically identical to the original monoclonal antibody which induced the anti-Id. Thus, by using antibodies to the idiotypic determinants of a mAb, it is possible to identify other clones expressing antibodies of identical specificity.

Production of Selective Binding Agents of IFNγ

When the selective binding agent of IFNγ to be prepared is a proteinaceous selective binding agent, such as an antibody or an antigen binding domain, various biological or chemical methods for producing said agent are available.

Biological methods are preferable for producing sufficient quantities of a selective binding agent for therapeutic use. Standard recombinant dna techniques are particularly useful for the production of antibodies and antigen binding domains of the invention. Exemplary expression vectors, host cells and methods for recovery of the expressed product are described below.

A nucleic acid molecule encoding an IFNγ antibody or antigen binding domain is inserted into an appropriate expression vector using standard ligation techniques. The vector is typically selected to be functional in the particular host cell employed (i.e., the vector is compatible with the host cell machinery such that amplification of the gene and/or expression of the gene can occur). A nucleic acid molecule encoding an anti-IFNγ antibody may be amplified/expressed in prokaryotic, yeast, insect (baculovirus systems) and/or eukaryotic host cells. Selection of the host cell will depend in part on whether an anti-IFNγ antibody is to be post-transitionally modified (e.g., glycosylated and/or phosphorylated). If so, yeast, insect, or mammalian host cells are preferable. For a review of expression vectors, see Meth. Enz. V. 185, D. V. Goeddel, ed. Academic Press Inc., San Diego, Calif. (1990).

Typically, expression vectors used in any host cells will contain one or more of the following components: a promoter, one or more enhancer sequences, an origin of replication, a transcriptional termination sequence, a complete intron sequence containing a donor and acceptor splice site, a leader sequence for secretion, a ribosome binding site, a polyadenylation sequence, a polylinker region for inserting the nucleic acid encoding the polypeptide to be expressed, and a selectable marker element. Each of these sequences is discussed in more detail below.

The vector components may be homologous (i.e., from the same species and/or strain as the host cell), heterologous (i.e., from a species other than the host cell species or strain), hybrid (i.e., a combination of different sequences from more than one source), synthetic, or native sequences which normally function to regulate immunoglobulin expression. As such, a source of vector components may be any prokaryotic or eukaryotic organism, any vertebrate or invertebrate organism, or any plant, provided that the components are functional in, and can be activated by, the host cell machinery.

An origin of replication is selected based upon the type of host cell being used for expression. For example, the origin of replication from the plasmid pbr322 (product no. 303-3s, New England Biolabs, Beverly, Mass.) is suitable for most gram-negative bacteria while various origins from SV40, polyoma, adenovirus, vesicular stomatitus virus (VSV) or papillomaviruses (such as HPV or BPV) are useful for cloning vectors in mammalian cells. Generally, the origin of replication component is not needed for mammalian expression vectors (for example, the SV40 origin is often used only because it contains the early promoter).

A transcription termination sequence is typically located 3' of the end of a polypeptide coding regions and serves to terminate transcription. Usually, a transcription termination sequence in prokaryotic cells is a G-C rich fragment followed by a poly T sequence. While the sequence is easily cloned from a library or even purchased commercially as part of a vector, it can also be readily synthesized using methods for nucleic acid synthesis such as those described above.

A selectable marker gene element encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells, (b) complement auxotrophic deficiencies of the cell; or (c) supply critical nutrients not available from complex media. Preferred selectable markers are the kanamycin resistance gene, the ampicillin resistance gene, and the tetracycline resistance gene. A neomycin resistance gene may also be used for selection in prokaryotic and eukaryotic host cells.

Other selection genes may be used to amplify the gene which will be expressed. Amplification is the process wherein genes which are in greater demand for the production of a protein critical for growth are reiterated in tandem within the chromosomes of successive generations of recombinant cells. Examples of suitable selectable markers for mammalian cells include dihydrofolate reductase (DHFR) and thymidine kinase. The mammalian cell transformants are placed under selection pressure which only the transformants are uniquely adapted to survive by virtue of the marker present in the vector. Selection pressure is imposed by culturing the transformed cells under conditions in which the concentration of selection agent in the medium is successively changed, thereby leading to amplification of both the selection gene and the DNA that encodes an anti-IFNγ antibody. As a result, increased quantities of an antibody are synthesized from the amplified DNA.

A ribosome binding site is usually necessary for translation initiation of mrna and is characterized by a Shine-Dalgarno sequence (prokaryotes) or a Kozak sequence (eukaryotes). The element is typically located 3' to the promoter and 5' to the coding sequence of the polypeptide to be expressed. The Shine-Dalgarno sequence is varied but is typically a polypurine (i.e., having a high A-G content). Many Shine-Dalgarno sequences have been identified, each of which can be readily synthesized using methods set forth above and used in a prokaryotic vector.

A leader, or signal, sequence is used to direct secretion of a polypeptide. A signal sequence may be positioned within or directly at the 5' end of a polypeptide coding region. Many signal sequences have been identified and may be selected based upon the host cell used for expression. In the present invention, a signal sequence may be homologous (naturally occurring) or heterologous to a nucleic acid sequence encoding an anti-IFNγ antibody or antigen binding domain. A heterologous signal sequence selected should be one that is recognized and processed, i.e., cleaved, by a signal peptidase, by the host cell. For prokaryotic host cells that do not recognize and process a native immunoglobulin signal sequence, the signal sequence is substituted by a prokaryotic signal sequence selected, for example, from the group of the alkaline phosphatase, penicillinase, or heat-stable enterotoxin II leaders. For yeast secretion, a native immunoglobulin signal sequence may be substituted by the yeast invertase, alpha factor, or acid phosphatase leaders. In mammalian cell expression the native signal sequence is satisfactory, although other mammalian signal sequences may be suitable.

In most cases, secretion of an anti-IFNγ antibody or antigen binding domain from a host cell will result in the removal of the signal peptide from the antibody. Thus the mature antibody will lack any leader or signal sequence.

In some cases, such as where glycosylation is desired in a eukaryotic host cell expression system, one may manipulate the various presequences to improve glycosylation or yield. For example, one may alter the peptidase cleavage site of a particular signal peptide, or add prosequences, which also may affect glycosylation. The final protein product may have, in the −1 position (relative to the first amino acid of the mature protein) one or more additional amino acids incident to expression, which may not have been totally removed. For example, the final protein product may have one or two amino acid found in the peptidase cleavage site, attached to the N terminus. Alternatively, use of some enzyme cleavage sites may result in a slightly truncated form of the desired IFNγ polypeptide, if the enzyme cuts at such area within the mature polypeptide.

The expression vectors of the present invention will typically contain a promoter that is recognized by the host organism and operably linked to a nucleic acid molecule encoding an anti-IFNγ antibody or antigen binding domain. Either a native or heterologous promoter may be used depending the host cell used for expression and the yield of protein desired.

Promoters suitable for use with prokaryotic hosts include the beta-lactamase and lactose promoter systems; alkaline phosphatase, a tryptophan (trp) promoter system; and hybrid promoters such as the tac promoter. Other known bacterial promoters are also suitable. Their sequences have been published, thereby enabling one skilled in the art to ligate them to the desired DNA sequences), using linkers or adapters as needed to supply any required restriction sites.

Suitable promoters for use with yeast hosts are also well known in the art. Yeast enhancers are advantageously used with yeast promoters. Suitable promoters for use with mammalian host cells are well known and include those obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40). Other suitable mammalian promoters include heterologous mammalian promoters, e.g., heat-shock promoters and the actin promoter.

Additional promoters which may be used for expressing the selective binding agents of the invention include, but are not limited to: the SV40 early promoter region; Bernoist and Chambon, *Nature,* 290:304–310 (1981), the CMV promoter, the promoter contained in the 3' long terminal repeat of Rous sarcoma virus; Yamamoto, et al., *Cell,* 22:787–797 (1980), the herpes thymidine kinase promoter; Wagner et al., *Proc. Natl. Acad. Sci. U.S.A.,* 78:144–1445 (1981), the regulatory sequences of the metallothionine gene; Brinster et al., *Nature,* 296:39–42 (1982), prokaryotic expression vectors such as the beta-lactamase promoter; Villa-Kamaroff, et al., *Proc. Natl. Acad. Sci. U.S.A.,* 75:3727–3731 (1978), or the tac promoter; DeBoer, et al., *Proc. Natl. Acad. Sci. U.S.A.,* 80:21–25 (1983).

Also of interest are the following animal transcriptional control regions, which exhibit tissue specificity and have been utilized in transgenic animals: the elastase I gene control region which is active in pancreatic acinar cells; Swift et al., *Cell,* 38:639–646, (1984); Ornitz et al., Cold Spring Harbor Symp. Quant. Biol. 50:399–409 (1986); MacDonald, *Hepatology,* 7:425–515 (1987), the insulin gene control region which is active in pancreatic beta cells; Hanahan, *Nature,* 315:115–122 (1985), the immunoglobulin gene control region which is active in lymphoid cells; Grosschedl et al., *Cell,* 38:647–658 (1984); Adames et al., *Nature,* 318:533–538 (1985); Alexander et al., *Mol. Cell. Biol.,* 7:1436–1444 (1987), the mouse mammary tumor virus control region which is active in testicular, breast, lymphoid and mast cells; Leder et al., *Cell,* 45:485–495 (1986), the albumin gene control region which is active in liver; Pinkert et al., *Genes and Devel.,* 1:268–276 (1987), the alphafetoprotein gene control region which is active in liver; Krumlauf et al., *Mol. Cell. Biol.,* 5:1639–1648 (1985); Hammer et al., *Science,* 235:53–58 (1987), the alpha 1-antitrypsin gene control region which is active in the liver; Kelsey et al., *Genes and Devel.,* 1:161–171 (1987); the beta-globin gene control region which is active in myeloid cells; Mogram et al., *Nature,* 315:338–340 (1985); Kollias et al., *Cell,* 46:89–94 (1986), the myelin basic protein gene control region which is active in oligodendrocyte cells in the brain; Readhead et al., *Cell,* 48:703–712 (1987), the myosin light chain-2 gene control region which is active in skeletal muscle; Sani, *Nature,* 314:283–286 (1985), and the gonadotropic releasing hormone gene control region which is active in the hypothalamus; Mason et al., *Science,* 234: 1372–1378 (1986).

An enhancer sequence may be inserted into the vector to increase transcription in eucaryotic host cells. Several enhancer sequences available from mammalian genes are known (e.g., globin, elastase, albumin, alpha-feto-protein and insulin). Typically, however, an enhancer from a virus will be used. The Sv40 enhancer, the cytomegalovirus early promoter enhancer, the polyoma enhancer, and adenovirus enhancers are exemplary enhancing elements for the activation of eukaryotic promoters. While an enhancer may be spliced into the vector at a position 5' or 3' to the polypeptide coding region, it is typically located at a site 5' from the promoter.

Preferred vectors for practicing this invention are those which are compatible with bacterial, insect, and mammalian host cells. Such vectors include, inter alia, pCRII, pCR3, and pcDNA3.1 (Invitrogen Company, San Diego, Calif.), pBSII (Stratagene Company, La Jolla, Calif.), pET15 (Novagen, Madison, Wis.), pGEX (Pharmacia Biotech, Piscataway, N.J.), pEGFP-N2 (Clontech, Palo Alto, Calif.), pETL (BlueBacII; Invitrogen Carlsbad, Calif.), pDSR-alpha (PCT Publication No. WO90/14363) and pFastBacDual (Gibco/BRL, Grand Island, N.Y.).

Additional possible vectors include, but are not limited to, cosmids, plasmids or modified viruses, but the vector system must be compatible with the selected host cell. Such vectors include, but are not limited to plasmids such as Bluescript® plasmid derivatives (a high copy number ColE1-based phagemid, Stratagene Cloning Systems Inc., La Jolla Calif.), PCR cloning plasmids designed for cloning Taq-amplified PCR products (e.g., TOPO™ TA Cloning® Kit, PCR2.1® plasmid derivatives, Invitrogen, Carlsbad, Calif.), and mammalian, yeast or virus vectors such as a baculovirus expression system (pBacPAK plasmid derivatives, Clontech, Palo Alto, Calif.). The recombinant molecules can be introduced into host cells via transformation, transfection, infection, electroporation, or other known techniques.

Host cells of the invention may be prokaryotic host cells (such as E. coli) or eukaryotic host cells (such as a yeast cell, an insect cell, or a vertebrate cell). The host cell, when cultured under appropriate conditions, expresses an antibody or antigen binding domain of the invention which can subsequently be collected from the culture medium (if the host cell secretes it into the medium) or directly from the host cell producing it (if it is not secreted). Selection of an appropriate host cell will depend upon various factors, such as desired expression levels, polypeptide modifications that are desirable or necessary for activity, such as glycosylation or phosphorylation, and ease of folding into a biologically active molecule.

A number of suitable host cells are known in the art and many are available from the American Type Culture Collection (ATCC), Manassas, Va. Examples include mammalian cells, such as Chinese hamster ovary cells (CHO) (ATCC No. CCL61) CHO DHFR-cells; Urlaub et al., *Proc. Natl. Acad. Sci. USA*, 97:4216–4220 (1980), human embryonic kidney (HEK) 293 or 293T cells (ATCC No. CRL1573), or 3T3 cells (ATCC No. CCL92). The selection of suitable mammalian host cells and methods for transformation, culture, amplification, screening and product production and purification are known in the art. Other suitable mammalian cell lines, are the monkey COS-1 (ATCC No. CRL1650) and COS-7 cell lines (ATCC No. CRL1651), and the CV-1 cell line (ATCC No. CCL70). Further exemplary mammalian host cells include primate cell lines and rodent cell lines, including transformed cell lines. Normal diploid cells, cell strains derived from in vitro culture of primary tissue, as well as primary explants, are also suitable. Candidate cells may be genotypically deficient in the selection gene, or may contain a dominantly acting selection gene. Other suitable mammalian cell lines include but are not limited to, mouse neuroblastoma N2A cells, HeLa, mouse L-929 cells, 3T3 lines derived from Swiss, Balb-c or NIH mice, BHK or HaK hamster cell lines, which are available from the American Type Culture Collection, Manassas, Va.). Each of these cell lines is known by and available to those skilled in the art of protein expression.

Similarly useful as host cells suitable for the present invention are bacterial cells. For example, the various strains of E. coli (e.g., HB101, (ATCC No. 33694) DH5α, DH10, and MC1061 (ATCC No. 53338) are well-known as host cells in the field of biotechnology. Various strains of *B. subtilis*, *Pseudomonas* spp., other *Bacillus* spp., *Streptomyces* spp., and the like may also be employed in this method.

Many strains of yeast cells known to those skilled in the art are also available as host cells for expression of the polypeptides of the present invention. Preferred yeast cells include, for example, *saccharomyces cerivisae*.

Additionally, where desired, insect cell systems may be utilized in the methods of the present invention. Such systems are described for example in Kitts et al., *Biotechniques*, 14:810–817 (1993), Lucklow, Curr. Opin. Biotechnol., 4:564–572 (1993) and Lucklow et al., *J. Virol.*, 67:4566–4579 (1993). Preferred insect cells are Sf-9 and Hi5 (Invitrogen, Carlsbad, Calif.).

Transformation or transfection of a nucleic acid molecule encoding an anti-IFNγ antibody or antigen binding domain into a selected host cell may be accomplished by well known methods including methods such as calcium chloride, electroporation, microinjection, lipofection or the deae-dextran method. The method selected will in part be a function of the type of host cell to be used. These methods and other suitable methods are well known to the skilled artisan, and are set forth, for example, in Sambrook et al., supra.

One may also use transgenic animals to express glycosylated selective binding agents, such as antibodies and antigen binding domain. For example, one may use a transgenic milk-producing animal (a cow or goat, for example) and obtain glycosylated binding agents in the animal milk. Alternatively, one may use plants to produce glycosylated selective binding agents.

Host cells comprising (i.e., transformed or transfected) an expression vector encoding a selective binding agent of IFNγ may be cultured using standard media well known to the skilled artisan. The media will usually contain all nutrients necessary for the growth and survival of the cells. Suitable media for culturing E. coli cells are for example, luria broth (LB) and/or terrific broth (TB). Suitable media for culturing eukaryotic cells are RPMI 1640, MEM, DMEM, all of which may be supplemented with serum and/or growth factors as required by the particular cell line being cultured. A suitable medium for insect cultures is Grace's medium supplemented with yeastolate, lactalbumin hydrolysate, and/or fetal calf serum as necessary.

Typically, an antibiotic or other compound useful for selective growth of transfected or transformed cells is added as a supplement to the media. The compound to be used will be dictated by the selectable marker element present on the plasmid with which the host cell was transformed. For example, where the selectable marker element is kanamycin resistance, the compound added to the culture medium will be kanamycin. Other compounds for selective growth include ampicillin, tetracycline and neomycin.

The amount of an anti-IFNγ antibody or antigen binding domain produced by a host cell can be evaluated using standard methods known in the art. Such methods include, without limitation, Western blot analysis, SDS-polyacrylamide gel electrophoresis, non-denaturing gel electrophoresis, HPLC separation, immunoprecipitation, and/or activity assays.

Purification of an anti-IFNγ antibody or antigen binding domain which has been secreted into the cell media can be accomplished using a variety of techniques including affinity, immunoaffinity or ion exchange chromatography, molecular sieve chromatography, preparative gel electrophoresis or isoelectric focusing, chromatofocusing, and high pressure liquid chromatography. For example, antibodies comprising a Fc region may be conveniently purified by affinity chromatography with Protein A, which selectively binds the fc region. Modified forms of an antibody or antigen binding domain may be prepared with affinity tags, such as hexahistidine or other small peptide such as FLAG (Eastman Kodak Co., New Haven, Conn.) or myc (Invitrogen) at either its carboxyl or amino terminus and purified by a one-step affinity column. For example, polyhistidine binds with great affinity and specificity to nickel, thus an affinity column of nickel (such as the Qiagen® nickel columns) can be used for purification of polyhistidine-tagged selective binding agents; see e.g., Ausubel et al., eds., *Current Protocols in Molecular Biology*, section 10.11.8, John Wiley & Sons, New York (1993). In some instances, more than one purification step may be required.

Selective binding agents of the invention which are expressed in procaryotic host cells may be present in soluble form either in the periplasmic space or in the cytoplasm or in an insoluble form as part of intracellular inclusion bodies. Selective binding agents can be extracted from the host cell using any standard technique known to the skilled artisan. For example, the host cells can be lysed to release the contents of the periplasm/cytoplasm by french press, homogenization, and/or sonication followed by centrifugation.

Soluble forms of an anti-IFNγ antibody or antigen binding domain present either in the cytoplasm or released from the periplasmic space may be further purified using methods known in the art, for example Fab fragments are released from the bacterial periplasmic space by osmotic shock techniques. If an antibody or antigen binding domain has formed inclusion bodies, they can often bind to the inner and/or outer cellular membranes and thus will be found primarily in the pellet material after centrifugation. The pellet material can then be treated at pH extremes or with chaotropic agent such as a detergent, guanidine, guanidine derivatives, urea, or urea derivatives in the presence of a reducing agent such as dithiothreitol at alkaline pH or tris carboxyethyl phosphine at acid pH to release, break apart, and solubilize the inclusion bodies. The soluble selective binding agent can then be analyzed using gel electrophoresis, immunoprecipitation or the like. If it is desired to isolate a solublized antibody or antigen binding domain, isolation may be accomplished using standard methods such as those set forth below and in Marston et al., *Meth. Enz.*, 182: 264–275 (1990).

In some cases, an antibody or antigen binding domain may not be biologically active upon isolation. Various methods for "refolding" or converting the polypeptide to its tertiary structure and generating disulfide linkages, can be used to restore biological activity. Such methods include exposing the solubilized polypeptide to a pH usually above 7 and in the presence of a particular concentration of a chaotrope. The selection of chaotrope is very similar to the choices used for inclusion body solubilization, but usually the chaotrope is used at a lower concentration and is not necessarily the same as chaotropes used for the solubilization. In most cases the refolding/oxidation solution will also contain a reducing agent or the reducing agent plus its oxidized form in a specific ratio to generate a particular redox potential allowing for disulfide shuffling to occur in the formation of the protein's cysteine bridge(s). Some of the commonly used redox couples include cysteine/cystamine, glutathione (GSH)/dithiobis GSH, cupric chloride, dithiothreitol (DTT)/dithiane DTT, and 2-mercaptoethanol (bME)/dithio-b(ME). In many instances, a cosolvent may be used or may be needed to increase the efficiency of the refolding and the more common reagents used for this purpose include glycerol, polyethylene glycol of various molecular weights, arginine and the like.

Antibodies and antigen binding domains of the invention may also be prepared by chemical synthesis methods (such as solid phase peptide synthesis) using techniques known in the art such as those set forth by Merrifield et al., *J. Am. Chem. Soc.*, 85:2149 (1963); Houghten et al., *Proc Natl Acad. Sci. USA*, 82:5132 (1985), and Stewart and Young (Solid Phase Peptide Synthesis, Pierce Chemical Co., Rockford, Ill. (1984). Such polypeptides may be synthesized with or without a methionine on the amino terminus. Chemically synthesized antibodies and antigen binding domains may be oxidized using methods set forth in these references to form disulfide bridges. Antibodies so prepared will retain at least one biological activity associated with a native or recombinantly produced anti-opgbp antibody or antigen binding domain.

Assays for Selective Binding Agents of IFNγ

Screening methods for identifying selective binding agents which partially or completely inhibits at least one biological activity of IFNγ are provided by the invention. Inhibiting the biological activity of IFNγ includes, but is not limited to, inhibiting binding of IFNγ to its cognate receptor, IFNγ-R, inhibiting anti-proliferative activity of IFNγ on A549 cells in vitro, and inhibiting activation of monocytes by IFNγ in vitro and in vivo. Selective binding agents of the invention include anti-IFNγ antibodies, and fragments, variants, derivatives and fusion thereof, peptides, peptidomimetic compounds or organo-mimetic compounds. Screening methods for identifying selective binding agents which can partially or completely inhibit a biological activity of IFNγ can include in vitro or in vivo assays. In vitro assays include those that detect binding of IFNγ to IFNγ-R and may be used to screen selective binding agents of IFNγ for their ability to increase or decrease the rate or extent of IFNγ binding to IFNγ-R. In one type of assay, an IFNγ polypeptide, preferably a soluble form of IFNγ such as an extracellular domain, is immobilized on a solid support (e.g., agarose or acrylic beads) and an IFNγ-R polypetpide is the added either in the presence or absence of a selective binding agent of IFNγ. The extent of binding of IFNγ and IFNγ-R with or without a selective binding agent present is measured. Binding can be detected by for example radioactive labeling, fluorescent labeling or enzymatic reaction.

Alternatively, the binding reaction may be carried out using a surface plasmon resonance detector system such as the BIAcore assay system (Pharmacia, Piscataway, N.J.). Binding reactions may be carried out according to the manufacturer's protocol.

In vitro assays such as those described above may be used advantageously to screen rapidly large numbers of selective binding agents for effects on binding of IFNγ to IFNγ-R. The assays may be automated to screen compounds generated in phage display, synthetic peptide and chemical synthesis libraries.

Selective binding agents increase or decrease binding of IFNγ to IFNγ-R may also be screened in cell culture using cells and cell lines expressing either polypeptide. Cells and cell lines may be obtained from any mammal, but preferably will be from human or other primate, canine, or rodent sources. As an example, the binding of IFNγ to cells expressing IFNγ-R on the surface is evaluated in the presence or absence of selective binding agents and the extent of binding may be determined by, for example, flow cytometry using a biotinylated antibody to IFNγ.

In vitro activity assays may also be used to identify selective binding agents which inhibit IFNγ activity. Examples of assays include A549 cell proliferation assay and THP-1 HLA-DR expression assay.

In vivo assays are also available to determine whether a selective binding agent is capable of delaying development of proteinurea and increasing survival time in NZB×NZW F1 mouse model.

For diagnostic applications, in certain embodiments, selective binding agents of IFNγ, such as antibodies and antigen binding domains thereof, typically will be labeled with a detectable moiety. The detectable moiety can be any one which is capable of producing, either directly or indirectly, a detectable signal. For example, the detectable moiety may be a radioisotope, such as $^3H$, $^{14}C$, $^{32}P$, $^{35}S$, or $^{125}I$, a fluorescent or chemiluminescent compound, such as fluorescein isothiocyanate, rhodamine, or luciferin; or an enzyme, such as alkaline phosphatase, β-galactosidase or horseradish peroxidase; Bayer et. al., *Meth. Enz.,* 184: 138–163 (1990).

The selective binding agents of the invention may be employed in any known assay method, such as radioimmunoassays, competitive binding assays, direct and indirect sandwich assays (ELISAs), and immunoprecipitation assays (Sola, Monoclonal Antibodies: A Manual of Techniques, pp. 147–158 (CRC Press, 1987)) for detection and quantitation of IFNγ polypeptides. The antibodies will bind IFNγ polypeptides with an affinity which is appropriate for the assay method being employed.

The selective binding agents of the invention also are useful for in vivo imaging, wherein for example a selective binding agent labeled with a detectable moiety is administered to an animal, preferably into the bloodstream, and the presence and location of the labeled antibody in the host is assayed. The agent may be labeled with any moiety that is detectable in an animal, whether by nuclear magnetic resonance, radiology, or other detection means known in the art.

The invention also relates to a kit comprising a selective binding agent of IFNγ, such as an antibody or antigen binding domain, and other reagents useful for detecting IFNγ levels in biological samples. Such reagents may include a secondary activity, a detectable label, blocking serum, positive and negative control samples, and detection reagents.

Therapeutic Uses of IFNγ Selective Binding Agents

Selective binding agents of the invention may be used as therapeutics. Therapeutic selective binding agents may be IFNγ agonists or antagonists and, in one embodiment, are anti-IFNγ antagonist antibodies which inhibit at least one of the biological activities of an IFNγ polypeptide in vitro or in vivo. For example, an antagonist of IFNγ will inhibit the binding of IFNγ to IFNγ-R. Alternatively, an IFNγ antagonist will stimulate the proliferation of human lung carcinoma in vitro as indicated by measurable ND50 (a concentration giving 50% proliferation) in a A549 cell proliferation assay such as that described in Example 1.

IFNγ antagonists, such as anti-IFNγ antagonist antibodies and antigen binding domains, may be used to prevent or treat auto-immune diseases and inflammatory conditions including, but not limited to the following: acute pancreatitis; ALS; Alzheimer's disease; cachexia/anorexia, including AIDS-induced cachexia; asthma and other pulmonary diseases; atherosclerosis; chronic fatigue syndrome; *Clostridium* associated illnesses, including *Clostridium*-associated diarrhea; coronary conditions and indications, including congestive heart failure, coronary restenosis, myocardial infarction, myocardial dysfunction (e.g., related to sepsis), and coronary artery bypass graft; cancer, such as multiple myeloma and myelogenous (e.g., AML and CML) and other leukemias, as well as tumor metastasis; fever; glomerulonephritis; graft versus host disease/transplant rejection; hemohorragic shock; inflammatory eye disease, as may be associated with, for example, corneal transplant; ischemia, including cerebral ischemia (e.g., brain injury as a result of trauma, epilepsy, hemorrhage or stroke, each of which may lead to neurodegeneration); learning impairment; multiple sclerosis; myopathies (e.g., muscle protein metabolism, esp. in sepsis); neurotoxicity (e.g., as induced by HIV); osteoporosis; pain, including cancer-related pain; Parkinson's disease; periodontal disease; neurotoxicity; pre-term labor; psoriasis; reperfusion injury; septic shock; side effects from radiation therapy; temporal mandibular joint disease; sleep disturbance; uveitis; or an inflammatory condition resulting from strain, sprain, cartilage damage, trauma, orthopedic surgery, infection or other disease processes; diabetes, including juvenile onset Type 1, diabetes mellitus, and insulin resistance (e.g., as associated with obesity); endometriosis, endometritis, and related conditions; fibromyalgia or analgesia; hyperalgesia; inflammatory bowel diseases, including Crohn's disease; lung diseases (e.g., adult respiratory distress syndrome, and pulmonary fibrosis); neuroinflammatory diseases; ocular diseases and conditions, including ocular degeneration and uveitis; Pityriasis rubra pilaris (PRP); prostatitis (bacterial or non-bacterial) and related conditions; psoriasis and related conditions; pulmonary fibrosis; reperfusion injury; inflammatory conditions of a joint and rheumatic diseases, including, osteoarthritis, rheumatoid arthritis, juvenile (rheumatoid) arthritis, seronegative polyarthritis, ankylosing spondylitis, Reiter's syndrome and reactive arthritis, Still's disease, psoriatic arthritis, enteropathic arthritis, polymyositis, dermatomyositis, scleroderma, systemic sclerosis, vasculitis (e.g., Kawasaki's disease), cerebral vasculitis, Lyme disease, staphylococcal-induced ("septic") arthritis, Sjögren's syndrome, rheumatic fever, polychondritis and polymyalgia rheumatica and giant cell arteritis; septic shock; systemic lupus erythematosus (SLE) nephritis; side effects from radiation therapy; temporal mandibular joint disease; thyroiditis; tissue transplantation or an inflammatory condition resulting from strain, sprain, cartilage damage, trauma, and orthopedic surgery.

More specifically, the IFNγ antagonists, such as anti-IFNγ antagonist antibodies and antigen binding domains, may be used to prevent or treat arthritis (particularly rheumatoid arthritis), systemic lupus erythematosus (SLE), graft versus host disease (GvHD), multiple sclerosis and diabetes.

IFNγ antagonists of the invention, including antagonist antibodies and antigen binding domains, are administered alone or in combination with other therapeutic agents IFNγ antagonists, such as anti-IFNγ antagonist antibodies and antigen binding domains, may be used to prevent or treat to treat various inflammatory conditions, autoimmune conditions, and other conditions leading to bone loss. Depending on the condition and the desired level of treatment, two, three, or more agents may be administered. These agents may be provided together by inclusion in the same formulation or inclusion in a treatment kit, or they may be provided separately. When administered by gene therapy, the genes encoding the protein agents may be included in the same vector, optionally under the control of the same promoter region, or in separate vectors. Particularly preferred molecules in the aforementioned classes are as follows.

IL-1 inhibitors: IL-1ra proteins and soluble IL-1 receptors. The most preferred IL-1 inhibitor is anakinra.

TNF-α inhibitors: soluble tumor necrosis factor receptor type I (sTNF-RI; -RI is also called the p55 receptor); soluble tumor necrosis factor receptor type II (also called the p75 receptor); and monoclonal antibodies that bind the TNF receptor. Most preferred is STNF-RI as described in WO 98/24463, etanercept (Enbrel®), and Avakine®. Exemplary TNF-α inhibitors are described in EP 422 339, EP 308 378, EP 393 438, EP 398 327, and EP 418 014.

serine protease inhibitors: SLPI, ALP, MPI, HUSI-I, BMI, and CUSI. These inhibitors also may be viewed as exemplary LPS modulators, as SLPI has been shown to inhibit LPS responses. Jin et al. (1997), *Cell* 88(3): 417–26 (incorporated by reference).

PHARMACEUTICAL COMPOSITIONS

Pharmaceutical compositions of IFNγ selective binding agents are within the scope of the present invention. Such compositions comprise a therapeutically or prophylactically effective amount of an IFNγ selective binding agent such as an antibody, or a fragment, variant, derivative or fusion thereof, in admixture with a pharmaceutically acceptable agent. In a preferred embodiment, pharmaceutical compositions comprise anti-IFNγ antagonist antibodies which inhibit partially or completely at least one biological activity of IFNγ in admixture with a pharmaceutically acceptable agent. Typically, the antibodies will be sufficiently purified for administration to an animal.

Pharmaceutically acceptable agents for use in the compositions of the invention include carriers, excipients, diluents, antioxidants, preservatives, coloring, flavoring and diluting agents, emulsifying agents, suspending agents, solvents, fillers, bulking agents, buffers, delivery vehicles, tonicity agents, cosolvents, wetting agents, complexing agents, buffering agents, antimicrobials and surfactants, as are well known in the art.

Neutral buffered saline or saline mixed with serum albumin are exemplary appropriate carriers. Also included in the compositions are antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, pluronics or polyethylene glycol. Also by way of example, suitable tonicity enhancing agents include alkali metal halides (preferably sodium or potassium chloride), mannitol, sorbitol and the like. Suitable preservatives include, but are not limited to, benzalkonium chloride, thimerosal, phenethyl alcohol, methylparaben, propylparaben, chlorhexidine, sorbic acid and the like. Hydrogen peroxide may also be used as preservative.

Suitable cosolvents are for example glycerin, propylene glycol, and polyethylene glycol. Suitable complexing agents are for example caffeine, polyvinylpyrrolidone, beta-cyclodextrin or hydroxy-propyl-beta-cyclodextrin. Suitable surfactants or wetting agents include sorbitan esters, polysorbates such as polysorbate 80, tromethamine, lecithin, cholesterol, tyloxapal and the like. The buffers can be conventional buffers such as acetate, borate, citrate, phosphate, bicarbonate, or Tris-HCl. Acetate buffer may be around pH 4.0–5.5 and Tris buffer may be around pH 7.0–8.5. Additional pharmaceutical agents are set forth in *Remington's Pharmaceutical Sciences,* 18th Edition, A. R. Gennaro, ed., Mack Publishing Company 1990, the relevant portions of which are hereby incorporated by reference.

The compositions may be in liquid form or in a lyophilized or freeze-dried form. Lypophilized forms may include excipients such as sucrose. The compositions of the invention are suitable for parenteral administration. In preferred embodiments, the compositions are suitable for injection or infusion into an animal by any route available to the skilled worker, such as subcutaneous, intravenous, intramuscular, intraperitoneal, intracerebral (intraparenchymal), intracerebroventricular, intramuscular, intraocular, intraarterial, or intralesional routes. A parenteral formulation will typically be a sterile, pyrogen-free, isotonic aqueous solution, optionally containing pharmaceutically acceptable preservatives.

The optimal pharmaceutical formulation may be readily determined by one skilled in the art depending upon the intended route of administration, delivery format and desired dosage.

Other formulations are also contemplated by the invention. The pharmaceutical compositions also may include particulate preparations of polymeric compounds such as polylactic acid, polyglycolic acid, etc. or the introduction of an IFNγ selective binding agent (such as an antibody) into liposomes. Hyaluronic acid may also be used, and this may have the effect of promoting sustained duration in the circulation. Pharmaceutical compositions also include the formulation of IFNγ selective binding agents (such as antibodies) with an agent, such as injectable microspheres, bio-erodible particles or beads, or liposomes, that provides for the controlled or sustained release of a selective binding agent which may then be delivered as a depot injection. Other suitable means for delivery include implantable delivery devices.

A pharmaceutical composition comprising and IFNγ selective binding agent (such as an antibody) may be formulated as a dry powder for inhalation. Such inhalation solutions may also be formulated in a liquefied propellant for aerosol delivery. In yet another formulation, solutions may be nebulized. It is also contemplated that certain formulations containing IFNγ selective binding agents may be administered orally. Formulations administered in this fashion may be formulated with or without those carriers customarily used in the compounding of solid dosage forms such as tablets and capsules. For example, a capsule may be designed to release the active portion of the formulation at the point in the gastrointestinal tract when bioavailability is maximized and pre-systemic degradation is minimized. Additional agents may be included to facilitate absorption of a selective binding agent. Diluents, flavorings, low melting point waxes, vegetable oils, lubricants, suspending agents, tablet disintegrating agents, and binders may also be employed.

Another preparation may involve an effective quantity of an IFNγ selective binding agent in a mixture with non-toxic excipients which are suitable for the manufacture of tablets. By dissolving the tablets in sterile water, or another appropriate vehicle, solutions can be prepared in unit dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional formulations will be evident to those skilled in the art, including formulations involving IFNγ selective binding agents in combination with one or more other therapeutic agents. Techniques for formulating a variety of other sustained- or controlled-delivery means, such as liposome carriers, bio-erodible microparticles or porous beads and depot injections, are also known to those skilled in the art. See, for example, the Supersaxo et al. description of controlled release porous polymeric microparticles for the delivery of pharmaceutical compositions (See WO 93/15722 (PCT/US93/00829) the disclosure of which is hereby incorporated by reference.

Regardless of the manner of administration, the specific dose may be calculated according to body weight, body surface area or organ size. Further refinement of the calculations necessary to determine the appropriate dosage for treatment involving each of the above mentioned formulations is routinely made by those of ordinary skill in the art and is within the ambit of tasks routinely performed by them. Appropriate dosages may be ascertained through use of appropriate dose-response data.

One may further administer the present pharmaceutical compositions by pulmonary administration, see, e.g., PCT WO94/20069, which discloses pulmonary delivery of chemically modified proteins, herein incorporated by reference. For pulmonary delivery, the particle size should be suitable for delivery to the distal lung. For example, the particle size may be from 1 μm to 5 μm, however, larger particles may be used, for example, if each particle is fairly porous.

Alternatively or additionally, the compositions may be administered locally via implantation into the affected area of a membrane, sponge, or other appropriate material on to which an IFNγ selective binding agent has been absorbed or encapsulated. Where an implantation device is used, the device may be implanted into any suitable tissue or organ, and delivery of an IFNγ selective binding agent may be directly through the device via bolus, or via continuous administration, or via catheter using continuous infusion.

Pharmaceutical compositions of the invention may also be administered in a sustained release formulation or preparation. Suitable examples of sustained-release preparations include semipermeable polymer matrices in the form of shaped articles, e.g. films, or microcapsules. Sustained release matrices include polyesters, hydrogels, polylactides (See e.g., U.S. Pat. No. 3,773,919, EP 58,481), copolymers of L-glutamic acid and gamma ethyl-L-glutamate (Sidman et al, *Biopolymers*, 22: 547–556 (1983), poly (2-hydroxyethyl-methacrylate) (Langer et al., *J. Biomed. Mater. Res.*, 15: 167–277 (1981) and Langer, *Chem. Tech.*, 12: 98–105 (1982), ethylene vinyl acetate, or poly-D(–)-3-hydroxybutyric acid. Sustained-release compositions also may include liposomes, which can be prepared by any of several methods known in the art. See e.g., Eppstein et al., *Proc. Natl. Acad. Sci. USA*, 82: 3688–3692 (1985); EP 36,676; EP 88,046; and EP 143,949.

It may be desirable in some instances to use a pharmaceutical composition comprising an IFNγ selective binding agent compositions in an ex vivo manner. Here, cells, tissues, or organs that have been removed from the patient are exposed to pharmaceutical compositons comprising IFNγ selective binding agents after which the cells, tissues and/or organs are subsequently implanted back into the patient.

In other cases, a composition comprising an IFNγ selective binding agent may be delivered through implanting into patients certain cells that have been genetically engineered, using methods such as those described herein, to express and secrete the polypeptides, selective binding agents, fragments, variants, or derivatives. Such cells may be animal or human cells, and may be derived from the patient's own tissue or from another source, either human or non-human. Optionally, the cells may be immortalized. However, in order to decrease the chance of an immunological response, it is preferred that the cells be encapsulated to avoid infiltration of surrounding tissues. The encapsulation materials are typically biocompatible, semi-permeable polymeric enclosures or membranes that allow release of the protein product(s) but prevent destruction of the cells by the patient's immune system or by other detrimental factors from the surrounding tissues.

Methods used for membrane encapsulation of cells are familiar to the skilled artisan, and preparation of encapsulated cells and their implantation in patients may be accomplished without undue experimentation. See, e.g., U.S. Pat. Nos. 4,892,538, 5,011,472, and 5,106,627. A system for encapsulating living cells is described in PCT WO 91/10425 (Aebischer et al.). Techniques for formulating a variety of other sustained or controlled delivery means, such as liposome carriers, bio-erodible particles or beads, are also known to those in the art, and are described. The cells, with or without encapsulation, may be implanted into suitable body tissues or organs of the patient.

A therapeutically or prophylactically effective amount of a pharmaceutical composition comprising an IFNγ selective binding agent (such as an anti-IFNγ antibody, or fragment, variant, derivative, and fusion thereof) will depend, for example, upon the therapeutic objectives such as the indication for which the composition is being used, the route of administration, and the condition of the subject. IFNγ antagonist antibodies or antigen binding domains of the invention are administered in a therapeutically or prophylactically effective amount to prevent and/or treat an autoimmune and/or inflammatory condition.

The following examples are offered to more fully illustrate the invention but are not construed as limiting the scope thereof.

EXAMPLE 1

Reagents and Assays

The screening targets used in these studies were hIFNγ prepared from: 1) expression of a cDNA encoding hIFNγ in *E. coli* as described in EP 0423845, or PCT Publication WO 83/04053; or, 2) expression of a cDNA encoding hIFNγ in a CHO host cell as follows: PCR (standard conditions) was used to amplify the full-length sequence encoding the human IFNγ using human spleen marathon ready cDNA (Clontech) as a template. The sequence was subcloned into an expression plasmid and DNA transformed into DH10B cells (Gibco Life Sciences), DNA prepared, and transfected into CHO cells by the calcium phosphate method (Speciality Media, Inc.). A high-expressing cell line clone was used to generate serum-free conditioned media.

CHO cell conditioned media containing hINFγ was concentrated, dialyzed, and then purified through several chromatography steps. The $1^{st}$ step was Q-HP (Pharmacia) chromatography using a standard NaCl gradient to separate highly glycosylated vs. unglycosylated hIFNγ forms. The Q-HP pool was further purified through a wheat germ agglutinin chromatography (EY Laboratories). The purified material was greater than 95% pure judged by both Coomassie-blue and silver-stained SDS-PAGE. The material was of low endotoxin level as assayed by the gel-clot method (Limulus Amebocyte Lysate). The identity of hINFγ was confirmed by western blot, using goat anti-hIFNγ neutralizing antibody from R & D Systems (catalog number AF-285-NA, lot number ZW019011). The final protein concentration was determined using the extinction coefficient method (0.66). Two lots of material were generated respectively. The yield was 40 mg/l. Final materials were formulated in PBS.

Expression of Human IFNγR1-Fc Protein in CHO Cells

The human IFNγR1-Fc protein used for elution of phage antibodies from target in these studies were prepared as follows: PCR (standard conditions) was used to amplify the full-length sequence encoding the human IFNγR1 using human lymphoid marathon ready cDNA (purchased from Clontech) as a template. PCR (standard conditions) was used to amplify the sequence encoding the Fc portion of human IgG1. Overlap PCR was used to generate a sequence encoding the IFNγR1-Fc fusion construct (Amino acids 1 Ser$^{246}$ of the IFNγR1) and the sequence was subcloned into an expression plasmid. DNA was transformed into DH10B cells (Gibco Life Sciences), DNA prepared, and transfected into CHO cells by the calcium phosphate method (Speciality Media, Inc). A high-expressing cell line clone was used to generate serum-free conditioned media.

CHO cell conditioned media containing hINFγR1-Fc was concentrated and purified through standard Protein-G Fast-Flow column (Pharmacia). Final concentration was determined by $A_{280}$ using 1.44 as the extinction coefficient. The identity of the purified sample was confirmed through N-terminal sequencing analysis. The material was formulated in PBS.

Antibodies

Monoclonal anti-hIFNγ antibody, clone 2578.111, was purchased from R&D Systems (catalog number MAB285, lot number KW07). Monoclonal anti-hIFNγ antibody, clone MMHG-1, was purchased from Biosource (catalog number AHC4834, lot number 10803-015). Recombinant human IFNγ Receptor1 (rhIFNγ R1) was purchased from R&D Systems (catalog number 673-IR). The calculated molecular weight of the rhIFNγ R1 is 25,000 daltons. As a result of glycosylation, the recombinant protein migrates as a 40–50 kDa protein on SDS-PAGE.

A549 Cell Proliferation Assay

The A549 cell proliferation assay used to evaluate antibody neutralization of IFNγ is a 96 well assay and is generally described as follows: on day 1, 1) dilute Ab serially 1:2 from highest concentration in Assay Media (F12K, 5% FBS, 1×Pen/strep L-Glutamine). Do a total of 10 dilutions at 4× the concentration desired in Assay. For duplicates, at least 200 μl final is needed for each dilution; 2) dilute IFNγ to appropriate concentration for spike, based on 90% of the effective dose in a dose response curve. Make IFNγ spike 4× the concentration desired in assay; 3) combine 150 μl of each 4×Ab dilution with 150 μl 4×IFNγ spike in titertek tubes. Mix by pipetting. Cover and incubate 1 hour at room temperature. (Note: Concentration of Ab and IFNγ now at 2×assay concentration); 4)(Optional) while Ab and IFNγ incubate, dilute IFNγ for titration curve. Do 12 1:3 dilutions starting at 4000 ng/ml. Since 300 μl is needed for triplicates in assay, volume needed at end of dilution should be at least 400 μl. Store at 4° C. until needed; 5) before incubation is completed, trypsinize A549 cells in 5 ml trypsin. Add 20 ml Assay Media to flask and transfer to 50 ml conical and centrifuge at ½ to ¾ speed in IEC, RT; 6) aspirate cells. Resuspend in 7.5 ml Assay Media. Count 1:1 in trypan Blue; 7) dilute Cells in assay media to $2.5 \times 10^4$ cells/ml. Seed 0.1 ml into 96 well falcon for each sample for $2.5 \times 10^3$ cells/well; 8) at one hour, add 100 μl Ab/IFNγ mix to each of two wells for duplicates; and 9) incubate for 5 days at 37° C., 5% $CO_2$ and high humidity. On day 5:1) add 20 μl Alamar Blue per well. Incubate for 3–4 hours at 37° C., 5% $CO_2$ and high humidity; 2) turn on FL500 fluorescent plate reader. Remove lids from plates and shake for 10 minutes, without lid; and 3) read on FL500. Settings: Shake 3 seconds at medium, excitation at 530/25, emission at 590/35, sensitivity of 34.

EXAMPLE 2

Screening of a Human Fab Library

Screening Procedure

General procedures for construction and screening human Fab libraries were described in de Haard et al. (*Advanced Drug Delivery Reviews*, 31:5–31 (1998); *J. Biol. Chem.*, 274:18218–18230 (1999)). The library was screened for Fab fragments which bind to hIFNγ by the following procedures.

Nunc immunotube was coated with 4 ml of hIFNγ at 0.39 μg/ml in 0.1 M Na carbonate, pH 9.6 at room temperature on Nutator for 2 hrs. After thawing, glycerol (15%) was removed from an aliquot of Target Quest, Nev. (Amsterdam, Netherlands) frozen phage library stock ($4 \times 10^{12}$ pfu in 750 μl per tube) by adding ⅕ vol. (150 μl) of PEG solution (20% polyetheylene glycol 8000, 2.5 M NaCl, autoclaved) and leaving the tube on ice for 1 hr to precipitate the phage. The precipitated phage particles were pelleted at 4000 rpm for 15 min at 4° C., then resuspended into 500 μl PBS, pH 7.4. IFNγ-coated immunotube was washed 3×s with 4 ml PBS and blocked with 4 ml 2% MPBS at RT for 1 hr on Nutator. At the same time, 500 μl 4% MPBS was added to the phage suspension and incubated for 30 min-1 hr at room temperature to allow pre-blocking of the phage particles. The blocked immunotube was washed with 2×PBST(0.1% Tween20 in PBS) and 2× with PBS. The pre-blocked phage mixture was added to the washed immunotube containing 3 ml of 2% MPBS. After 30 minutes of incubation on a rotator followed by 1.5 hr of standing incubation at room temperature, the phage mixture was discarded. The tube was washed first 20× with PBST, then 20× with PBS. The bound phage particles were eluted by incubation with 1 ml of specific elution reagent (hIFNγ, GPNA, RDMA, BSMA, or rhIFNγ R1, respectively) at 1 μM in 0.4% MPBS, pH 7.4 for 90 min on a rotator. The eluted phage particles were transferred to sterile 50 ml conical polypropylene tube and stored on ice. About 20 μl of each phage elution was set aside for titering. For amplification, the remaining eluted phage particles were added to a 50 ml conical tube containing 5 ml of TG1 culture ($OD_{590}$ about 0.5) and 4 ml 2×YT. The IFNection mixture was incubated at 37° C. without shaking for 30 min, then spun at 3500 rpm for 20 min. The cell pellet was suspended into 1500 μl 2×YT-AG broth and plated 300 μl/plate on five SOBCG plates. The plates were incubated at 30° C. overnight. After 20 hours of incubation, the cells were recovered with cell scraper from the plates, to which 4 ml per plate of 2×YT-AG were added. The step was repeated three times. A small portion of the recovered cells was used for phage rescue (see below). The remaining cell suspension was spun at 3500 rpm for 20 min. The cell pellet was suspended into ½ volume of the pellet size of 50% glycerol to make glycerol stocks and stored at −80° C.

Phage rescue from amplified cell suspension was performed as follows. About 0.5 ml of recovered plated-amplified cell suspension was used to inoculate 50 ml of 2×YT-AG to $OD_{590}$ about 0.3. The culture was incubated at 37° C. on a shaker to $OD_{590}$ 0.5. 10 ml of the culture was IFNected with 1 ml of M13KO7 helper phage (GIBCO BRL, catalog # 18311-019, $1.1 \times 10^{11}$ pfu/ml) at M.O.I. 20. and incubate in the incubator at 37° C. for 30 min. The IFNected cells were spun down at 4000 rpm for 20 min. The cell pellet was re-suspended into 50 ml of 2×YT-AK, transferred to a 250-ml flask and incubated at 30° C. with shaking at 270 rpm for 20 hours. The over-night culture was spun at 4000 rpm for 20 min to removal cell debris. The supernatant was centrifuge again to ensure the removal of cell debris. About ⅕ volume of PEG solution (20% PEG 8000, 2.5 M NaCl) was added to the supernatant to precipitate the phage particles. The mixture was incubated on ice for at least 1 hour, then centrifuged at 4000 rpm for 20 min to collect the precipitated phage particles. The phage pellet was re-suspended into 1 ml of PBS and transferred to a microfuge tube. The phage suspension was left on ice for 1 hour to allow complete suspension of phage particles, then spun at 14,000 rpm for 2 min to remove the residual cell debris. Phage precipitation step was repeated. The final phage pellet was suspended into 1.1 ml of PBS and left on ice for an extended period to ensure complete suspension of phage particles. The phage suspension was centrifuged at 14,000 rpm for 2 min to remove residual cell debris. 500 μl of rescued phage suspension was used to make a glycerol stock by addition of 250 μl of 50% glycerol. 100 μl of rescued phage suspension was reserved for phage pool ELISA (see below). The remaining 500 μl of the rescued phage was used for next round of panning.

Phage Pool ELISA

Phage pool ELISA was performed as follows: *E. coli* expressed hIFNγ was plated, 100 μl/well, at 0.39 μg/ml in 0.1 M Na carbonate, pH 9.6 in Nunc MaxiSorb Immuno plate at room temperature with gentle rocking for 2 hrs. The coated plate was washed 3 times with PBS, then blocked with 300 μl/well of 2% MPBS at room temperature on the rocker for one hour. For negative control, another Nunc Immuno plate which has not been coated with the antigen was also blocked with 2% MPBS. Meanwhile, 120 μl of each rescued phage pool with was pre-blocked with 120 μl of 0.8%MTBS in a 96-well Costar 3790 plate and left at room temperature until ready to use. Both blocked plates were washed 5 times with 0.1%TBST (TBS: 10 mM Tris-HCl, pH 7.5, 1 mM EDTA, 150 mM NaCl; Tween-20. 0.1%). Pre-blocked phage dilution was distributed (100 μl/well) to both antigen-coated plate and the negative control plate, and incubated at room temperature on rocker for one hour. After the plates were washed as described, 100 μl/well of 1:1000 fold diluted HRP/Anti-M13 monoclonal Conjugate (Amersham Pharmacia Biotech, catalog number 27-9421-01) in 0.4% MTBS was distributed, and incubated at room temperature on rocker for one hour. The plates were washed as described. After 100 μl/well of the substrate 1-Step™ ABTS (Pierce, catalog number 37615) was added, the plates were incubated for one hour. $OD_{405}$ was measured for signal detection. ELISA positive phage pools were used as the source of individual clones for further analysis.

EXAMPLE 3

Identification of IFNγ Binding Fab Phage Clones

DNA Fingerprinting

Polymerase chain reaction (PCR) was performed in a 96-well Thermowell plate in order to identify full-length clones containing both heavy chain and light chain from ELISA positive phage pools. Typically, each well contains 25 μl of PCR reaction mix (2.5 μl 10×PCR buffer, 21.625 μl water, 0.25 μl dNTPs at 25 mM, 0.25 μl primer 870-02 (shown below) at 10 pmol/μl, 0.25 μl primer 2182-83 (shown below) at 10 pmol/μl, 0.125 μl Taq polymerase at 5 units/μl).

870-02 5'-CCG ACT TTG CAC CTA GTT (SEQ ID NO:109)

2182-83 5'-TTT GTC GTC TTT CCA GAC GTT AGT (SEQ ID NO:110)

Individual colonies were picked and resuspended first into a well in the PCR plate, then resuspended into the corresponding well in a 96-deep well block filled with 300 μl/well of 2×YT-AG broth (2×YT broth: 10 g yeast extract, 16 g bacto-tryptone, 5 g NaCl per liter of water containing 100 μg/ml ampicillin and 2% glucose). The PCR reaction conditions were one denature cycle of 5 min at 94° C., 40 cycles of 45 sec at 94° C., 45 sec at 55° C., 1.5 min at 72° C., followed by one extension cycle at 72° C. for 10 min. After completion of PCR reaction, 3 μl/well of PCR reaction mixture were run on a 1% extra long 4×(24+2) TAE gels containing 0.5 ul/ml ethidium bromide (Embi Tec, catalog # GE-3820) at 120 volts for one hour. By comparison to the 1 kb plus DNA ladder (Gibco BRL, catalog # 10787-018), clones with inserts greater than 1.6 kb were identified as full-length clones.

Identification of unique full-length clones was performed as follows: BstNI digestion was performed on PCR amplified inserts of the identified full-length clones. To 16 μl of PCR reaction mixture per sample in a 96-well Thermowell plate, 14 μl of BstNI digestion master solution containing 3 μl 10×Buffer 2 (NEBL), 0.3 μl BSA at 10 mg/ml, 10 μl water and 0.7 μl BstNI (NEBL) was added. The plates were incubated at 60° C. for 3 hours. Digested samples, 13 μl each, were run on 4% extra long 2×(24+2) TAE gels containing 0.5 ul/ml ethidium bromide (Embi Tec, catalog # GE-3817) at 100 volts for 3 hours. Unique clones were identified based on the difference in BstNI fragment patterns.

Clonal Phase ELISA

Fab phages of identified unique full-length clones were rescued in the 96-well format. In 96-well 2-ml deep-well block, 480 μl/well 2×YTAG broth was inoculated with 20 μl of overnight cultures of the selected unique full-length clones, then incubated at 37° C., 300 rpm for 3 hours. To each well, 100 μl of 1:10 diluted M13KO7 helper phage dilution were added to IFNect the cells. The block was incubated at 37° C. without shaking for 30 minutes, then shaken gently for another 30 minutes at 150 rpm. The block was centrifuged at 3600 rpm for 20 minutes to pellet the IFNected cells. The cell pellet in each well was suspended into 480 μl of 2×YTAK (2×YT broth containing 100 μg/ml ampicillin and 40 μg/ml kanamycin), then incubated at 30° C. overnight for about 20 hours. The cell debris was separated by centrifugation at 3600 rpm for 20 minutes. The rescued phage supernatant was carefully transfer into another sterile 96-well block. The rescued phages were used to perform clonal phase ELISA exactly the same as described in Example 2, Phage pool ELISA. Clones that give ≧0.2 net $OD_{405}$ were considered as IFNγ-binding candidates.

Large Scale Phage Rescue ELISA

Specific IFNγ-binding of the identified unique Fab phage clones was confirmed by demonstration of concentration-dependent Fab phage binding to IFNγ in ELISA. Fab phages were obtained by large scale rescue.

Large-scale rescue of individual clones was performed as follows: Fab phages of identified unique IFNγ-binding clones were rescued in large scale. In a 250-ml sterile flask, 50 ml of 2×YT-AG broth was inoculated with 200 μl of overnight culture of the selected IFNγ-binding clone, and incubated at 37° C., 2700 rpm until the $OD_{590}$ of the culture reacheed 0.5. Five ml of M13KO7 helper phage (GIBCO BRL, catalog #18311-019, 1.1×10$^{11}$ pfu/ml) were added to infect the cells at M.O.I of 20. The cell/helper phage mixture was incubated at 37° C. without shaking for 30 minutes, then centrifuged at 4000 rpm for 20 minutes to pellet the infected cells. The cell pellet was suspended in 50 ml of 2×YTAK broth (2×YT broth containing 100 µg/ml ampicillin and 40 µg/ml kanamycin), then incubated at 30° C. with shaking at 270 rpm overnight for about 20 hours. The overnight culture was centrifuged at 4000 rpm for 20 minutes to remove the cell debris. The supernatant was centrifuged again to ensure the removal of cell debris. To the supernatant, 10 ml (⅕ vol.) of PEG solution (20% PEG 8000, 2.5 M NaCl) was added to precipitate the phage particles. The mixture was incubated on ice for at least 1 hour, and centrifuged at 4000 rpm for 20 min to collect the precipitated phage particles. The phage pellet was re-suspended in 1 ml of PBS and transferred to a microfuge tube. The phage suspension was left on ice for 1 hour to allow complete suspension of phage particles, then spun at 14,000 rpm for 2 min to remove the residual cell debris. Phage precipitation step was repeated. The final phage pellet was suspended into 1 ml of PBS and left on ice for an extended period to ensure complete suspension of phage particles. The phage suspension was centrifuged at 14,000 rpm for 2 min to remove residual cell debris. The final phage suspension was stored at 4° C. Phage ELISA was performed as described in Example 2, phage pool ELISA. At least six different concentrations of large-scale rescued phages, typically from 1×10$^9$ pfu/well to 1×10$^{11}$ pfu/well, were added to the corresponding wells.

Figure 2:
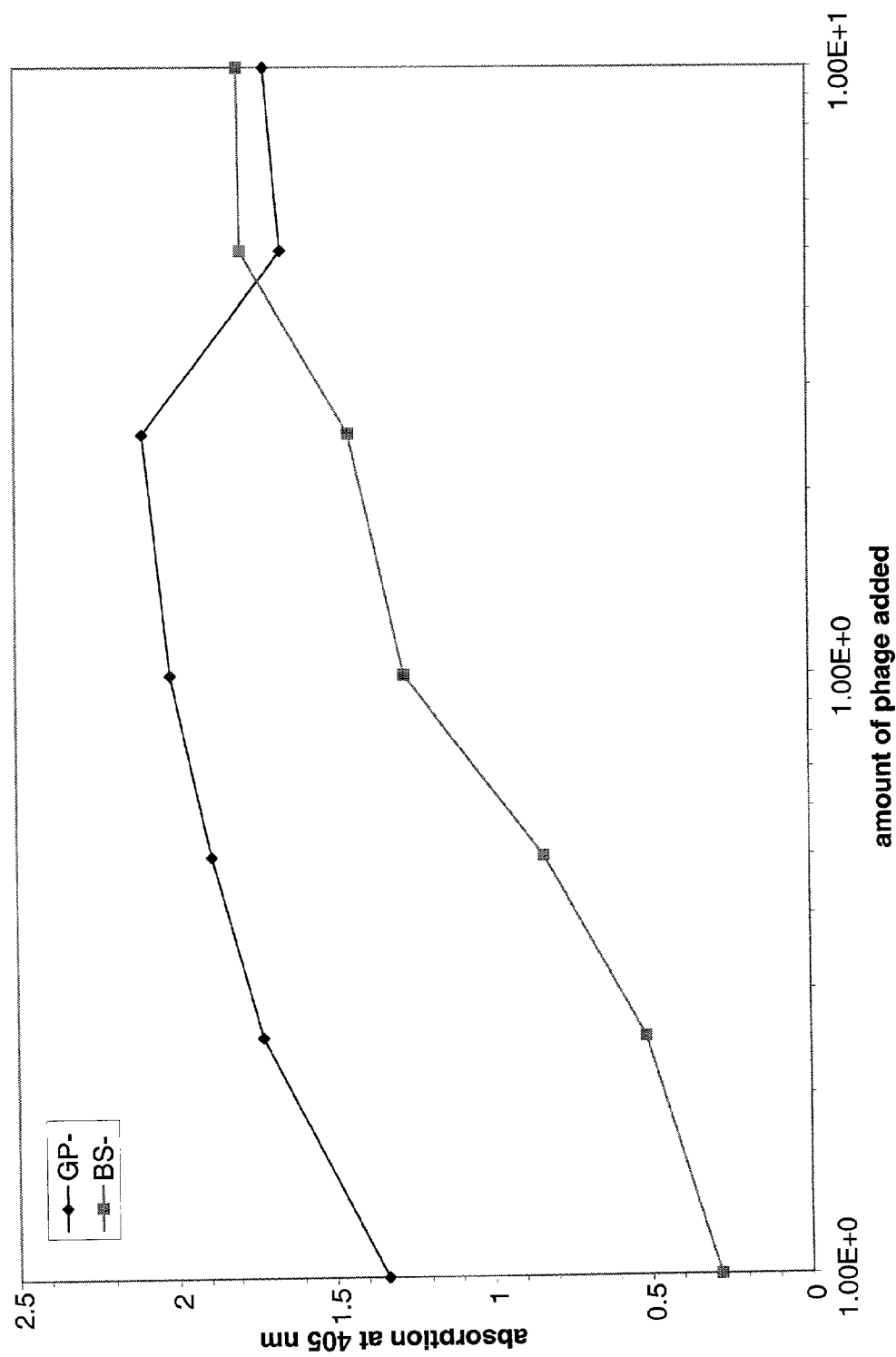
FIG. 2 is a graph depicting the results of a dose dependent clonal phage ELISA of predominant Fabs "GP-A" and "BS-B" clones for reactivity to hIFNγ. Phage dilutions were performed using a maximum of 100 μl of phage suspension pre-blocked with 2% MPBS per well to given a typical range of $10^9$–$10^{11}$ phage/well in the ELISA. Phage stocks for ELISA were prepared as described in Example 3. Values were from single point determinations and $OD_{405}$ was measured for signal detection.

A total of eleven Fab clones were identified. Fab clones "IFN-A", "57E", and "57D" were identified from phage pool with *E. coli* hIFN-γ elution. Fab clones "GP-A" and "58C" were identified from phage pool with GPNA elution. Fab clones "RD-A2", "RD-B" and "59-A2" were identified from phage pool with RDMA elution. Fab clones "BS-A" and "BS-B" were identified from phage pool with BSMA elution. Fab clone "67C" was identified from phage pool with hIFN-γ R1 elution. Concentration dependent clonal phage ELISA of nine unique clones was performed on large-scale rescued phage preparations and illustrated in FIG. 1 and FIG. 2. These Fab phages can be grouped into three groups based on their ELISA profiles. Group A includes Fab clones "GP-A" and "BS-B". These two Fab phages are strong binders, with ELISA signals reaching saturation at 5E9 pfu/well. Group B includes Fab clones "BS-A", "RD-A2", "INF-A" and "57E". These are strong to moderate binders that show good concentration-dependent binding curves. Group C includes Fab clones "57D", "58C", "RD-B" and "67C". These are weak yet specific and concentration-dependent binders of IFNγ.

Sequence Analysis of Fab Clones

Confirmation of unique IFNγ binding Fab phage clones was performed as follows: Plasmid DNAs of representatives of each unique Fab BstNI digestion pattern were prepared using QIAfilter™ Plasmid midi kit (Qiagen, catalog #12245) and sent for sequencing. Sequences of all Fab BstNI patterns confirmed their uniqueness and revealed their individual heavy chain and light chain sequence (see FIGS. 3–24).

The DNA and predicted amino acid sequences for the heavy chains of Fabs "BS-A", "BS-B", "RD-B1", "RD-A2", "58C", "GP-A", "57D", "57E", "IFN-A", "67C" and "59-A2" (SEQ ID Nos:65–86, respectively) were shown in FIGS. 3–13, respectively. The DNA and predicted amino acid sequences for the light chains of Fabs "BS-A", "BS-B", "RD-B1", "RD-A2", "58C", "GP-A", "57D", "57E", "IFN-A", "67C", and "59-A2" (SEQ ID Nos:87–108, respectively) were shown in FIGS. 14–24, respectively. The amino acid sequences of the heavy chains and the light chains of all eleven Fabs were compared, as shown in FIG. 31. GCG's "BestFit" program was used to obtain percentage of identity and similarity between each pair of Fabs. The closest matches in the heavy chains are in "BS-A", "RD-A2" and "IFN-A". The heavy chain sequences of "BS-A" and "RD-A2" have identical framework and CDR1 and CDR2. They differ only in CDR3, and have 92.6% identity and 93.4% similarity. With the exception of the 1$^{st}$ amino acid, the heavy chain sequences of "BS-A" and "IFN-A" have identical framework and CDR1 and CDR2 and different CDR3. They share 93.5% identity and 95.1% similarity. The same is true for the heavy chain sequences of "IFN-A" and "RD-A2", with identity of 90.5% and similarity of 92.1%. The Amino acid sequence of heavy chain of Fab "57E" shows 88.1% identity and 89.0% similarity to the heavy chain sequence of "BS-A", 88.8% identity and 90.0% similarity to the heavy chain sequence of "RD-A2", and 89.0 identity and 90.7% similarity to the heavy chain sequence of IFN-A. The Amino acid sequence of heavy chain of Fab "BS-B" shows 88.6% identity and 90.4% similarity to the heavy chain sequence of "57D", 81.7% identity and 83.3% similarity to the heavy chain sequence of "GP-A", and 83.9% identity and 84.7% similarity to the heavy chain sequence of 58C. The closet matches in the light chains are between "59-A2" and "BS-A" with 90.8% identity and 91.7% similarity, between "BS-A" and "BS-B" with 89.0% identity and 90.9% similarity, between "57E" and "BS-A" with 88.2% identity and 90.9% similarity, between "57E" and "BS-B" with 89.7% identity and 91.5% similarity, and between "59-A2" and"BS-B" with 88.2% identity and 88.2% similarity. Only three pairs of Fabs, "59-A2"/"BS-B", "57E"/"BS-A" and "IFN-A"/"RD-A2", are closely matched in both heavy chain and light chain.

A comparison of amino acid sequences of complementary determining regions (CDRs) is shown in FIG. 25. The heavy-chain CDR3s of the eleven anti-IFNγ Fabs share little similarities. The Fabs can be grouped according to the similarities of either the heavy chain CDRs or the light chain CDRs, as shown in FIG. 32. Clones "BS-A", "IFN-A" and "RD-A2" have identical heavy chain CDR1 and CDR2. However, beside the same last three residues (FDY), their heavy chain CDR3s are very different. Interestingly, IFN-A and RD-A2 also share closely matched light chain CDR1 (11/16 identical residues), CDR2 (5/7 identical resudes), and CDR3 (8/9 identical residues). Clones "BS-B", "59-A2", "GP-A", and "57D" have similar heavy chain CDR1 and CDR2. Clones "BS-B" and "59-A2" have identical heavy chain CDR1 and CDR2, yet very different heavy chain CDR3. All three light chain CDRs of clones "59-A2", "BS-A", "BS-B" and "57E" are very similar.

EXAMPLE 4

Expression and Purification of Soluble Fabs

*E. coli* strain HB2151 (Pharmacia) was transformed with plasmid DNA of a unique binder. Overnight cultures of the transformed HB2151 were grown in 2×YT-AG broth at 30° C. 750 ml of 2×YT containing 100 µg/ml ampicillin and 0.1% glucose were inoculated with 7.5 ml of overnight culture and incubated at 37° C. with shaking (270 rpm) for about 2 hours. When OD$_{590}$ reached 0.8–1.0, IPTG was added to 1 mM for induction. The culture was continued to grow at 30° C. for 4 hours while shaking. The culture was centrifuged at 4000 rpm for 20 min and the supernatant was discarded. Periplasmic release of Fab was achieved using Osmotic shock approach. Cells were suspended in 8 ml of ice cold TES (0.2 M Tris, 0.5 mM EDTA, 17.1% sucrose, pH 8.0) and incubated on ice for 5–10 min with occasional gentle shaking. The empty tube was rinsed with 8.8 ml TES/H$_2$O (1:3), which was pooled to the cell suspension.

The cell suspension was incubated on ice for another 20 min, and centrifuged at 4,000 rpm for 15 min. The supernatant was carefully transferred into another tube and centrifuged again at 8000 rpm for 20 min. The resulted supernatant was the TES-released periplasmic fraction. The cell pellet was resuspended in 10 ml TES/15 mM MgSO$_4$, incubated on ice for 15 min, then centrifuged twice as described above. The final supernatant was the Mg-released periplasmic fraction and was pooled together with the TES-released periplasmic fraction.

BSA was added as a carrier and stabilizer to the periplasmic fraction to a final concentration of 1 mg/ml. The periplasmic fraction was dialyzed with one change against 2 L of sonification buffer (20 mM Tris-HCl/0.1M NaCl, pH 8.5) plus protease inhibitors at 4° C. The periplasmic fraction was added to $\frac{1}{10}^{th}$ volume of pre-equilibrated TALON resin (Clontech) and incubated at 4° C. with gentle rocking for 1 hour. The resin mixture was centrifuged at 1300 rpm for 3 min, and the supernatant was removed as much as possible. The resin was wash with 10 volumes of sonification buffer, then centrifuged at 1300 rpm for 3 min. The supernatant was discarded. The washed resin was suspended into one bed volume of sonification buffer and packed into a column, which was washed with three bed volumes of sonification buffer. The Fab was eluted with 2 bed volumns of 200 mM imidazole. Purified Fab was dialyzed into PBS, pH 7.4.

EXAMPLE 5

Cloning and Expression of Full-length Human IFNγAntibodies

FAb clones were converted to full-length antibodies by the following procedures.

Construction of pDSRα19:hIgG1 CH

The plasmid pDSRα19:anti human OPGL IgG1 was digested with HindIII and BsmBI to remove the coding region for anti-human OPGL variable region. The linear plasmid pDSRα19:hIgG1 CH containing the 1.0 kbp human IgG1 constant region domain (C$_H$1, hinge, C$_H$2 and C$_H$3 domains) was gel isolated and used to accept FAb derived anti IFN-gamma variable regions.

Construction of pDSRα19:Anti-IFN Gamma BS-A Heavy Chain

The anti-IFN-gamma FAb heavy chain cDNAs were cloned into pDSRα19:hIgG1 CH to convert the FAbs into full length IgGs. The construction of a plasmid encoding "BS-A" heavy chain is described here. The other FAb heavy chains were cloned using similar procedures. To generate the FAb with a signal sequence, a three-step PCR was performed. First, primers 2485-51 (shown below) and 2465-68 (shown below) were used with the FAb cDNA template. Conditions were: 94° C. for 1 min, (94° C. for 20 sec., 48° C. for 30 sec., 74° C. for 30 sec.) for 4 cycles, (94° C. for 20 sec., 66° C. for 30 sec., 74° C. for 30 sec.) for 25 cycles and 74° C. for 5 min. with Pfu polymerase and the appropriate buffer and nucleotides. The PCR product was then amplified with primers 2148-98 (shown below) and 2465-68 (shown below) followed by amplification with primers 2489-36 (shown below) and 2465-68 (shown below). The final PCR product was Qiagen purified, cut with HindIII and BsmBI, and Qiagen purified. This fragment containing the FAb with a 5' Kozak (translational initiation) site and the following signal sequence for mammalian expression:

MDMRVPAQLLGLLLLWLRGARC (SEQ ID NO:111), was ligated into pDSRα19:hIgG1 CH.

2489-36
(SEQ ID NO:112)
5'-CAG CAG AAG CTT CTA GAC CAC CAT GGA CAT GAG GGT CCC CGC TCA GCT CCT GGG 2148-98
(SEQ ID NO:113)
5'-CCG CTC AGC TCC TGG GGC TCC TGC TAT TGT GGT TGA GAG GTG CCA GAT 2485-51
(SEQ ID NO:114)
5'-G TGG TTG AGA GGT GCC AGA TGT CAG GTG CAG CTG CAG GAG-3'

2465-68
(SEQ ID NO:115)
5'-GT GGA GGC ACT AGA GAC GGT GAC CAG GGT 3'

Construction of pDSRα19: Anti-IFN Gamma BS-A Heavy Chain

The FAb light chain cDNAs were cloned into pDSRα19 to convert the FAbs into full-length antibodies. The construction of a plasmid encoding the "BS-A" light chain is described here. The other FAbs were cloned using similar procedures. To generate FAb "BS-A" with a signal sequence, a three-step PCR was performed. First, primers 2525-43 (shown below) and 2578-27 (shown below) were used with the FAb cDNA template. The PCR conditions were: 94° C. for 1 min, (94° C. for 20 sec., 48° C. for 30 sec., 74° C. for 30 sec.) for 4 cycles, (94° C. for 20 sec., 66° C. for 30 sec., 74° C. for 30 sec.) for 25 cycles and 74° C. for 5 min. with Pfu polymerase and the appropriate buffer and nucleotides. The PCR product was then gel purified and then amplified with primers 2148-98 (shown below) and 2578-27 (shown below). Second, primers 2578-26 (shown below) and 2469-67 (shown below) were used again with the FAb cDNA template. The PCR conditions were: 94° C. for 1 min, (94° C. for 20 sec., 48° C. for 30 sec., 74° C. for 30 sec.) for 4 cycles, (94° C. for 20 sec., 66° C. for 30 sec., 74° C. for 30 sec.) for 25 cycles and 74° C. for 5 min. with Pfu polymerase and the appropriate buffer and nucleotides. The PCR product was gel isolated and re-amplified using the same conditions. Finally, the gel isolated PCR products were mixed and amplified with primers 2489-36 (shown below) and 2469-67 (shown below). The final PCR product was Qiagen purified, cut with XbaI and SalI, and Qiagen purified. This fragment containing the FAb with a 5' Kozak (translational initiation) site and the following signal sequence for mammalian expression:

MDMRVPAQLLGLLLLWLRGARC (SEQ ID NO:111), was ligated into pDSRα19.

2489-36
(SEQ ID NO:116)
5'-C AGC AGA AGC TTC TAG ACC ACC ATG GAC ATG AGG GTC CCC GCT CAG CTC CTG GG-3'

-continued 2525-43
(SEQ ID NO:117)
5'-TGG TTG AGA GGT GCC AGA TGT AAT TTT ATG CTG ACT
CAG CCC-3'

2578-27
(SEQ ID NO:118)
5'GGC CGC GTA CTT GTT GTT GCT TTG TTT GGA G-3'

2148-98
(SEQ ID NO:119)
5'-CC GCT CAG CTC CTG GGG CTC CTG CTA TTG TGG TTG
AGA GGT GCC AGA T-3'

2578-26
(SEQ ID NO:120)
5'-AGC AAC AAC AAG TAC GCG GCC AGC AGC TAC-3'

2469-67
(SEQ ID NO:121)
5'-GA AGT CGA CTA TGA ACA TTC TGT AGG AGC-3'

Antibody Preparation

Expression vectors containing cDNA encoding heavy and light chain full-length antibodies were transfected into CHO cells and cultured under conditions to allow expression of heavy and light chains and secretion into the cell media. The conditioned media was filtered through a 0.45 μm cellulose acetate filter (Corning, Acton, Mass.) and applied to a Protein G sepharose (Amersham Pharmacia Biotech, Piscataway, N.J.) column which had been equilibrated with PBS—Dulbecco's Phosphate Buffered Saline without calcium chloride and without magnesium chloride (Gibco BRL Products, Grand Island, N.Y.). After sample application the column was washed with PBS until absorbency at 280 nm reached baseline. Elution of protein was achieved using 100 mM Glycine, pH 2.5. Fractions were collected and immediately neutralized by addition of 1M Tris-HCl, pH 9.2. Antibodies were detected by SDS-polyacrylamide gels visualized by Commassie staining.

Fractions containing antibody were pooled, concentrated and diafiltered into PBS using either Centricon 10 (Amicon) or for larger volumes Centriprep 10 (Amicon).

The isolated antibody was characterized by gel filtration on Superose 6 (Amersham Pharmacia Biotech, Piscataway, N.J.) and was shown to run as a monomeric IgG.

EXAMPLE 6

Affinity Measurements of Fab and IgG

The binding constant (Kd), the on rate constant (ka) and off rate constant (kd) were determined by surface plasmon resonance techniques (BIAcore, Pharmacia, Piscataway, N.J.). BIAcore analysis of Fab and antibody was performed as follows: The experiments were carried out using BIACORE 2000 (BIACORE Inc.) at room temperature. CHO expressed hIFNγ was immobilized on a CM5 chip. The Fab or Fab IgG at various concentrations were injected over the hu-IFNγ surface. The data was analyzed using BIAEVALUATION 3.1 software (BIACORE, Inc.). The results are shown in FIG. 30.

EXAMPLE 7

Activity Measurements of Fab and IgG

BIAcore Neutralization Assay

Figure 29:
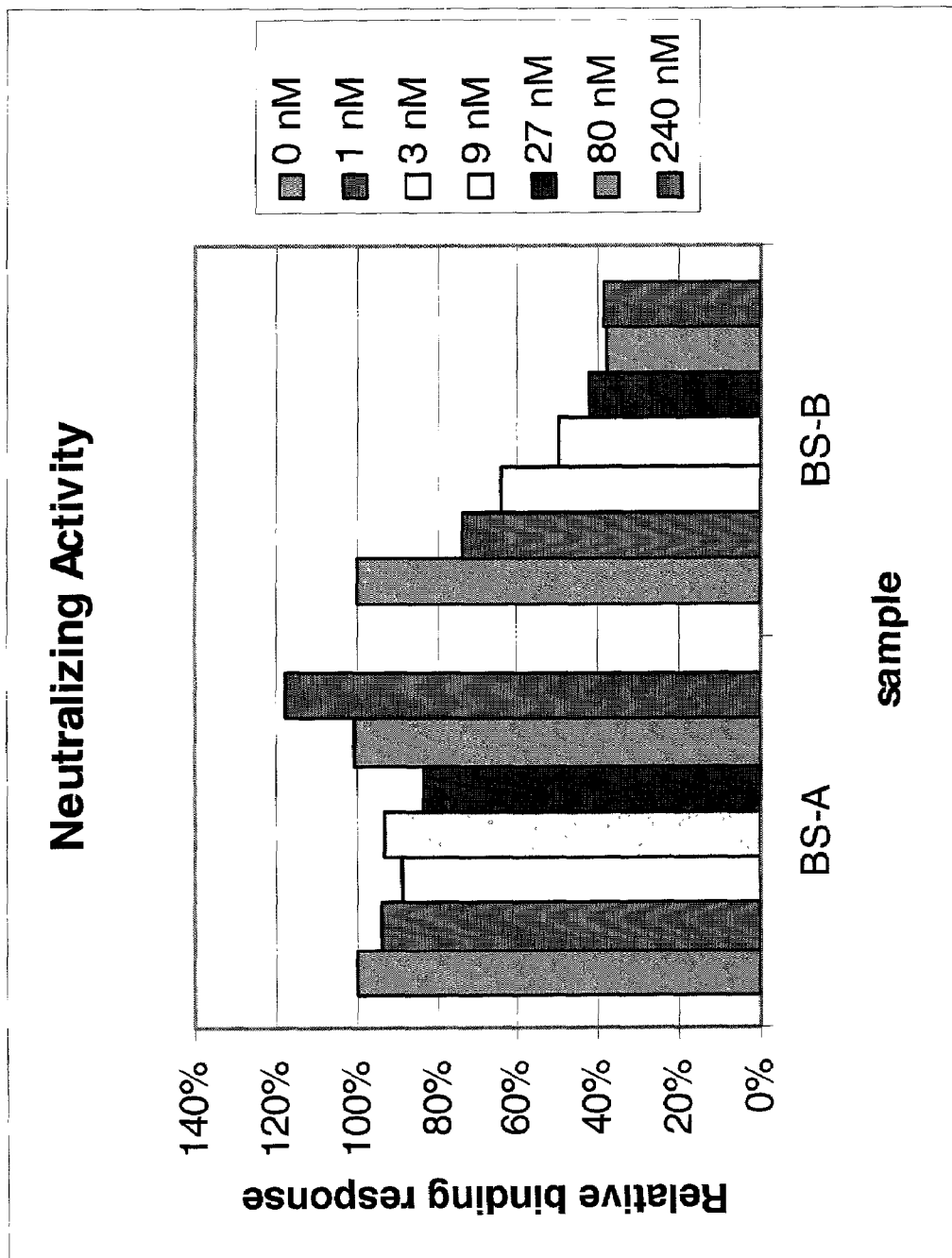
FIG. 29 is a graph depicting the neutralization activity of "BS-A" IgG and "BS-B" IgG as measured by BIACore. Relative binding response (%) is plotted vs. concentration of sample (nM).

Neutralization activity of of Fab converted IgGs was tested on BIAcore (see Example 6). The results are shown in FIG. 29. A concentration depedent inhibition of hu IFNγ binding to IFNγ-R1 with an IC50 of 9 nM was observed for BS-B IgG.

A549 Cell Proliferation Assay

Figure 26:
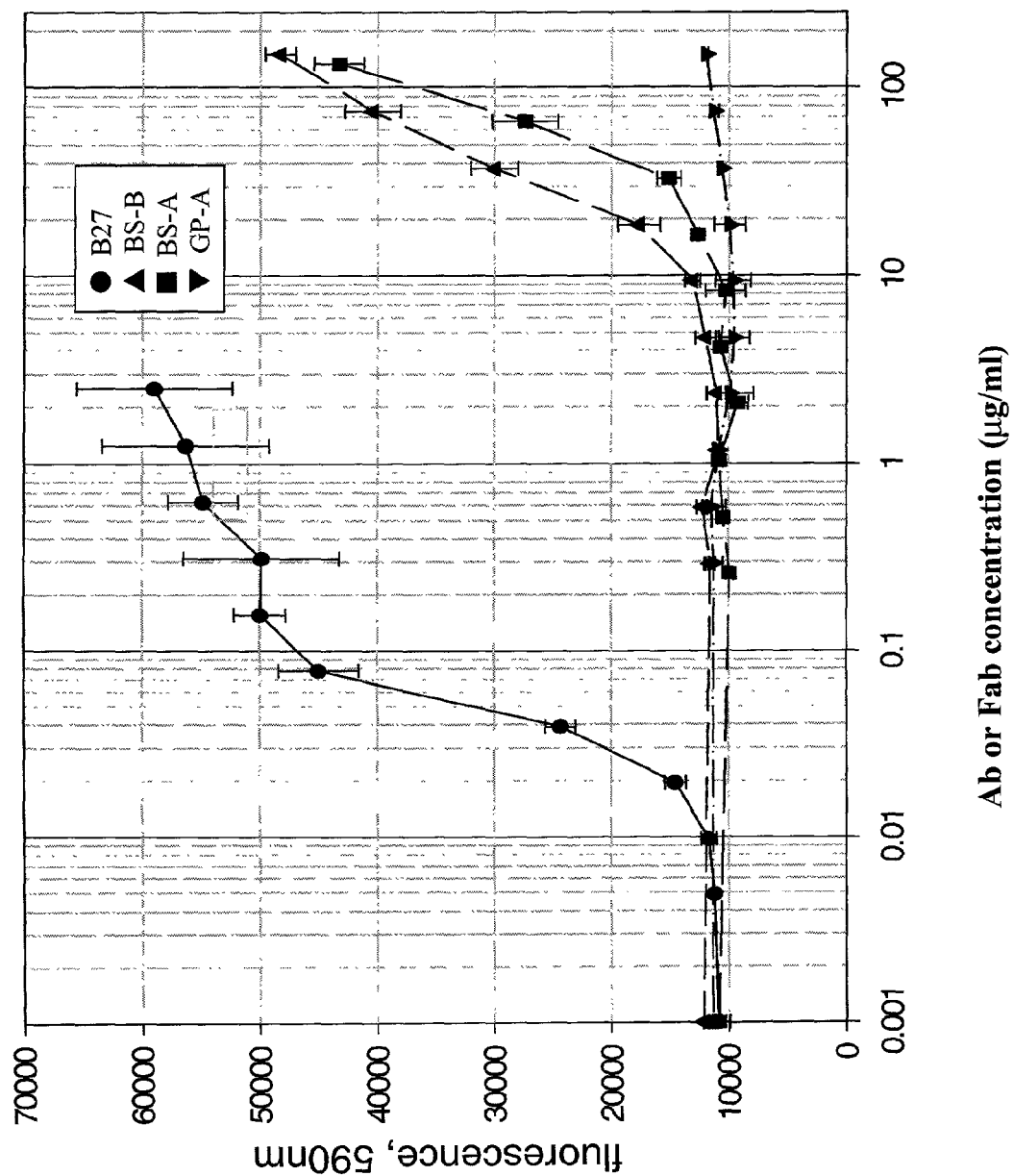
FIG. 26 is a graph depicting the neutralization activity of Fabs "BS-A" and "BS-B" as measured in the A549 cell assay. Fabs were purified as described in Example 4 and added at Fab concentrations ranging from 0.3–150 μg/ml. Pharmingen B27 Ab (concentrations ranging from 0.01–5 μg/ml) was used as a positive control. Cells were stained with Alamar Blue 5 days post treatment, and analyzed 4 hours post staining on a FL500 plate reader.
Figure 27:
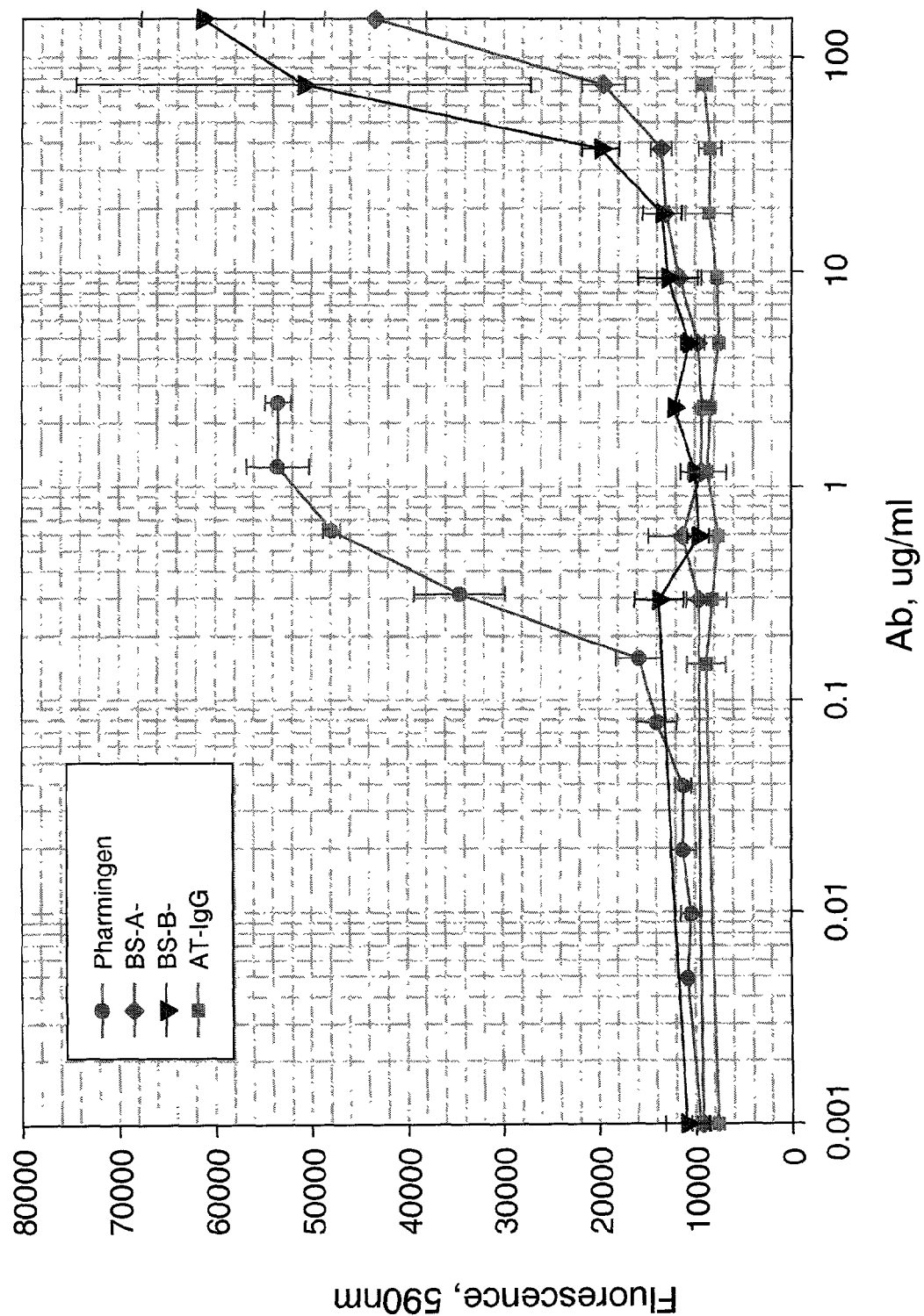
FIG. 27 is a graph depicting the neutralization activity of "BS-A" IgG and "BS-B" IgG as measured in the A549 cell assay. IgGs were purified as described in Example 4 and added at IgG concentrations ranging from 0.1–100 μg/ml. Pharmingen B27 Ab (concentrations ranging from 0.01–5 μg/ml) was used as a positive control. An irrelevant Ab, AT-IgG (concentrations ranging from 0.01–5 μg/ml), that does not react with hIFNγ was used as a negative control. Cells were stained with Alamar Blue 5 days post treatment, and analyzed 4 hours post staining on a FL500 plate reader.

Neutralization activity of Fab and IgG measured in A549 proliferation assay (described in Example 1) was performed as follows: A549 cells were treated with a mixture of a targeted Fab or IgG (various concentrations) and CHO expressed hIFNγ (2 ng/ml or 5 ng/ml). Fab concentrations ranged from 0.3–150 μg/ml. IgG concentrations ranged from 0.1–100 μg/ml. Positive control Ab (Pharmingen B27) concentrations ranged from 0.01–5 μg/ml. Cells were stained with Alamar Blue 5 days post treatment, and analyzed 4 hours post staining on an FL500 plate reader. The results are shown in FIG. 26 for BS-A Fab, BS-B Fab and GP-A Fab and in FIG. 27 for BS-A IgG and BS-B IgG. BS-A Fab and BS-B Fab in FIG. 26 and BS-A IgG and BS-B IgG in FIG. 27 were shown to have neutralization activity, measured as proliferation activity, at high concentrations, about two orders of magnitude higher than the positive control.

While the present invention has been described in terms of preferred embodiments, it was understood that variations and modifications will occur to those skilled in the art. Therefore, it was intended that the appended claims cover all such equivalent variations which would come within the scope of the invention as claimed.

What is claimed is:

1. An isolated antibody or antibody fragment that includes an antigen binding region comprising all or part of a heavy chain variable region consisting of an amino acid sequence at least 90% identical to at least one of the following sequences: SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NQ:84, and SEQ ID NO:86;
   wherein the antigen binding region binds to an interferon gamma protein.

2. The antibody or antibody fragment of claim 1, wherein the antigen binding region further comprises a kappa or lambda light chain or a fragment thereof comprising a light chain variable region.

3. The antibody or antibody fragment of claim 1 further comprising a human Fc region.

4. The antibody or antibody fragment of claim 1, wherein the heavy chain variable region comprises a CDR3 comprising a sequence selected from the group consisting of:
   GRARNWRSRFDY (SEQ ID NO:54);
   TSWNAGGPIDY (SEQ ID NO:55);
   DRVGYSSSLLDY (SEQ ID NO:56);
   DKGSRITIFGVVGSAGFDY (SEQ ID NO:57);
   LLLYEGFDP (SEQ ID NO:58);
   DLVLTMTSRRAAFDI (SEQ ID NO:59);
   DQWGTISGNDY (SEQ ID NO:60);
   GWPTYVWGSYRPKGYFDY (SEQ ID NO:61);
   GDWGYFDY (SEQ ID NO:62);
   DADGGDYGY (SEQ ID NO:63); and
   RLVRYGGYSTGGFDV (SEQ ID NO:64).

5. The antibody or antibody fragment of claim 1, wherein the amino acid sequence is at least 98% identical to SEQ ID NO:68.

6. An isolated antibody or antigen-binding antibody fragment that includes an antigen binding region comprising all or part of a heavy chain variable region which includes a heavy chain CDR3 comprising a first amino acid sequence selected from a first group consisting of:
   GRARNWRSRFDY (SEQ ID NO:54) or a variant of this sequence comprising not more than four alterations relative to this sequence;
   TSWNAGGPIDY (SEQ ID NO:55), DRVGYSSSLLDY (SEQ ID NO:56), DQWGTISGNDY (SEQ ID NO:60), or DADGGDYGY (SEQ ID NO:63), or a variant of any one of these sequences comprising not more than two alterations relative to one of these sequences;
   DKGSRITIFGVVGSAGFDY (SEQ ID NO:57) or a variant of this sequence comprising not more than eight alterations relative to this sequence;
   LLLYEGFDP (SEQ ID NO:58) or a variant of this sequence comprising not more than one alteration relative to this sequence;
   GWPTYVWGSYRPKGYFDY (SEQ ID NO:61) or a variant of this sequence comprising not more than five alterations relative to this sequence;
   GDWGYFDY (SEQ ID NO:62); and
   RLVRYGGYSTGGFDV (SEQ ID NO:64) or DLVLTMTSRRAAFDI (SEQ ID NO:59), or a variant of one of these sequences comprising not more than six alterations relative to one of these sequences;
   wherein an alteration is the substitution, deletion, or insertion of a single amino acid; and
   wherein the antigen binding region binds to a human interferon gamma protein.

7. An isolated antibody or antigen-binding antibody fragment comprising an antigen binding region comprising an amino acid sequence as shown in FIG. 3 (SEQ ID NO:66), FIG. 4 (SEQ ID NO:68), FIG. 5 (SEQ ID NO:70), FIG. 6 (SEQ ID NQ:72), FIG. 7 (SEQ ID NO:74), FIG. 8 (SEQ ID NO:76), FIG. 9 (SEQ ID NO:78), FIG. 10 (SEQ ID NO:80), FIG. 11 (SEQ ID NO:82), FIG. 12 (SEQ ID NO:84), or FIG. 13 (SEQ ID NO:86), or an antigen-binding fragment of one of these sequences,
   wherein the antigen binding region binds to a human interferon gamma protein.

8. The antibody or antigen-binding antibody fragment of claim 7, wherein the antigen binding region further comprises an amino acid sequence as shown in FIG. 14 (SEQ ID NO:88), FIG. 15 (SEQ ID NO:90), FIG. 16 (SEQ ID NO:92), FIG. 17 (SEQ ID NO:94), FIG. 18 (SEQ ID NO:96), FIG. 19 (SEQ ID NO:98), FIG. 20 (SEQ ID NO:100), FIG. 21 (SEQ ID NO:102), FIG. 22 (SEQ ID NO: 104), FIG. 23 (SEQ ID NO: 106), or FIG. 24 (SEQ ID NO: 108), or a fragment of one of these sequences.

9. The antibody or antigen-binding antibody fragment of claim 6, further comprising a human Fc region.

10. The antibody or antigen-binding antibody fragment of claim 8, further comprising a human Fc region.

11. The antibody or antigen-binding antibody fragment of claim 10, wherein the antigen binding region consists of part or all of both amino acid sequences in a pair of amino acid sequences, wherein the pair is selected from the group consisting of:

SEQ ID NO:66 and SEQ ID NO:88;
SEQ ID NO:68 and SEQ ID NO:90;
SEQ ID NO:70 and SEQ ID NO:92;
SEQ ID NO:72 and SEQ ID NO:94;
SEQ ID NO:74 and SEQ ID NO:96;
SEQ ID NO:76 and SEQ ID NO:98;
SEQ ID NO:78 and SEQ ID NO:100;
SEQ ID NO:80 and SEQ ID NO:102;
SEQ ID NO:82 and SEQ ID NO:104;
SEQ ID NO:84 and SEQ ID NO:106; and
SEQ ID NO:86 and SEQ ID NO:108.

12. The antibody or antigen-binding antibody fragment of claim 11, wherein the antigen binding region consists of all or part of SEQ ID NO:68 and SEQ ID NO:90.

13. The antibody or antigen-binding antibody fragment of any one of claims 3, 9, and 10 wherein the isotype of the antibody is selected from the group consisting of IgG, IgM, IgA, IgE and IgD.

14. The antibody or antigen-binding antibody fragment of claim 13 wherein the isotype is IgG$_1$, IgG$_2$, IgG$_3$ or IgG$_4$.

15. A pharmaceutical composition comprising the antibody or antigen-binding antibody fragment of any of claims 7, 1, and 6, and a pharmaceutically acceptable carrier.

16. A method for treating inflammation associated with an inflammatoiy condition, the method comprising administering to a mammal an effective amount of the composition of claim 15.

17. A method for treating inflammation associated with an auto-immune disease, the method comprising administering to a mammal an effective amount of the composition of claim 15.

18. The method of claim 17, wherein the autoimmune disease is selected from the group consisting of psoriasis, rheumatoid arthritis, juvenile rheumatoid arthritis, inflammatory bowel disease, and systemic lupus erythematosus.

19. The antibody or antigen-binding antibody fragment of claim 6, wherein the antigen binding region further comprises all or part of a light chain variable region which includes a light chain CDR3 comprising a second amino acid sequence selected from a third group of sequences or a variant of such a sequence, wherein the third group consists of:
QSYDSSNQWV (SEQ ID NO:23);
QSYDGSAWV (SEQ ID NO:24);
QSYDRNSLV (SEQ ID NO:25);
MQALQLPPT (SEQ ID NO:26);
MQATQLPYT (SEQ ID NO:27);
YSAADNRGV (SEQ ID NO:28);
QVWDGSSDQRV (SEQ ID NO:29);
MQALQTPRT (SEQ ID NO:30);
QSYDNSNSFVV (SEQ ID NO:31);
QQYGSSPIT (SEQ ID NO:32); and
VHGVHIPYT (SEQ ID NO:33);
wherein the variant comprises no more than two alterations relative to a sequence in the third group.

20. The antibody or antigen-binding antibody fragment of claim 19, wherein the first amino acid sequence is SEQ ID NO:56 and the second amino acid sequence is SEQ ID NO:25.

21. The antibody or antigen-binding antibody fragment of claim 19, wherein the light chain variable region further includes a light chain CDR1 comprising an amino acid sequence selected from the group consisting of:
TGSSGSIASHYVQ (SEQ ID NO:01),
TGSSGSIASNYVQ (SEQ ID NO:02),
TRSSGSIASYYVQ (SEQ ID NO:03),
RATQSLLHGNGHNYLD (SEQ ID NO:04),
RSSQSLVHSDGNTYLS (SEQ ID NO:05),
SGDYLARKYAR (SEQ ID NO:06),
GGDNLGGKSLH (SEQ ID NO:07),
RSSQSLLHTNEYNYLD (SEQ ID NO:08),
TGSSGSIANNYVH (SEQ ID NO:09).
RASQYVSSNSLA (SEQ ID NO: 10), and
RSSQSLLRSNGYNYLA (SEQ ID NO:11).

22. The antibody or antigen-binding antibody fragment of claim 21, wherein the light chain variable region further includes a light chain CDR2 comprising an amino acid sequence selected from the group consisting of EDKERPS (SEQ ID NO:12), EDNQRPS (SEQ ID NO:13), EDDQRPS (SEQ ID NO:14), MGSNRAS (SEQ ID NO:15), KISNRFS (SEQ ID NO:16), KDRERPS (SEQ ID NO:17), DDSDRPS (SEQ ID NO:18), LGSNRAP (SEQ ID NO:19), EDDQRPS (SEQ ID NO:20), GASNRAT (SEQ ID NO:21), and LASNRAS (SEQ ID NO:22).

23. The antibody or antigen-binding antibody fragment of claim 6, wherein the first amino acid sequence is selected from a second group consisting of:
GRARNWRSRFDY (SEQ ID NO:54);
TSWNAGGPIDY (SEQ ID NO:55);
DRVGYSSSLLDY (SEQ ID NO:56);
DKGSRITIFGVVGSAGFDY (SEQ ID NO:57);
LLLYEGFDP (SEQ ID NO:58);
DLVLTMTSRRAAFDI (SEQ ID NO:59);
DQWGTISGNDY (SEQ ID NO:60);
GWPTYVWGSYRPKGYFDY (SEQ ID NO:61);
GDWGYFDY (SEQ ID NO:62);
DADGGDYGY (SEQ ID NO:63); and
RLVRYGGYSTGGFDV (SEQ ID NO:64).

24. The antibody or antigen-binding antibody fragment of claim 23, wherein the heavy chain variable region further includes a heavy chain CDR1 comprising an amino acid sequence selected from the group consisting of GYYWS (SEQ ID NO:34), SYAMS (SEQ ID NO:35), GYYWS (SEQ ID NO:36), NARMGVS (SEQ ID NO:37), SYAMH (SEQ ID NO:38), SYSMN (SEQ ID NO:39), GYYWS (SEQ ID NO:40), SGGYSWS (SEQ ID NO:41), SNYMS (SEQ ID NO:42), and SNEAGVG (SEQ ID NO:43).

25. The antibody or antigen-binding antibody fragment of claim 24, wherein the heavy chain variable region further includes a heavy chain CDR2 comprising an amino acid sequence selected from the group consisting of EINHSGSTNYNPSLKS (SEQ ID NO:44), AISGSGGSTYYADSVKG (SEQ ID NO:45), EINHSGSTNYNPSLKS (SEQ ID NO:46), HIFSNDEESYSTSLKS (SEQ ID NO:47), VISYDGSNKYYADSVKG (SEQ ID NO:48), SISSGSSYRYDADSVKG (SEQ ID NO:49), EINHSGSTNYNPSLKS (SEQ ID NO:50), YIYHSGSTYYNPSLKS (SEQ ID NO:51), VIYSGGSTYYADSVKG (SEQ ID NO:52), and LLYWDDDKRYSPSLRS (SEQ ID NO:53).

26. The antibody or antibody fragment of claim 1, wherein the amino acid sequence is
at least 95% identical to at least one of:
SEQ ID NO:72, SEQ ID NO:74, SEQ ID NO:76, SEQ ID NO:78, SEQ ID NO:80, SEQ ID NO:82, and SEQ ID NO:86; or
at least 98% identical to at least one of:
SEQ ID NO:66 and SEQ ID NO:68.

27. The antibody or antibody fragment of claim 12, wherein the amino acid sequence is identical to SEQ ID NO:66, SEQ ID NO:68, SEQ ID NO:70, SEQ ID NO:72, SEQ ID NO:74, SEQ ID NO:76, SEQ ID) NO:78, SEQ ID NO:80, SEQ ID NO:82, SEQ ID NO:84, or SEQ ID NO:86.

28. The antibody or antibody fragment of claim 26, wherein the antigen binding region further comprises a light chain variable region comprising an amino acid sequence at least 90% identical to SEQ ID NO:88, and wherein the heavy chain variable region comprises an amino acid sequence at least 98% identical to SEQ ID NO:66.

29. The antibody or antibody fragment of claim 26, wherein the antigen binding region further comprises a light chain variable region comprising an amino acid sequence at least 90% identical to SEQ ID NO:90, and wherein the heavy chain variable region comprises an amino acid sequence at least 98% identical to SEQ ID NO:68.

30. The antibody or antibody fragment of claim 26, wherein the antigen binding region further comprises a light chain variable region comprising an amino acid sequence at least 90% identical to SEQ ID NO:92, and wherein the heavy chain variable region comprises an amino acid sequence at least 90% identical to SEQ ID NO:70.

31. The antibody or antibody fragment of claim 26, wherein the antigen binding region further comprises a light chain variable region comprising an amino acid sequence at least 90% identical to SEQ ID NO:94, and wherein the heavy chain variable region comprises an amino acid sequence at least 95% identical to SEQ ID NO:72.

32. The antibody or antibody fragment of claim 26, wherein the antigen binding region further comprises a light chain variable region comprising an amino acid sequence at least 90% identical to SEQ ID NO:96, and wherein the heavy chain variable region comprises an amino acid sequence at least 95% identical to SEQ ID NO:74.

33. The antibody or antibody fragment of claim 26, wherein the antigen binding region further comprises a light chain variable region comprising an amino acid sequence at least 90% identical to SEQ ID NO:98, and wherein the heavy chain variable region comprises an amino acid sequence at least 95% identical to SEQ ID NO:76.

34. The antibody or antibody fragment of claim 26, wherein the antigen binding region further comprises a light chain variable region comprising an amino acid sequence at least 90% identical to SEQ ID NO:100, and wherein the heavy chain variable region comprises an amino acid sequence at least 95% identical to SEQ ID NO:78.

35. The antibody or antibody fragment of claim 26, wherein the antigen binding region further comprises a light chain variable region comprising an amino acid sequence at least 90% identical to SEQ ID NO:102, and wherein the heavy chain variable region comprises an amino acid sequence at least 95% identical to SEQ ID NO:80.

36. The antibody or antibody fragment of claim 26, wherein the antigen binding region further comprises a light chain variable region comprising an amino acid sequence at least 90% identical to SEQ ID NO:104, and wherein the heavy chain variable region comprises an amino acid sequence at least 95% identical to SEQ ID NO:82.

37. The antibody or antibody fragment of claim 26, wherein the antigen binding region further comprises a light chain variable region comprising an amino acid sequence at least 90% identical to SEQ ID NO:106, and wherein the heavy chain variable region comprises an amino acid sequence at least 90% identical to SEQ ID NO:84.

38. The antibody or antibody fragment of claim 26, wherein the antigen binding region further comprises a light chain variable region comprising an amino acid sequence at least 90% identical to SEQ ID NO:108, and wherein the heavy chain variable region comprises an amino acid sequence at least 95% identical to SEQ ID NO:86.

* * * * *

SEQUENCE LISTING

<160> NUMBER OF SEQ ID NOS: 135

<210> SEQ ID NO 1
<211> LENGTH: 13
<212> TYPE: PRT
<213> ORGANISM: Homo sapiens

<400> SEQUENCE: 1

Thr Gly Ser Ser Gly Ser Ile Ala Ser His Tyr Val Gln
1               5                   10

```
<210> SEQ ID NO 2
<211> LENGTH: 13
<212> TYPE: PRT
<213> ORGANISM: Homo sapiens

<400> SEQUENCE: 2

Thr Gly Ser Ser Gly Ser Ile Ala Ser Asn Tyr Val Gln
1               5                   10

<210> SEQ ID NO 3
<211> LENGTH: 13
<212> TYPE: PRT
<213> ORGANISM: Homo sapiens

<400> SEQUENCE: 3

Thr Arg Ser Ser Gly Ser Ile Ala Ser Tyr Tyr Val Gln
1               5                   10

<210> SEQ ID NO 4
<211> LENGTH: 16
<212> TYPE: PRT
<213> ORGANISM: Homo sapiens

<400> SEQUENCE: 4

Arg Ala Thr Gln Ser Leu Leu His Gly Asn Gly His Asn Tyr Leu Asp
1               5                   10                  15

<210> SEQ ID NO 5
<211> LENGTH: 16
<212> TYPE: PRT
<213> ORGANISM: Homo sapiens

<400> SEQUENCE: 5

Arg Ser Ser Gln Ser Leu Val His Ser Asp Gly Asn Thr Tyr Leu Ser
1               5                   10                  15

<210> SEQ ID NO 6
<211> LENGTH: 11
<212> TYPE: PRT
<213> ORGANISM: Homo sapiens

<400> SEQUENCE: 6

Ser Gly Asp Val Leu Ala Arg Lys Tyr Ala Arg
1               5                   10

<210> SEQ ID NO 7
<211> LENGTH: 11
<212> TYPE: PRT
<213> ORGANISM: Homo sapiens

<400> SEQUENCE: 7

Gly Gly Asp Asn Leu Gly Gly Lys Ser Leu His
1               5                   10

<210> SEQ ID NO 8
<211> LENGTH: 16
<212> TYPE: PRT
<213> ORGANISM: Homo sapiens

<400> SEQUENCE: 8

Arg Ser Ser Gln Ser Leu Leu His Thr Asn Glu Tyr Asn Tyr Leu Asp
1               5                   10                  15

<210> SEQ ID NO 9
<211> LENGTH: 13
```

```
<212> TYPE: PRT
<213> ORGANISM: Homo sapiens

<400> SEQUENCE: 9

Thr Gly Ser Ser Gly Ser Ile Ala Asn Asn Tyr Val His
1               5                   10

<210> SEQ ID NO 10
<211> LENGTH: 12
<212> TYPE: PRT
<213> ORGANISM: Homo sapiens

<400> SEQUENCE: 10

Arg Ala Ser Gln Tyr Val Ser Ser Asn Ser Leu Ala
1               5                   10

<210> SEQ ID NO 11
<211> LENGTH: 16
<212> TYPE: PRT
<213> ORGANISM: Homo sapiens

<400> SEQUENCE: 11

Arg Ser Ser Gln Ser Leu Leu Arg Ser Asn Gly Tyr Asn Tyr Leu Ala
1               5                   10                  15

<210> SEQ ID NO 12
<211> LENGTH: 7
<212> TYPE: PRT
<213> ORGANISM: Homo sapiens

<400> SEQUENCE: 12

Glu Asp Lys Glu Arg Pro Ser
1               5

<210> SEQ ID NO 13
<211> LENGTH: 7
<212> TYPE: PRT
<213> ORGANISM: Homo sapiens

<400> SEQUENCE: 13

Glu Asp Asn Gln Arg Pro Ser
1               5

<210> SEQ ID NO 14
<211> LENGTH: 7
<212> TYPE: PRT
<213> ORGANISM: Homo sapiens

<400> SEQUENCE: 14

Glu Asp Asp Gln Arg Pro Ser
1               5

<210> SEQ ID NO 15
<211> LENGTH: 7
<212> TYPE: PRT
<213> ORGANISM: Homo sapiens

<400> SEQUENCE: 15

Met Gly Ser Asn Arg Ala Ser
1               5

<210> SEQ ID NO 16
<211> LENGTH: 7
<212> TYPE: PRT
<213> ORGANISM: Homo sapiens
```

```
<400> SEQUENCE: 16

Lys Ile Ser Asn Arg Phe Ser
1               5

<210> SEQ ID NO 17
<211> LENGTH: 7
<212> TYPE: PRT
<213> ORGANISM: Homo sapiens

<400> SEQUENCE: 17

Lys Asp Arg Glu Arg Pro Ser
1               5

<210> SEQ ID NO 18
<211> LENGTH: 7
<212> TYPE: PRT
<213> ORGANISM: Homo sapiens

<400> SEQUENCE: 18

Asp Asp Ser Asp Arg Pro Ser
1               5

<210> SEQ ID NO 19
<211> LENGTH: 7
<212> TYPE: PRT
<213> ORGANISM: Homo sapiens

<400> SEQUENCE: 19

Leu Gly Ser Asn Arg Ala Pro
1               5

<210> SEQ ID NO 20
<211> LENGTH: 7
<212> TYPE: PRT
<213> ORGANISM: Homo sapiens

<400> SEQUENCE: 20

Glu Asp Asp Gln Arg Pro Ser
1               5

<210> SEQ ID NO 21
<211> LENGTH: 7
<212> TYPE: PRT
<213> ORGANISM: Homo sapiens

<400> SEQUENCE: 21

Gly Ala Ser Asn Arg Ala Thr
1               5

<210> SEQ ID NO 22
<211> LENGTH: 7
<212> TYPE: PRT
<213> ORGANISM: Homo sapiens

<400> SEQUENCE: 22

Leu Ala Ser Asn Arg Ala Ser
1               5

<210> SEQ ID NO 23
<211> LENGTH: 10
<212> TYPE: PRT
<213> ORGANISM: Homo sapiens

<400> SEQUENCE: 23
```

-continued

Gln Ser Tyr Asp Ser Ser Asn Gln Trp Val
1               5                   10

<210> SEQ ID NO 24
<211> LENGTH: 9
<212> TYPE: PRT
<213> ORGANISM: Homo sapiens

<400> SEQUENCE: 24

Gln Ser Tyr Asp Gly Ser Ala Trp Val
1               5

<210> SEQ ID NO 25
<211> LENGTH: 9
<212> TYPE: PRT
<213> ORGANISM: Homo sapiens

<400> SEQUENCE: 25

Gln Ser Tyr Asp Arg Asn Ser Leu Val
1               5

<210> SEQ ID NO 26
<211> LENGTH: 9
<212> TYPE: PRT
<213> ORGANISM: Homo sapiens

<400> SEQUENCE: 26

Met Gln Ala Leu Gln Leu Pro Pro Thr
1               5

<210> SEQ ID NO 27
<211> LENGTH: 9
<212> TYPE: PRT
<213> ORGANISM: Homo sapiens

<400> SEQUENCE: 27

Met Gln Ala Thr Gln Leu Pro Tyr Thr
1               5

<210> SEQ ID NO 28
<211> LENGTH: 9
<212> TYPE: PRT
<213> ORGANISM: Homo sapiens

<400> SEQUENCE: 28

Tyr Ser Ala Ala Asp Asn Arg Gly Val
1               5

<210> SEQ ID NO 29
<211> LENGTH: 11
<212> TYPE: PRT
<213> ORGANISM: Homo sapiens

<400> SEQUENCE: 29

Gln Val Trp Asp Gly Ser Ser Asp Gln Arg Val
1               5                   10

<210> SEQ ID NO 30
<211> LENGTH: 9
<212> TYPE: PRT
<213> ORGANISM: Homo sapiens

<400> SEQUENCE: 30

Met Gln Ala Leu Gln Thr Pro Arg Thr

```
<210> SEQ ID NO 31
<211> LENGTH: 11
<212> TYPE: PRT
<213> ORGANISM: Homo sapiens

<400> SEQUENCE: 31

Gln Ser Tyr Asp Asn Ser Asn Ser Phe Val Val
1               5                   10

<210> SEQ ID NO 32
<211> LENGTH: 9
<212> TYPE: PRT
<213> ORGANISM: Homo sapiens

<400> SEQUENCE: 32

Gln Gln Tyr Gly Ser Ser Pro Ile Thr
1               5

<210> SEQ ID NO 33
<211> LENGTH: 9
<212> TYPE: PRT
<213> ORGANISM: Homo sapiens

<400> SEQUENCE: 33

Val His Gly Val His Ile Pro Tyr Thr
1               5

<210> SEQ ID NO 34
<211> LENGTH: 5
<212> TYPE: PRT
<213> ORGANISM: Homo sapiens

<400> SEQUENCE: 34

Gly Tyr Tyr Trp Ser
1               5

<210> SEQ ID NO 35
<211> LENGTH: 5
<212> TYPE: PRT
<213> ORGANISM: Homo sapiens

<400> SEQUENCE: 35

Ser Tyr Ala Met Ser
1               5

<210> SEQ ID NO 36
<211> LENGTH: 5
<212> TYPE: PRT
<213> ORGANISM: Homo sapiens

<400> SEQUENCE: 36

Gly Tyr Tyr Trp Ser
1               5

<210> SEQ ID NO 37
<211> LENGTH: 7
<212> TYPE: PRT
<213> ORGANISM: Homo sapiens

<400> SEQUENCE: 37

Asn Ala Arg Met Gly Val Ser
1               5
```

```
<210> SEQ ID NO 38
<211> LENGTH: 5
<212> TYPE: PRT
<213> ORGANISM: Homo sapiens

<400> SEQUENCE: 38

Ser Tyr Ala Met His
1               5

<210> SEQ ID NO 39
<211> LENGTH: 5
<212> TYPE: PRT
<213> ORGANISM: Homo sapiens

<400> SEQUENCE: 39

Ser Tyr Ser Met Asn
1               5

<210> SEQ ID NO 40
<211> LENGTH: 5
<212> TYPE: PRT
<213> ORGANISM: Homo sapiens

<400> SEQUENCE: 40

Gly Tyr Tyr Trp Ser
1               5

<210> SEQ ID NO 41
<211> LENGTH: 7
<212> TYPE: PRT
<213> ORGANISM: Homo sapiens

<400> SEQUENCE: 41

Ser Gly Gly Tyr Ser Trp Ser
1               5

<210> SEQ ID NO 42
<211> LENGTH: 5
<212> TYPE: PRT
<213> ORGANISM: Homo sapiens

<400> SEQUENCE: 42

Ser Asn Tyr Met Ser
1               5

<210> SEQ ID NO 43
<211> LENGTH: 7
<212> TYPE: PRT
<213> ORGANISM: Homo sapiens

<400> SEQUENCE: 43

Ser Asn Glu Ala Gly Val Gly
1               5

<210> SEQ ID NO 44
<211> LENGTH: 16
<212> TYPE: PRT
<213> ORGANISM: Homo sapiens

<400> SEQUENCE: 44

Glu Ile Asn His Ser Gly Ser Thr Asn Tyr Asn Pro Ser Leu Lys Ser
1               5                   10                  15

<210> SEQ ID NO 45
```

```
<211> LENGTH: 17
<212> TYPE: PRT
<213> ORGANISM: Homo sapiens

<400> SEQUENCE: 45

Ala Ile Ser Gly Ser Gly Gly Ser Thr Tyr Tyr Ala Asp Ser Val Lys
1               5                   10                  15
Gly

<210> SEQ ID NO 46
<211> LENGTH: 16
<212> TYPE: PRT
<213> ORGANISM: Homo sapiens

<400> SEQUENCE: 46

Glu Ile Asn His Ser Gly Ser Thr Asn Tyr Asn Pro Ser Leu Lys Ser
1               5                   10                  15

<210> SEQ ID NO 47
<211> LENGTH: 16
<212> TYPE: PRT
<213> ORGANISM: Homo sapiens

<400> SEQUENCE: 47

His Ile Phe Ser Asn Asp Glu Glu Ser Tyr Ser Thr Ser Leu Lys Ser
1               5                   10                  15

<210> SEQ ID NO 48
<211> LENGTH: 17
<212> TYPE: PRT
<213> ORGANISM: Homo sapiens

<400> SEQUENCE: 48

Val Ile Ser Tyr Asp Gly Ser Asn Lys Tyr Tyr Ala Asp Ser Val Lys
1               5                   10                  15
Gly

<210> SEQ ID NO 49
<211> LENGTH: 17
<212> TYPE: PRT
<213> ORGANISM: Homo sapiens

<400> SEQUENCE: 49

Ser Ile Ser Ser Gly Ser Ser Tyr Arg Tyr Asp Ala Asp Ser Val Lys
1               5                   10                  15
Gly

<210> SEQ ID NO 50
<211> LENGTH: 16
<212> TYPE: PRT
<213> ORGANISM: Homo sapiens

<400> SEQUENCE: 50

Glu Ile Asn His Ser Gly Ser Thr Asn Tyr Asn Pro Ser Leu Lys Ser
1               5                   10                  15

<210> SEQ ID NO 51
<211> LENGTH: 16
<212> TYPE: PRT
<213> ORGANISM: Homo sapiens

<400> SEQUENCE: 51

Tyr Ile Tyr His Ser Gly Ser Thr Tyr Tyr Asn Pro Ser Leu Lys Ser
```

<210> SEQ ID NO 52
<211> LENGTH: 16
<212> TYPE: PRT
<213> ORGANISM: Homo sapiens

<400> SEQUENCE: 52

Val Ile Tyr Ser Gly Gly Ser Thr Tyr Tyr Ala Asp Ser Val Lys Gly
1               5                   10                  15

<210> SEQ ID NO 53
<211> LENGTH: 16
<212> TYPE: PRT
<213> ORGANISM: Homo sapiens

<400> SEQUENCE: 53

Leu Leu Tyr Trp Asp Asp Lys Arg Tyr Ser Pro Ser Leu Arg Ser
1               5                   10                  15

<210> SEQ ID NO 54
<211> LENGTH: 12
<212> TYPE: PRT
<213> ORGANISM: Homo sapiens

<400> SEQUENCE: 54

Gly Arg Ala Arg Asn Trp Arg Ser Arg Phe Asp Tyr
1               5                   10

<210> SEQ ID NO 55
<211> LENGTH: 11
<212> TYPE: PRT
<213> ORGANISM: Homo sapiens

<400> SEQUENCE: 55

Thr Ser Trp Asn Ala Gly Gly Pro Ile Asp Tyr
1               5                   10

<210> SEQ ID NO 56
<211> LENGTH: 12
<212> TYPE: PRT
<213> ORGANISM: Homo sapiens

<400> SEQUENCE: 56

Asp Arg Val Gly Tyr Ser Ser Ser Leu Leu Asp Tyr
1               5                   10

<210> SEQ ID NO 57
<211> LENGTH: 19
<212> TYPE: PRT
<213> ORGANISM: Homo sapiens

<400> SEQUENCE: 57

Asp Lys Gly Ser Arg Ile Thr Ile Phe Gly Val Val Gly Ser Ala Gly
1               5                   10                  15

Phe Asp Tyr

<210> SEQ ID NO 58
<211> LENGTH: 9
<212> TYPE: PRT
<213> ORGANISM: Homo sapiens

<400> SEQUENCE: 58

Leu Leu Leu Tyr Glu Gly Phe Asp Pro

<210> SEQ ID NO 59
<211> LENGTH: 15
<212> TYPE: PRT
<213> ORGANISM: Homo sapiens

<400> SEQUENCE: 59

Asp Leu Val Leu Thr Met Thr Ser Arg Arg Ala Ala Phe Asp Ile
1               5                   10                  15

<210> SEQ ID NO 60
<211> LENGTH: 11
<212> TYPE: PRT
<213> ORGANISM: Homo sapiens

<400> SEQUENCE: 60

Asp Gln Trp Gly Thr Ile Ser Gly Asn Asp Tyr
1               5                   10

<210> SEQ ID NO 61
<211> LENGTH: 18
<212> TYPE: PRT
<213> ORGANISM: Homo sapiens

<400> SEQUENCE: 61

Gly Trp Pro Thr Tyr Val Trp Gly Ser Tyr Arg Pro Lys Gly Tyr Phe
1               5                   10                  15

Asp Tyr

<210> SEQ ID NO 62
<211> LENGTH: 8
<212> TYPE: PRT
<213> ORGANISM: Homo sapiens

<400> SEQUENCE: 62

Gly Asp Trp Gly Tyr Phe Asp Tyr
1               5

<210> SEQ ID NO 63
<211> LENGTH: 9
<212> TYPE: PRT
<213> ORGANISM: Homo sapiens

<400> SEQUENCE: 63

Asp Ala Asp Gly Gly Asp Tyr Gly Tyr
1               5

<210> SEQ ID NO 64
<211> LENGTH: 15
<212> TYPE: PRT
<213> ORGANISM: Homo sapiens

<400> SEQUENCE: 64

Arg Leu Val Arg Tyr Gly Gly Tyr Ser Thr Gly Gly Phe Asp Val
1               5                   10                  15

<210> SEQ ID NO 65
<211> LENGTH: 669
<212> TYPE: DNA
<213> ORGANISM: Homo sapiens
<220> FEATURE:
<221> NAME/KEY: CDS
<222> LOCATION: (1)..(669)

<400> SEQUENCE: 65

| cag gtg cag ctg cag cag tgg ggc gca gga ctg ttg aag cct tcg gag | 48 |
| Gln Val Gln Leu Gln Gln Trp Gly Ala Gly Leu Leu Lys Pro Ser Glu | |
| 1               5                   10                  15 | |

| acc ctg tcc ctc acc tgc gct gtc tat ggt ggg tcc ttc agt ggt tac | 96 |
| Thr Leu Ser Leu Thr Cys Ala Val Tyr Gly Gly Ser Phe Ser Gly Tyr | |
|         20                  25                  30 | |

| tac tgg agc tgg atc cgc cag ccc cca ggg aag ggg ctg gag tgg att | 144 |
| Tyr Trp Ser Trp Ile Arg Gln Pro Pro Gly Lys Gly Leu Glu Trp Ile | |
|     35                  40                  45 | |

| ggg gaa atc aat cat agt gga agc acc aac tac aac ccg tcc ctc aag | 192 |
| Gly Glu Ile Asn His Ser Gly Ser Thr Asn Tyr Asn Pro Ser Leu Lys | |
| 50                  55                  60 | |

| agt cga gtc acc ata tca gta gac acg tcc aag aac cag ttc tcc ctg | 240 |
| Ser Arg Val Thr Ile Ser Val Asp Thr Ser Lys Asn Gln Phe Ser Leu | |
| 65                  70                  75                  80 | |

| aag ctg agc tct gtg acc gcc gcg gac acg gct gtg tat tac tgt gcg | 288 |
| Lys Leu Ser Ser Val Thr Ala Ala Asp Thr Ala Val Tyr Tyr Cys Ala | |
|             85                  90                  95 | |

| aga ggc cgg gca cgg aac tgg aga tcg cgt ttt gac tac tgg ggc cag | 336 |
| Arg Gly Arg Ala Arg Asn Trp Arg Ser Arg Phe Asp Tyr Trp Gly Gln | |
|         100                 105                 110 | |

| gga acc ctg gtc acc gtc tct agt gcc tcc acc aag ggc cca tcg gtc | 384 |
| Gly Thr Leu Val Thr Val Ser Ser Ala Ser Thr Lys Gly Pro Ser Val | |
|     115                 120                 125 | |

| ttc ccc ctg gca ccc tcc tcc aag agc acc tct ggg ggc aca gcg gcc | 432 |
| Phe Pro Leu Ala Pro Ser Ser Lys Ser Thr Ser Gly Gly Thr Ala Ala | |
| 130                 135                 140 | |

| ctg ggc tgc ctg gtc aag gac tac ttc ccc gaa ccg gtg acg gtg tcg | 480 |
| Leu Gly Cys Leu Val Lys Asp Tyr Phe Pro Glu Pro Val Thr Val Ser | |
| 145                 150                 155                 160 | |

| tgg aac tca ggc gcc ctg acc agc ggc gtg cac acc ttc ccg gct gtc | 528 |
| Trp Asn Ser Gly Ala Leu Thr Ser Gly Val His Thr Phe Pro Ala Val | |
|             165                 170                 175 | |

| cta cag tcc tca gga ctc tac tcc ctc agc agc gtg gtg acc gtg ccc | 576 |
| Leu Gln Ser Ser Gly Leu Tyr Ser Leu Ser Ser Val Val Thr Val Pro | |
|         180                 185                 190 | |

| tcc agc agc ttg ggc acc cag acc tac atc tgc aac gtg aat cac aag | 624 |
| Ser Ser Ser Leu Gly Thr Gln Thr Tyr Ile Cys Asn Val Asn His Lys | |
|     195                 200                 205 | |

| ccc agc aac acc aag gtg gac aag aaa gtt gag ccc aaa tct tgt | 669 |
| Pro Ser Asn Thr Lys Val Asp Lys Lys Val Glu Pro Lys Ser Cys | |
| 210                 215                 220 | |

<210> SEQ ID NO 66
<211> LENGTH: 223
<212> TYPE: PRT
<213> ORGANISM: Homo sapiens

<400> SEQUENCE: 66

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu

-continued

```
                65                  70                  75                  80
        Lys Leu Ser Ser Val Thr Ala Ala Asp Thr Ala Val Tyr Tyr Cys Ala
                        85                  90                  95
        Arg Gly Arg Ala Arg Asn Trp Arg Ser Arg Phe Asp Tyr Trp Gly Gln
                    100                 105                 110
        Gly Thr Leu Val Thr Val Ser Ser Ala Ser Thr Lys Gly Pro Ser Val
                    115                 120                 125
        Phe Pro Leu Ala Pro Ser Ser Lys Ser Thr Ser Gly Gly Thr Ala Ala
                130                 135                 140
        Leu Gly Cys Leu Val Lys Asp Tyr Phe Pro Glu Pro Val Thr Val Ser
        145                 150                 155                 160
        Trp Asn Ser Gly Ala Leu Thr Ser Gly Val His Thr Phe Pro Ala Val
                        165                 170                 175
        Leu Gln Ser Ser Gly Leu Tyr Ser Leu Ser Ser Val Val Thr Val Pro
                    180                 185                 190
        Ser Ser Ser Leu Gly Thr Gln Thr Tyr Ile Cys Asn Val Asn His Lys
                    195                 200                 205
        Pro Ser Asn Thr Lys Val Asp Lys Lys Val Glu Pro Lys Ser Cys
                210                 215                 220

<210> SEQ ID NO 67
<211> LENGTH: 672
<212> TYPE: DNA
<213> ORGANISM: Homo sapiens
<220> FEATURE:
<221> NAME/KEY: CDS
<222> LOCATION: (1)..(672)

<400> SEQUENCE: 67 gag gtg cag ctg gtg gag tct ggg gga ggc ttg gta cag cct ggg ggg       48
Glu Val Gln Leu Val Glu Ser Gly Gly Gly Leu Val Gln Pro Gly Gly
1               5                   10                  15 tcc ctg aga ctc tcc tgt gca gcc tct gga ttc acc ttt agc agc tat       96
Ser Leu Arg Leu Ser Cys Ala Ala Ser Gly Phe Thr Phe Ser Ser Tyr
            20                  25                  30 gcc atg agc tgg gtc cgc cag gct cca ggg aag ggg ctg gag tgg gtc      144
Ala Met Ser Trp Val Arg Gln Ala Pro Gly Lys Gly Leu Glu Trp Val
        35                  40                  45 tca gct att agt ggt agt ggt ggt agc aca tac tac gca gac tcc gtg      192
Ser Ala Ile Ser Gly Ser Gly Gly Ser Thr Tyr Tyr Ala Asp Ser Val
    50                  55                  60 aag ggc cgg ttc acc atc tcc aga gac aat tcc aag aac acg ctg tat      240
Lys Gly Arg Phe Thr Ile Ser Arg Asp Asn Ser Lys Asn Thr Leu Tyr
65                  70                  75                  80 ctg caa atg aac agc ctg aga gcc gag gac acg gcc gta tat tac tgt      288
Leu Gln Met Asn Ser Leu Arg Ala Glu Asp Thr Ala Val Tyr Tyr Cys
                85                  90                  95 gcg aaa gat cgg gtg ggg tat agc agc agc ctt ctt gac tac tgg ggc      336
Ala Lys Asp Arg Val Gly Tyr Ser Ser Ser Leu Leu Asp Tyr Trp Gly
            100                 105                 110 cag gga acc ctg gtc acc gtc tct agt gcc tcc acc aag ggc cca tcg      384
Gln Gly Thr Leu Val Thr Val Ser Ser Ala Ser Thr Lys Gly Pro Ser
        115                 120                 125 gtc ttc ccc ctg gca ccc tcc tcc aag agc acc tct ggg ggc aca gcg      432
Val Phe Pro Leu Ala Pro Ser Ser Lys Ser Thr Ser Gly Gly Thr Ala
    130                 135                 140 gcc ctg ggc tgc ctg gtc aag gac tac ttc ccc gaa ccg gtg acg gtg      480
Ala Leu Gly Cys Leu Val Lys Asp Tyr Phe Pro Glu Pro Val Thr Val
145                 150                 155                 160
```

```
tcg tgg aac tca ggc gcc ctg acc agc ggc gtg cac acc ttc ccg gct      528
Ser Trp Asn Ser Gly Ala Leu Thr Ser Gly Val His Thr Phe Pro Ala
            165                 170                 175 gtc cta cag tcc tca gga ctc tac tcc ctc agc agc gtg gtg acc gtg      576
Val Leu Gln Ser Ser Gly Leu Tyr Ser Leu Ser Ser Val Val Thr Val
        180                 185                 190 ccc tcc agc agc ttg ggc acc cag acc tac atc tgc aac gtg aat cac      624
Pro Ser Ser Ser Leu Gly Thr Gln Thr Tyr Ile Cys Asn Val Asn His
    195                 200                 205 aag ccc agc aac acc aag gtg gac aag aaa gtt gag ccc aaa tct tgt      672
Lys Pro Ser Asn Thr Lys Val Asp Lys Lys Val Glu Pro Lys Ser Cys
210                 215                 220

<210> SEQ ID NO 68
<211> LENGTH: 224
<212> TYPE: PRT
<213> ORGANISM: Homo sapiens

<400> SEQUENCE: 68

Glu Val Gln Leu Val Glu Ser Gly Gly Gly Leu Val Gln Pro Gly Gly
1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Val Gly Tyr Ser Ser Ser Leu Leu Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

<210> SEQ ID NO 69
<211> LENGTH: 666
<212> TYPE: DNA
<213> ORGANISM: Homo sapiens
<220> FEATURE:
<221> NAME/KEY: CDS
<222> LOCATION: (1)..(666)

<400> SEQUENCE: 69 cag gtc acc ttg aag gag tct ggt cct gtg ctg gtg aaa ccc aca gag      48
```

```
                Gln Val Thr Leu Lys Glu Ser Gly Pro Val Leu Val Lys Pro Thr Glu
                  1               5                  10                  15 acc ctc acg ctg acc tgc acc gtg tct ggg ttc tca ctc agc aat gct        96
Thr Leu Thr Leu Thr Cys Thr Val Ser Gly Phe Ser Leu Ser Asn Ala
                 20                  25                  30 aga atg ggt gtg agt tgg atc cgt cag ccc cca ggg aag gcc ctg gag       144
Arg Met Gly Val Ser Trp Ile Arg Gln Pro Pro Gly Lys Ala Leu Glu
             35                  40                  45 tgg ctt gca cac att ttt tcg aat gac gaa gaa tcc tac agc aca tct       192
Trp Leu Ala His Ile Phe Ser Asn Asp Glu Glu Ser Tyr Ser Thr Ser
         50                  55                  60 ctg aag agc agg ctc acc atc tcc aag gac acc tcc caa agc cag gtg       240
Leu Lys Ser Arg Leu Thr Ile Ser Lys Asp Thr Ser Gln Ser Gln Val
 65                  70                  75                  80 gtc ctt acc atg acc aac atg gac cct gtg gac aca gcc acg tat tac       288
Val Leu Thr Met Thr Asn Met Asp Pro Val Asp Thr Ala Thr Tyr Tyr
                 85                  90                  95 tgt gca cgg ctt tta ttg tac gag ggg ttc gac ccc tgg ggc cag gga       336
Cys Ala Arg Leu Leu Leu Tyr Glu Gly Phe Asp Pro Trp Gly Gln Gly
             100                 105                 110 acc ctg gtc acc gtc tct agt gcc tcc acc aag ggc cca tcg gtc ttc       384
Thr Leu Val Thr Val Ser Ser Ala Ser Thr Lys Gly Pro Ser Val Phe
         115                 120                 125 ccc ctg gca ccc tcc tcc aag agc acc tct ggg ggc aca gcg gcc ctg       432
Pro Leu Ala Pro Ser Ser Lys Ser Thr Ser Gly Gly Thr Ala Ala Leu
     130                 135                 140 ggc tgc ctg gtc aag gac tac ttc ccc gaa ccg gtg acg gtg tcg tgg       480
Gly Cys Leu Val Lys Asp Tyr Phe Pro Glu Pro Val Thr Val Ser Trp
145                 150                 155                 160 aac tca ggc gcc ctg acc agc ggc gtg cac acc ttc ccg gct gtc cta       528
Asn Ser Gly Ala Leu Thr Ser Gly Val His Thr Phe Pro Ala Val Leu
                 165                 170                 175 cag tcc tca gga ctc tac tcc ctc agc agc gtg gtg acc gtg ccc tcc       576
Gln Ser Ser Gly Leu Tyr Ser Leu Ser Ser Val Val Thr Val Pro Ser
             180                 185                 190 agc agc ttg ggc acc cag acc tac atc tgc aac gtg aat cac aag ccc       624
Ser Ser Leu Gly Thr Gln Thr Tyr Ile Cys Asn Val Asn His Lys Pro
         195                 200                 205 agc aac acc aag gtg gac aag aaa gtt gag ccc aaa tct tgt               666
Ser Asn Thr Lys Val Asp Lys Lys Val Glu Pro Lys Ser Cys
     210                 215                 220

<210> SEQ ID NO 70
<211> LENGTH: 222
<212> TYPE: PRT
<213> ORGANISM: Homo sapiens

<400> SEQUENCE: 70

Gln Val Thr Leu Lys Glu Ser Gly Pro Val Leu Val Lys Pro Thr Glu
  1               5                  10                  15

Thr Leu Thr Leu Thr Cys Thr Val Ser Gly Phe Ser Leu Ser Asn Ala
                 20                  25                  30

Arg Met Gly Val Ser Trp Ile Arg Gln Pro Pro Gly Lys Ala Leu Glu
             35                  40                  45

Trp Leu Ala His Ile Phe Ser Asn Asp Glu Glu Ser Tyr Ser Thr Ser
         50                  55                  60

Leu Lys Ser Arg Leu Thr Ile Ser Lys Asp Thr Ser Gln Ser Gln Val
 65                  70                  75                  80

Val Leu Thr Met Thr Asn Met Asp Pro Val Asp Thr Ala Thr Tyr Tyr
```

```
                85                  90                  95
Cys Ala Arg Leu Leu Tyr Glu Gly Phe Asp Pro Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys
        210                 215                 220

<210> SEQ ID NO 71
<211> LENGTH: 690
<212> TYPE: DNA
<213> ORGANISM: Homo sapiens
<220> FEATURE:
<221> NAME/KEY: CDS
<222> LOCATION: (1)..(690)

<400> SEQUENCE: 71
```

| | | | | | | | | | | | | | | | | |
|---|---|---|---|---|---|---|---|---|---|---|---|---|---|---|---|---|
| cag | gtg | cag | cta | cag | cag | tgg | ggc | gca | gga | ctg | ttg | aag | cct | tcg | gag | 48 |
| Gln | Val | Gln | Leu | Gln | Gln | Trp | Gly | Ala | Gly | Leu | Leu | Lys | Pro | Ser | Glu | |
| 1 | | | | 5 | | | | | 10 | | | | | 15 | | |
| acc | ctg | tcc | ctc | acc | tgc | gct | gtc | tat | ggt | ggg | tcc | ttc | agt | ggt | tac | 96 |
| Thr | Leu | Ser | Leu | Thr | Cys | Ala | Val | Tyr | Gly | Gly | Ser | Phe | Ser | Gly | Tyr | |
| | | | 20 | | | | | 25 | | | | | 30 | | | |
| tac | tgg | agc | tgg | atc | cgc | cag | ccc | cca | ggg | aag | ggg | ctg | gag | tgg | att | 144 |
| Tyr | Trp | Ser | Trp | Ile | Arg | Gln | Pro | Pro | Gly | Lys | Gly | Leu | Glu | Trp | Ile | |
| | | 35 | | | | | 40 | | | | | 45 | | | | |
| ggg | gaa | atc | aat | cat | agt | gga | agc | acc | aac | tac | aac | ccg | tcc | ctc | aag | 192 |
| Gly | Glu | Ile | Asn | His | Ser | Gly | Ser | Thr | Asn | Tyr | Asn | Pro | Ser | Leu | Lys | |
| | 50 | | | | | 55 | | | | | 60 | | | | | |
| agt | cga | gtc | acc | ata | tca | gta | gac | acg | tcc | aag | aac | cag | ttc | tcc | ctg | 240 |
| Ser | Arg | Val | Thr | Ile | Ser | Val | Asp | Thr | Ser | Lys | Asn | Gln | Phe | Ser | Leu | |
| 65 | | | | | 70 | | | | | 75 | | | | | 80 | |
| aag | ctg | agc | tct | gtg | acc | gcc | gcg | gac | acg | gct | gtg | tat | tac | tgt | gcg | 288 |
| Lys | Leu | Ser | Ser | Val | Thr | Ala | Ala | Asp | Thr | Ala | Val | Tyr | Tyr | Cys | Ala | |
| | | | | 85 | | | | | 90 | | | | | 95 | | |
| aga | gat | aag | ggc | tcc | cgt | att | acg | att | ttt | gga | gtg | gtt | ggg | tcc | gct | 336 |
| Arg | Asp | Lys | Gly | Ser | Arg | Ile | Thr | Ile | Phe | Gly | Val | Val | Gly | Ser | Ala | |
| | | | 100 | | | | | 105 | | | | | 110 | | | |
| ggc | ttt | gac | tac | tgg | ggc | cag | ggc | acc | ctg | gtc | acc | gtc | tct | agt | gcc | 384 |
| Gly | Phe | Asp | Tyr | Trp | Gly | Gln | Gly | Thr | Leu | Val | Thr | Val | Ser | Ser | Ala | |
| | | 115 | | | | | 120 | | | | | 125 | | | | |
| tcc | acc | aag | ggc | cca | tcg | gtc | ttc | ccc | ctg | gca | ccc | tcc | tcc | aag | agc | 432 |
| Ser | Thr | Lys | Gly | Pro | Ser | Val | Phe | Pro | Leu | Ala | Pro | Ser | Ser | Lys | Ser | |
| | 130 | | | | | 135 | | | | | 140 | | | | | |
| acc | tct | ggg | ggc | aca | gcg | gcc | ctg | ggc | tgc | ctg | gtc | aag | gac | tac | ttc | 480 |
| Thr | Ser | Gly | Gly | Thr | Ala | Ala | Leu | Gly | Cys | Leu | Val | Lys | Asp | Tyr | Phe | |
| 145 | | | | | 150 | | | | | 155 | | | | | 160 | |
| ccc | gaa | ccg | gtg | acg | gtg | tcg | tgg | aac | tca | ggc | gcc | ctg | acc | agc | ggc | 528 |
| Pro | Glu | Pro | Val | Thr | Val | Ser | Trp | Asn | Ser | Gly | Ala | Leu | Thr | Ser | Gly | |

```
                      165                 170                 175
gtg cac acc ttc ccg gct gtc cta cag tcc tca gga ctc tac tcc ctc    576
Val His Thr Phe Pro Ala Val Leu Gln Ser Ser Gly Leu Tyr Ser Leu
                  180                 185                 190 agc agc gtg gtg acc gtg ccc tcc agc agc ttg ggc acc cag acc tac    624
Ser Ser Val Val Thr Val Pro Ser Ser Ser Leu Gly Thr Gln Thr Tyr
            195                 200                 205 atc tgc aac gtg aat cac aag ccc agc aac acc aag gtg gac aag aaa    672
Ile Cys Asn Val Asn His Lys Pro Ser Asn Thr Lys Val Asp Lys Lys
        210                 215                 220 gtt gag ccc aaa tct tgt                                             690
Val Glu Pro Lys Ser Cys
225                 230

<210> SEQ ID NO 72
<211> LENGTH: 230
<212> TYPE: PRT
<213> ORGANISM: Homo sapiens

<400> SEQUENCE: 72

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Lys Gly Ser Arg Ile Thr Ile Phe Gly Val Val Gly Ser Ala
            100                 105                 110

Gly Phe Asp Tyr Trp Gly Gln Gly Thr Leu Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
    210                 215                 220

Val Glu Pro Lys Ser Cys
225                 230

<210> SEQ ID NO 73
<211> LENGTH: 666
<212> TYPE: DNA
<213> ORGANISM: Homo sapiens
<220> FEATURE:
<221> NAME/KEY: CDS
<222> LOCATION: (1)..(666)
```

<400> SEQUENCE: 73

```
gag gtg cag ctg ctg gag tct ggg gga ggc ctg gtc aag cct ggg ggg     48
Glu Val Gln Leu Leu Glu Ser Gly Gly Gly Leu Val Lys Pro Gly Gly
1               5                   10                  15 tcc ctg aga ctc tcc tgt gca gcc tct gga ttc acc ttc agt agc tat     96
Ser Leu Arg Leu Ser Cys Ala Ala Ser Gly Phe Thr Phe Ser Ser Tyr
            20                  25                  30 agc atg aac tgg gtc cgc cag gct cca ggg aag ggg ctg gag tgg gtc    144
Ser Met Asn Trp Val Arg Gln Ala Pro Gly Lys Gly Leu Glu Trp Val
        35                  40                  45 tca tcc att agt agt ggt agc agt tac aga tac gac gca gac tca gtg    192
Ser Ser Ile Ser Ser Gly Ser Ser Tyr Arg Tyr Asp Ala Asp Ser Val
    50                  55                  60 aag ggc cga ttc acc atc tcc aga gac aat tcc aag aac acg ctg tat    240
Lys Gly Arg Phe Thr Ile Ser Arg Asp Asn Ser Lys Asn Thr Leu Tyr
65                  70                  75                  80 ctg caa atg aat agc ctg aga gcc gag gac acg gcc ata tat tac tgt    288
Leu Gln Met Asn Ser Leu Arg Ala Glu Asp Thr Ala Ile Tyr Tyr Cys
                85                  90                  95 gcg gat cag atg ggt aca att agt ggc aat gac tac tgg ggc cag ggc    336
Ala Asp Gln Met Gly Thr Ile Ser Gly Asn Asp Tyr Trp Gly Gln Gly
            100                 105                 110 acc ctg gtc acc gtc tct agt gcc tcc acc aag ggc cca tcg gtc ttc    384
Thr Leu Val Thr Val Ser Ser Ala Ser Thr Lys Gly Pro Ser Val Phe
        115                 120                 125 ccc ctg gca ccc tcc tcc aag agc acc tct ggg ggc aca gcg gcc ctg    432
Pro Leu Ala Pro Ser Ser Lys Ser Thr Ser Gly Gly Thr Ala Ala Leu
    130                 135                 140 ggc tgc ctg gtc aag gac tac ttc ccc gaa ccg gtg acg gtg tcg tgg    480
Gly Cys Leu Val Lys Asp Tyr Phe Pro Glu Pro Val Thr Val Ser Trp
145                 150                 155                 160 aac tca ggc gcc ctg acc agc ggc gtg cac acc ttc ccg gct gtc cta    528
Asn Ser Gly Ala Leu Thr Ser Gly Val His Thr Phe Pro Ala Val Leu
                165                 170                 175 cag tcc tca gga ctc tac tcc ctc agc agc gtg gtg acc gtg ccc tcc    576
Gln Ser Ser Gly Leu Tyr Ser Leu Ser Ser Val Val Thr Val Pro Ser
            180                 185                 190 agc agc ttg ggc acc cag acc tac atc tgc aac gtg aat cac aag ccc    624
Ser Ser Leu Gly Thr Gln Thr Tyr Ile Cys Asn Val Asn His Lys Pro
        195                 200                 205 agc aac acc aag gtg gac aag aaa gtt gag ccc aaa tct tgt            666
Ser Asn Thr Lys Val Asp Lys Lys Val Glu Pro Lys Ser Cys
    210                 215                 220
```

<210> SEQ ID NO 74
<211> LENGTH: 222
<212> TYPE: PRT
<213> ORGANISM: Homo sapiens

<400> SEQUENCE: 74

```
Glu Val Gln Leu Leu Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Gly Ser Ser Tyr Arg Tyr Asp Ala Asp Ser Val
    50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Ile Tyr Tyr Cys
                 85                  90                  95

Ala Asp Gln Met Gly Thr Ile Ser Gly Asn Asp Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys
    210                 215                 220

<210> SEQ ID NO 75
<211> LENGTH: 681
<212> TYPE: DNA
<213> ORGANISM: Homo sapiens
<220> FEATURE:
<221> NAME/KEY: CDS
<222> LOCATION: (1)..(681)

<400> SEQUENCE: 75 cag gtg cag ctg gtg gag acc ggg gga ggc gtg gtc cag cct ggg agg      48
Gln Val Gln Leu Val Glu Thr Gly Gly Gly Val Val Gln Pro Gly Arg
1               5                   10                  15 tcc ctg aga ctc tcc tgt gca gcc tct gga ttc acc ttc agt agc tat      96
Ser Leu Arg Leu Ser Cys Ala Ala Ser Gly Phe Thr Phe Ser Ser Tyr
            20                  25                  30 gct atg cac tgg gtc cgc cag gct cca ggc aag ggg ctg gag tgg gtg     144
Ala Met His Trp Val Arg Gln Ala Pro Gly Lys Gly Leu Glu Trp Val
        35                  40                  45 gca gtt ata tca tat gat gga agc aat aaa tac tac gca gac tcc gtg     192
Ala Val Ile Ser Tyr Asp Gly Ser Asn Lys Tyr Tyr Ala Asp Ser Val
    50                  55                  60 aag ggc cga ttc acc atc tcc aga gac aat tcc aag aac acg ctg tat     240
Lys Gly Arg Phe Thr Ile Ser Arg Asp Asn Ser Lys Asn Thr Leu Tyr
65                  70                  75                  80 ctg caa atg aac agc ctg aga gct gag gac acg gct gtg tat tac tgt     288
Leu Gln Met Asn Ser Leu Arg Ala Glu Asp Thr Ala Val Tyr Tyr Cys
                85                  90                  95 gcg agc gac cta gtc ctt act atg acc tca cga cgg gct gct ttt gat     336
Ala Ser Asp Leu Val Leu Thr Met Thr Ser Arg Arg Ala Ala Phe Asp
            100                 105                 110 atc tgg ggc caa ggg aca atg gtc acc gtc tct agt gcc tcc acc aag     384
Ile Trp Gly Gln Gly Thr Met Val Thr Val Ser Ser Ala Ser Thr Lys
        115                 120                 125 ggc cca tcg gtc ttc ccc ctg gca ccc tcc tcc aag agc acc tct ggg     432
Gly Pro Ser Val Phe Pro Leu Ala Pro Ser Ser Lys Ser Thr Ser Gly
    130                 135                 140 ggc aca gcg gcc ctg ggc tgc ctg gtc aag gac tac ttc ccc gaa ccg     480
Gly Thr Ala Ala Leu Gly Cys Leu Val Lys Asp Tyr Phe Pro Glu Pro
```

```
                        145                 150                 155                 160
gtg acg gtg tcg tgg aac tca ggc gcc ctg acc agc ggc gtg cac acc            528
Val Thr Val Ser Trp Asn Ser Gly Ala Leu Thr Ser Gly Val His Thr
                165                 170                 175 ttc ccg gct gtc cta cag tcc tca gga ctc tac tcc ctc agc agc gtg            576
Phe Pro Ala Val Leu Gln Ser Ser Gly Leu Tyr Ser Leu Ser Ser Val
            180                 185                 190 gtg acc gtg ccc tcc agc agc ttg ggc acc cag acc tac atc tgc aac            624
Val Thr Val Pro Ser Ser Ser Leu Gly Thr Gln Thr Tyr Ile Cys Asn
        195                 200                 205 gtg aat cac aag ccc agc aac acc aag gtg gac aag aaa gtt gag ccc            672
Val Asn His Lys Pro Ser Asn Thr Lys Val Asp Lys Lys Val Glu Pro
    210                 215                 220 aaa tct tgt                                                                681
Lys Ser Cys
225

<210> SEQ ID NO 76
<211> LENGTH: 227
<212> TYPE: PRT
<213> ORGANISM: Homo sapiens

<400> SEQUENCE: 76

Gln Val Gln Leu Val Glu Thr Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Ser Asp Leu Val Leu Thr Met Thr Ser Arg Arg Ala Ala Phe Asp
        100                 105                 110

Ile Trp Gly Gln Gly Thr Met Val Thr Val Ser Ser Ala Ser Thr Lys
    115                 120                 125

Gly Pro Ser Val Phe Pro Leu Ala Pro Ser Ser Lys Ser Thr Ser Gly
130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys
225

<210> SEQ ID NO 77
<211> LENGTH: 660
<212> TYPE: DNA
```

<213> ORGANISM: Homo sapiens
<220> FEATURE:
<221> NAME/KEY: CDS
<222> LOCATION: (1)..(660)

<400> SEQUENCE: 77

| | | | | | | | | | | | | | | | | |
|---|---|---|---|---|---|---|---|---|---|---|---|---|---|---|---|---|
| gag | gtc | cag | ctg | gtg | cag | tct | ggg | gga | ggc | ttg | gtc | cag | cct | ggg | ggg | 48 |
| Glu | Val | Gln | Leu | Val | Gln | Ser | Gly | Gly | Gly | Leu | Val | Gln | Pro | Gly | Gly | |
| 1 | | | | 5 | | | | | 10 | | | | | 15 | | |
| tcc | ctg | aga | ctc | tcc | tgt | gca | gcc | tct | gga | ttc | acc | gtc | agt | agc | aac | 96 |
| Ser | Leu | Arg | Leu | Ser | Cys | Ala | Ala | Ser | Gly | Phe | Thr | Val | Ser | Ser | Asn | |
| | | | 20 | | | | | 25 | | | | | 30 | | | |
| tac | atg | agc | tgg | gtc | cgc | cag | gct | cca | ggg | aag | ggg | ctg | gag | tgg | gtc | 144 |
| Tyr | Met | Ser | Trp | Val | Arg | Gln | Ala | Pro | Gly | Lys | Gly | Leu | Glu | Trp | Val | |
| | | 35 | | | | | 40 | | | | | 45 | | | | |
| tca | gtt | att | tat | agc | ggt | ggt | agc | aca | tac | tac | gca | gac | tcc | gtg | aag | 192 |
| Ser | Val | Ile | Tyr | Ser | Gly | Gly | Ser | Thr | Tyr | Tyr | Ala | Asp | Ser | Val | Lys | |
| 50 | | | | | 55 | | | | | 60 | | | | | | |
| ggc | aga | ttc | acc | atc | tcc | aga | gac | aat | tcc | aag | aac | acg | ctg | tat | ctt | 240 |
| Gly | Arg | Phe | Thr | Ile | Ser | Arg | Asp | Asn | Ser | Lys | Asn | Thr | Leu | Tyr | Leu | |
| 65 | | | | 70 | | | | | 75 | | | | | 80 | | |
| caa | atg | aac | agc | ctg | aga | gcc | gag | gac | acg | gct | gtg | tat | tac | tgt | gcg | 288 |
| Gln | Met | Asn | Ser | Leu | Arg | Ala | Glu | Asp | Thr | Ala | Val | Tyr | Tyr | Cys | Ala | |
| | | | | 85 | | | | | 90 | | | | | 95 | | |
| aga | gat | tcg | gac | ggc | ggt | gac | tat | ggc | tac | tgg | ggc | cag | gga | acc | ctg | 336 |
| Arg | Asp | Ser | Asp | Gly | Gly | Asp | Tyr | Gly | Tyr | Trp | Gly | Gln | Gly | Thr | Leu | |
| | | | 100 | | | | | 105 | | | | | 110 | | | |
| gtc | acc | gtc | tct | agt | gcc | tcc | acc | aag | ggc | cca | tcg | gtc | ttc | ccc | ctg | 384 |
| Val | Thr | Val | Ser | Ser | Ala | Ser | Thr | Lys | Gly | Pro | Ser | Val | Phe | Pro | Leu | |
| | | | 115 | | | | | 120 | | | | | 125 | | | |
| gca | ccc | tcc | tcc | aag | agc | acc | tct | ggg | ggc | aca | gcg | gcc | ctg | ggc | tgc | 432 |
| Ala | Pro | Ser | Ser | Lys | Ser | Thr | Ser | Gly | Gly | Thr | Ala | Ala | Leu | Gly | Cys | |
| | 130 | | | | | 135 | | | | | 140 | | | | | |
| ctg | gtc | aag | gac | tac | ttc | ccc | gaa | ccg | gtg | acg | gtg | tcg | tgg | aac | tca | 480 |
| Leu | Val | Lys | Asp | Tyr | Phe | Pro | Glu | Pro | Val | Thr | Val | Ser | Trp | Asn | Ser | |
| 145 | | | | | 150 | | | | | 155 | | | | | 160 | |
| ggc | gcc | ctg | acc | agc | ggc | gtg | cac | acc | ttc | ccg | gct | gtc | cta | cag | tcc | 528 |
| Gly | Ala | Leu | Thr | Ser | Gly | Val | His | Thr | Phe | Pro | Ala | Val | Leu | Gln | Ser | |
| | | | | 165 | | | | | 170 | | | | | 175 | | |
| tca | gga | ctc | tac | tcc | ctc | agc | agc | gtg | gtg | acc | gtg | ccc | tcc | agc | agc | 576 |
| Ser | Gly | Leu | Tyr | Ser | Leu | Ser | Ser | Val | Val | Thr | Val | Pro | Ser | Ser | Ser | |
| | | | 180 | | | | | 185 | | | | | 190 | | | |
| ttg | ggc | acc | cag | acc | tac | atc | tgc | aac | gtg | aat | cac | aag | ccc | agc | aac | 624 |
| Leu | Gly | Thr | Gln | Thr | Tyr | Ile | Cys | Asn | Val | Asn | His | Lys | Pro | Ser | Asn | |
| | | | 195 | | | | | 200 | | | | | 205 | | | |
| acc | aag | gtg | gac | aag | aaa | gtt | gag | ccc | aaa | tct | tgt | | | | | 660 |
| Thr | Lys | Val | Asp | Lys | Lys | Val | Glu | Pro | Lys | Ser | Cys | | | | | |
| | 210 | | | | | 215 | | | | | 220 | | | | | |

<210> SEQ ID NO 78
<211> LENGTH: 220
<212> TYPE: PRT
<213> ORGANISM: Homo sapiens

<400> SEQUENCE: 78

| | | | | | | | | | | | | | | | |
|---|---|---|---|---|---|---|---|---|---|---|---|---|---|---|---|
| Glu | Val | Gln | Leu | Val | Gln | Ser | Gly | Gly | Gly | Leu | Val | Gln | Pro | Gly | Gly |
| 1 | | | | 5 | | | | | 10 | | | | | 15 | |
| Ser | Leu | Arg | Leu | Ser | Cys | Ala | Ala | Ser | Gly | Phe | Thr | Val | Ser | Ser | Asn |
| | | | 20 | | | | | 25 | | | | | 30 | | |
| Tyr | Met | Ser | Trp | Val | Arg | Gln | Ala | Pro | Gly | Lys | Gly | Leu | Glu | Trp | Val |
| | | 35 | | | | | 40 | | | | | 45 | | | |

-continued

```
Ser Val Ile Tyr Ser Gly Gly Ser Thr Tyr Tyr Ala Asp Ser Val Lys
 50                  55                  60
Gly Arg Phe Thr Ile Ser Arg Asp Asn Ser Lys Asn Thr Leu Tyr Leu
 65                  70                  75                  80
Gln Met Asn Ser Leu Arg Ala Glu Asp Thr Ala Val Tyr Tyr Cys Ala
                 85                  90                  95
Arg Asp Ser Asp Gly Gly Asp Tyr Gly Tyr Trp Gly Gln Gly Thr Leu
            100                 105                 110
Val Thr Val Ser Ser Ala Ser Thr Lys Gly Pro Ser Val Phe Pro Leu
        115                 120                 125
Ala Pro Ser Ser Lys Ser Thr Ser Gly Gly Thr Ala Ala Leu Gly Cys
130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
            180                 185                 190
Leu Gly Thr Gln Thr Tyr Ile Cys Asn Val Asn His Lys Pro Ser Asn
        195                 200                 205
Thr Lys Val Asp Lys Lys Val Glu Pro Lys Ser Cys
    210                 215                 220

<210> SEQ ID NO 79
<211> LENGTH: 663
<212> TYPE: DNA
<213> ORGANISM: Homo sapiens
<220> FEATURE:
<221> NAME/KEY: CDS
<222> LOCATION: (1)..(663)

<400> SEQUENCE: 79 cag gtg cag ctg cag gag tcg ggc cca gga ctg gtg aag cct tcg gag     48
Gln Val Gln Leu Gln Glu Ser Gly Pro Gly Leu Val Lys Pro Ser Glu
1               5                   10                  15 acc ctg tcc ctc acc tgc gct gtc tct ggt ggc tcc atc agc agt ggt     96
Thr Leu Ser Leu Thr Cys Ala Val Ser Gly Gly Ser Ile Ser Ser Gly
            20                  25                  30 ggt tac tcc tgg agc tgg atc cgg cag cca cca ggg aag ggc ctg gag    144
Gly Tyr Ser Trp Ser Trp Ile Arg Gln Pro Pro Gly Lys Gly Leu Glu
        35                  40                  45 tgg att ggg tac atc tat cat agt ggg agc acc tac tac aac ccg tcc    192
Trp Ile Gly Tyr Ile Tyr His Ser Gly Ser Thr Tyr Tyr Asn Pro Ser
    50                  55                  60 ctc aag agt cga gtc acc ata tca gta gac agg tcc aag aac cag ttc    240
Leu Lys Ser Arg Val Thr Ile Ser Val Asp Arg Ser Lys Asn Gln Phe
65                  70                  75                  80 tcc ctg aag ctg agc tct gtg acc gcc gcg gac acg gcc gtg tat tac    288
Ser Leu Lys Leu Ser Ser Val Thr Ala Ala Asp Thr Ala Val Tyr Tyr
                85                  90                  95 tgt gcc aga ggg gac tgg ggc tac ttt gac tac tgg ggc cag gga acc    336
Cys Ala Arg Gly Asp Trp Gly Tyr Phe Asp Tyr Trp Gly Gln Gly Thr
            100                 105                 110 ctg gtc acc gtc tct agt gcc tcc acc aag ggc cca tcg gtc ttc ccc    384
Leu Val Thr Val Ser Ser Ala Ser Thr Lys Gly Pro Ser Val Phe Pro
        115                 120                 125 ctg gca ccc tcc tcc aag agc acc tct ggg ggc aca gcg gcc ctg ggc    432
Leu Ala Pro Ser Ser Lys Ser Thr Ser Gly Gly Thr Ala Ala Leu Gly
```

```
          130                 135                 140
tgc ctg gtc aag gac tac ttc ccc gaa ccg gtg acg gtg tcg tgg aac       480
Cys Leu Val Lys Asp Tyr Phe Pro Glu Pro Val Thr Val Ser Trp Asn
145                 150                 155                 160 tca ggc gcc ctg acc agc ggc gtg cac acc ttc ccg gct gtc cta cag       528
Ser Gly Ala Leu Thr Ser Gly Val His Thr Phe Pro Ala Val Leu Gln
                165                 170                 175 tcc tca gga ctc tac tcc ctc agc agc gtg gtg acc gtg ccc tcc agc       576
Ser Ser Gly Leu Tyr Ser Leu Ser Ser Val Val Thr Val Pro Ser Ser
            180                 185                 190 agc ttg ggc acc cag acc tac atc tgc aac gtg aat cac aag ccc agc       624
Ser Leu Gly Thr Gln Thr Tyr Ile Cys Asn Val Asn His Lys Pro Ser
        195                 200                 205 aac acc aag gtg gac aag aaa gtt gag ccc aaa tct tgt                   663
Asn Thr Lys Val Asp Lys Lys Val Glu Pro Lys Ser Cys
    210                 215                 220
```

<210> SEQ ID NO 80
<211> LENGTH: 221
<212> TYPE: PRT
<213> ORGANISM: Homo sapiens

<400> SEQUENCE: 80

```
Gln Val Gln Leu Gln Glu Ser Gly Pro Gly Leu Val Lys Pro Ser Glu
1               5                   10                  15

Thr Leu Ser Leu Thr Cys Ala Val Ser Gly Gly Ser Ile Ser Ser Gly
            20                  25                  30

Gly Tyr Ser Trp Ser Trp Ile Arg Gln Pro Pro Gly Lys Gly Leu Glu
        35                  40                  45

Trp Ile Gly Tyr Ile Tyr His Ser Gly Ser Thr Tyr Tyr Asn Pro Ser
    50                  55                  60

Leu Lys Ser Arg Val Thr Ile Ser Val Asp Arg Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Asp Trp Gly Tyr Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys
    210                 215                 220
```

<210> SEQ ID NO 81
<211> LENGTH: 687
<212> TYPE: DNA
<213> ORGANISM: Homo sapiens
<220> FEATURE:
<221> NAME/KEY: CDS

```
<222> LOCATION: (1)..(687)

<400> SEQUENCE: 81 gag gtg cag cta cag cag tgg ggc gca gga ctg ttg aag cct tcg gag      48
Glu Val Gln Leu Gln Gln Trp Gly Ala Gly Leu Leu Lys Pro Ser Glu
1               5                   10                  15 acc ctg tcc ctc acc tgc gct gtc tat ggt ggg tcc ttc agt ggt tac      96
Thr Leu Ser Leu Thr Cys Ala Val Tyr Gly Gly Ser Phe Ser Gly Tyr
                20                  25                  30 tac tgg agc tgg atc cgc cag ccc cca ggg aag ggg ctg gag tgg att      144
Tyr Trp Ser Trp Ile Arg Gln Pro Pro Gly Lys Gly Leu Glu Trp Ile
            35                  40                  45 ggg gaa atc aat cat agt gga agc acc aac tac aac ccg tcc ctc aag      192
Gly Glu Ile Asn His Ser Gly Ser Thr Asn Tyr Asn Pro Ser Leu Lys
        50                  55                  60 agt cga gtc acc ata tca gta gac acg tcc aag aac cag ttc tcc ctg      240
Ser Arg Val Thr Ile Ser Val Asp Thr Ser Lys Asn Gln Phe Ser Leu
65                  70                  75                  80 aag ctg agc tct gtg acc gcc gcg gac acg gct gtg tat tac tgt gcg      288
Lys Leu Ser Ser Val Thr Ala Ala Asp Thr Ala Val Tyr Tyr Cys Ala
                85                  90                  95 aga ggc tgg ccc act tac gtt tgg ggg agt tat cgt ccc aaa ggc tac      336
Arg Gly Trp Pro Thr Tyr Val Trp Gly Ser Tyr Arg Pro Lys Gly Tyr
            100                 105                 110 ttt gac tac tgg ggc cag gga acc ctg gtc acc gtc tct agt gcc tcc      384
Phe Asp Tyr Trp Gly Gln Gly Thr Leu Val Thr Val Ser Ser Ala Ser
        115                 120                 125 acc aag ggc cca tcg gtc ttc ccc ctg gca ccc tcc tcc aag agc acc      432
Thr Lys Gly Pro Ser Val Phe Pro Leu Ala Pro Ser Ser Lys Ser Thr
    130                 135                 140 tct ggg ggc aca gcg gcc ctg ggc tgc ctg gtc aag gac tac ttc ccc      480
Ser Gly Gly Thr Ala Ala Leu Gly Cys Leu Val Lys Asp Tyr Phe Pro
145                 150                 155                 160 gaa ccg gtg acg gtg tcg tgg aac tca ggc gcc ctg acc agc ggc gtg      528
Glu Pro Val Thr Val Ser Trp Asn Ser Gly Ala Leu Thr Ser Gly Val
                165                 170                 175 cac acc ttc ccg gct gtc cta cag tcc tca gga ctc tac tcc ctc agc      576
His Thr Phe Pro Ala Val Leu Gln Ser Ser Gly Leu Tyr Ser Leu Ser
            180                 185                 190 agc gtg gtg acc gtg ccc tcc agc agc ttg ggc acc cag acc tac atc      624
Ser Val Val Thr Val Pro Ser Ser Ser Leu Gly Thr Gln Thr Tyr Ile
        195                 200                 205 tgc aac gtg aat cac aag ccc agc aac acc aag gtg gac aag aaa gtt      672
Cys Asn Val Asn His Lys Pro Ser Asn Thr Lys Val Asp Lys Lys Val
    210                 215                 220 gag ccc aaa tct tgt                                                  687
Glu Pro Lys Ser Cys
225

<210> SEQ ID NO 82
<211> LENGTH: 229
<212> TYPE: PRT
<213> ORGANISM: Homo sapiens

<400> SEQUENCE: 82

Glu Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
                20                  25                  30

Tyr Trp Ser Trp Ile Arg Gln Pro Pro Gly Lys Gly Leu Glu Trp Ile
```

-continued

```
                35                  40                  45
Gly Glu Ile Asn His Ser Gly Ser Thr Asn Tyr Asn Pro Ser Leu Lys
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Gly Trp Pro Thr Tyr Val Trp Gly Ser Tyr Arg Pro Lys Gly Tyr
                100                 105                 110

Phe Asp Tyr Trp Gly Gln Gly Thr Leu Val Thr Val Ser Ser Ala Ser
                115                 120                 125

Thr Lys Gly Pro Ser Val Phe Pro Leu Ala Pro Ser Ser Lys Ser Thr
130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
                180                 185                 190

Ser Val Val Thr Val Pro Ser Ser Ser Leu Gly Thr Gln Thr Tyr Ile
                195                 200                 205

Cys Asn Val Asn His Lys Pro Ser Asn Thr Lys Val Asp Lys Lys Val
210                 215                 220

Glu Pro Lys Ser Cys
225

<210> SEQ ID NO 83
<211> LENGTH: 684
<212> TYPE: DNA
<213> ORGANISM: Homo sapiens
<220> FEATURE:
<221> NAME/KEY: CDS
<222> LOCATION: (1)..(684)

<400> SEQUENCE: 83 gcc aat acc ctt gaa gag tct ggt cct acg ctg gtg caa ccg aca cag      48
Ala Asn Thr Leu Glu Glu Ser Gly Pro Thr Leu Val Gln Pro Thr Gln
 1               5                  10                  15 acc ctc acg ctg acc tgc tcc tac tct ggg ttc tca ctc agc agt aat      96
Thr Leu Thr Leu Thr Cys Ser Tyr Ser Gly Phe Ser Leu Ser Ser Asn
                20                  25                  30 gaa gcg ggt gtg ggc tgg atc cgt cag ccc cca gga aag gcc ccg gag     144
Glu Ala Gly Val Gly Trp Ile Arg Gln Pro Pro Gly Lys Ala Pro Glu
            35                  40                  45 tgg ctt gca ctt ctt tat tgg gat gat gat aag cgc tac agc ccg tct     192
Trp Leu Ala Leu Leu Tyr Trp Asp Asp Asp Lys Arg Tyr Ser Pro Ser
 50                  55                  60 ctg agg agc agg ctc atc gtt aac aag gac acc tcc aaa agc cag gtt     240
Leu Arg Ser Arg Leu Ile Val Asn Lys Asp Thr Ser Lys Ser Gln Val
 65                  70                  75                  80 gtc ctt aca atg acc aac atg gac cct gtg gac acg gcc aca tat tac     288
Val Leu Thr Met Thr Asn Met Asp Pro Val Asp Thr Ala Thr Tyr Tyr
                85                  90                  95 tgt gca cac aga ctc gtc aga tat ggt ggc tac tca acg ggt ggt ttt     336
Cys Ala His Arg Leu Val Arg Tyr Gly Gly Tyr Ser Thr Gly Gly Phe
                100                 105                 110 gat gtc tgg ggc caa ggg acc acg gtc acc gtc tca agc gcc tcc acc     384
Asp Val Trp Gly Gln Gly Thr Thr Val Thr Val Ser Ser Ala Ser Thr
```

```
              115                 120                 125
aag ggc cca tcg gtc ttc ccc ctg gca ccc tcc tcc aag agc acc tct      432
Lys Gly Pro Ser Val Phe Pro Leu Ala Pro Ser Ser Lys Ser Thr Ser
    130                 135                 140 ggg ggc aca gcg gcc ctg ggc tgc ctg gtc aag gac tac ttc ccc gaa      480
Gly Gly Thr Ala Ala Leu Gly Cys Leu Val Lys Asp Tyr Phe Pro Glu
145                 150                 155                 160 ccg gtg acg gtg tcg tgg aac tca ggc gcc ctg acc agc ggc gtc cac      528
Pro Val Thr Val Ser Trp Asn Ser Gly Ala Leu Thr Ser Gly Val His
                165                 170                 175 acc ttc ccg gct gtc cta cag tcc tca gga ctc tac tcc ctc agc agc      576
Thr Phe Pro Ala Val Leu Gln Ser Ser Gly Leu Tyr Ser Leu Ser Ser
            180                 185                 190 gta gtg acc gtg ccc tcc agc agc ttg ggc acc cag acc tac atc tgc      624
Val Val Thr Val Pro Ser Ser Ser Leu Gly Thr Gln Thr Tyr Ile Cys
        195                 200                 205 aac gtg aat cac aag ccc agc aac acc aag gtg gac aag aaa gtt gag      672
Asn Val Asn His Lys Pro Ser Asn Thr Lys Val Asp Lys Lys Val Glu
    210                 215                 220 ccc aaa tct tgt                                                       684
Pro Lys Ser Cys
225

<210> SEQ ID NO 84
<211> LENGTH: 228
<212> TYPE: PRT
<213> ORGANISM: Homo sapiens

<400> SEQUENCE: 84

Ala Asn Thr Leu Glu Glu Ser Gly Pro Thr Leu Val Gln Pro Thr Gln
1               5                   10                  15

Thr Leu Thr Leu Thr Cys Ser Tyr Ser Gly Phe Ser Leu Ser Ser Asn
            20                  25                  30

Glu Ala Gly Val Gly Trp Ile Arg Gln Pro Pro Gly Lys Ala Pro Glu
        35                  40                  45

Trp Leu Ala Leu Leu Tyr Trp Asp Asp Asp Lys Arg Tyr Ser Pro Ser
    50                  55                  60

Leu Arg Ser Arg Leu Ile Val Asn Lys Asp Thr Ser Lys Ser Gln Val
65                  70                  75                  80

Val Leu Thr Met Thr Asn Met Asp Pro Val Asp Thr Ala Thr Tyr Tyr
                85                  90                  95

Cys Ala His Arg Leu Val Arg Tyr Gly Gly Tyr Ser Thr Gly Gly Phe
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220
```

```
Pro Lys Ser Cys
225

<210> SEQ ID NO 85
<211> LENGTH: 669
<212> TYPE: DNA
<213> ORGANISM: Homo sapiens
<220> FEATURE:
<221> NAME/KEY: CDS
<222> LOCATION: (1)..(669)

<400> SEQUENCE: 85 gac gtg cag ctg gtg gag act ggg gga ggc ttg gta cag cct ggg ggg        48
Asp Val Gln Leu Val Glu Thr Gly Gly Gly Leu Val Gln Pro Gly Gly
1               5                   10                  15 tcc ctg aga ctc tcc tgt gcg gcc tct gga ttc acc ttt agc agc tat        96
Ser Leu Arg Leu Ser Cys Ala Ala Ser Gly Phe Thr Phe Ser Ser Tyr
            20                  25                  30 gcc atg agc tgg gtc cgc cag gct cca ggg aag ggg ctg gag tgg gtc       144
Ala Met Ser Trp Val Arg Gln Ala Pro Gly Lys Gly Leu Glu Trp Val
        35                  40                  45 tca gct att agt ggt agt ggt ggt agc aca tac tac gca gac tcc gtg       192
Ser Ala Ile Ser Gly Ser Gly Gly Ser Thr Tyr Tyr Ala Asp Ser Val
    50                  55                  60 aag ggc cgg ttc acc atc tcc aga gac aat tcc aag aac acg ctg tat       240
Lys Gly Arg Phe Thr Ile Ser Arg Asp Asn Ser Lys Asn Thr Leu Tyr
65                  70                  75                  80 ctg caa atg gac agc ctg aga gcc gag gac acg gcc gta tat tac tgt       288
Leu Gln Met Asp Ser Leu Arg Ala Glu Asp Thr Ala Val Tyr Tyr Cys
                85                  90                  95 gcg aag acg tcc tgg aac gca ggt ggc ccg att gac tac tgg ggc cag       336
Ala Lys Thr Ser Trp Asn Ala Gly Gly Pro Ile Asp Tyr Trp Gly Gln
            100                 105                 110 gga aac ctg gtc acc gtc tca agc gcc tcc acc aag ggc cca tcg gtc       384
Gly Asn Leu Val Thr Val Ser Ser Ala Ser Thr Lys Gly Pro Ser Val
        115                 120                 125 ttc ccc ctg gca ccc tcc tcc aag agc acc tct ggg ggc aca gcg gcc       432
Phe Pro Leu Ala Pro Ser Ser Lys Ser Thr Ser Gly Gly Thr Ala Ala
    130                 135                 140 ctg ggc tgc ctg gtc aag gac tac ttc ccc gaa ccg gtg acg gtg tcg       480
Leu Gly Cys Leu Val Lys Asp Tyr Phe Pro Glu Pro Val Thr Val Ser
145                 150                 155                 160 tgg aac tca ggc gcc ctg acc agc ggc gtg cac acc ttc ccg gct gtc       528
Trp Asn Ser Gly Ala Leu Thr Ser Gly Val His Thr Phe Pro Ala Val
                165                 170                 175 cta cag tcc tca gga ctc tac tcc ctc agc agc gta gtg acc gtg ccc       576
Leu Gln Ser Ser Gly Leu Tyr Ser Leu Ser Ser Val Val Thr Val Pro
            180                 185                 190 tcc agc agc ttg ggc acc cag acc tac atc tgc aac gtg aat cac aag       624
Ser Ser Ser Leu Gly Thr Gln Thr Tyr Ile Cys Asn Val Asn His Lys
        195                 200                 205 ccc agc aac acc aag gtg gac aag aaa gtt gag ccc aaa tct tgt           669
Pro Ser Asn Thr Lys Val Asp Lys Lys Val Glu Pro Lys Ser Cys
    210                 215                 220

<210> SEQ ID NO 86
<211> LENGTH: 223
<212> TYPE: PRT
<213> ORGANISM: Homo sapiens

<400> SEQUENCE: 86
```

```
Asp Val Gln Leu Val Glu Thr Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
50                      55                  60

Lys Gly Arg Phe Thr Ile Ser Arg Asp Asn Ser Lys Asn Thr Leu Tyr
65                  70                  75                  80

Leu Gln Met Asp Ser Leu Arg Ala Glu Asp Thr Ala Val Tyr Tyr Cys
                85                  90                  95

Ala Lys Thr Ser Trp Asn Ala Gly Gly Pro Ile Asp Tyr Trp Gly Gln
            100                 105                 110

Gly Asn Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys
        210                 215                 220

<210> SEQ ID NO 87
<211> LENGTH: 651
<212> TYPE: DNA
<213> ORGANISM: Homo sapiens
<220> FEATURE:
<221> NAME/KEY: CDS
<222> LOCATION: (1)..(651)

<400> SEQUENCE: 87 aat ttt atg ctg act cag ccc cac tct gtg tcg gag tct ccg ggg aag      48
Asn Phe Met Leu Thr Gln Pro His Ser Val Ser Glu Ser Pro Gly Lys
1               5                   10                  15 acg gta acc atc tcc tgc acc ggc agc agt ggc agc att gcc agc cac      96
Thr Val Thr Ile Ser Cys Thr Gly Ser Ser Gly Ser Ile Ala Ser His
            20                  25                  30 tat gtg cag tgg tac cag cag cgc ccg ggc agt gcc ccc act aat gtg     144
Tyr Val Gln Trp Tyr Gln Gln Arg Pro Gly Ser Ala Pro Thr Asn Val
        35                  40                  45 att tat gag gat aag gaa aga ccc tct ggg gtc cct gat cgg ttc tct     192
Ile Tyr Glu Asp Lys Glu Arg Pro Ser Gly Val Pro Asp Arg Phe Ser
50                  55                  60 ggc tcc atc gac agc tcc acc aac tct gcc tcc ctc acc atc tct gga     240
Gly Ser Ile Asp Ser Ser Thr Asn Ser Ala Ser Leu Thr Ile Ser Gly
65                  70                  75                  80 ctg aag act gag gac gag gct gac tac tat tgt cag tct tat gat agc     288
Leu Lys Thr Glu Asp Glu Ala Asp Tyr Tyr Cys Gln Ser Tyr Asp Ser
                85                  90                  95 agc aat cag tgg gtg ttc ggc gga ggg acc aag ctg acc gtc cta ggt     336
Ser Asn Gln Trp Val Phe Gly Gly Gly Thr Lys Leu Thr Val Leu Gly
```

```
            100                 105                 110
cag ccc aag gct gcc ccc tcg gtc act ctg ttc ccg ccc tcc tct gag      384
Gln Pro Lys Ala Ala Pro Ser Val Thr Leu Phe Pro Pro Ser Ser Glu
            115                 120                 125 gag ctt caa gcc aac aag gcc aca ctg gtg tgt ctc ata agt gac ttc      432
Glu Leu Gln Ala Asn Lys Ala Thr Leu Val Cys Leu Ile Ser Asp Phe
    130                 135                 140 tac ccg gga gcc gtg aca gtg gcc tgg aag gca gat agc agc ccc gtc      480
Tyr Pro Gly Ala Val Thr Val Ala Trp Lys Ala Asp Ser Ser Pro Val
145                 150                 155                 160 aag gcg gga gtg gag acc acc aca ccc tcc aaa caa agc aac aac aag      528
Lys Ala Gly Val Glu Thr Thr Thr Pro Ser Lys Gln Ser Asn Asn Lys
                165                 170                 175 tac gcg gcc agc agc tac ctg agc ctg acg cct gag cag tgg aag tcc      576
Tyr Ala Ala Ser Ser Tyr Leu Ser Leu Thr Pro Glu Gln Trp Lys Ser
            180                 185                 190 cac aga agc tac agc tgc cag gtc acg cat gaa ggg agc acc gtg gag      624
His Arg Ser Tyr Ser Cys Gln Val Thr His Glu Gly Ser Thr Val Glu
        195                 200                 205 aag aca gtg gct cct aca gaa tgt tca                                  651
Lys Thr Val Ala Pro Thr Glu Cys Ser
    210                 215

<210> SEQ ID NO 88
<211> LENGTH: 217
<212> TYPE: PRT
<213> ORGANISM: Homo sapiens

<400> SEQUENCE: 88

Asn Phe Met Leu Thr Gln Pro His Ser Val Ser Glu Ser Pro Gly Lys
1               5                   10                  15

Thr Val Thr Ile Ser Cys Thr Gly Ser Ser Gly Ser Ile Ala Ser His
            20                  25                  30

Tyr Val Gln Trp Tyr Gln Gln Arg Pro Gly Ser Ala Pro Thr Asn Val
        35                  40                  45

Ile Tyr Glu Asp Lys Glu Arg Pro Ser Gly Val Pro Asp Arg Phe Ser
    50                  55                  60

Gly Ser Ile Asp Ser Ser Thr Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Ser Asn Gln Trp Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215
```

<210> SEQ ID NO 89
<211> LENGTH: 648
<212> TYPE: DNA
<213> ORGANISM: Homo sapiens
<220> FEATURE:
<221> NAME/KEY: CDS
<222> LOCATION: (1)..(648)

<400> SEQUENCE: 89

| aat | ttt | atg | ctg | act | cag | ccc | cac | tct | gtg | tcg | gag | tct | ccg | ggg | aag | 48 |
|---|---|---|---|---|---|---|---|---|---|---|---|---|---|---|---|---|
| Asn | Phe | Met | Leu | Thr | Gln | Pro | His | Ser | Val | Ser | Glu | Ser | Pro | Gly | Lys | |
| 1 | | | | 5 | | | | | 10 | | | | | 15 | | |

| acg | gta | acc | atc | tcc | tgc | acc | cgc | agc | agc | ggc | agc | att | gcc | agc | tac | 96 |
|---|---|---|---|---|---|---|---|---|---|---|---|---|---|---|---|---|
| Thr | Val | Thr | Ile | Ser | Cys | Thr | Arg | Ser | Ser | Gly | Ser | Ile | Ala | Ser | Tyr | |
| | | | 20 | | | | | 25 | | | | | 30 | | | |

| tat | gtg | cag | tgg | tac | cag | cag | cgc | ccg | ggc | agt | tcc | ccc | acc | act | gtg | 144 |
|---|---|---|---|---|---|---|---|---|---|---|---|---|---|---|---|---|
| Tyr | Val | Gln | Trp | Tyr | Gln | Gln | Arg | Pro | Gly | Ser | Ser | Pro | Thr | Thr | Val | |
| | | | 35 | | | | | 40 | | | | | 45 | | | |

| atc | tat | gaa | gat | gac | caa | aga | ccc | tct | ggg | gtc | cct | gat | cga | ttc | tct | 192 |
|---|---|---|---|---|---|---|---|---|---|---|---|---|---|---|---|---|
| Ile | Tyr | Glu | Asp | Asp | Gln | Arg | Pro | Ser | Gly | Val | Pro | Asp | Arg | Phe | Ser | |
| 50 | | | | | 55 | | | | | 60 | | | | | | |

| ggc | tcc | atc | gac | agt | gcc | tcc | aac | tca | gcc | tcc | ctc | acc | atc | tct | ggc | 240 |
|---|---|---|---|---|---|---|---|---|---|---|---|---|---|---|---|---|
| Gly | Ser | Ile | Asp | Ser | Ala | Ser | Asn | Ser | Ala | Ser | Leu | Thr | Ile | Ser | Gly | |
| 65 | | | | 70 | | | | | 75 | | | | | 80 | | |

| ctg | cag | act | gag | gac | gag | gct | gac | tac | tat | tgt | cag | tct | tat | gac | agg | 288 |
|---|---|---|---|---|---|---|---|---|---|---|---|---|---|---|---|---|
| Leu | Gln | Thr | Glu | Asp | Glu | Ala | Asp | Tyr | Tyr | Cys | Gln | Ser | Tyr | Asp | Arg | |
| | | | 85 | | | | | 90 | | | | | 95 | | | |

| aac | agt | ctg | gtg | ttc | ggc | ggg | ggg | acc | aag | ctg | acc | gtc | ctg | ggt | cag | 336 |
|---|---|---|---|---|---|---|---|---|---|---|---|---|---|---|---|---|
| Asn | Ser | Leu | Val | Phe | Gly | Gly | Gly | Thr | Lys | Leu | Thr | Val | Leu | Gly | Gln | |
| | | | 100 | | | | | 105 | | | | | 110 | | | |

| ccc | aag | gct | gcc | ccc | tcg | gtc | act | ctg | ttc | ccg | ccc | tcc | tct | gag | gag | 384 |
|---|---|---|---|---|---|---|---|---|---|---|---|---|---|---|---|---|
| Pro | Lys | Ala | Ala | Pro | Ser | Val | Thr | Leu | Phe | Pro | Pro | Ser | Ser | Glu | Glu | |
| | | | 115 | | | | | 120 | | | | | 125 | | | |

| ctt | caa | gcc | aac | aag | gcc | aca | ctg | gtg | tgt | ctc | ata | agt | gac | ttc | tac | 432 |
|---|---|---|---|---|---|---|---|---|---|---|---|---|---|---|---|---|
| Leu | Gln | Ala | Asn | Lys | Ala | Thr | Leu | Val | Cys | Leu | Ile | Ser | Asp | Phe | Tyr | |
| | 130 | | | | | 135 | | | | | 140 | | | | | |

| ccg | gga | gcc | gtg | aca | gtg | gcc | tgg | aag | gca | gat | agc | agc | ccc | gtc | aag | 480 |
|---|---|---|---|---|---|---|---|---|---|---|---|---|---|---|---|---|
| Pro | Gly | Ala | Val | Thr | Val | Ala | Trp | Lys | Ala | Asp | Ser | Ser | Pro | Val | Lys | |
| 145 | | | | | 150 | | | | | 155 | | | | | 160 | |

| gcg | gga | gtg | gag | acc | acc | aca | ccc | tcc | aaa | caa | agc | aac | aac | aag | tac | 528 |
|---|---|---|---|---|---|---|---|---|---|---|---|---|---|---|---|---|
| Ala | Gly | Val | Glu | Thr | Thr | Thr | Pro | Ser | Lys | Gln | Ser | Asn | Asn | Lys | Tyr | |
| | | | | 165 | | | | | 170 | | | | | 175 | | |

| gcg | gcc | agc | agc | tac | ctg | agc | ctg | acg | cct | gag | cag | tgg | aag | tcc | cac | 576 |
|---|---|---|---|---|---|---|---|---|---|---|---|---|---|---|---|---|
| Ala | Ala | Ser | Ser | Tyr | Leu | Ser | Leu | Thr | Pro | Glu | Gln | Trp | Lys | Ser | His | |
| | | | 180 | | | | | 185 | | | | | 190 | | | |

| aaa | agc | tac | agc | tgc | cag | gtc | acg | cat | gaa | ggg | agc | acc | gtg | gag | aag | 624 |
|---|---|---|---|---|---|---|---|---|---|---|---|---|---|---|---|---|
| Lys | Ser | Tyr | Ser | Cys | Gln | Val | Thr | His | Glu | Gly | Ser | Thr | Val | Glu | Lys | |
| | | 195 | | | | | 200 | | | | | 205 | | | | |

| aca | gtg | gct | cct | aca | gaa | tgt | tca | | | | | | | | | 648 |
|---|---|---|---|---|---|---|---|---|---|---|---|---|---|---|---|---|
| Thr | Val | Ala | Pro | Thr | Glu | Cys | Ser | | | | | | | | | |
| | 210 | | | | | 215 | | | | | | | | | | |

<210> SEQ ID NO 90
<211> LENGTH: 216
<212> TYPE: PRT
<213> ORGANISM: Homo sapiens

<400> SEQUENCE: 90

Asn Phe Met Leu Thr Gln Pro His Ser Val Ser Glu Ser Pro Gly Lys
1               5                   10                  15

```
Thr Val Thr Ile Ser Cys Thr Arg Ser Ser Gly Ser Ile Ala Ser Tyr
            20                  25                  30

Tyr Val Gln Trp Tyr Gln Gln Arg Pro Gly Ser Ser Pro Thr Thr Val
        35                  40                  45

Ile Tyr Glu Asp Asp Gln Arg Pro Ser Gly Val Pro Asp Arg Phe Ser
50                  55                  60

Gly Ser Ile Asp Ser Ala Ser Asn Ser Ala Ser Leu Thr Ile Ser Gly
65                  70                  75                  80

Leu Gln Thr Glu Asp Glu Ala Asp Tyr Tyr Cys Gln Ser Tyr Asp Arg
                85                  90                  95

Asn Ser Leu Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Lys Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 91
<211> LENGTH: 657
<212> TYPE: DNA
<213> ORGANISM: Homo sapiens
<220> FEATURE:
<221> NAME/KEY: CDS
<222> LOCATION: (1)..(657)

<400> SEQUENCE: 91 gat att gtg atg acc cac act cca ctc tcc tca cct gtc acc ctt gga      48
Asp Ile Val Met Thr His Thr Pro Leu Ser Ser Pro Val Thr Leu Gly
1               5                   10                  15 cag ccg gcc tcc atc tcc tgc agg tct agt cag agc ctc gta cac agt      96
Gln Pro Ala Ser Ile Ser Cys Arg Ser Ser Gln Ser Leu Val His Ser
            20                  25                  30 gat gga aac acc tac ttg agt tgg ctt cac cag agg cca ggc cag cct     144
Asp Gly Asn Thr Tyr Leu Ser Trp Leu His Gln Arg Pro Gly Gln Pro
        35                  40                  45 cca aga ctc cta att tat aag att tct aac cgg ttc tct ggg gtc cca     192
Pro Arg Leu Leu Ile Tyr Lys Ile Ser Asn Arg Phe Ser Gly Val Pro
50                  55                  60 gac aga ttc agt ggc agt ggg gca ggg aca gat ttc aca ctg aaa atc     240
Asp Arg Phe Ser Gly Ser Gly Ala Gly Thr Asp Phe Thr Leu Lys Ile
65                  70                  75                  80 agc agg gtg gaa gct gag gat gtc ggg ctt tat tac tgc atg caa gct     288
Ser Arg Val Glu Ala Glu Asp Val Gly Leu Tyr Tyr Cys Met Gln Ala
                85                  90                  95 aca caa ctt ccg tac act ttt ggc cag ggg acc aag ctg gag atc aaa     336
Thr Gln Leu Pro Tyr Thr Phe Gly Gln Gly Thr Lys Leu Glu Ile Lys
            100                 105                 110 cga act gtg gct gca cca tct gtc ttc atc ttc ccg cca tct gat gag     384
```

```
Arg Thr Val Ala Ala Pro Ser Val Phe Ile Phe Pro Ser Asp Glu
        115                 120                 125 cag ttg aaa tct gga act gcc tct gtt gtg tgc ctg ctg aat aac ttc      432
Gln Leu Lys Ser Gly Thr Ala Ser Val Val Cys Leu Leu Asn Asn Phe
    130                 135                 140 tat ccc aga gag gcc aaa gta cag tgg aag gtg gat aac gcc ctc caa      480
Tyr Pro Arg Glu Ala Lys Val Gln Trp Lys Val Asp Asn Ala Leu Gln
145                 150                 155                 160 tcg ggt aac tcc cag gag agt gtc aca gag cag gac agc aag gac agc      528
Ser Gly Asn Ser Gln Glu Ser Val Thr Glu Gln Asp Ser Lys Asp Ser
                165                 170                 175 acc tac agc ctc agc agc acc ctg acg ctg agc aaa gca gac tac gag      576
Thr Tyr Ser Leu Ser Ser Thr Leu Thr Leu Ser Lys Ala Asp Tyr Glu
            180                 185                 190 aaa cac aaa gtc tac gcc tgc gaa gtc acc cat cag ggc ctg agc tcg      624
Lys His Lys Val Tyr Ala Cys Glu Val Thr His Gln Gly Leu Ser Ser
        195                 200                 205 ccc gtc aca aag agt ttc aac agg gga gag tgt                          657
Pro Val Thr Lys Ser Phe Asn Arg Gly Glu Cys
    210                 215

<210> SEQ ID NO 92
<211> LENGTH: 219
<212> TYPE: PRT
<213> ORGANISM: Homo sapiens

<400> SEQUENCE: 92

Asp Ile Val Met Thr His Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu His Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Leu Tyr Tyr Cys Met Gln Ala
                85                  90                  95

Thr Gln Leu Pro Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 93
```

<211> LENGTH: 657
<212> TYPE: DNA
<213> ORGANISM: Homo sapiens
<220> FEATURE:
<221> NAME/KEY: CDS
<222> LOCATION: (1)..(657)

<400> SEQUENCE: 93

| | | | | | | | | | | | | | | | | |
|---|---|---|---|---|---|---|---|---|---|---|---|---|---|---|---|---|
| gat | gtt | gtg | atg | act | cag | tct | cca | ctc | tcc | ctg | ccc | gtc | acc | cct | gga | 48 |
| Asp | Val | Val | Met | Thr | Gln | Ser | Pro | Leu | Ser | Leu | Pro | Val | Thr | Pro | Gly | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| gag | ccg | gcc | tcc | atc | tcc | tgc | agg | gca | act | cag | agc | ctc | ctg | cat | gga | 96 |
| Glu | Pro | Ala | Ser | Ile | Ser | Cys | Arg | Ala | Thr | Gln | Ser | Leu | Leu | His | Gly | |
| | | | 20 | | | | | 25 | | | | | 30 | | | |

| | | | | | | | | | | | | | | | | |
|---|---|---|---|---|---|---|---|---|---|---|---|---|---|---|---|---|
| aat | gga | cac | aac | tat | ttg | gat | tgg | tac | ctg | cag | aag | cca | ggg | cag | tct | 144 |
| Asn | Gly | His | Asn | Tyr | Leu | Asp | Trp | Tyr | Leu | Gln | Lys | Pro | Gly | Gln | Ser | |
| | | | 35 | | | | | 40 | | | | | 45 | | | |

| | | | | | | | | | | | | | | | | |
|---|---|---|---|---|---|---|---|---|---|---|---|---|---|---|---|---|
| cca | cac | ctc | ctg | atc | tat | atg | ggt | tct | aat | cgg | gcc | tcc | ggg | gtc | cct | 192 |
| Pro | His | Leu | Leu | Ile | Tyr | Met | Gly | Ser | Asn | Arg | Ala | Ser | Gly | Val | Pro | |
| | | 50 | | | | | 55 | | | | | 60 | | | | |

| | | | | | | | | | | | | | | | | |
|---|---|---|---|---|---|---|---|---|---|---|---|---|---|---|---|---|
| ggc | agg | ttc | agt | ggc | act | gaa | tca | ggc | aga | aat | ttt | aca | ctg | aag | atc | 240 |
| Gly | Arg | Phe | Ser | Gly | Thr | Glu | Ser | Gly | Arg | Asn | Phe | Thr | Leu | Lys | Ile | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| agc | aga | gtg | gag | gct | gag | gat | gtt | ggg | gtc | tat | tac | tgt | atg | cag | gct | 288 |
| Ser | Arg | Val | Glu | Ala | Glu | Asp | Val | Gly | Val | Tyr | Tyr | Cys | Met | Gln | Ala | |
| | | | | 85 | | | | | 90 | | | | | 95 | | |

| | | | | | | | | | | | | | | | | |
|---|---|---|---|---|---|---|---|---|---|---|---|---|---|---|---|---|
| cta | caa | ctt | cct | ccg | acg | ttc | ggc | caa | ggt | acc | agg | gtg | gat | atc | aaa | 336 |
| Leu | Gln | Leu | Pro | Pro | Thr | Phe | Gly | Gln | Gly | Thr | Arg | Val | Asp | Ile | Lys | |
| | | | 100 | | | | | 105 | | | | | 110 | | | |

| | | | | | | | | | | | | | | | | |
|---|---|---|---|---|---|---|---|---|---|---|---|---|---|---|---|---|
| cga | act | gtg | gct | gca | cca | tct | gtc | ttc | atc | ttc | ccg | cca | tct | gat | gag | 384 |
| Arg | Thr | Val | Ala | Ala | Pro | Ser | Val | Phe | Ile | Phe | Pro | Pro | Ser | Asp | Glu | |
| | | | 115 | | | | | 120 | | | | | 125 | | | |

| | | | | | | | | | | | | | | | | |
|---|---|---|---|---|---|---|---|---|---|---|---|---|---|---|---|---|
| cag | ttg | aaa | tct | gga | act | gcc | tct | gtt | gtg | tgc | ctg | ctg | aat | aac | ttc | 432 |
| Gln | Leu | Lys | Ser | Gly | Thr | Ala | Ser | Val | Val | Cys | Leu | Leu | Asn | Asn | Phe | |
| | 130 | | | | | 135 | | | | | 140 | | | | | |

| | | | | | | | | | | | | | | | | |
|---|---|---|---|---|---|---|---|---|---|---|---|---|---|---|---|---|
| tat | ccc | aga | gag | gcc | aaa | gta | cag | tgg | aag | gtg | gat | aac | gcc | ctc | caa | 480 |
| Tyr | Pro | Arg | Glu | Ala | Lys | Val | Gln | Trp | Lys | Val | Asp | Asn | Ala | Leu | Gln | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| tcg | ggt | aac | tcc | cag | gag | agt | gtc | aca | gag | cag | gac | agc | aag | gac | agc | 528 |
| Ser | Gly | Asn | Ser | Gln | Glu | Ser | Val | Thr | Glu | Gln | Asp | Ser | Lys | Asp | Ser | |
| | | | | 165 | | | | | 170 | | | | | 175 | | |

| | | | | | | | | | | | | | | | | |
|---|---|---|---|---|---|---|---|---|---|---|---|---|---|---|---|---|
| acc | tac | agc | ctc | agc | agc | acc | ctg | acg | ctg | agc | aaa | gca | gac | tac | gag | 576 |
| Thr | Tyr | Ser | Leu | Ser | Ser | Thr | Leu | Thr | Leu | Ser | Lys | Ala | Asp | Tyr | Glu | |
| | | | 180 | | | | | 185 | | | | | 190 | | | |

| | | | | | | | | | | | | | | | | |
|---|---|---|---|---|---|---|---|---|---|---|---|---|---|---|---|---|
| aaa | cac | aaa | gtc | tac | gcc | tgc | gaa | gtc | acc | cat | cag | ggc | ctg | agc | tcg | 624 |
| Lys | His | Lys | Val | Tyr | Ala | Cys | Glu | Val | Thr | His | Gln | Gly | Leu | Ser | Ser | |
| | | | 195 | | | | | 200 | | | | | 205 | | | |

| | | | | | | | | | | |
|---|---|---|---|---|---|---|---|---|---|---|
| ccc | gtc | aca | aag | agc | ttc | aac | agg | gga | gag | tgt | 657 |
| Pro | Val | Thr | Lys | Ser | Phe | Asn | Arg | Gly | Glu | Cys | |
| | 210 | | | | | 215 | | | | | |

<210> SEQ ID NO 94

<211> LENGTH: 219
<212> TYPE: PRT
<213> ORGANISM: Homo sapiens

<400> SEQUENCE: 94

Asp Val Val Met Thr Gln Ser Pro Leu Ser Leu Pro Val Thr Pro Gly
1               5                   10                  15

Glu Pro Ala Ser Ile Ser Cys Arg Ala Thr Gln Ser Leu Leu His Gly
            20                  25                  30

```
Asn Gly His Asn Tyr Leu Asp Trp Tyr Leu Gln Lys Pro Gly Gln Ser
             35                  40                  45

Pro His Leu Leu Ile Tyr Met Gly Ser Asn Arg Ala Ser Gly Val Pro
         50                  55                  60

Gly Arg Phe Ser Gly Thr Glu Ser Gly Arg Asn Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Leu Pro Pro Thr Phe Gly Gln Gly Thr Arg Val Asp Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
            130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
    210                 215
```

<210> SEQ ID NO 95
<211> LENGTH: 642
<212> TYPE: DNA
<213> ORGANISM: Homo sapiens
<220> FEATURE:
<221> NAME/KEY: CDS
<222> LOCATION: (1)..(642)

<400> SEQUENCE: 95

```
cag tct gtg ctt acg cag ccg ccc tcg gtg tct gtg gcc cca gga aag        48
Gln Ser Val Leu Thr Gln Pro Pro Ser Val Ser Val Ala Pro Gly Lys
 1               5                  10                  15 acg gcc act att acc tgt ggg gga gac aac ctt gga ggt aaa agt cta        96
Thr Ala Thr Ile Thr Cys Gly Gly Asp Asn Leu Gly Gly Lys Ser Leu
             20                  25                  30 cac tgg tac cag cag aag cca ggc cag gcc cct gta ctg gtc gtc tac       144
His Trp Tyr Gln Gln Lys Pro Gly Gln Ala Pro Val Leu Val Val Tyr
         35                  40                  45 gat gat agc gac cgg ccc tca ggg atc cct gag cga ttt tct ggc tcc       192
Asp Asp Ser Asp Arg Pro Ser Gly Ile Pro Glu Arg Phe Ser Gly Ser
     50                  55                  60 aac tct ggg aac acg gcc acc ctg acc att gat agg gtc gaa gac ggg       240
Asn Ser Gly Asn Thr Ala Thr Leu Thr Ile Asp Arg Val Glu Asp Gly
 65                  70                  75                  80 gat gag gcc gac tat tat tgt cag gtg tgg gat ggt agt agt gat caa       288
Asp Glu Ala Asp Tyr Tyr Cys Gln Val Trp Asp Gly Ser Ser Asp Gln
                 85                  90                  95 cga gtc ttc ggc gga ggg acc agg ctg acc gtc cta ggt cag ccc aag       336
Arg Val Phe Gly Gly Gly Thr Arg Leu Thr Val Leu Gly Gln Pro Lys
            100                 105                 110 gct gcc ccc tcg gtc act ctg ttc ccg ccc tcc tct gag gag ctt caa       384
Ala Ala Pro Ser Val Thr Leu Phe Pro Pro Ser Ser Glu Glu Leu Gln
            115                 120                 125
```

-continued

```
gcc aac aag gcc aca ctg gtg tgt ctc ata agt gac ttc tac ccg gga    432
Ala Asn Lys Ala Thr Leu Val Cys Leu Ile Ser Asp Phe Tyr Pro Gly
    130                 135                 140 gcc gtg aca gtg gcc tgg aag gca gat agc agc ccc gtc aag gcg gga    480
Ala Val Thr Val Ala Trp Lys Ala Asp Ser Ser Pro Val Lys Ala Gly
145                 150                 155                 160 gtg gag acc acc aca ccc tcc aaa caa agc aac aac aag tac gcg gcc    528
Val Glu Thr Thr Thr Pro Ser Lys Gln Ser Asn Asn Lys Tyr Ala Ala
                165                 170                 175 agc agc tat ctg agc ctg acg cct gag cag tgg aag tcc cac aga agc    576
Ser Ser Tyr Leu Ser Leu Thr Pro Glu Gln Trp Lys Ser His Arg Ser
            180                 185                 190 tac agc tgc cag gtc acg cat gaa ggg agc acc gtg gag aag aca gtg    624
Tyr Ser Cys Gln Val Thr His Glu Gly Ser Thr Val Glu Lys Thr Val
        195                 200                 205 gct cct aca gaa tgt tca                                            642
Ala Pro Thr Glu Cys Ser
    210
```

<210> SEQ ID NO 96
<211> LENGTH: 214
<212> TYPE: PRT
<213> ORGANISM: Homo sapiens

<400> SEQUENCE: 96

```
Gln Ser Val Leu Thr Gln Pro Pro Ser Val Ser Val Ala Pro Gly Lys
1               5                   10                  15

Thr Ala Thr Ile Thr Cys Gly Gly Asp Asn Leu Gly Lys Ser Leu
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Asp Arg Val Glu Asp Gly
65                  70                  75                  80

Asp Glu Ala Asp Tyr Tyr Cys Gln Val Trp Asp Gly Ser Ser Asp Gln
                85                  90                  95

Arg Val Phe Gly Gly Gly Thr Arg Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210
```

<210> SEQ ID NO 97
<211> LENGTH: 636
<212> TYPE: DNA

```
<213> ORGANISM: Homo sapiens
<220> FEATURE:
<221> NAME/KEY: CDS
<222> LOCATION: (1)..(636)

<400> SEQUENCE: 97 tcc tat gag ctg act cag cca ccc tct gtg tca gtg tct ccg gga cag      48
Ser Tyr Glu Leu Thr Gln Pro Pro Ser Val Ser Val Ser Pro Gly Gln
1               5                   10                  15 aca gcc agg atc acc tgc tca gga gat gta ctg gca aga aaa tat gct      96
Thr Ala Arg Ile Thr Cys Ser Gly Asp Val Leu Ala Arg Lys Tyr Ala
            20                  25                  30 cgg tgg ttc cag cag aag cca ggc cag gcc cct gtg ctg gtg att tat     144
Arg Trp Phe Gln Gln Lys Pro Gly Gln Ala Pro Val Leu Val Ile Tyr
        35                  40                  45 aaa gac cgt gag cgg ccc tca ggg atc cct gag cga ttc tcc ggc tcc     192
Lys Asp Arg Glu Arg Pro Ser Gly Ile Pro Glu Arg Phe Ser Gly Ser
50                  55                  60 acc tca ggg acc aca gtc acc ttg acc atc agc ggg gcc cag gtt gaa     240
Thr Ser Gly Thr Thr Val Thr Leu Thr Ile Ser Gly Ala Gln Val Glu
65                  70                  75                  80 gat gag gct gac tat tac tgt tac tct gcg gct gac aac agg ggg gtg     288
Asp Glu Ala Asp Tyr Tyr Cys Tyr Ser Ala Ala Asp Asn Arg Gly Val
                85                  90                  95 ttc ggc gga ggg acc aag ctg acc gtc cta cgt cag ccc aag gct gcc     336
Phe Gly Gly Gly Thr Lys Leu Thr Val Leu Arg Gln Pro Lys Ala Ala
            100                 105                 110 ccc tcg gtc act ctg ttc cca ccc tcc tct gag gag ctt caa gcc aac     384
Pro Ser Val Thr Leu Phe Pro Pro Ser Ser Glu Glu Leu Gln Ala Asn
        115                 120                 125 aag gcc aca ctg gtg tgt ctc ata agt gac ttc tac ccg gga gcc gtg     432
Lys Ala Thr Leu Val Cys Leu Ile Ser Asp Phe Tyr Pro Gly Ala Val
130                 135                 140 aca gtg gcc tgg aag gca gat agc agt ccc gtc aag gcg gga gtg gag     480
Thr Val Ala Trp Lys Ala Asp Ser Ser Pro Val Lys Ala Gly Val Glu
145                 150                 155                 160 acc acc aca ccc tcc aaa caa agc aac aac aag tac gcg gcc agc agc     528
Thr Thr Thr Pro Ser Lys Gln Ser Asn Asn Lys Tyr Ala Ala Ser Ser
                165                 170                 175 tac ctg agc ctg acg cct gag cag tgg aag tcc cac aaa agc tac agc     576
Tyr Leu Ser Leu Thr Pro Glu Gln Trp Lys Ser His Lys Ser Tyr Ser
            180                 185                 190 tgc cag gtc acg cat gaa ggg agc acc gtg gag aag aca gtg gct cct     624
Cys Gln Val Thr His Glu Gly Ser Thr Val Glu Lys Thr Val Ala Pro
        195                 200                 205 aca gaa tgt tca                                                     636
Thr Glu Cys Ser
    210

<210> SEQ ID NO 98
<211> LENGTH: 212
<212> TYPE: PRT
<213> ORGANISM: Homo sapiens

<400> SEQUENCE: 98

Ser Tyr Glu Leu Thr Gln Pro Pro Ser Val Ser Val Ser Pro Gly Gln
1               5                   10                  15

Thr Ala Arg Ile Thr Cys Ser Gly Asp Val Leu Ala Arg Lys Tyr Ala
            20                  25                  30

Arg Trp Phe Gln Gln Lys Pro Gly Gln Ala Pro Val Leu Val Ile Tyr
        35                  40                  45
```

```
Lys Asp Arg Glu Arg Pro Ser Gly Ile Pro Glu Arg Phe Ser Gly Ser
 50                  55                  60

Thr Ser Gly Thr Thr Val Thr Leu Thr Ile Ser Gly Ala Gln Val Glu
 65                  70                  75                  80

Asp Glu Ala Asp Tyr Tyr Cys Tyr Ser Ala Ala Asp Asn Arg Gly Val
             85                  90                  95

Phe Gly Gly Gly Thr Lys Leu Thr Val Leu Arg Gln Pro Lys Ala Ala
            100                 105                 110

Pro Ser Val Thr Leu Phe Pro Pro Ser Glu Glu Leu Gln Ala Asn
            115                 120                 125

Lys Ala Thr Leu Val Cys Leu Ile Ser Asp Phe Tyr Pro Gly Ala Val
130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Lys Ser Tyr Ser
            180                 185                 190

Cys Gln Val Thr His Glu Gly Ser Thr Val Glu Lys Thr Val Ala Pro
            195                 200                 205

Thr Glu Cys Ser
    210

<210> SEQ ID NO 99
<211> LENGTH: 645
<212> TYPE: DNA
<213> ORGANISM: Homo sapiens
<220> FEATURE:
<221> NAME/KEY: CDS
<222> LOCATION: (1)..(645)

<400> SEQUENCE: 99 gaa att gtg ctc acg cag tct cca ggc acc ctg tct ttg tct cca ggg        48
Glu Ile Val Leu Thr Gln Ser Pro Gly Thr Leu Ser Leu Ser Pro Gly
  1               5                  10                  15 gaa aga gcc acc ctc tcc tgc cgg gcc agt cag tat gtt agc agc aac        96
Glu Arg Ala Thr Leu Ser Cys Arg Ala Ser Gln Tyr Val Ser Ser Asn
             20                  25                  30 tcc tta gcc tgg tac cag cag aaa gct ggc cag gct ccc agg ctc ctc       144
Ser Leu Ala Trp Tyr Gln Gln Lys Ala Gly Gln Ala Pro Arg Leu Leu
         35                  40                  45 atc tat ggt gca tcc aac agg gcc act ggc atc cca gac agg ttc agt       192
Ile Tyr Gly Ala Ser Asn Arg Ala Thr Gly Ile Pro Asp Arg Phe Ser
     50                  55                  60 ggc agt ggg tct ggg aca gac ttc act ctc acc atc agc aga ctg gag       240
Gly Ser Gly Ser Gly Thr Asp Phe Thr Leu Thr Ile Ser Arg Leu Glu
 65                  70                  75                  80 cct gaa gat ttt gca gtg tat tac tgt cag cag tat ggt agc tcg ccg       288
Pro Glu Asp Phe Ala Val Tyr Tyr Cys Gln Gln Tyr Gly Ser Ser Pro
                 85                  90                  95 atc acc ttc ggc caa ggg aca cga ctg gag att aaa cga act gtg gct       336
Ile Thr Phe Gly Gln Gly Thr Arg Leu Glu Ile Lys Arg Thr Val Ala
            100                 105                 110 gca cca tct gtc ttc atc ttc ccg cca tct gat gag cag ttg aaa tct       384
Ala Pro Ser Val Phe Ile Phe Pro Pro Ser Asp Glu Gln Leu Lys Ser
        115                 120                 125 gga act gcc tct gtt gtg tgc ctg ctg aat aac ttc tat ccc aga gag       432
Gly Thr Ala Ser Val Val Cys Leu Leu Asn Asn Phe Tyr Pro Arg Glu
```

```
                130             135             140
gcc aaa gta cag tgg aag gtg gat aac gcc ctc caa tcg ggt aac tcc   480
Ala Lys Val Gln Trp Lys Val Asp Asn Ala Leu Gln Ser Gly Asn Ser
145                 150             155                 160 cag gag agt gtc aca gag cag gac agc aag gac agc acc tac agc ctc   528
Gln Glu Ser Val Thr Glu Gln Asp Ser Lys Asp Ser Thr Tyr Ser Leu
            165                 170                 175 agc agc acc ctg acg ctg agc aaa gca gac tac gag aaa cac aaa gtc   576
Ser Ser Thr Leu Thr Leu Ser Lys Ala Asp Tyr Glu Lys His Lys Val
        180                 185                 190 tac gcc tgc gaa gtc acc cat cag ggc ctg agc tcg ccc gtc aca aag   624
Tyr Ala Cys Glu Val Thr His Gln Gly Leu Ser Ser Pro Val Thr Lys
    195                 200                 205 agc ttc aac agg gga gag tgt                                        645
Ser Phe Asn Arg Gly Glu Cys
    210                 215
```

<210> SEQ ID NO 100
<211> LENGTH: 215
<212> TYPE: PRT
<213> ORGANISM: Homo sapiens

<400> SEQUENCE: 100

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Tyr Val Ser Ser Asn
            20                  25                  30

Ser Leu Ala Trp Tyr Gln Gln Lys Ala Gly Gln Ala Pro Arg Leu Leu
        35                  40                  45

Ile Tyr Gly Ala Ser Asn Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Ile Thr Phe Gly Gln Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 101
<211> LENGTH: 654
<212> TYPE: DNA
<213> ORGANISM: Homo sapiens
<220> FEATURE:
<221> NAME/KEY: CDS

<222> LOCATION: (1)..(654)

<400> SEQUENCE: 101

| aat | ttt | atg | ctg | act | cag | ccc | cac | tct | gtg | tcg | gag | tct | ccg | ggg | aag | 48 |
| Asn | Phe | Met | Leu | Thr | Gln | Pro | His | Ser | Val | Ser | Glu | Ser | Pro | Gly | Lys | |
| 1 | | | | 5 | | | | | 10 | | | | | 15 | | |

| acg | gta | acc | atc | tcc | tgc | acc | ggc | agc | agt | ggc | agc | att | gcc | aac | aac | 96 |
| Thr | Val | Thr | Ile | Ser | Cys | Thr | Gly | Ser | Ser | Gly | Ser | Ile | Ala | Asn | Asn | |
| | | | 20 | | | | | 25 | | | | | 30 | | | |

| tat | gtt | cac | tgg | tac | cag | caa | cgc | ccg | ggc | agt | gcc | ccc | acc | act | gtg | 144 |
| Tyr | Val | His | Trp | Tyr | Gln | Gln | Arg | Pro | Gly | Ser | Ala | Pro | Thr | Thr | Val | |
| | | 35 | | | | | 40 | | | | | 45 | | | | |

| atc | ttt | gag | gat | gac | caa | aga | ccc | tct | gga | gtc | cct | gat | cgg | ttc | tct | 192 |
| Ile | Phe | Glu | Asp | Asp | Gln | Arg | Pro | Ser | Gly | Val | Pro | Asp | Arg | Phe | Ser | |
| 50 | | | | | 55 | | | | | 60 | | | | | | |

| ggc | tcc | gtc | gac | agc | tcc | tcc | aac | tct | gcc | tcc | ctc | agc | att | tct | gga | 240 |
| Gly | Ser | Val | Asp | Ser | Ser | Ser | Asn | Ser | Ala | Ser | Leu | Ser | Ile | Ser | Gly | |
| 65 | | | | | 70 | | | | | 75 | | | | | 80 | |

| ctg | aag | act | gag | gac | gag | gct | gac | tac | tac | tgt | cag | tct | tat | gat | aac | 288 |
| Leu | Lys | Thr | Glu | Asp | Glu | Ala | Asp | Tyr | Tyr | Cys | Gln | Ser | Tyr | Asp | Asn | |
| | | | | 85 | | | | | 90 | | | | | 95 | | |

| agc | aat | tca | ttt | gtg | gtg | ttc | ggc | gga | ggg | acc | aag | ctg | acc | gtc | cta | 336 |
| Ser | Asn | Ser | Phe | Val | Val | Phe | Gly | Gly | Gly | Thr | Lys | Leu | Thr | Val | Leu | |
| | | | 100 | | | | | 105 | | | | | 110 | | | |

| ggt | cag | ccc | aag | gct | gcc | ccc | tcg | gtc | act | ctg | ttc | ccg | ccc | tcc | tct | 384 |
| Gly | Gln | Pro | Lys | Ala | Ala | Pro | Ser | Val | Thr | Leu | Phe | Pro | Pro | Ser | Ser | |
| | | 115 | | | | | 120 | | | | | 125 | | | | |

| gag | gag | ctt | caa | gcc | aac | aag | gcc | aca | ctg | gtg | tgt | ctc | ata | agt | gac | 432 |
| Glu | Glu | Leu | Gln | Ala | Asn | Lys | Ala | Thr | Leu | Val | Cys | Leu | Ile | Ser | Asp | |
| 130 | | | | | 135 | | | | | 140 | | | | | | |

| ttc | tac | ccg | gga | gcc | gtg | aca | gtg | gcc | tgg | aag | gca | gat | agc | agc | ccc | 480 |
| Phe | Tyr | Pro | Gly | Ala | Val | Thr | Val | Ala | Trp | Lys | Ala | Asp | Ser | Ser | Pro | |
| 145 | | | | | 150 | | | | | 155 | | | | | 160 | |

| gtc | aag | gcg | gga | gtg | gag | acc | acc | aca | ccc | tcc | aaa | caa | agc | aac | aac | 528 |
| Val | Lys | Ala | Gly | Val | Glu | Thr | Thr | Thr | Pro | Ser | Lys | Gln | Ser | Asn | Asn | |
| | | | | 165 | | | | | 170 | | | | | 175 | | |

| aag | tac | gcg | gcc | agc | agc | tac | ctg | agc | ctg | acg | cct | gag | cag | tgg | aag | 576 |
| Lys | Tyr | Ala | Ala | Ser | Ser | Tyr | Leu | Ser | Leu | Thr | Pro | Glu | Gln | Trp | Lys | |
| | | | 180 | | | | | 185 | | | | | 190 | | | |

| tcc | cac | aaa | agc | tac | agc | tgc | cag | gtc | acg | cat | gaa | ggg | agc | acc | gtg | 624 |
| Ser | His | Lys | Ser | Tyr | Ser | Cys | Gln | Val | Thr | His | Glu | Gly | Ser | Thr | Val | |
| | | 195 | | | | | 200 | | | | | 205 | | | | |

| gag | aag | aca | gtg | gcc | cct | aca | gaa | tgc | tct | | | | | | | 654 |
| Glu | Lys | Thr | Val | Ala | Pro | Thr | Glu | Cys | Ser | | | | | | | |
| | 210 | | | | | 215 | | | | | | | | | | |

<210> SEQ ID NO 102
<211> LENGTH: 218
<212> TYPE: PRT
<213> ORGANISM: Homo sapiens

<400> SEQUENCE: 102

| Asn | Phe | Met | Leu | Thr | Gln | Pro | His | Ser | Val | Ser | Glu | Ser | Pro | Gly | Lys |
| 1 | | | | 5 | | | | | 10 | | | | | 15 | |

| Thr | Val | Thr | Ile | Ser | Cys | Thr | Gly | Ser | Ser | Gly | Ser | Ile | Ala | Asn | Asn |
| | | | 20 | | | | | 25 | | | | | 30 | | |

| Tyr | Val | His | Trp | Tyr | Gln | Gln | Arg | Pro | Gly | Ser | Ala | Pro | Thr | Thr | Val |
| | | 35 | | | | | 40 | | | | | 45 | | | |

| Ile | Phe | Glu | Asp | Asp | Gln | Arg | Pro | Ser | Gly | Val | Pro | Asp | Arg | Phe | Ser |
| 50 | | | | | 55 | | | | | 60 | | | | | |

```
Gly Ser Val Asp Ser Ser Asn Ser Ala Ser Leu Ser Ile Ser Gly
 65                  70                  75                  80

Leu Lys Thr Glu Asp Glu Ala Asp Tyr Tyr Cys Gln Ser Tyr Asp Asn
                 85                  90                  95

Ser Asn Ser Phe Val Val Phe Gly Gly Gly Thr Lys Leu Thr Val Leu
            100                 105                 110

Gly Gln Pro Lys Ala Ala Pro Ser Val Thr Leu Phe Pro Pro Ser Ser
        115                 120                 125

Glu Glu Leu Gln Ala Asn Lys Ala Thr Leu Val Cys Leu Ile Ser Asp
    130                 135                 140

Phe Tyr Pro Gly Ala Val Thr Val Ala Trp Lys Ala Asp Ser Ser Pro
145                 150                 155                 160

Val Lys Ala Gly Val Glu Thr Thr Thr Pro Ser Lys Gln Ser Asn Asn
                165                 170                 175

Lys Tyr Ala Ala Ser Ser Tyr Leu Ser Leu Thr Pro Glu Gln Trp Lys
            180                 185                 190

Ser His Lys Ser Tyr Ser Cys Gln Val Thr His Glu Gly Ser Thr Val
        195                 200                 205

Glu Lys Thr Val Ala Pro Thr Glu Cys Ser
    210                 215

<210> SEQ ID NO 103
<211> LENGTH: 657
<212> TYPE: DNA
<213> ORGANISM: Homo sapiens
<220> FEATURE:
<221> NAME/KEY: CDS
<222> LOCATION: (1)..(657)

<400> SEQUENCE: 103 gaa att gtg ctg act cag tct cca ctc tcc ctt ccc gtc acc cct gga      48
Glu Ile Val Leu Thr Gln Ser Pro Leu Ser Leu Pro Val Thr Pro Gly
  1               5                  10                  15 gag ccg gcc tcc atc tcc tgc agg tct agt cag agc ctc ctg cat act      96
Glu Pro Ala Ser Ile Ser Cys Arg Ser Ser Gln Ser Leu Leu His Thr
             20                  25                  30 aat gaa tac aac tat ttg gat tgg tac ctg cag aag cca ggg cag tct     144
Asn Glu Tyr Asn Tyr Leu Asp Trp Tyr Leu Gln Lys Pro Gly Gln Ser
         35                  40                  45 cca cag ctc ctc atc tat ttg ggt tct aat cgg gcc ccc ggg gtc cct     192
Pro Gln Leu Leu Ile Tyr Leu Gly Ser Asn Arg Ala Pro Gly Val Pro
     50                  55                  60 gac agg ttc agt ggc agt gga tca ggc aca gat ttt aca ctg aga atc     240
Asp Arg Phe Ser Gly Ser Gly Ser Gly Thr Asp Phe Thr Leu Arg Ile
 65                  70                  75                  80 agc agg gtg gag gct gac gat gtt ggg gtt tac tac tgc atg caa gct     288
Ser Arg Val Glu Ala Asp Asp Val Gly Val Tyr Tyr Cys Met Gln Ala
                 85                  90                  95 cta caa act cct cgt act ttt ggc cag ggg acc aag ctg gag atc aaa     336
Leu Gln Thr Pro Arg Thr Phe Gly Gln Gly Thr Lys Leu Glu Ile Lys
            100                 105                 110 cga act gtg gct gca cca tct gtc ttc atc ttc ccg cca tct gat gag     384
Arg Thr Val Ala Ala Pro Ser Val Phe Ile Phe Pro Pro Ser Asp Glu
        115                 120                 125 cag ttg aaa tct gga act gcc tct gtt gtg tgc ctg ctg aat aac ttc     432
Gln Leu Lys Ser Gly Thr Ala Ser Val Val Cys Leu Leu Asn Asn Phe
    130                 135                 140 tat ccc aga gag gcc aaa gta cag tgg aag gtg gat aac gcc ctc caa     480
Tyr Pro Arg Glu Ala Lys Val Gln Trp Lys Val Asp Asn Ala Leu Gln
```

```
Tyr Pro Arg Glu Ala Lys Val Gln Trp Lys Val Asp Asn Ala Leu Gln
145                 150                 155                 160 tcg ggt aac tcc cag gag agt gtc aca gag cag gac agc aag gac agc      528
Ser Gly Asn Ser Gln Glu Ser Val Thr Glu Gln Asp Ser Lys Asp Ser
                165                 170                 175 acc tac agc ctc agc agc acc ctg acg ctg agc aaa gca gac tac gag      576
Thr Tyr Ser Leu Ser Ser Thr Leu Thr Leu Ser Lys Ala Asp Tyr Glu
            180                 185                 190 aaa cac aaa gtc tac gcc tgc gaa gtc acc cat cag ggc ctg agc tcg      624
Lys His Lys Val Tyr Ala Cys Glu Val Thr His Gln Gly Leu Ser Ser
        195                 200                 205 ccc gtc aca aag agc ttc aac agg gga gag tgt                          657
Pro Val Thr Lys Ser Phe Asn Arg Gly Glu Cys
    210                 215

<210> SEQ ID NO 104
<211> LENGTH: 219
<212> TYPE: PRT
<213> ORGANISM: Homo sapiens

<400> SEQUENCE: 104

Glu Ile Val Leu Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Thr
            20                  25                  30

Asn Glu Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Pro Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Asp Asp Val Gly Val Tyr Tyr Cys Met Gln Ala
                85                  90                  95

Leu Gln Thr Pro Arg Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 105
<211> LENGTH: 657
<212> TYPE: DNA
<213> ORGANISM: Homo sapiens
<220> FEATURE:
<221> NAME/KEY: CDS
<222> LOCATION: (1)..(657)

<400> SEQUENCE: 105
```

```
gat att gtg atg acc cac act cca ctc tcc ctg ccc gtc acc cct gga      48
Asp Ile Val Met Thr His Thr Pro Leu Ser Leu Pro Val Thr Pro Gly
1               5                   10                  15 gag ccg gcc tcc atc tcc tgc agg tcc agt cag agc ctc ctg cgt agt      96
Glu Pro Ala Ser Ile Ser Cys Arg Ser Ser Gln Ser Leu Leu Arg Ser
                20                  25                  30 aat gga tac aac tat ttg gct tgg tac gtg cag aag cca ggg cag tct     144
Asn Gly Tyr Asn Tyr Leu Ala Trp Tyr Val Gln Lys Pro Gly Gln Ser
            35                  40                  45 cca caa ctc ctg atc tac ttg gct tct aat cgg gcc tcc ggg gtc cct     192
Pro Gln Leu Leu Ile Tyr Leu Ala Ser Asn Arg Ala Ser Gly Val Pro
50                  55                  60 gac agg ttt agt ggc agt gga tca ggc aca gat ttt aca ctg aag atc     240
Asp Arg Phe Ser Gly Ser Gly Ser Gly Thr Asp Phe Thr Leu Lys Ile
65                  70                  75                  80 agc agc gtg gag gct gag gat gtt ggg gtg tat tac tgc gtg cat ggt     288
Ser Ser Val Glu Ala Glu Asp Val Gly Val Tyr Tyr Cys Val His Gly
                85                  90                  95 gta cac att ccc tac act ttt ggc cag ggg acc aag ctg gag atc aaa     336
Val His Ile Pro Tyr Thr Phe Gly Gln Gly Thr Lys Leu Glu Ile Lys
            100                 105                 110 cga act gtg gct gca cca tct gtc ttc atc ttc ccg cca tct gat gag     384
Arg Thr Val Ala Ala Pro Ser Val Phe Ile Phe Pro Pro Ser Asp Glu
            115                 120                 125 cag ttg aaa tct gga act gcc tct gtt gtg tgc ctg ctg aat aac ttc     432
Gln Leu Lys Ser Gly Thr Ala Ser Val Val Cys Leu Leu Asn Asn Phe
        130                 135                 140 tat ccc aga gag gcc aaa gta cag tgg aag gtg gat aac gcc ctc caa     480
Tyr Pro Arg Glu Ala Lys Val Gln Trp Lys Val Asp Asn Ala Leu Gln
145                 150                 155                 160 tcg ggt aac tcc cag gag agt gtc aca gag cag gac agc aag gac agc     528
Ser Gly Asn Ser Gln Glu Ser Val Thr Glu Gln Asp Ser Lys Asp Ser
                165                 170                 175 acc tac agc ctc agc agc acc ctg acg ctg agc aaa gca gac tac gag     576
Thr Tyr Ser Leu Ser Ser Thr Leu Thr Leu Ser Lys Ala Asp Tyr Glu
            180                 185                 190 aaa cac aaa gtc tac gcc tgc gaa gtc acc cat cag ggc ctg agc tcg     624
Lys His Lys Val Tyr Ala Cys Glu Val Thr His Gln Gly Leu Ser Ser
        195                 200                 205 ccc gtc aca aag agc ttc aac agg gga gag tgt                         657
Pro Val Thr Lys Ser Phe Asn Arg Gly Glu Cys
    210                 215

<210> SEQ ID NO 106
<211> LENGTH: 219
<212> TYPE: PRT
<213> ORGANISM: Homo sapiens

<400> SEQUENCE: 106

Asp Ile Val Met Thr His Thr Pro Leu Ser Leu Pro Val Thr Pro Gly
1               5                   10                  15

Glu Pro Ala Ser Ile Ser Cys Arg Ser Ser Gln Ser Leu Leu Arg Ser
                20                  25                  30

Asn Gly Tyr Asn Tyr Leu Ala Trp Tyr Val Gln Lys Pro Gly Gln Ser
            35                  40                  45

Pro Gln Leu Leu Ile Tyr Leu Ala Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80
```

```
Ser Ser Val Glu Ala Glu Asp Val Gly Val Tyr Tyr Cys Val His Gly
                85                  90                  95

Val His Ile Pro Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 107
<211> LENGTH: 648
<212> TYPE: DNA
<213> ORGANISM: Homo sapiens
<220> FEATURE:
<221> NAME/KEY: CDS
<222> LOCATION: (1)..(648)

<400> SEQUENCE: 107 aat ttt atg ctg act cag ccc cac tct gtg tcg gag tct ccg ggg aag      48
Asn Phe Met Leu Thr Gln Pro His Ser Val Ser Glu Ser Pro Gly Lys
1               5                   10                  15 acg gta acc atc tcc tgc acc ggc agc agt ggc agc att gcc agc aac      96
Thr Val Thr Ile Ser Cys Thr Gly Ser Ser Gly Ser Ile Ala Ser Asn
            20                  25                  30 tat gtg cag tgg tac cag cag cgc ccg ggc agt gcc ccc acc act gtg     144
Tyr Val Gln Trp Tyr Gln Gln Arg Pro Gly Ser Ala Pro Thr Thr Val
        35                  40                  45 atc tat gag gat aac caa aga ccc tct ggg gtc cct cct cgg ttc tct     192
Ile Tyr Glu Asp Asn Gln Arg Pro Ser Gly Val Pro Pro Arg Phe Ser
    50                  55                  60 ggc tcc atc gac agg tcc tcc aac tct gcc tcc ctc acc atc tcc gga     240
Gly Ser Ile Asp Arg Ser Ser Asn Ser Ala Ser Leu Thr Ile Ser Gly
65                  70                  75                  80 ctg aag agt gag gac gag gct gac tac tac tgt caa tct tat gat ggc     288
Leu Lys Ser Glu Asp Glu Ala Asp Tyr Tyr Cys Gln Ser Tyr Asp Gly
                85                  90                  95 agc gct tgg gtg ttc ggc gga ggg acc aag ctg acc gtc cta ggt cag     336
Ser Ala Trp Val Phe Gly Gly Gly Thr Lys Leu Thr Val Leu Gly Gln
            100                 105                 110 ccc aag gct gcc ccc tcg gtc act ctg ttc cca ccc tcc tct gag gag     384
Pro Lys Ala Ala Pro Ser Val Thr Leu Phe Pro Pro Ser Ser Glu Glu
        115                 120                 125 ctt caa gcc aac aag gcc aca ctg gtg tgt ctc ata agt gac ttc tac     432
Leu Gln Ala Asn Lys Ala Thr Leu Val Cys Leu Ile Ser Asp Phe Tyr
    130                 135                 140 ccg gga gcc gtg aca gtg gcc tgg aag gca gat agc agc ccc gtc aag     480
Pro Gly Ala Val Thr Val Ala Trp Lys Ala Asp Ser Ser Pro Val Lys
145                 150                 155                 160
```

```
gcg gga gtg gag acc acc gca ccc tcc aaa caa agc aac aac aag tac    528
Ala Gly Val Glu Thr Thr Ala Pro Ser Lys Gln Ser Asn Asn Lys Tyr
            165                 170                 175 gcg gcc agc agc tac ctg agc ctg acg cct gag cag tgg aag tcc cac    576
Ala Ala Ser Ser Tyr Leu Ser Leu Thr Pro Glu Gln Trp Lys Ser His
        180                 185                 190 aaa agc tac agc tgc cag gtc acg cat gaa ggg agc acc gtg gag aag    624
Lys Ser Tyr Ser Cys Gln Val Thr His Glu Gly Ser Thr Val Glu Lys
        195                 200                 205 aca gtg gcc cct gca gaa tgc tct                                    648
Thr Val Ala Pro Ala Glu Cys Ser
    210                 215

<210> SEQ ID NO 108
<211> LENGTH: 216
<212> TYPE: PRT
<213> ORGANISM: Homo sapiens

<400> SEQUENCE: 108

Asn Phe Met Leu Thr Gln Pro His Ser Val Ser Glu Ser Pro Gly Lys
1               5                   10                  15

Thr Val Thr Ile Ser Cys Thr Gly Ser Ser Gly Ser Ile Ala Ser Asn
            20                  25                  30

Tyr Val Gln Trp Tyr Gln Gln Arg Pro Gly Ser Ala Pro Thr Thr Val
        35                  40                  45

Ile Tyr Glu Asp Asn Gln Arg Pro Ser Gly Val Pro Pro Arg Phe Ser
    50                  55                  60

Gly Ser Ile Asp Arg Ser Ser Asn Ser Ala Ser Leu Thr Ile Ser Gly
65                  70                  75                  80

Leu Lys Ser Glu Asp Glu Ala Asp Tyr Tyr Cys Gln Ser Tyr Asp Gly
                85                  90                  95

Ser Ala Trp Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Ala Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Lys Ser Tyr Ser Cys Gln Val Thr His Glu Gly Ser Thr Val Glu Lys
        195                 200                 205

Thr Val Ala Pro Ala Glu Cys Ser
    210                 215

<210> SEQ ID NO 109
<211> LENGTH: 18
<212> TYPE: DNA
<213> ORGANISM: Homo sapiens

<400> SEQUENCE: 109
ccgactttgc acctagtt                                                18

<210> SEQ ID NO 110
<211> LENGTH: 24
```

```
<212> TYPE: DNA
<213> ORGANISM: Homo sapiens

<400> SEQUENCE: 110
tttgtcgtct ttccagacgt tagt                                              24

<210> SEQ ID NO 111
<211> LENGTH: 22
<212> TYPE: PRT
<213> ORGANISM: Homo sapiens

<400> SEQUENCE: 111

Met Asp Met Arg Val Pro Ala Gln Leu Leu Gly Leu Leu Leu Leu Trp
1               5                   10                  15

Leu Arg Gly Ala Arg Cys
            20

<210> SEQ ID NO 112
<211> LENGTH: 53
<212> TYPE: DNA
<213> ORGANISM: Homo sapiens

<400> SEQUENCE: 112
cagcagaagc ttctagacca ccatggacat gagggtcccc gctcagccct ggg             53

<210> SEQ ID NO 113
<211> LENGTH: 48
<212> TYPE: DNA
<213> ORGANISM: Homo sapiens

<400> SEQUENCE: 113
ccgctcagct cctggggctc ctgctattgt ggttgagagg tgccagat                   48

<210> SEQ ID NO 114
<211> LENGTH: 40
<212> TYPE: DNA
<213> ORGANISM: Homo sapiens

<400> SEQUENCE: 114
gtggttgaga ggtgccagat gtcaggtgca gctgcaggag                            40

<210> SEQ ID NO 115
<211> LENGTH: 29
<212> TYPE: DNA
<213> ORGANISM: Homo sapiens

<400> SEQUENCE: 115
gtggaggcac tagagacggt gaccagggt                                        29

<210> SEQ ID NO 116
<211> LENGTH: 54
<212> TYPE: DNA
<213> ORGANISM: Homo sapiens

<400> SEQUENCE: 116
cagcagaagc ttctagacca ccatggacat gagggtcccc gctcagctcc tggg            54

<210> SEQ ID NO 117
<211> LENGTH: 42
<212> TYPE: DNA
<213> ORGANISM: Homo sapiens

<400> SEQUENCE: 117
```

```
tggttgagag gtgccagatg taattttatg ctgactcagc cc                    42
```

<210> SEQ ID NO 118
<211> LENGTH: 31
<212> TYPE: DNA
<213> ORGANISM: Homo sapiens

<400> SEQUENCE: 118

```
ggccgcgtac ttgttgttgc tttgtttgga g                               31
```

<210> SEQ ID NO 119
<211> LENGTH: 48
<212> TYPE: DNA
<213> ORGANISM: Homo sapiens

<400> SEQUENCE: 119

```
ccgctcagct cctggggctc ctgctattgt ggttgagagg tgccagat              48
```

<210> SEQ ID NO 120
<211> LENGTH: 30
<212> TYPE: DNA
<213> ORGANISM: Homo sapiens

<400> SEQUENCE: 120

```
agcaacaaca agtacgcggc cagcagctac                                  30
```

<210> SEQ ID NO 121
<211> LENGTH: 29
<212> TYPE: DNA
<213> ORGANISM: Homo sapiens

<400> SEQUENCE: 121

```
gaagtcgact atgaacattc tgtaggagc                                   29
```

<210> SEQ ID NO 122
<211> LENGTH: 102
<212> TYPE: PRT
<213> ORGANISM: Homo sapiens
<220> FEATURE:
<221> NAME/KEY: Misc.
<222> LOCATION: (32)..(32)
<223> OTHER INFORMATION: Unidentifiable
<221> NAME/KEY: Misc.
<222> LOCATION: (33)..(33)
<223> OTHER INFORMATION: Unidentifiable
<221> NAME/KEY: Misc.
<222> LOCATION: (56)..(56)
<223> OTHER INFORMATION: Unidentifiable
<221> NAME/KEY: Misc.
<222> LOCATION: (57)..(57)
<223> OTHER INFORMATION: Unidentifiable
<221> NAME/KEY: Misc.
<222> LOCATION: (58)..(58)
<223> OTHER INFORMATION: Unidentifiable

<400> SEQUENCE: 122

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Xaa
            20                  25                  30

Xaa Tyr Tyr Trp Ser Trp Ile Arg Gln Pro Pro Gly Lys Gly Leu Glu
        35                  40                  45

Trp Ile Gly Glu Ile Asn His Xaa Xaa Xaa Ser Gly Ser Thr Asn Tyr
    50                  55                  60

Asn Pro Ser Leu Lys Ser Arg Val Thr Ile Ser Val Asp Thr Ser Lys
```

```
                65                  70                  75                  80
Asn Gln Phe Ser Leu Lys Leu Ser Val Thr Ala Ala Asp Thr Ala
                    85                  90                  95

Val Tyr Tyr Cys Ala Arg
            100

<210> SEQ ID NO 123
<211> LENGTH: 102
<212> TYPE: PRT
<213> ORGANISM: Homo sapiens
<220> FEATURE:
<221> NAME/KEY: Misc.
<222> LOCATION: (32)..(32)
<223> OTHER INFORMATION: Unidentifiable
<221> NAME/KEY: Misc.
<222> LOCATION: (33)..(33)
<223> OTHER INFORMATION: Unidentifiable
<221> NAME/KEY: Misc.
<222> LOCATION: (56)..(56)
<223> OTHER INFORMATION: Unidentifiable
<221> NAME/KEY: Misc.
<222> LOCATION: (57)..(57)
<223> OTHER INFORMATION: Unidentifiable

<400> SEQUENCE: 123

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Xaa
            20                  25                  30

Xaa Tyr Ala Met Ser Trp Val Arg Gln Ala Pro Gly Lys Gly Leu Glu
        35                  40                  45

Trp Val Ser Ala Ile Ser Gly Xaa Xaa Ser Gly Gly Ser Thr Tyr Tyr
    50                  55                  60

Ala Asp Ser Val Lys Gly Arg Phe Thr Ile Ser Arg Asp Asn Ser Lys
65                  70                  75                  80

Asn Thr Leu Tyr Leu Gln Met Asn Ser Leu Arg Ala Glu Asp Thr Ala
                85                  90                  95

Val Tyr Tyr Cys Ala Arg
            100

<210> SEQ ID NO 124
<211> LENGTH: 102
<212> TYPE: PRT
<213> ORGANISM: Homo sapiens
<220> FEATURE:
<221> NAME/KEY: Misc.
<222> LOCATION: (55)..(55)
<223> OTHER INFORMATION: Unidentifiable
<221> NAME/KEY: Misc.
<222> LOCATION: (56)..(56)
<223> OTHER INFORMATION: Unidentifiable
<221> NAME/KEY: Misc.
<222> LOCATION: (57)..(57)
<223> OTHER INFORMATION: Unidentifiable

<400> SEQUENCE: 124

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Asn Ala
            20                  25                  30

Arg Met Gly Val Ser Trp Ile Arg Gln Pro Pro Gly Lys Ala Leu Glu
        35                  40                  45

Trp Leu Ala His Ile Phe Xaa Xaa Xaa Ser Asn Asp Glu Lys Ser Tyr
    50                  55                  60
```

```
Ser Thr Ser Leu Lys Ser Arg Leu Thr Ile Ser Lys Asp Thr Ser Lys
 65                  70                  75                  80

Ser Gln Val Val Leu Thr Met Thr Asn Met Asp Pro Val Asp Thr Ala
                 85                  90                  95

Thr Tyr Tyr Cys Ala Arg
            100

<210> SEQ ID NO 125
<211> LENGTH: 102
<212> TYPE: PRT
<213> ORGANISM: Homo sapiens
<220> FEATURE:
<221> NAME/KEY: Misc.
<222> LOCATION: (32)..(32)
<223> OTHER INFORMATION: Unidentified
<221> NAME/KEY: Misc.
<222> LOCATION: (33)..(33)
<223> OTHER INFORMATION: Unidentified
<221> NAME/KEY: Misc.
<222> LOCATION: (56)..(56)
<223> OTHER INFORMATION: Unidentified
<221> NAME/KEY: Misc.
<222> LOCATION: (57)..(57)
<223> OTHER INFORMATION: Unidentified

<400> SEQUENCE: 125

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Xaa
             20                  25                  30

Xaa Tyr Ser Met Asn Trp Val Arg Gln Ala Pro Gly Lys Gly Leu Glu
         35                  40                  45

Trp Val Ser Ser Ile Ser Ser Xaa Xaa Ser Ser Ser Tyr Ile Tyr Tyr
     50                  55                  60

Ala Asp Ser Val Lys Gly Arg Phe Thr Ile Ser Arg Asp Asn Ala Lys
 65                  70                  75                  80

Asn Ser Leu Tyr Leu Gln Met Asn Ser Leu Arg Ala Glu Asp Thr Ala
                 85                  90                  95

Val Tyr Tyr Cys Ala Arg
            100

<210> SEQ ID NO 126
<211> LENGTH: 102
<212> TYPE: PRT
<213> ORGANISM: Homo sapiens
<220> FEATURE:
<221> NAME/KEY: Misc.
<222> LOCATION: (32)..(32)
<223> OTHER INFORMATION: Unidentified
<221> NAME/KEY: Misc.
<222> LOCATION: (33)..(33)
<223> OTHER INFORMATION: Unidentified
<221> NAME/KEY: Misc.
<222> LOCATION: (56)..(56)
<223> OTHER INFORMATION: Unidentified
<221> NAME/KEY: Misc.
<222> LOCATION: (57)..(57)
<223> OTHER INFORMATION: Unidentified

<400> SEQUENCE: 126

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Xaa
             20                  25                  30
```

```
Xaa Tyr Ala Met His Trp Val Arg Gln Ala Pro Gly Lys Gly Leu Glu
        35                  40                  45

Trp Val Ala Val Ile Ser Tyr Xaa Xaa Asp Gly Ser Asn Lys Tyr Tyr
 50                  55                  60

Ala Asp Ser Val Lys Gly Arg Phe Thr Ile Ser Arg Asp Asn Ser Lys
 65                  70                  75                  80

Asn Thr Leu Tyr Leu Gln Met Asn Ser Leu Arg Ala Glu Asp Thr Ala
                 85                  90                  95

Val Tyr Tyr Cys Ala Arg
            100

<210> SEQ ID NO 127
<211> LENGTH: 102
<212> TYPE: PRT
<213> ORGANISM: Homo sapiens
<220> FEATURE:
<221> NAME/KEY: Misc.
<222> LOCATION: (32)..(32)
<223> OTHER INFORMATION: Unidentified
<221> NAME/KEY: Misc.
<222> LOCATION: (33)..(33)
<223> OTHER INFORMATION: Unidentified
<221> NAME/KEY: Misc.
<222> LOCATION: (55)..(55)
<223> OTHER INFORMATION: Unidentified
<221> NAME/KEY: Misc.
<222> LOCATION: (56)..(56)
<223> OTHER INFORMATION: Unidentified
<221> NAME/KEY: Misc.
<222> LOCATION: (57)..(57)
<223> OTHER INFORMATION: Unidentified

<400> SEQUENCE: 127

Glu Val Gln Leu Val Glu Ser Gly Gly Gly Leu Ile Gln Pro Gly Gly
 1               5                  10                  15

Ser Leu Arg Leu Ser Cys Ala Ala Ser Gly Phe Thr Val Ser Ser Xaa
             20                  25                  30

Xaa Asn Tyr Met Ser Trp Val Arg Gln Ala Pro Gly Lys Gly Leu Glu
        35                  40                  45

Trp Val Ser Val Ile Tyr Xaa Xaa Xaa Ser Gly Gly Ser Thr Tyr Tyr
 50                  55                  60

Ala Asp Ser Val Lys Gly Arg Phe Thr Ile Ser Arg Asp Asn Ser Lys
 65                  70                  75                  80

Asn Thr Leu Tyr Leu Gln Met Asn Ser Leu Arg Ala Glu Asp Thr Ala
                 85                  90                  95

Val Tyr Tyr Cys Ala Arg
            100

<210> SEQ ID NO 128
<211> LENGTH: 102
<212> TYPE: PRT
<213> ORGANISM: Homo sapiens
<220> FEATURE:
<221> NAME/KEY: Misc.
<222> LOCATION: (55)..(55)
<223> OTHER INFORMATION: Unidentified
<221> NAME/KEY: Misc.
<222> LOCATION: (56)..(56)
<223> OTHER INFORMATION: Unidentified
<221> NAME/KEY: Misc.
<222> LOCATION: (57)..(57)
<223> OTHER INFORMATION: Unidentified

<400> SEQUENCE: 128

Gln Val Gln Leu Gln Glu Ser Gly Pro Gly Leu Val Lys Pro Ser Glu
```

```
                1               5                  10                   15
Thr Leu Ser Leu Thr Cys Thr Val Ser Gly Gly Ser Val Ser Ser Gly
                20                  25                  30

Gly Tyr Tyr Trp Ser Trp Ile Arg Gln Pro Pro Gly Lys Gly Leu Glu
                35                  40                  45

Trp Ile Gly Tyr Ile Tyr Xaa Xaa Xaa Tyr Ser Gly Ser Thr Asn Tyr
        50                  55                  60

Asn Pro Ser Leu Lys Ser Arg Val Thr Ile Ser Val Asp Thr Ser Lys
65                  70                  75                  80

Asn Gln Phe Ser Leu Lys Leu Ser Ser Val Thr Ala Ala Asp Thr Ala
                85                  90                  95

Val Tyr Tyr Cys Ala Arg
                100
```

<210> SEQ ID NO 129
<211> LENGTH: 102
<212> TYPE: PRT
<213> ORGANISM: Homo sapiens
<220> FEATURE:
<221> NAME/KEY: Misc.
<222> LOCATION: (55)..(55)
<223> OTHER INFORMATION: Unidentified
<221> NAME/KEY: Misc.
<222> LOCATION: (56)..(56)
<223> OTHER INFORMATION: Unidentified
<221> NAME/KEY: Misc.
<222> LOCATION: (57)..(57)
<223> OTHER INFORMATION: Unidentified

<400> SEQUENCE: 129

```
Gln Ile Thr Leu Lys Glu Ser Gly Pro Thr Leu Val Lys Pro Thr Gln
1               5                  10                  15

Thr Leu Thr Leu Thr Cys Thr Phe Ser Gly Phe Ser Leu Ser Thr Ser
                20                  25                  30

Gly Val Gly Val Gly Trp Ile Arg Gln Pro Pro Gly Lys Ala Leu Glu
                35                  40                  45

Trp Leu Ala Leu Ile Tyr Xaa Xaa Xaa Trp Asn Asp Asp Lys Arg Tyr
        50                  55                  60

Ser Pro Ser Leu Lys Ser Arg Leu Thr Ile Thr Lys Asp Thr Ser Lys
65                  70                  75                  80

Asn Gln Val Val Leu Thr Met Thr Asn Met Asp Pro Val Asp Thr Ala
                85                  90                  95

Thr Tyr Tyr Cys Ala His
                100
```

<210> SEQ ID NO 130
<211> LENGTH: 103
<212> TYPE: PRT
<213> ORGANISM: Homo sapiens
<220> FEATURE:
<221> NAME/KEY: Misc.
<222> LOCATION: (7)..(7)
<223> OTHER INFORMATION: Unidentified
<221> NAME/KEY: Misc.
<222> LOCATION: (33)..(33)
<223> OTHER INFORMATION: Unidentified
<221> NAME/KEY: Misc.
<222> LOCATION: (34)..(34)
<223> OTHER INFORMATION: Unidentified
<221> NAME/KEY: Misc.
<222> LOCATION: (35)..(35)
<223> OTHER INFORMATION: Unidentified
<221> NAME/KEY: Misc.
<222> LOCATION: (36)..(36)

<223> OTHER INFORMATION: Unidentified

<400> SEQUENCE: 130

Asn Phe Met Leu Thr Gln Xaa Pro His Ser Val Ser Glu Ser Pro Gly
1               5                   10                  15

Lys Thr Val Thr Ile Ser Cys Thr Arg Ser Ser Gly Ser Ile Ala Ser
            20                  25                  30

Xaa Xaa Xaa Xaa Asn Tyr Val Gln Trp Tyr Gln Arg Pro Gly Ser
        35                  40                  45

Ser Pro Thr Thr Val Ile Tyr Glu Asp Asn Arg Pro Ser Gly Val
    50                  55                  60

Pro Asp Arg Phe Ser Gly Ser Ile Asp Ser Ser Asn Ser Ala Ser
65              70                  75                  80

Leu Thr Ile Ser Gly Leu Lys Thr Glu Asp Glu Ala Asp Tyr Tyr Cys
                85                  90                  95

Gln Ser Tyr Asp Ser Ser Asn
                100

<210> SEQ ID NO 131
<211> LENGTH: 101
<212> TYPE: PRT
<213> ORGANISM: Homo sapiens
<220> FEATURE:
<221> NAME/KEY: Misc.
<222> LOCATION: (33)..(33)
<223> OTHER INFORMATION: Unidentified

<400> SEQUENCE: 131

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Xaa Asp Gly Asn Thr Tyr Leu Ser Trp Leu Gln Arg Pro Gly Gln
        35                  40                  45

Pro Pro Arg Leu Leu Ile Tyr Lys Ile Ser Asn Arg Phe Ser Gly Val
    50                  55                  60

Pro Asp Arg Phe Ser Gly Ser Gly Ala Gly Thr Asp Phe Thr Leu Lys
65              70                  75                  80

Ile Ser Arg Val Glu Ala Glu Asp Val Gly Val Tyr Tyr Cys Met Gln
                85                  90                  95

Ala Thr Gln Phe Pro
                100

<210> SEQ ID NO 132
<211> LENGTH: 101
<212> TYPE: PRT
<213> ORGANISM: Homo sapiens
<220> FEATURE:
<221> NAME/KEY: Misc.
<222> LOCATION: (33)..(33)
<223> OTHER INFORMATION: Unidentified

<400> SEQUENCE: 132

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Xaa Asn Gly Tyr Asn Tyr Leu Asp Trp Tyr Leu Gln Lys Pro Gly Gln
        35                  40                  45

Ser Pro Gln Leu Leu Ile Tyr Leu Gly Ser Asn Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Ala Leu Gln Thr Pro
            100

<210> SEQ ID NO 133
<211> LENGTH: 106
<212> TYPE: PRT
<213> ORGANISM: Homo sapiens
<220> FEATURE:
<221> NAME/KEY: Misc.
<222> LOCATION: (10)..(10)
<223> OTHER INFORMATION: Unidentified
<221> NAME/KEY: Misc.
<222> LOCATION: (26)..(26)
<223> OTHER INFORMATION: Unidentified
<221> NAME/KEY: Misc.
<222> LOCATION: (29)..(29)
<223> OTHER INFORMATION: Unidentified
<221> NAME/KEY: Misc.
<222> LOCATION: (34)..(34)
<223> OTHER INFORMATION: Unidentified
<221> NAME/KEY: Misc.
<222> LOCATION: (55)..(55)
<223> OTHER INFORMATION: Unidentified
<221> NAME/KEY: Misc.
<222> LOCATION: (56)..(56)
<223> OTHER INFORMATION: Unidentified
<221> NAME/KEY: Misc.
<222> LOCATION: (57)..(57)
<223> OTHER INFORMATION: Unidentified
<221> NAME/KEY: Misc.
<222> LOCATION: (58)..(58)
<223> OTHER INFORMATION: Unidentified
<221> NAME/KEY: Misc.
<222> LOCATION: (76)..(76)
<223> OTHER INFORMATION: Unidentified
<221> NAME/KEY: Misc.
<222> LOCATION: (77)..(77)
<223> OTHER INFORMATION: Unidentified

<400> SEQUENCE: 133

Ser Tyr Val Leu Thr Gln Pro Pro Ser Xaa Val Ser Val Ala Pro Gly
1               5                   10                  15

Lys Thr Ala Arg Ile Thr Cys Gly Gly Xaa Asn Asn Xaa Ile Gly Ser
                20                  25                  30

Lys Xaa Ser Val His Trp Tyr Gln Gln Lys Pro Gly Gln Ala Pro Val
            35                  40                  45

Leu Val Val Tyr Asp Asp Xaa Xaa Xaa Ser Asp Arg Pro Ser Gly
    50                  55                  60

Ile Pro Glu Arg Phe Ser Gly Ser Asn Ser Gly Xaa Xaa Asn Thr Ala
65                  70                  75                  80

Thr Leu Thr Ile Ser Arg Val Glu Ala Gly Asp Glu Ala Asp Tyr Tyr
                85                  90                  95

Cys Gln Val Trp Asp Ser Ser Ser Asp His
            100                 105

<210> SEQ ID NO 134
<211> LENGTH: 104
<212> TYPE: PRT
<213> ORGANISM: Homo sapiens
<220> FEATURE:
<221> NAME/KEY: Misc.

```
<222> LOCATION: (10)..(10)
<223> OTHER INFORMATION: Unidentified
<221> NAME/KEY: Misc.
<222> LOCATION: (26)..(26)
<223> OTHER INFORMATION: Unidentified
<221> NAME/KEY: Misc.
<222> LOCATION: (29)..(29)
<223> OTHER INFORMATION: Unidentified
<221> NAME/KEY: Misc.
<222> LOCATION: (34)..(34)
<223> OTHER INFORMATION: Unidentified
<221> NAME/KEY: Misc.
<222> LOCATION: (55)..(55)
<223> OTHER INFORMATION: Unidentified
<221> NAME/KEY: Misc.
<222> LOCATION: (56)..(56)
<223> OTHER INFORMATION: Unidentified
<221> NAME/KEY: Misc.
<222> LOCATION: (57)..(57)
<223> OTHER INFORMATION: Unidentified
<221> NAME/KEY: Misc.
<222> LOCATION: (58)..(58)
<223> OTHER INFORMATION: Unidentified
<221> NAME/KEY: Misc.
<222> LOCATION: (76)..(76)
<223> OTHER INFORMATION: Unidentified
<221> NAME/KEY: Misc.
<222> LOCATION: (77)..(77)
<223> OTHER INFORMATION: Unidentified

<400> SEQUENCE: 134

Ser Tyr Glu Leu Thr Gln Pro Ser Ser Xaa Val Ser Val Ser Pro Gly
1               5                   10                  15

Gln Thr Ala Arg Ile Thr Cys Ser Gly Xaa Asp Val Xaa Leu Ala Lys
            20                  25                  30

Lys Xaa Tyr Ala Arg Trp Phe Gln Gln Lys Pro Gly Gln Ala Pro Val
        35                  40                  45

Leu Val Ile Tyr Lys Asp Xaa Xaa Xaa Ser Glu Arg Pro Ser Gly
    50                  55                  60

Ile Pro Glu Arg Phe Ser Gly Ser Ser Ser Gly Xaa Xaa Thr Thr Val
65                  70                  75                  80

Thr Leu Thr Ile Ser Gly Ala Gln Val Glu Asp Glu Ala Asp Tyr Tyr
                85                  90                  95

Cys Tyr Ser Ala Ala Asp Asn Asn
            100

<210> SEQ ID NO 135
<211> LENGTH: 101
<212> TYPE: PRT
<213> ORGANISM: Homo sapiens
<220> FEATURE:
<221> NAME/KEY: Misc.
<222> LOCATION: (33)..(33)
<223> OTHER INFORMATION: Unidentified
<221> NAME/KEY: Misc.
<222> LOCATION: (34)..(34)
<223> OTHER INFORMATION: Unidentified
<221> NAME/KEY: Misc.
<222> LOCATION: (35)..(35)
<223> OTHER INFORMATION: Unidentified
<221> NAME/KEY: Misc.
<222> LOCATION: (36)..(36)
<223> OTHER INFORMATION: Unidentified
<221> NAME/KEY: Misc.
<222> LOCATION: (37)..(37)
<223> OTHER INFORMATION: Unidentified

<400> SEQUENCE: 135

Glu Ile Val Leu Thr Gln Ser Pro Gly Thr Leu Ser Leu Ser Pro Gly
1               5                   10                  15
```

-continued

```
Glu Arg Ala Thr Leu Ser Cys Arg Ala Ser Gln Ser Val Ser Ser Ser
             20                  25                  30

Xaa Xaa Xaa Xaa Xaa Tyr Leu Ala Trp Tyr Gln Gln Lys Pro Gly Gln
         35                  40                  45

Ala Pro Arg Leu Leu Ile Tyr Gly Ala Ser Ser Arg Ala Thr Gly Ile
    50                  55                  60

Pro Asp Arg Phe Ser Gly Ser Gly Ser Gly Thr Asp Phe Thr Leu Thr
65                  70                  75                  80

Ile Ser Arg Leu Glu Pro Glu Asp Phe Ala Val Tyr Tyr Cys Gln Gln
             85                  90                  95

Tyr Gly Ser Ser Pro
            100
```